(12) United States Patent
Kapust et al.

(10) Patent No.: US 9,180,270 B2
(45) Date of Patent: Nov. 10, 2015

(54) METHODS, SYSTEMS AND DEVICES FOR NON-INVASIVE OPEN VENTILATION WITH GAS DELIVERY NOZZLES WITHIN AN OUTER TUBE

(75) Inventors: Gregory Kapust, San Ramon, CA (US); Todd Allum, Livermore, CA (US); Anthony D. Wondka, Thousand Oaks, CA (US); Joseph Cipollone, Mission Viejo, CA (US); Joey Aguirre, San Ramon, CA (US); Darius Eghbal, Oakland, CA (US); Anthony Gerber, Denver, CA (US); Lutz Freitag, Hemer (DE)

(73) Assignee: Breathe Technologies, Inc., Irvine, CA (US)

(*) Notice: Subject to any disclaimer, the term of this patent is extended or adjusted under 35 U.S.C. 154(b) by 1159 days.

(21) Appl. No.: 12/753,851

(22) Filed: Apr. 2, 2010

(65) Prior Publication Data
US 2010/0252040 A1    Oct. 7, 2010

Related U.S. Application Data

(60) Provisional application No. 61/166,150, filed on Apr. 2, 2009, provisional application No. 61/239,728, filed on Sep. 3, 2009, provisional application No. 61/255,760, filed on Oct. 28, 2009, provisional application No. 61/294,363, filed on Jan. 12, 2010.

(51) Int. Cl.
*A61M 16/00* (2006.01)
*A61M 16/06* (2006.01)
(Continued)

(52) U.S. Cl.
CPC ....... *A61M 16/0666* (2013.01); *A61M 16/0677* (2014.02); *A61M 16/0683* (2013.01);
(Continued)

(58) Field of Classification Search
CPC ............. A61M 2016/0021; A61M 2016/0024; A61M 2016/0027; A61M 16/0666; A61M 16/06; A61M 16/0666; A61M 16/0677; A61M 16/0683; A61M 16/0688; A61M 16/0858; A61M 16/101; A61M 16/127; A61M 16/16; A61M 16/205; A61M 2205/17; A61M 2205/8206

USPC ............ 128/204.18, 204.23, 204.25, 206.28, 128/207.13, 207.18, 204.21, 204.22, 128/204.24, 204.26–204.28, 205.11, 128/205.13–205.18, 205.22, 205.24, 128/206.21, 207.12
See application file for complete search history.

(56) References Cited

U.S. PATENT DOCUMENTS

| 50,641 A | 10/1865 | Stone |
| 428,592 A | 5/1890 | Chapman |

(Continued)

FOREIGN PATENT DOCUMENTS

| DE | 19626924 | 1/1998 |
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Lynne Anderson
*Assistant Examiner* — Mark K Han
(74) *Attorney, Agent, or Firm* — Stetina Brunda Garred & Brucker

(57) ABSTRACT

A non-invasive ventilation system may include at least one outer tube with a proximal lateral end of the outer tube adapted to extend to a side of a nose. The at least one outer tube may also include a throat section. At least one coupler may be located at a distal section of the outer tube for impinging at least one nostril and positioning the at least one outer tube relative to the at least one nostril. At least one jet nozzle may be positioned within the outer tube at the proximal lateral end and in fluid communication with a pressurized gas supply. At least one opening in the distal section may be adapted to be in fluid communication with the nostril. At least one aperture in the at least one outer tube may be in fluid communication with ambient air. The at least one aperture may be in proximity to the at least one jet nozzle.

28 Claims, 89 Drawing Sheets

(51) Int. Cl.
*A61M 16/08* (2006.01)
*A61M 16/10* (2006.01)
*A61M 16/12* (2006.01)
*A61M 16/16* (2006.01)
*A61M 16/20* (2006.01)

(52) U.S. Cl.
CPC ....... *A61M16/0688* (2014.02); *A61M 16/0858* (2014.02); *A61M 16/101* (2014.02); *A61M 16/127* (2014.02); *A61M 16/16* (2013.01); *A61M 16/208* (2013.01); *A61M 2016/0021* (2013.01); *A61M 2016/0024* (2013.01); *A61M 2205/17* (2013.01); *A61M 2205/8206* (2013.01)

(56) References Cited

U.S. PATENT DOCUMENTS

| | | | |
|---|---|---|---|
| 697,181 | A | 4/1902 | Smith |
| 718,785 | A | 1/1903 | McNary |
| 853,439 | A | 5/1907 | Clark |
| 859,156 | A | 7/1907 | Warnken |
| 909,002 | A | 1/1909 | Lambert |
| 1,125,542 | A | 1/1915 | Humphries |
| 1,129,619 | A | 2/1915 | Zapf |
| 1,331,297 | A | 2/1920 | Walker |
| 2,178,800 | A | 11/1939 | Lombard |
| 2,259,817 | A | 10/1941 | Hawkins |
| 2,552,595 | A | 5/1951 | Seeler |
| 2,663,297 | A | 12/1953 | Turnberg |
| 2,693,800 | A | 11/1954 | Caldwell |
| 2,735,432 | A | 2/1956 | Hudson |
| 2,792,000 | A | 5/1957 | Richardson |
| 2,843,122 | A | 7/1958 | Hudson |
| 2,859,748 | A | 11/1958 | Hudson |
| 2,931,358 | A | 4/1960 | Sheridan |
| 2,947,938 | A | 8/1960 | Bennett |
| 3,172,407 | A | 3/1965 | Von Pechmann |
| 3,267,935 | A | 8/1966 | Andreasen et al. |
| 3,319,627 | A | 5/1967 | Windsor |
| 3,357,424 | A | 12/1967 | Schreiber |
| 3,357,427 | A | 12/1967 | Wittke et al. |
| 3,357,428 | A | 12/1967 | Carlson |
| 3,437,274 | A | 4/1969 | Apri |
| 3,460,533 | A | 8/1969 | Plá |
| 3,493,703 | A | 2/1970 | Finan |
| 3,513,844 | A | 5/1970 | Smith |
| 3,610,247 | A | 10/1971 | Jackson |
| 3,625,206 | A | 12/1971 | Charnley |
| 3,625,207 | A | 12/1971 | Agnew |
| 3,631,438 | A | 12/1971 | Lewin |
| 3,643,660 | A | 2/1972 | Hudson et al. |
| 3,657,740 | A | 4/1972 | Cialone |
| 3,682,171 | A | 8/1972 | Dali et al. |
| 3,721,233 | A | 3/1973 | Montgomery et al. |
| 3,726,275 | A | 4/1973 | Jackson et al. |
| 3,727,606 | A | 4/1973 | Sielaff |
| 3,733,008 | A | 5/1973 | Churchill et al. |
| 3,741,208 | A | 6/1973 | Jonsson et al. |
| 3,754,552 | A | 8/1973 | King |
| 3,794,026 | A | 2/1974 | Jacobs |
| 3,794,072 | A | 2/1974 | Diedrich et al. |
| 3,802,431 | A | 4/1974 | Farr |
| 3,831,596 | A | 8/1974 | Cavallo |
| 3,881,480 | A | 5/1975 | Lafourcade |
| 3,896,800 | A | 7/1975 | Cibulka |
| 3,903,881 | A | 9/1975 | Weigl |
| 3,905,362 | A | 9/1975 | Eyrick et al. |
| 3,949,749 | A | 4/1976 | Stewart |
| 3,951,143 | A | 4/1976 | Kitrilakis et al. |
| 3,961,627 | A | 6/1976 | Ernst et al. |
| 3,972,327 | A | 8/1976 | Ernst et al. |
| 3,985,131 | A | 10/1976 | Buck et al. |
| 3,991,790 | A | 11/1976 | Russell |
| 4,003,377 | A | 1/1977 | Dahl |
| 4,036,253 | A | 7/1977 | Fegan et al. |
| 4,054,133 | A | 10/1977 | Myers |
| 4,067,328 | A | 1/1978 | Manley |
| 4,106,505 | A | 8/1978 | Salter et al. |
| 4,146,885 | A | 3/1979 | Lawson, Jr. |
| 4,206,754 | A | 6/1980 | Cox et al. |
| 4,211,086 | A | 7/1980 | Leonard et al. |
| 4,216,769 | A | 8/1980 | Grimes |
| 4,231,363 | A | 11/1980 | Grimes |
| 4,231,365 | A | 11/1980 | Scarberry |
| 4,248,218 | A * | 2/1981 | Fischer .................. 128/204.18 |
| 4,256,101 | A | 3/1981 | Ellestad |
| 4,261,355 | A | 4/1981 | Glazener |
| 4,263,908 | A | 4/1981 | Mizerak |
| 4,265,237 | A | 5/1981 | Schwanbom et al. |
| 4,266,540 | A * | 5/1981 | Panzik et al. ............ 128/207.13 |
| 4,273,124 | A | 6/1981 | Zimmerman |
| 4,274,162 | A | 6/1981 | Joy et al. |
| 4,278,082 | A | 7/1981 | Blackmer |
| 4,282,869 | A | 8/1981 | Zidulka |
| 4,306,567 | A | 12/1981 | Krasner |
| 4,323,064 | A | 4/1982 | Hoenig et al. |
| 4,354,488 | A | 10/1982 | Bartos |
| 4,365,636 | A | 12/1982 | Barker |
| 4,367,735 | A | 1/1983 | Dali |
| 4,377,162 | A | 3/1983 | Staver |
| 4,393,869 | A | 7/1983 | Boyarsky et al. |
| 4,406,283 | A | 9/1983 | Bir |
| 4,411,267 | A | 10/1983 | Heyman |
| 4,413,514 | A | 11/1983 | Bowman |
| 4,421,113 | A | 12/1983 | Gedeon et al. |
| 4,422,456 | A | 12/1983 | Tiep |
| 4,449,523 | A | 5/1984 | Szachowicz et al. |
| 4,454,880 | A | 6/1984 | Muto et al. |
| 4,462,398 | A | 7/1984 | Durkan et al. |
| 4,469,097 | A | 9/1984 | Kelman |
| 4,481,944 | A | 11/1984 | Bunnell |
| 4,488,548 | A | 12/1984 | Agdanowski |
| 4,495,946 | A | 1/1985 | Lemer |
| 4,506,666 | A | 3/1985 | Durkan |
| 4,506,667 | A | 3/1985 | Ansite |
| 4,519,387 | A | 5/1985 | Durkan et al. |
| 4,520,812 | A | 6/1985 | Freitag et al. |
| 4,527,557 | A | 7/1985 | DeVries et al. |
| 4,535,766 | A | 8/1985 | Baum |
| 4,537,188 | A | 8/1985 | Phuc |
| 4,539,984 | A | 9/1985 | Kiszel et al. |
| 4,548,590 | A | 10/1985 | Green |
| 4,559,940 | A | 12/1985 | McGinnis |
| 4,570,631 | A | 2/1986 | Durkan |
| 4,571,741 | A | 2/1986 | Guillaumot |
| 4,584,996 | A | 4/1986 | Blum |
| 4,590,951 | A | 5/1986 | O'Connor |
| 4,592,349 | A | 6/1986 | Bird |
| 4,621,632 | A | 11/1986 | Bartels et al. |
| 4,630,606 | A | 12/1986 | Weerda et al. |
| 4,630,614 | A | 12/1986 | Atlas |
| 4,644,947 | A | 2/1987 | Whitwam et al. |
| 4,648,395 | A | 3/1987 | Sato et al. |
| 4,648,398 | A | 3/1987 | Agdanowski et al. |
| 4,658,832 | A | 4/1987 | Brugnoli |
| 4,660,555 | A | 4/1987 | Payton |
| 4,682,591 | A | 7/1987 | Jones |
| 4,684,398 | A | 8/1987 | Dunbar et al. |
| 4,686,974 | A | 8/1987 | Sato et al. |
| 4,686,975 | A | 8/1987 | Naimon et al. |
| 4,688,961 | A | 8/1987 | Shioda et al. |
| 4,705,034 | A | 11/1987 | Perkins |
| 4,744,356 | A | 5/1988 | Greenwood |
| 4,747,403 | A | 5/1988 | Gluck et al. |
| 4,753,233 | A | 6/1988 | Grimes |
| 4,773,411 | A | 9/1988 | Downs |
| 4,776,333 | A | 10/1988 | Miyamae |
| 4,782,832 | A | 11/1988 | Trimble et al. |
| 4,784,130 | A | 11/1988 | Kenyon et al. |
| 4,803,981 | A | 2/1989 | Vickery |
| 4,807,616 | A | 2/1989 | Adahan |
| 4,807,617 | A | 2/1989 | Nesti |
| 4,808,160 | A | 2/1989 | Timmons et al. |
| 4,813,431 | A | 3/1989 | Brown |

(56) References Cited

U.S. PATENT DOCUMENTS

| | | |
|---|---|---|
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |

(56) References Cited

U.S. PATENT DOCUMENTS

| | | |
|---|---|---|
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |

(56) References Cited

U.S. PATENT DOCUMENTS

| | | |
|---|---|---|
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |

(56) References Cited

U.S. PATENT DOCUMENTS

| | | |
|---|---|---|
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy, Jr. |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0066976 A1* | 3/2005 | Wondka .................. 128/207.18 |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |

(56) References Cited

U.S. PATENT DOCUMENTS

| | | |
|---|---|---|
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1* | 6/2007 | Pierro et al. ............ 128/204.23 |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunaratnam et al. |
| 2008/0092905 A1 | 4/2008 | Gunaratnam et al. |
| 2008/0092906 A1 | 4/2008 | Gunaratnam et al. |
| 2008/0099024 A1 | 5/2008 | Gunaratnam et al. |
| 2008/0099027 A1 | 5/2008 | Gunaratnam et al. |
| 2008/0105264 A1 | 5/2008 | Gunaratnam et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |

(56) References Cited

U.S. PATENT DOCUMENTS

| | | |
|---|---|---|
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | Mcauley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | s63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | 2004105846 | 12/2004 |
| WO | 2005007056 | 1/2005 |
| WO | WO-2005/014091 | 2/2005 |
| WO | WO-2005/018524 | 3/2005 |
| WO | 2006088007 | 8/2006 |
| WO | WO-2006/138580 | 12/2006 |
| WO | WO 2006133493 A1 * | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO2008060295 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO 2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO 2009/151791 | 12/2009 |
| WO | WO-2010/000135 | 1/2010 |
| WO | WO-2010/021556 | 2/2010 |
| WO | WO-2010/022363 | 2/2010 |

(56) References Cited

FOREIGN PATENT DOCUMENTS

| WO | WO-2010/039989 | 4/2010 |
|---|---|---|
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Office Action in re: Application No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, *Ex Parte Quayle* Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
AMBROSINO, "Exercise and noninvasive ventilatory support," *Monaldi Arch Chest Dis.*, 2000: 55(3): 242-246.
AMBROSINO, "Weaning and Respiratory Muscle Dysfunction: The Egg Chicken Dilemma," *Chest*, 2005: 128(2), pp. 481-483.

(56) References Cited

OTHER PUBLICATIONS

Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-222.
Bauer et al., "Adam Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
ENRIGHT, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.

Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," FDA Consumer Magazine, Jun. 1992, pp. 33-37.
Limberg et al., "Changes in Supplemental Oxygen Prescription in Pulmonary Rehabilitation," *Resp. Care*, 2006:51(11), p. 1302.
MacInryre, "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the Scoop(R) System," *Pneumologie*, 1996: 50(10), pp. 700-02. (English Abstract provided.).

(56) References Cited

OTHER PUBLICATIONS

Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," Chest, 1983: 83(1), pp. 144-145.
Sinderby et al., "Neural control of mechanical ventilation in respiratory failure," Nat. Med., 1999: 5(12), pp. 1433-1436.
Somfay et al., "Dose-Response Effect of Oxygen on Hyperinflation and Exercise Endurance in Nonhypoxaemic COPD Patients," Eur. Resp. J., 2001: 18, pp. 77-84.
Sullivan et al., "Reversal of Obstructive Sleep Apnoea by Continuous Positive Airway Pressure Applied Through the Nares," The Lancet, 1981: 1(8225), pp. 862-865.
Sullivan, "Home treatment of obstructive sleep apnoea with continuous positive airway pressure applied through a nose-mask," Bull Eur Physiopathol Respir., 1984: 20(1), pp. 49-54.
Tiep et al., "Pulsed nasal and transtracheal oxygen delivery," Chest, 1990: 97, pp. 364-368.
Tsuboi et al., "Ventilatory Support During Exercise in Patients With Pulmonary Tuberculosis Sequelae," Chest, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," Cochrane Database Syst. Rev., 2002, 3: 1-22.
Yaeger et al., "Oxygen Therapy Using Pulse and Continuous Flow With a Transtracheal Catheter and a Nasal Cannula," Chest, 1994: 106, pp. 854-860.
Walsh, "McGraw Hill Pocket reference Machinists' and Metalworker' Pocket Reference," New York McGraw-Hill, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in co-pending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.
JP Office Action, 8 Pages.
English Traslation JP Office Action, Application No. 2012-503763, 5 Pages.
CN Office Action, Application No. 100140, Dec. 31, 2013, 4 Pages.
English Traslation CN Office Action, Application No. 201080024596, 2 Pages.
CN Office Action, 5 Pages.
English Traslation CN Office Action, Application No. 201080024596.9, 4 Pages.
English Translation of Chinese Office Action for Chinese Patent Application No. 201080024596.9.
Extended European Search Report and Supplemental Search Report for European Patent Application No. EP 10 75 9520; mailed Aug. 21, 2015.

\* cited by examiner

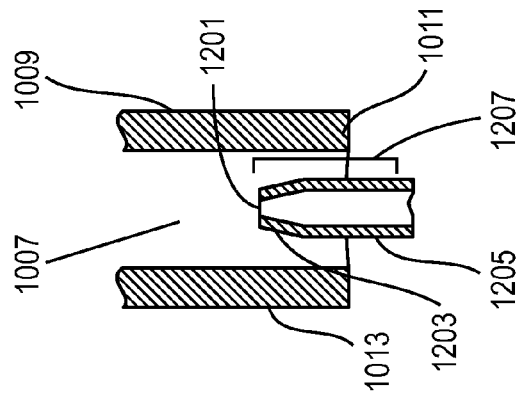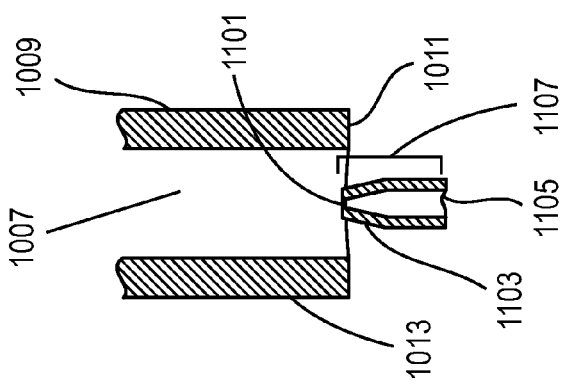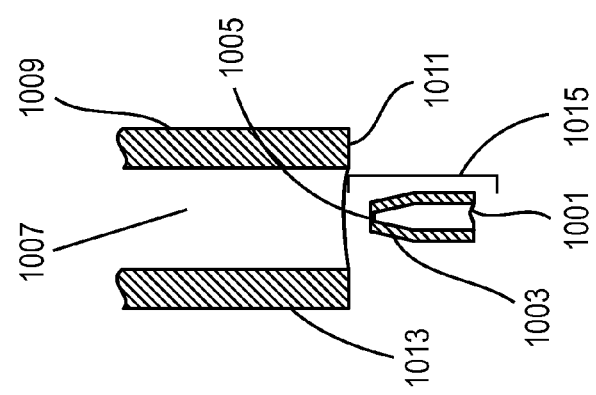

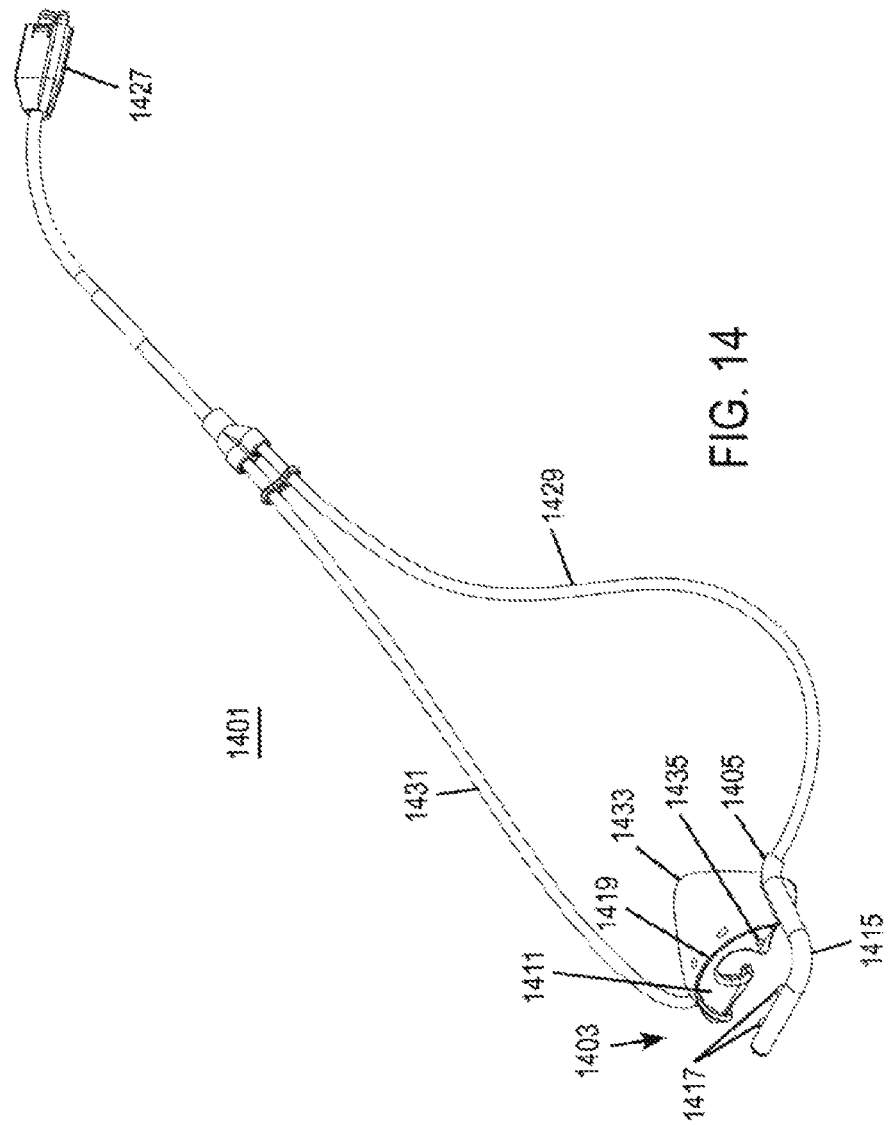

FIG. 61B
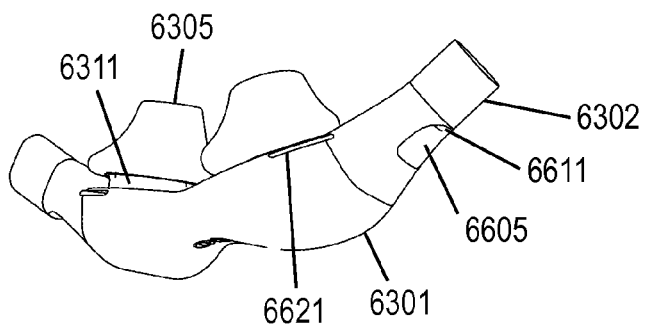
FIG. 62A
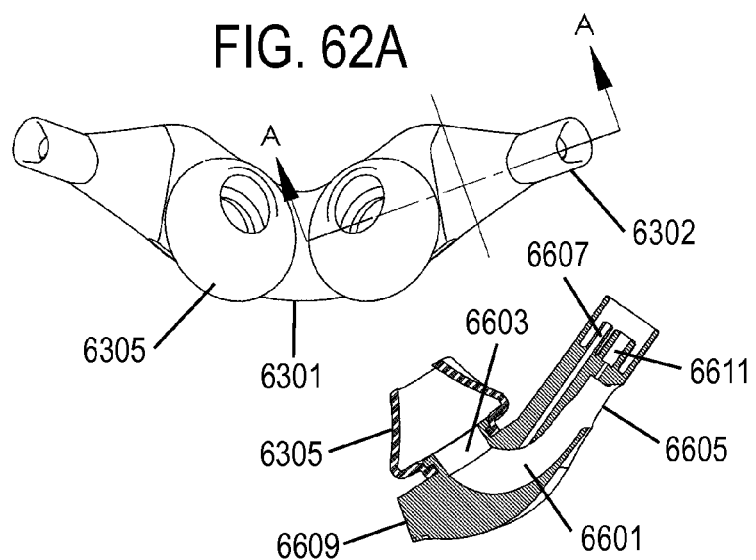
SECTION A-A
FIG. 62B

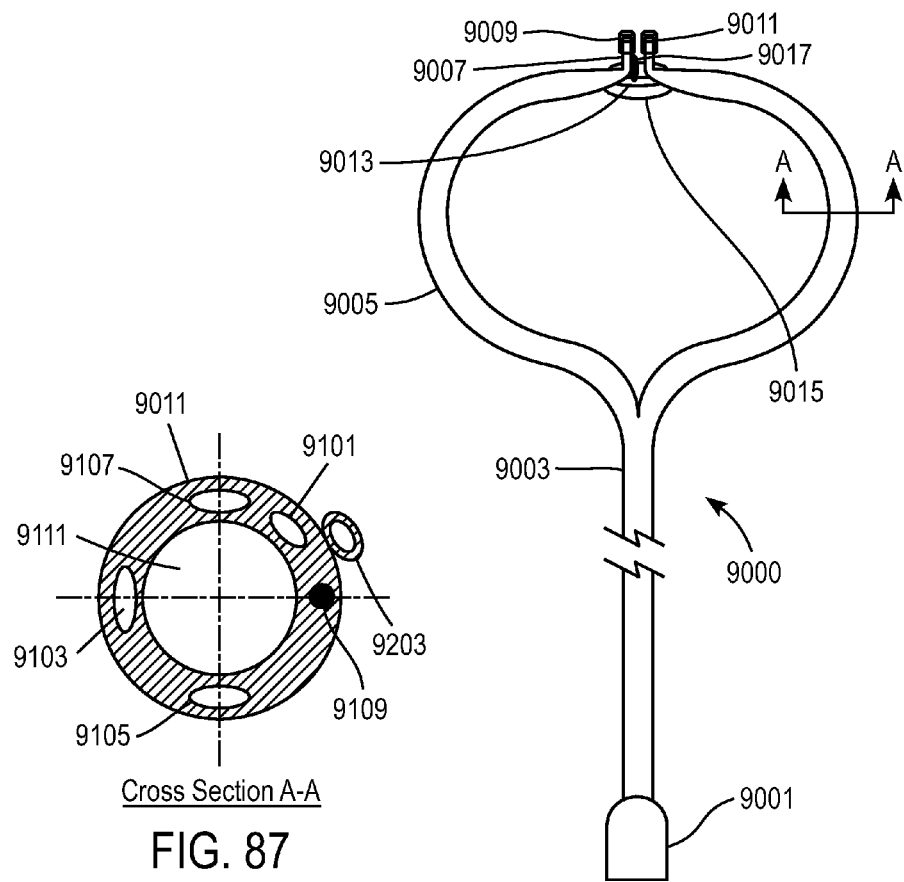
FIG. 86
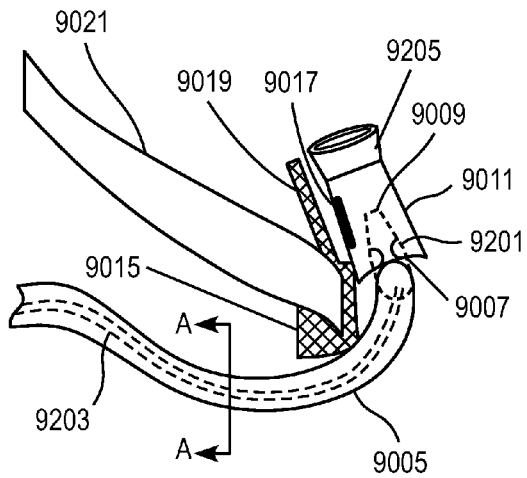
FIG. 87
FIG. 88

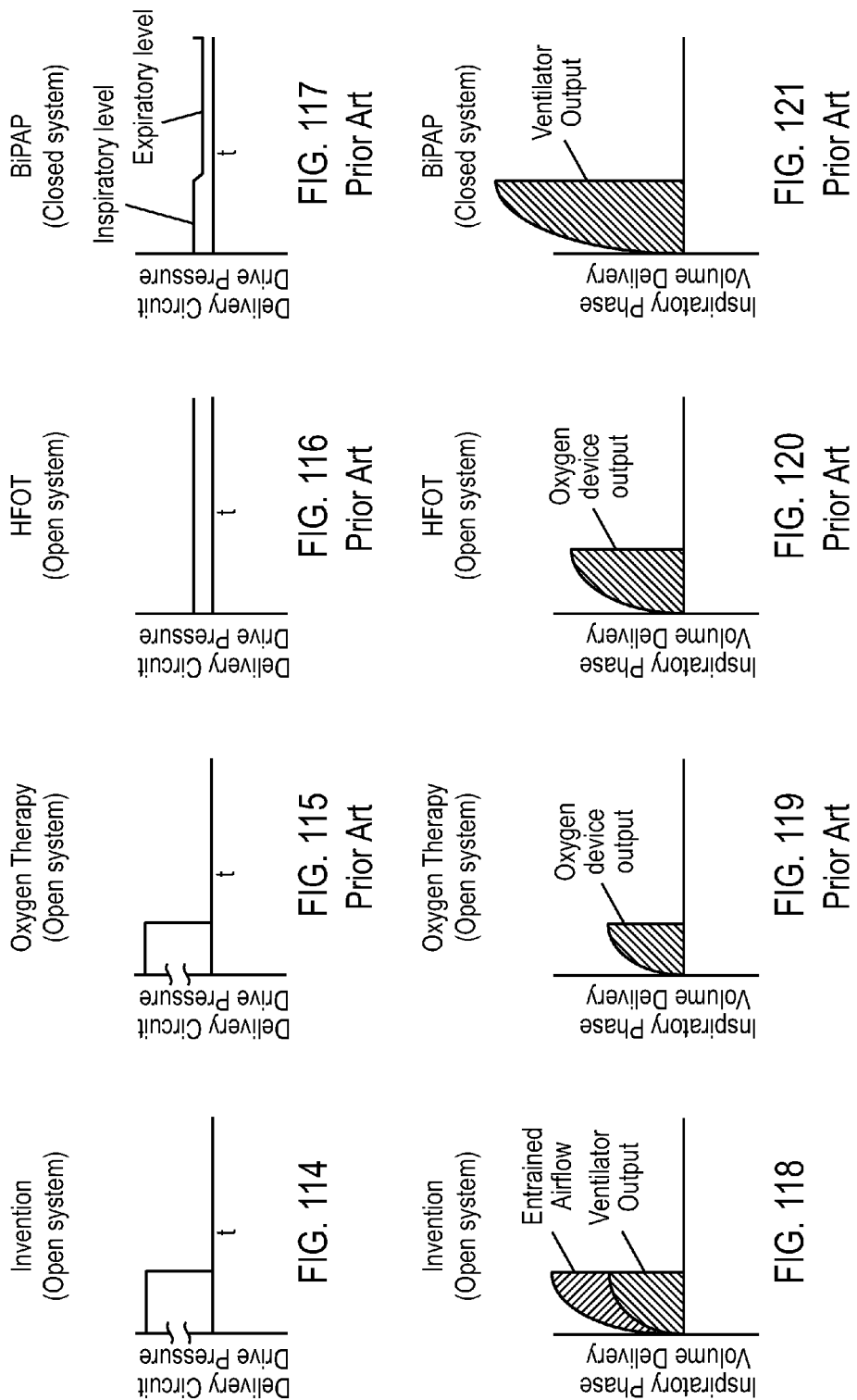

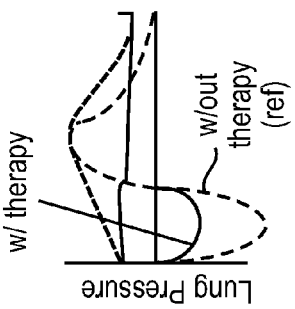
FIG. 122
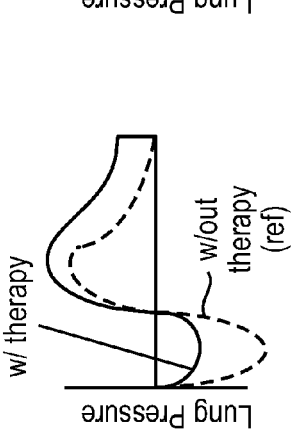
FIG. 123 PRIOR ART
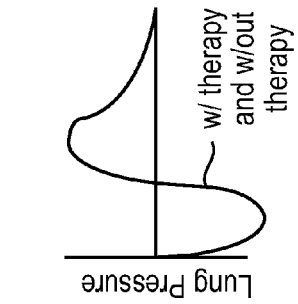
FIG. 124 PRIOR ART
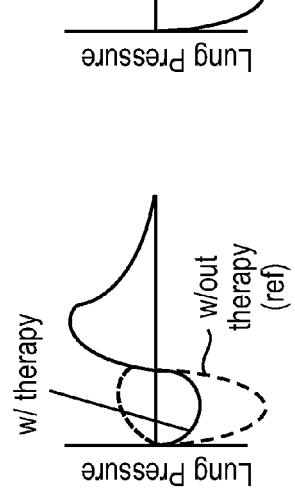
FIG. 125 PRIOR ART
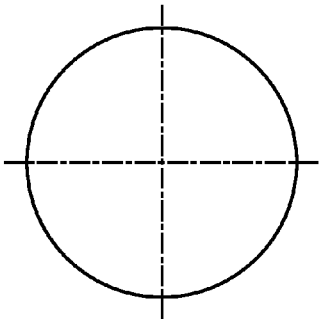
FIG. 126
FIG. 127 PRIOR ART
FIG. 128 PRIOR ART
FIG. 129 PRIOR ART

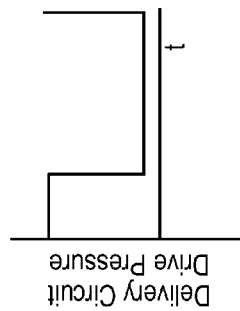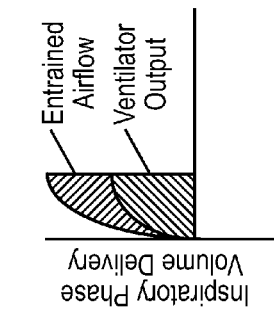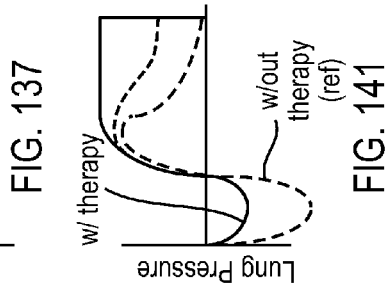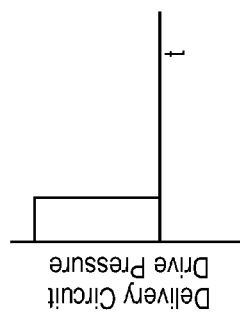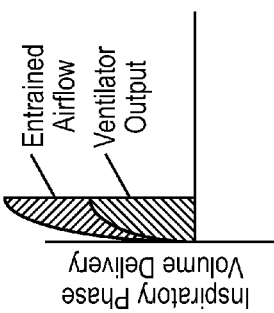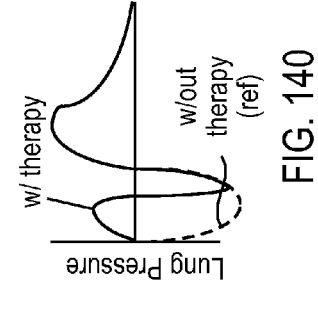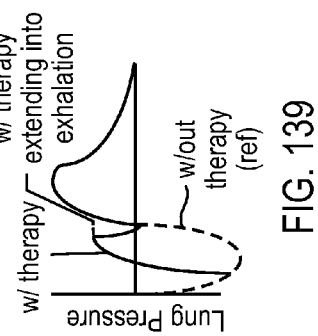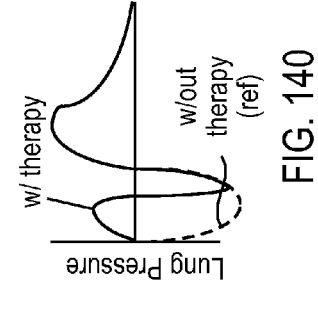

METHODS, SYSTEMS AND DEVICES FOR NON-INVASIVE OPEN VENTILATION WITH GAS DELIVERY NOZZLES WITHIN AN OUTER TUBE

CROSS-REFERENCE TO RELATED APPLICATIONS

This application claims the benefit of U.S. Provisional Patent Application No. 61/166,150, filed Apr. 2, 2009, U.S. Provisional Patent Application No. 61/239,728, filed Sep. 3, 2009, and U.S. Provisional Patent Application No. 61/255,760, filed Oct. 28, 2009, and U.S. Provisional Patent Application No. 61/294,363, filed Jan. 12, 2010; the contents of which are incorporated by reference herein in their entireties.

FIELD OF THE INVENTION

The present invention relates to the field of ventilation therapy for persons suffering from respiratory and breathing disorders, such as respiratory insufficiency and sleep apnea. More specifically, the present invention relates to methods and apparatus for non-invasive open nasal interfaces.

BACKGROUND OF INVENTION

There are a range of clinical syndromes that require some form of ventilation therapy. These syndromes may include hypoxemia, various forms of respiratory insufficiency and airway disorders. There are also non-respiratory and non-airway diseases that require ventilation therapy, such as congestive heart failure and neuromuscular disease, respectively.

Different and separate from ventilation therapy, is oxygen therapy, used for less severe forms of respiratory insufficiency. The standard of care for oxygen therapy or long term oxygen therapy (LTOT) includes administering supplemental oxygen to the patient with a small bore nasal cannula, using a metering device known as an oxygen conserver that releases the oxygen in boluses during a patient's inspiratory phase. This therapy is not considered ventilation therapy or respiratory support, because it does not mechanically help in the work of breathing.

Some entrainment mask systems have been developed and used for the purpose of delivering proper mixtures of air and therapeutic gas. For example, oxygen reservoir systems exist that include a mask with ports to entrain room air. Or, high flow oxygen delivery systems exist that include an air-entrainment mask containing a jet orifice and air entrainment ports, are designed to fit over the patient's nose and mouth, and connect to oxygen supply tubing. Oxygen under pressure is forced through a small jet orifice entering the mask. The velocity increases causing a shearing effect distal to the jet orifice, which causes room air to be entrained into the mask. These oxygen therapy entrainment systems do not support the work of breathing of the patient, rather they are used to deliver proper mixtures of air and oxygen.

Recently, a variant of oxygen therapy has been employed, known as high flow oxygen therapy (HFOT). In this case, the oxygen flow rate is increased beyond standard LTOT, for example, above 10 LPM. Because of the high flow rate, the oxygen must be humidified to prevent drying out the patient's airway. It has been reported that HFOT can reduce the patient's pleural pressure during spontaneous breathing. These systems are inefficient in that they are not precise in delivery of the therapy, and they consume a significant quantity of oxygen, which is often a drawback because the system cannot be mobile.

Respiratory support and ventilation therapies provide mechanical ventilation (MV) to the patient, and mechanically contribute to the work of breathing. MV therapies interface with the patient by intubating the patient with a cuffed or uncuffed tracheal tube, or a sealing face mask, sealing nasal mask or sealing nasal cannula. While helpful in supporting the work of breathing, the patient interfaces used for MV are obtrusive and/or invasive to the user, and MV does not facilitate mobility or activities of daily living and is therefore a drawback to many potential users.

Non-invasive ventilation (NIV) is used to ventilate a patient without requiring intubation. This is a significant advantage in that the patient does not require sedation for the therapy. However, the patient cannot use their upper airway because the interface makes an external seal against the nose and/or mouth, and the system is not mobile, the combination of which does not enable activities of daily living.

Minimally invasive ventilation (MIV) has been described to ventilate a patient with a catheter based delivery system that does not close the airway, and the patient can breathe ambient air freely and naturally through their normal passage ways. MIV differs from NIV because in NIV the patient interface does not enter the person's body, or minimally enters the body, and no unnatural channels are required to gain access to the airway, whereas MIV requires a slightly penetrating catheter or interface into an airway, and/or requires an unnatural channel to be created for airway access. MIV therapies have some promise; however, the patient needs to tolerate a transcutaneous catheter, for example a percutaneous transtracheal catheter, which can be beneficial for those whom are already trached or for those whom wish to conceal the interface underneath clothing.

For treating obstructive sleep apnea (OSA), the gold standard ventilation therapy is continuous positive airway pressure (CPAP) or bilevel positive airway pressure (BiPAP), which is a variant to NIV in that the patient partially exhales through exhaust ports in the mask and exhales the balance back into the large deadspace mask and large gas delivery tubing. The continuous positive pressure being applied from the ventilator opens the upper airway, using a patient interface mask that seals over the nose and or mouth, or seals inside the nose. While highly effective in treating OSA, this therapy has poor patient compliance because the patient interface is obtrusive to the patient, and because the patient unnaturally breathes through a mask and gas delivery circuit. A lesser obtrusive BiPAP and CPAP patient interface has been described by Wondka (U.S. Pat. No. 7,406,966), which is used for both NIV and OSA, in which the interface is low profile and allows for an adjustable fitment and alignment with the user's face and nose. The interface solves many of the preexisting problems associated with NIV masks and OSA masks, namely leaks, comfort, tolerance, sleep position, pressure drop and noise, and compatibility with a variety of anatomical shapes.

In summary, existing therapies and prior art have the following disadvantages: they do not offer respiratory support or airway support in a manner that (1) is non-invasive, and un-obtrusive such that it allows for mobility and activities of daily living, (2) allows the sensation of breathing from the ambient surroundings normally, and (3) is provided in an easily portable system or a system that can be easily borne or worn by the patient.

SUMMARY OF INVENTION

The invention may provide ventilation to a patient using non-invasive open ventilation (NIOV) with a non-invasive nasal interface that does not completely cover or seal the opening of the patient's mouth or nose. The invention can be used to treat respiratory insufficiency by providing MV to support the work of breathing of a patient, or can be used to treat OSA by pressurizing or providing flow to the airway. The nasal interface may include a novel jet pump nasal catheter design, with the nozzle of the catheter positioned near the entrance of the nostrils, and designed with a geometric configuration which optimizes the fluid dynamics of the system to improve the efficiency of the system and efficacy of the therapy. A pressurized gas, such as a therapeutic gas like oxygen-rich gas or simply pressurized air, may be delivered through the catheter, and when exiting the catheter distal tip, may entrain an amount of ambient air that is 25-250% of the gas exiting the catheter due to the configuration of the catheter, so that a combination of ventilator-delivered gas and entrained gas is delivered to the patient. Embodiments of the present invention can, for example, create an increase of 2-40 cmH2O in the upper airway, and 1-30 cmH2O in the lung. A ventilator-delivered gas volume of 50 ml can entrain for example 50 ml, so that 100 ml is delivered to the patient, with a sufficient driving pressure so that a significant amount of the 100 ml volume reaches the airway or lung to increase pressure in those areas, thus mechanically supporting respiration, or preventing airway collapse. In the subsequent descriptions, nasal cannula, nasal catheter, jet nozzle, and ventilation interface are often used interchangeably when pertaining to the present invention. Also, jet nozzle, gas delivery port and gas exit port may be used interchangeably in the invention.

A non-invasive ventilation system may include an interface. The interface may include at least one gas delivery jet nozzle adapted to be positioned in free space and aligned to directly deliver ventilation gas into an entrance of a nose. The at least one gas delivery jet nozzle may be connected to a pressurized gas supply. The ventilation gas may entrain ambient air to elevate lung pressure, elevate lung volume, decrease the work of breathing or increase airway pressure, and wherein the ventilation gas is delivered in synchrony with phases of breathing. A support for the at least one gas delivery jet nozzle may be provided. A breath sensor may be in close proximity to the entrance of the nose. A patient may spontaneous breathe ambient air through the nose without being impeded by the interface.

The support may be a connector for coupling the system to a bridge of the nose and aligning the at least one gas delivery jet nozzle with the entrance of the nose. A gas delivery circuit may pass along one side of a face. A sensing tube may pass along an opposite side of the face. The connector may be a shell. The support may be a bracket. The support may be a skin pad between the nose and mouth. The at least one jet nozzle may be outside the entrance to the nose. The at least one jet nozzle may be substantially flush with the entrance to the nose. The at least one jet nozzle may be inside the entrance to the nose. The at least one jet nozzle may be positioned approximately 0 inches to approximately 1.5 inches outside the entrance to the nose. The at least one jet nozzle may be positioned within approximately 10 degrees of parallel with the entrance to the nose. Ventilation gas may be delivered during inspiration. The at least one jet nozzle may be aligned with a positioning arm. The at least one jet nozzle may be integrated with a manifold. The support may be a gas delivery circuit and a sensing tube. The support may be a headset. At least one sensor may be within the manifold. A sound baffle may be provided. A wearable ventilator and a portable gas supply may be provided. A ventilator may be provided where the ventilator includes a control unit, wherein the control unit adjusts an output of the ventilator to match a patient's needs based on information from the breath sensor. The system further may include a ventilator, the ventilator may include a control unit, and the control unit may include a speaking mode sensing system, and wherein the control unit adjusts an output of the ventilator while a patient is speaking to not be asynchronous with a patient's spontaneous breathing. The system may include a ventilator, the ventilator may include a control unit, and the control unit may include an apnea or hypopnea sensing system, and wherein the control unit adjusts an output of the ventilator according to apnea or hypopnea.

A non-invasive ventilation system may include a ventilator; a control unit; a gas delivery circuit in fluid communication with the ventilator; a sensing tube in communication with the control unit; a shell for coupling to a bridge of a nose; a connector for coupling the gas delivery circuit and the sensing tube to the shell; and one or more nozzles at a distal end of the gas delivery circuit, wherein the one or more nozzles are positioned in free space below an entrance to one or more nostrils, and wherein the one or more nozzles are aligned with the entrance to the one or more nostrils.

The system may include a ledge for contacting a rim of the one or more nostrils and positioning the system. The ledge may include a sensing port connected to the sensing tube. The system may include a portable gas supply, and wherein ventilator is wearable. The control unit may adjust an output of the ventilator to match a patient's needs based on information from the sensing tube. The control unit may include a speaking mode sensing system, and wherein the control unit adjusts an output of the ventilator while a patient is speaking to not be asynchronous with a patient's spontaneous breathing. The control unit may include an apnea or hypopnea sensing system, and wherein the control unit adjusts an output of the ventilator according to apnea or hypopnea.

A method for providing respiratory support may include providing a non-invasive ventilation system including a ventilator; a gas delivery circuit; at least one jet nozzle positioned in free space and aligned to directly deliver ventilation gas into an entrance of a nose; at least one sensor; and a support for the at least one jet nozzle. The method may include measuring spontaneous respiration with the at least one sensor placed in close proximity to the nostril; and activating the ventilator to supply ventilation gas in synchrony with phases of breathing through the gas delivery circuit and to the at least one jet nozzle such that the ventilation gas entrains ambient air. The ventilation gas may entrain ambient air to elevate lung pressure, elevate lung volume, decrease the work of breathing or increase airway pressure.

The at least one jet nozzle may be outside the entrance to the nose. The at least one jet nozzle may be positioned approximately 0 inches to approximately 1.5 inches outside the entrance to the nose. The at least one jet nozzle may be positioned within approximately 10 degrees of parallel with the entrance to the nose. The at least one jet nozzle may be within a manifold. The non-invasive ventilation system may also include a portable gas supply where the ventilator is wearable. The supply of ventilation gas may be adjusted to meet the needs of a patient based on information from the at least one sensor. The method may also include detecting speaking where the supply of ventilation gas is adjusted based on whether or not a patient is speaking. The method may also include detecting apnea or hypopnea where the supply of ventilation gas is adjusted based on apnea or hypopnea.

A non-invasive ventilation system may include at least one outer tube with a proximal lateral end of the outer tube adapted to extend to a side of a nose. The at least one outer tube may also include a throat section. At least one coupler may be located at a distal section of the outer tube for impinging at least one nostril and positioning the at least one outer tube relative to the at least one nostril. At least one jet nozzle may be positioned within the outer tube at the proximal lateral end and in fluid communication with a pressurized gas supply. At least one opening in the distal section may be adapted to be in fluid communication with the nostril. At least one aperture in the at least one outer tube may be in fluid communication with ambient air. The at least one aperture may be in proximity to the at least one jet nozzle.

The outer tube may include a first outer tube and a second outer tube extending in substantially opposite directions. At least one jet nozzle may be positioned within the first outer tube and at least one jet nozzle may be positioned within the second outer tube. The first outer tube may be separated from the second outer tube by a divider. The at least one outer tube may be a manifold. A gas flow path may be within the manifold may be curved and devoid of abrupt angles and corners. At least one coupler may be a nasal pillow. At least one coupler may seal the nostril such that a patient spontaneously breathes through the at least one aperture. The distal tip of the at least one jet nozzle may be positioned at the at least one aperture. The at least one jet nozzle may direct pressurized gas in a substantially parallel direction with ambient air entering from the at least one aperture. At least one secondary aperture may be in the outer tube. The at least one jet nozzle may direct pressured gas coaxially to a primary gas flow pathway. A filter may be included. At least one gas flow path may be included through the outer tube, and pressurized gas may be directed toward a wall of the gas flow path. At least one sensor may be provided for sensing spontaneous respiration. A ventilator may deliver pressurized gas in synchrony with phases of breathing. A cross sectional area of the at least one aperture may be larger than a cross sectional area of the throat section. A wearable ventilator and a portable gas supply may be provided. A ventilator may be provided, the ventilator may include a control unit, and wherein the control unit adjusts an output of the ventilator to match a patient's ventilation needs based on information from at least one sensor. A ventilator may be provided, the ventilator may include a control unit, and the control unit may include a speaking mode sensing system, and wherein the control unit adjusts an output of the ventilator while the patient is speaking to not be asynchronous with a patient's spontaneous breathing. A ventilator may be provided, the ventilator may include a control unit, and the control unit may include an apnea or hypopnea sensing system, and wherein the control unit adjusts an output of the ventilator according to apnea or hypopnea. The outer tube may include sound reduction features selected from the group consisting of: a secondary aperture, a filter for the aperture, textured surfaces, a muffler, sound absorbing materials, an angled jet nozzle, non-concentric jet nozzle positions, and combinations thereof.

A non-invasive ventilation system may include a ventilator; a gas delivery circuit in fluid communication with the ventilator, wherein the gas delivery circuit is bifurcated; a manifold in fluid communication with the ventilator, wherein each lateral proximate end of the manifold is in fluid communication with the gas delivery circuit; a gas delivery path from each lateral proximal end of the manifold to a distal end of the manifold; at least one aperture in each lateral proximal end of the manifold between the gas delivery path and ambient air; at least one jet nozzle within each gas delivery path and aligned in parallel with each gas delivery path, wherein the at least one jet nozzle supplies ventilation gas proximate to the at least one aperture; tubular extensions at the distal end of the manifold, wherein the tubular extensions comprise a throat section; and a septum separating each gas delivery path.

The system may include at least one sensor. The tubular extensions may include nasal cushions. The ventilation gas and entrained ambient air may elevate lung pressure, elevate lung volume, decrease work of breathing or increase airway pressure. A cross sectional area of the at least one aperture may be larger than a cross sectional area of the throat section. A portable gas supply may be provided, and the ventilator may be portable. The ventilator may include a control unit, and the control unit may adjust an output of the ventilator to match a patient's ventilation needs based on information from at least one sensor. The ventilator may include a control unit, and the control unit may include a speaking mode sensing system, and the control unit may adjust an output of the ventilator while a patient is speaking to not be asynchronous with a patient's spontaneous breathing. The ventilator may include a control unit, and the control unit may include an apnea or hypopnea sensing system, and the control unit may adjust an output of the ventilator according to apnea or hypopnea. The manifold may include sound reduction features selected from the group consisting of: a secondary aperture, a filter for the aperture, textured surfaces, a muffler, sound absorbing materials, an angled jet nozzle, non-concentric jet nozzle positions, and combinations thereof.

A method of providing respiratory support may include providing a non-invasive ventilation system including a ventilator; a gas delivery circuit; an outer tube; at least one gas delivery path through the outer tube; at least one aperture between the at least one gas delivery tube and ambient air, wherein the at least one aperture is at a proximal lateral end of the at least one gas delivery path; at least one jet nozzle within the gas delivery path proximate to the at least one aperture; at least one sensor; and at least one nasal cushion at a distal end of the outer tube for impinging a nostril. The method may include measuring spontaneous respiration with the at least one sensor; and activating the ventilator to supply ventilation gas in synchrony with phases of breathing through the gas delivery circuit and to the at least one jet nozzle such that the ventilation gas entrains ambient air, wherein the ventilation gas entrains ambient air.

The ventilation gas and entrained ambient air may elevate lung pressure, elevate lung volume, decrease work of breathing or increase airway pressure. The non-invasive ventilation system may include a portable gas supply, where the ventilator is wearable. The supply of ventilation gas may be adjusted to meet the needs of a patient based on information from the at least one sensor. The method may include detecting speaking, and the supply of ventilation gas may be adjusted based on whether or not a patient is speaking. The method may include detecting apnea or hypopnea, and the supply of ventilation gas may be adjusted based on apnea or hypopnea.

A non-invasive ventilation system may include a nasal interface. The nasal interface may include a left outer tube with a left distal end adapted to impinge a left nostril, at least one left opening in the left distal end in pneumatic communication with the left nostril, and a left proximal end of the left outer tube in fluid communication with ambient air. The left proximal end of the left outer tube may curve laterally away from a midline of a face. A right outer tube may be similarly provided. One or more left jet nozzles may direct ventilation gas into the left outer tube, and one or more right jet nozzles may direct ventilation gas into the right outer tube. The jet nozzles may be in fluid communication with the pressurized gas supply.

The one or more left jet nozzles, the one or more right jet nozzles, or both may be directed toward an inner wall of the left outer tube, the right outer tube, or both. The left outer tube and the right outer tube may include a jet pump throat and a jet pump diffuser. The one or more left jet nozzles may be flush with an entrance of the left outer tube and the one or more right jet nozzles may be flush with an entrance of the right outer tube. The one or more left jet nozzles may be within an entrance of the left outer tube and the one or more right jet nozzles may be within an entrance of the right outer tube. The one or more left jet nozzles may be outside an entrance of the left outer tube and the one or more right jet nozzles may be outside an entrance of the right outer tube. The system may include at least one sensing lumen, and/or at least one secondary sensing lumen, and/or a drug delivery lumen, and/or a humidity delivery lumen, and/or a coupler between the left outer tube and the right outer tube. A ventilator may deliver ventilation gas in synchrony with phases of breathing. Ambient air may be entrained through the outer tube. The ventilation gas and the entrained ambient air may elevate lung pressure, elevate lung volume, decrease work of breathing or increase airway pressure. The left outer tube and the right outer tube may be stabilized against a face. A wearable ventilator and a portable gas supply may be provided. A ventilator may be provided, the ventilator may include a control unit, and wherein the control unit may adjust an output of the ventilator to match a patient's needs based on information from at least one sensor. A ventilator may be provided, the ventilator may include a control unit, the control unit may include a speaking mode sensing system, and wherein the control unit may adjust an output of the ventilator while the patient is speaking to not be asynchronous with a patient's spontaneous breathing. A ventilator may be provided, the ventilator may include a control unit, the control unit may include an apnea or hypopnea sensing system, and wherein the control unit adjusts an output of the ventilator based on apnea or hypopnea. The left outer tube or the right outer tube may include sound reduction features selected from the group of: a secondary aperture, a filter for the aperture, textured surfaces, a muffler, sound absorbing materials, an angled jet nozzle, non-concentric jet nozzle positions, and combinations thereof.

A non-invasive ventilation system may include a ventilator; a gas delivery circuit comprising a left gas path and a right gas path; and a nasal interface comprising a left outer tube receiving ventilation gas from at least one nozzle on a distal end of the left gas path and a right outer tube receiving ventilation gas from at least one nozzle on a distal end of the right gas path; wherein the left outer tube and the right outer tube curve laterally away from a midline of a nose.

Ventilation gas may be directed toward an inner wall of the left outer tube and the right outer tube. The at least one nozzle on the distal end of the left gas path may be within the left outer tube and the at least one nozzle on the distal end of the right gas path may be within the right outer tube. The at least one nozzle on the distal end of the left gas path may be flush with the left outer tube and the at least one nozzle on the distal end of the right gas path may be flush with the right outer tube. The at least one nozzle on the distal end of the left gas path may be outside the left outer tube and the at least one nozzle on the distal end of the right gas path may be outside the right outer tube. The left gas path and the right gas path may be stabilized against a face. A portable gas supply may be provided, and the ventilator may be portable. The ventilator may include a control unit, and the control unit may adjust an output of the ventilator to match a patient's needs based on information from at least one sensor. The ventilator may include a control unit, the control unit may include a speaking mode sensing system, and the control unit may adjust an output of the ventilator while the patient is speaking to not be asynchronous with a patient's spontaneous breathing. The ventilator may include a control unit, the control unit may include an apnea or hypopnea sensing system, and the control unit may adjust an output of the ventilator based on apnea or hypopnea. The left gas path or the right gas path may include sound reduction features selected from the group of: a secondary aperture, a filter for the aperture, textured surfaces, a muffler, sound absorbing materials, an angled jet nozzle, non-concentric jet nozzle positions, and combinations thereof.

A method of providing ventilation gas may include providing a nasal interface system including a ventilator; a gas delivery circuit; at least one jet nozzle at a distal end of the gas delivery circuit; at least one outer tube proximate to the distal end of the gas delivery circuit for receiving ventilation gas from the at least one jet nozzle, and wherein the at least one outer tube curves laterally away from a midline of a nose; at least one sensor; measuring spontaneous respiration with the at least one sensor; and activating the ventilator to supply ventilation gas in synchrony with phases of breathing through the gas delivery circuit and to the at least one jet nozzle such that the ventilation gas entrains ambient air, wherein the ventilation gas entrains ambient air.

The ventilation gas and entrained ambient air may elevate lung pressure, elevate lung volume, decrease work of breathing or increase airway pressure. Ventilation gas may be directed toward an inner wall of the at least one outer tube. The at least one nozzle may be within the at least one outer tube. The at least one nozzle may be flush with the at least one outer tube. The at least one nozzle may be outside the at least one outer tube. The nasal interface system may include a portable gas supply, where the ventilator is portable. The supply of ventilation gas may be adjusted to meet the needs of a patient based on information from the at least one sensor. The method may include detecting speaking, and the supply of ventilation gas may be adjusted based on whether or not a patient is speaking. The method may include detecting apnea or hypopnea, and the supply of ventilation gas may be adjusted based on apnea or hypopnea.

A system for providing ventilation support to a patient may include a ventilator, a control unit, a gas delivery circuit with a proximal end in fluid communication with the ventilator and a distal end in fluid communication with a nasal interface, and a nasal interface. The nasal interface may include at least one jet nozzle at the distal end of the gas delivery circuit; and at least one spontaneous respiration sensor for detecting respiration in communication with the control unit. The system may be open to ambient. The control unit may receive signals from the at least one spontaneous respiration sensor and determine gas delivery requirements. The ventilator may deliver gas at a velocity to entrain ambient air and increase lung volume or lung pressure above spontaneously breathing levels to assist in work of breathing, and deliver ventilation gas in a cyclical delivery pattern synchronized with a spontaneous breathing pattern.

The at least one jet nozzle may be adapted to be positioned in free space and may be aligned to directly deliver ventilation gas into an entrance of a nose. The nasal interface may include a support for the at least one jet nozzle. A patient may spontaneous breathe ambient air through the nose. The nasal interface may include at least one outer tube with a proximal lateral end of the outer tube adapted to extend toward a side of a nose; at least one coupler at a distal section of the outer tube for impinging at least one nostril and positioning the at least one outer tube relative to the at least one nostril; at least one opening in the distal section adapted to be in fluid communication with the nostril; and at least one aperture in the at least one outer tube in fluid communication with ambient air, wherein the at least one aperture is in proximity to the at least one jet nozzle, and wherein the at least one jet nozzle is positioned within the outer tube at the proximal lateral end and in fluid communication with a pressurized gas supply. The at least one coupler may be a nasal cushion. The nasal interface may include a left outer tube comprising a left distal end adapted to impinge a left nostril, at least one left opening in the left distal end in pneumatic communication with the left nostril, a left proximal end of the left outer tube in fluid communication with ambient air, and wherein the left proximal end of the left outer tube curves laterally away from a midline of a face; and a right outer tube comprising a right distal end adapted to impinge a right nostril, at least one right opening in the right distal end in pneumatic communication with the right nostril, a right proximal end of the right outer tube in fluid communication with ambient air, and wherein the right proximal end of the right outer tube curves laterally away from the midline of the face. Ambient air may be entrained through the left outer tube or the right outer tube. Ventilation gas may be provided at the beginning of respiration. Ventilation gas may be provided by ramping. The control unit may adjust an output of the ventilator to match a patient's needs based on information from the at least one respiration sensor. The control unit may include a speaking mode sensing system, and the control unit may adjust an output of the ventilator while the patient is speaking to not be asynchronous with the patient's spontaneous breathing. The nasal interface may include an outer tube, and wherein the outer tube comprises sound reduction features selected from the group consisting of: a secondary aperture, a filter for the aperture, textured surfaces, a muffler, sound absorbing materials, an angled jet nozzle, non-concentric jet nozzle positions, and combinations thereof.

A device for providing ventilatory support to a patient may include a ventilator with a control system; a gas supply; a nasal interface open to ambient comprising at least one jet nozzle and at least one breathing sensor; and a gas delivery circuit pneumatically connecting the ventilator to the at least one jet nozzle for delivering ventilation gas, and wherein the nasal interface is adapted to locate the at least one breathing sensor in proximity to a nostril entrance, and is adapted to locate the at least one jet nozzle a distance away from the nostril entrance distal to the at least one breathing sensor.

The ventilator may deliver ventilation gas at a velocity to entrain ambient air and increase lung volume or lung pressure above spontaneously breathing levels to assist in work of breathing. The ventilator may deliver ventilation gas in a cyclical delivery pattern synchronized with a spontaneous breathing pattern. The at least one jet nozzle may be adapted to be positioned in free space and may be aligned to directly deliver ventilation gas into an entrance of a nose. The nasal interface may include a support for the at least one jet nozzle. A patient may spontaneous breathe ambient air through the nose. The nasal interface may include at least one outer tube with a proximal lateral end of the outer tube adapted to extend toward a side of a nose; at least one coupler at a distal section of the outer tube for impinging at least one nostril and positioning the at least one outer tube relative to the at least one nostril; at least one opening in the distal section adapted to be in fluid communication with the nostril; and at least one aperture in the at least one outer tube in fluid communication with ambient air, wherein the at least one aperture is in proximity to the at least one jet nozzle, and wherein the at least one jet nozzle is positioned within the outer tube at the proximal lateral end and in fluid communication with a pressurized gas supply. The at least one coupler may be a nasal cushion. The nasal interface may include a left outer tube comprising a left distal end adapted to impinge a left nostril, at least one left opening in the left distal end in pneumatic communication with the left nostril, a left proximal end of the left outer tube in fluid communication with ambient air, and wherein the left proximal end of the left outer tube curves laterally away from a midline of a face; and a right outer tube comprising a right distal end adapted to impinge a right nostril, at least one right opening in the right distal end in pneumatic communication with the right nostril, a right proximal end of the right outer tube in fluid communication with ambient air, and wherein the right proximal end of the right outer tube curves laterally away from the midline of the face. Ambient air may be entrained through the left outer tube or the right outer tube. Ventilation gas may be provided at the beginning of respiration. Ventilation gas may be provided by ramping. The control unit may adjust an output of the ventilator to match a patient's needs based on information from the at least one respiration sensor. The control unit may include a speaking mode sensing system, and the control unit may adjust an output of the ventilator while the patient is speaking to not be asynchronous with the patient's spontaneous breathing. The nasal interface may include an outer tube, and wherein the outer tube comprises sound reduction features selected from the group consisting of: a secondary aperture, a filter for the aperture, textured surfaces, a muffler, sound absorbing materials, an angled jet nozzle, non-concentric jet nozzle positions, and combinations thereof.

A method for providing ventilation support may include providing a nasal interface for positioning at least one jet nozzle; delivering ventilation gas from a ventilator to a gas delivery circuit in fluid communication with the at least one jet nozzle; delivering ventilation gas to a patient nasal airway through the at least one jet nozzle; sensing spontaneous respiration with at least one sensor in communication with a control unit; determining ventilation gas delivery requirements; modifying the delivery of ventilation gas based upon phases of breathing in a cyclical pattern synchronized with the phases of breathing; wherein the ventilation gas increases lung volume or lung pressure above spontaneously breathing levels to assist in work of breathing, wherein the ventilation gas entrains ambient air, and wherein the patient nasal airway is open to ambient.

The at least one jet nozzle may be adapted to be positioned in free space and may be aligned to directly deliver the ventilation gas into an entrance of a nose. The nasal interface may include a support for the at least one jet nozzle. The nasal interface may include at least one outer tube with a proximal lateral end of the outer tube adapted to extend toward a side of a nose; at least one coupler at a distal section of the outer tube for impinging at least one nostril and positioning the at least one outer tube relative to the at least one nostril; at least one opening in the distal section adapted to be in fluid communication with the nostril; and at least one aperture in the at least one outer tube in fluid communication with ambient air, wherein the at least one aperture is in proximity to the at least one jet nozzle, and wherein the at least one jet nozzle is positioned within the outer tube at the proximal lateral end and in fluid communication with a pressurized gas supply. The at least one coupler may be a nasal cushion. The nasal interface may include a left outer tube comprising a left distal end adapted to impinge a left nostril, at least one left opening in the left distal end in pneumatic communication with the left nostril, a left proximal end of the left outer tube in fluid communication with ambient air, and wherein the left proximal end of the left outer tube curves laterally away from a midline of a face; and a right outer tube comprising a right distal end adapted to impinge a right nostril, at least one right opening in the right distal end in pneumatic communication with the right nostril, a right proximal end of the right outer tube in fluid communication with ambient air, and wherein the right proximal end of the right outer tube curves laterally away from the midline of the face. Ambient air may be entrained through the left outer tube or the right outer tube. Ventilation gas may be provided at the beginning of respiration. Ventilation gas may be provided by ramping. The nasal interface may be adapted to locate the at least one sensor in proximity to a nostril entrance, and may be adapted to locate the at least one jet nozzle a distance away from the nostril entrance distal to the at least one sensor. The method may include providing a portable gas supply where the ventilator is wearable. The supply of ventilation gas may be adjusted to meet the needs of a patient based on information from the at least one sensor. The method may include detecting speaking where the supply of ventilation gas may be adjusted based on whether or not a patient is speaking.

A system for reducing airway obstructions of a patient may include a ventilator, a control unit, a gas delivery circuit with a proximal end in fluid communication with the ventilator and a distal end in fluid communication with a nasal interface, and a nasal interface. The nasal interface may include at least one jet nozzle, and at least one spontaneous respiration sensor in communication with the control unit for detecting a respiration effort pattern and a need for supporting airway patency. The system may be open to ambient. The control unit may determine more than one gas output velocities. The more than one gas output velocities may be synchronized with different parts of a spontaneous breath effort cycle, and a gas output velocity may be determined by a need for supporting airway patency.

The at least one jet nozzle may be adapted to be positioned in free space and may be aligned to directly deliver pressurized gas into an entrance of a nose. The nasal interface may include a support for the at least one jet nozzle. A patient may spontaneous breathe ambient air through the nose. The nasal interface may include at least one outer tube with a proximal lateral end of the outer tube adapted to extend toward a side of a nose; at least one coupler at a distal section of the outer tube for impinging at least one nostril and positioning the at least one outer tube relative to the at least one nostril; and at least one opening in the distal section adapted to be in fluid communication with the nostril; and at least one aperture in the at least one outer tube in fluid communication with ambient air, wherein the at least one aperture is in proximity to the at least one jet nozzle, wherein the at least one jet nozzle is positioned within the outer tube at the proximal lateral end and in fluid communication with a pressurized gas supply. The at least one coupler may be a nasal cushion. The nasal interface may include a left outer tube comprising a left distal end adapted to impinge a left nostril, at least one left opening in the left distal end in pneumatic communication with the left nostril, a left proximal end of the left outer tube in fluid communication with ambient air, and wherein the left proximal end of the left outer tube curves laterally away from a midline of a face; and a right outer tube comprising a right distal end adapted to impinge a right nostril, at least one right opening in the right distal end in pneumatic communication with the right nostril, a right proximal end of the right outer tube in fluid communication with ambient air, and wherein the right proximal end of the right outer tube curves laterally away from the midline of the face. Ambient air may be entrained through the outer tube. Pressurized gas may be provided at the beginning of respiration. Pressurized gas may be provided by ramping. A portable ventilation gas supply may be provided where the ventilator is portable. The control unit may adjust an output of the ventilator to match a patient's needs based on information from the at least one respiration sensor. The control unit may include a speaking mode sensing system, and the control unit may adjust an output of the ventilator while the patient is speaking to not be asynchronous with the patient's spontaneous breathing. The control unit may include an apnea or hypopnea sensing system, and the control unit may adjust an output of the ventilator based on apnea or hypopnea. The nasal interface further may include an outer tube, and wherein the outer tube comprises sound reduction features selected from the group consisting of: a secondary aperture, a filter for the aperture, textured surfaces, a muffler, sound absorbing materials, an angled jet nozzle, non-concentric jet nozzle positions, and combinations thereof.

A device for treating sleep apnea may include a ventilator with a control system; a gas supply; a nasal interface comprising a manifold adapted to be placed under the nose, the manifold may include a gas flow path; a gas chamber in the gas flow path; tubular nasal cushions adapted to be in communication with the nostril gas flow path and in communication with the manifold gas flow path; a pressure sensing port in communication with the gas chamber; a spontaneous breathing aperture in communication with the gas flow path wherein the patient can exhale completely through the spontaneous breathing aperture, and inspire through the spontaneous breathing aperture; and a jet gas delivery nozzle in communication with the gas delivery circuit and in communication with the manifold gas flow path; and a gas delivery circuit pneumatically connecting the ventilator to the nasal interface; wherein gas flows from the ventilator through the gas delivery circuit, out the nozzle into the manifold gas flow path, into the chamber, and through the nasal cushions to the nasal airways, and wherein the gas delivery into the chamber of the manifold creates a positive pressure in the chamber, and wherein the positive pressure is controlled at a desired positive pressure by the control system.

The nose may be in fluid communication with ambient air. The control system may determine more than one gas output velocities, wherein the more than one gas output velocities are synchronized with different parts of a spontaneous breath effort cycle, and a gas output velocity is determined by a need for supporting airway patency. The control system may adjust an output of the ventilator to match a patient's needs based on information from the pressure sensing port. The control system may include a speaking mode sensing system, and the control system may adjust an output of the ventilator while the patient is speaking to not be asynchronous with the patient's spontaneous breathing. The control system may include an apnea or hypopnea sensing system, and the control system may adjust an output of the ventilator based on apnea or hypopnea. The nasal interface may include an outer tube, and wherein the outer tube comprises sound reduction features selected from the group consisting of: a secondary aperture, a filter for the aperture, textured surfaces, a muffler, sound absorbing materials, an angled jet nozzle, non-concentric jet nozzle positions, and combinations thereof.

A device for treating sleep apnea may include a ventilator with a control system; a gas supply; a nasal interface open to ambient comprising at least one jet nozzle and at least one breathing sensor; and a gas delivery circuit pneumatically connecting the ventilator to the at least one jet nozzle for delivering ventilation gas, and wherein the nasal interface is adapted to locate the at least one breathing sensor in proximity to a nostril entrance, and is adapted to locate the at least one jet nozzle a distance away from the nostril entrance distal to the at least one breathing sensor.

The at least one jet nozzle may be adapted to be positioned in free space and may be aligned to directly deliver ventilation gas into an entrance of a nose. The nasal interface may include a support for the at least one jet nozzle. A patient may spontaneous breathe ambient air through the nose. The nasal interface may include at least one outer tube with a proximal lateral end of the outer tube adapted to extend toward a side of a nose; at least one coupler at a distal section of the outer tube for impinging at least one nostril and positioning the at least one outer tube relative to the at least one nostril; at least one opening in the distal section adapted to be in fluid communication with the nostril; and at least one aperture in the at least one outer tube in fluid communication with ambient air, wherein the at least one aperture is in proximity to the at least one jet nozzle, and wherein the at least one jet nozzle is positioned within the outer tube at the proximal lateral end and in fluid communication with a pressurized gas supply.

The at least one coupler may be a nasal cushion. The nasal interface may include a left outer tube comprising a left distal end adapted to impinge a left nostril, at least one left opening in the left distal end in pneumatic communication with the left nostril, a left proximal end of the left outer tube in fluid communication with ambient air, and wherein the left proximal end of the left outer tube curves laterally away from a midline of a face; and a right outer tube comprising a right distal end adapted to impinge a right nostril, at least one right opening in the right distal end in pneumatic communication with the right nostril, a right proximal end of the right outer tube in fluid communication with ambient air, and wherein the right proximal end of the right outer tube curves laterally away from the midline of the face. Ambient air may be entrained through the left outer tube or the right outer tube. Ventilation gas may be provided at the beginning of respiration. Ventilation gas may be provided by ramping. The control system may adjust an output of the ventilator to match a patient's needs based on information from the pressure sensing port. The control system may include a speaking mode sensing system, and the control system may adjust an output of the ventilator while the patient is speaking to not be asynchronous with the patient's spontaneous breathing. The control system may include an apnea or hypopnea sensing system, and the control system may adjust an output of the ventilator based on apnea or hypopnea. The nasal interface may include an outer tube, and the outer tube may include sound reduction features selected from the group consisting of: a secondary aperture, a filter for the aperture, textured surfaces, a muffler, sound absorbing materials, an angled jet nozzle, non-concentric jet nozzle positions, and combinations thereof.

A method for reducing airway obstructions of a patient may include: providing a nasal interface for positioning at least one jet nozzle; delivering pressurized gas from a ventilator to a gas delivery circuit in fluid communication with the at least one jet nozzle; delivering pressurized gas to a patient nasal airway through the at least one jet nozzle; sensing a respiration effort pattern and a need for supporting airway patency with at least one sensor in communication with a control unit; determining pressurized gas output velocities, wherein the more than one gas output velocities are synchronized with different parts of a spontaneous breath effort cycle, and a gas output velocity is determined by a need for supporting airway patency; and modifying the delivery of pressurized gas based upon phases of breathing in a cyclical pattern synchronized with the phases of breathing; wherein the pressurized gas increases airway pressure, wherein the pressurized gas entrains ambient air, and wherein the patient nasal airway is open to ambient.

The at least one jet nozzle may be adapted to be positioned in free space and may be aligned to directly deliver the pressurized gas into an entrance of a nose. The nasal interface may include a support for the at least one jet nozzle. The nasal interface may include at least one outer tube with a proximal lateral end of the outer tube adapted to extend toward a side of a nose; at least one coupler at a distal section of the outer tube for impinging at least one nostril and positioning the at least one outer tube relative to the at least one nostril; at least one opening in the distal section adapted to be in fluid communication with the nostril; and at least one aperture in the at least one outer tube in fluid communication with ambient air, wherein the at least one aperture is in proximity to the at least one jet nozzle, wherein the at least one jet nozzle is positioned within the outer tube at the proximal lateral end and in fluid communication with a pressurized gas source.

The at least one coupler may be a nasal cushion. The nasal interface may include a left outer tube comprising a left distal end adapted to impinge a left nostril, at least one left opening in the left distal end in pneumatic communication with the left nostril, a left proximal end of the left outer tube in fluid communication with ambient air, and wherein the left proximal end of the left outer tube curves laterally away from a midline of a face; and a right outer tube comprising a right distal end adapted to impinge a right nostril, at least one right opening in the right distal end in pneumatic communication with the right nostril, a right proximal end of the right outer tube in fluid communication with ambient air, and wherein the right proximal end of the right outer tube curves laterally away from the midline of the face. Ambient air may be entrained through the outer tube. The pressurized gas may be provided at the beginning of respiration. The pressurized gas may be provided by ramping. A tip of the at least one jet nozzle may be directed toward an inner wall of an outer tube. The nasal interface may include a sound reducer. The method may include turning a pressurized gas source on, and monitoring for a predetermined time without delivering therapy. The method may include, after the predetermined time, activating the pressurized gas source to deliver a therapeutic gas flow. The supply of ventilation gas may be adjusted to meet the needs of a patient based on information from the at least one sensor. The method may include detecting speaking, and the supply of ventilation gas may be adjusted based on whether or not a patient is speaking. The method may include detecting apnea or hypopnea, and the supply of ventilation gas may be adjusted based on apnea or hypopnea.

A method of treating sleep apnea may include providing a ventilator, a gas delivery circuit, and a nasal interface; connecting a proximal end of the gas delivery circuit to the ventilator; connecting a distal end of the gas delivery circuit to the nasal interface; attaching the nasal interface to a user's face, wherein the nasal interface allows the user to inhale and exhale ambient air across or through the nasal interface without breathing being restricted; turning ventilator power on causing the ventilator to enter a mode of patient monitoring without delivering therapy; and wherein after a delay after turning the ventilator power on, at a predetermined time, the ventilator delivers a therapeutic gas flow of ventilation gas to a user's nasal airway through the gas delivery circuit and the nasal interface.

The therapeutic gas flow may be adjusted to meet the needs of the user based on information from at least one sensor. The method may include detecting speaking, and the supply therapeutic gas flow may be adjusted based on whether or not a patient is speaking. The method may include detecting apnea or hypopnea, and the therapeutic gas flow may be adjusted based on apnea or hypopnea.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention.

FIG. 10 shows a cross-sectional view of an exemplary nasal interface with a nozzle outside the nose.

FIG. 11 shows a cross-sectional view of an exemplary nasal interface with a nozzle flush with the nose.

FIG. 12 shows a cross-sectional view of an exemplary nasal interface with a nozzle inside the nose.

FIG. 14 illustrates an isometric view of a non-invasive open ventilation (NIOV) nasal interface assembly.

FIG. 61B shows a front-side view of the manifold of FIG. 59.

FIG. 62A shows a rear view of the manifold of FIG. 59.

FIG. 62B shows a sectional view of the manifold of FIG. 62A along a mid-line A-A showing a gas flow path.

FIG. 86 shows an overall view of a nasal ventilation interface.

FIG. 87 describes an exemplary cross section of the cannula of the nasal interface at line A-A indicated in FIG. 86.

FIG. 88 describe a more detailed side view of the distal end of the nasal interface shown in FIG. 86.

FIGS. 114-117 compare delivery circuit drive pressure of NIOV to the prior art.

FIGS. 118-121 compare inspiratory phase volume delivery of NIOV to the prior art.

FIGS. 122-125 compare lung pressure of NIOV to the prior art.

FIGS. 126-129 compare typical outer diameter of a delivery circuit of NIOV to the prior art.

FIGS. 130-153 graphically show different alternative ventilator output waveforms of the present invention, and the effect of the ventilator output on the patient's lung mechanics.

Figure 154:
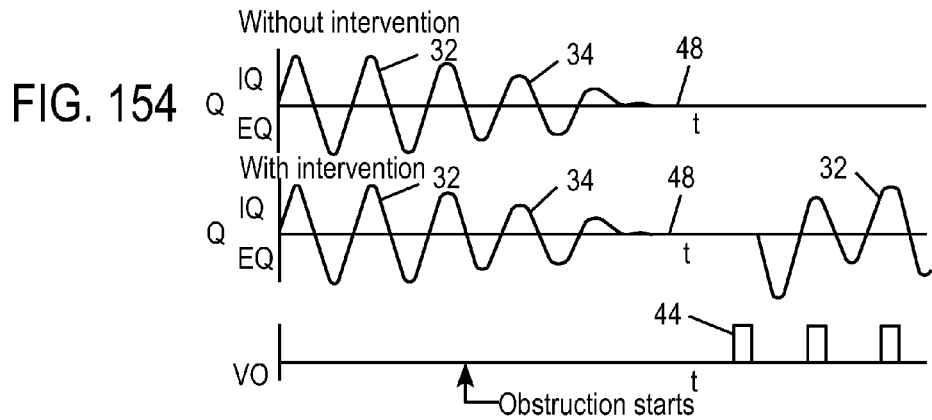

FIG. 154 shows a reaction and correction algorithm where the spontaneous breathing sensor may detect a shift in nasal airflow from a normal airflow signal to a reduced airflow signal.

Figure 155:
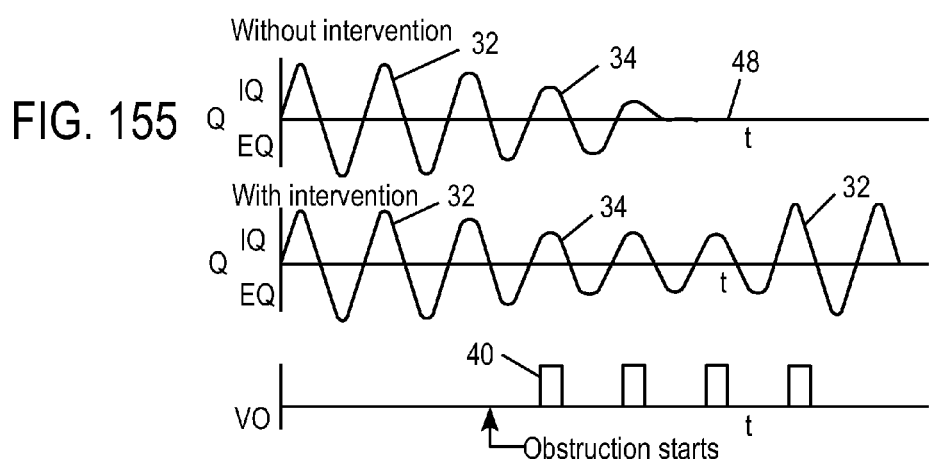

FIG. 155 shows a preemption algorithm where the breathing sensor detects a shift in nasal airflow from a normal airflow signal to a reduced airflow signal.

Figure 156:
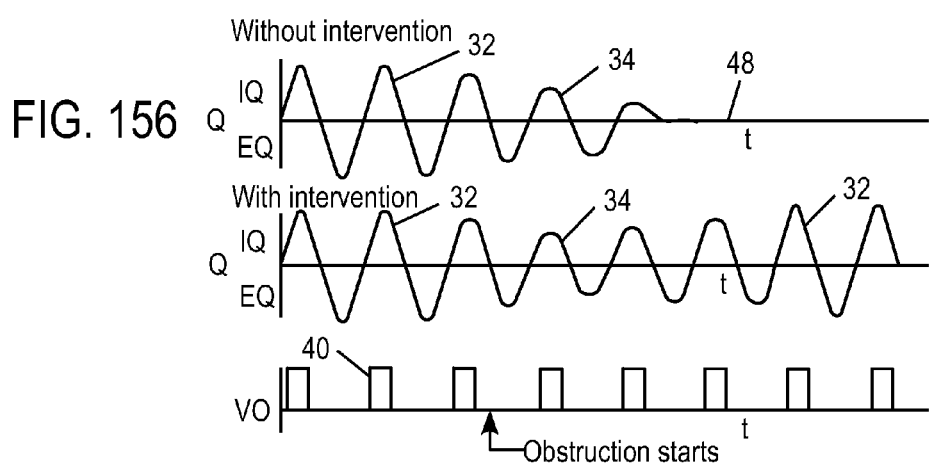

FIG. 156 shows a prevention algorithm where ventilator gas flow is delivered in synchrony with the patient's spontaneous breathing, and when a reduction in airflow occurs due to the onset of an obstruction, the cyclical rate of the ventilator prevents the obstruction from fully developing, and the breathing returns to normal.

Figure 157:
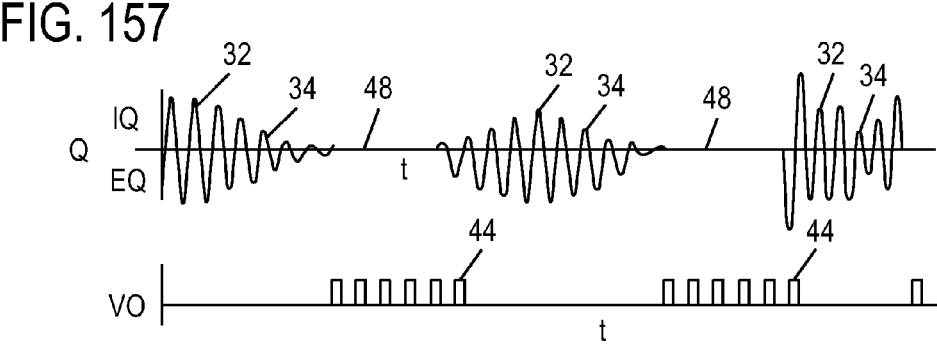

FIG. 157 graphically shows the patient and ventilator waveforms over a period of time, in which the ventilator is activated during the precursor to an apnea or during periods of apnea or airway obstruction, and then is deactivated when normal breathing is restored.

Figure 158:
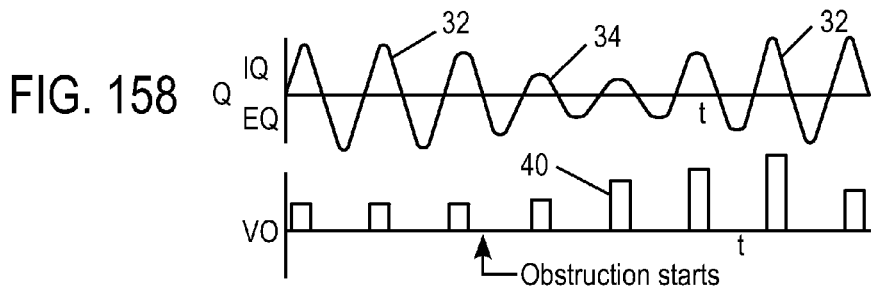

FIG. 158 shows that the ventilator output may be increased in response to a weakening airflow or breathing signal, thus preventing obstruction and restoring normal airflow.

Figure 159:
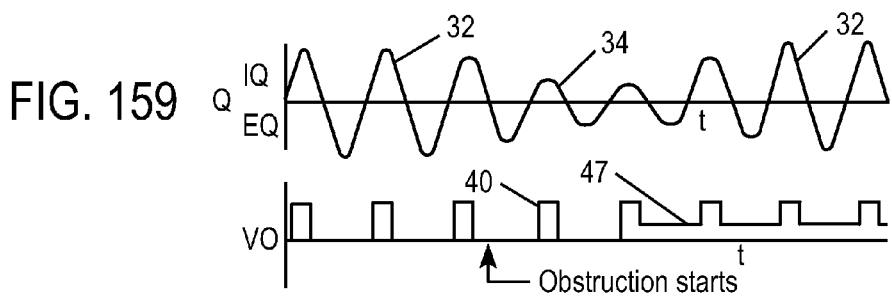

FIG. 159 shows that the ventilator output may switch from a synchronized cyclical on and off output to delivering a continuous flow between cycles, when the onset of an obstruction is detected.

Figure 160:
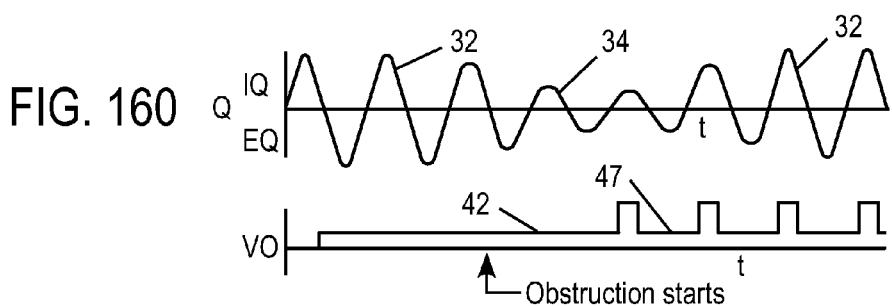

FIG. 160 shows that the ventilator may emit a continuous flow or pressure output until the precursor to an apnea is detected, at which time the ventilator boosts its output to deliver a greater amplitude of pressure, flow or volume synchronized with inspiration, while the reduced airflow representing the partial obstruction is present.

Figure 161:
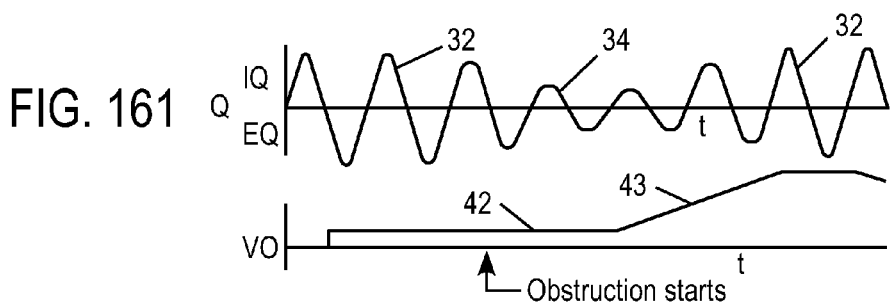

FIG. 161 shows that a variable ventilator pressure or continuous flow output may be delivered, which ramps to a greater amplitude until the reduced airflow signal is returned to a normal signal, after which time, the ventilator output can ramp down to its baseline value.

Figure 162:
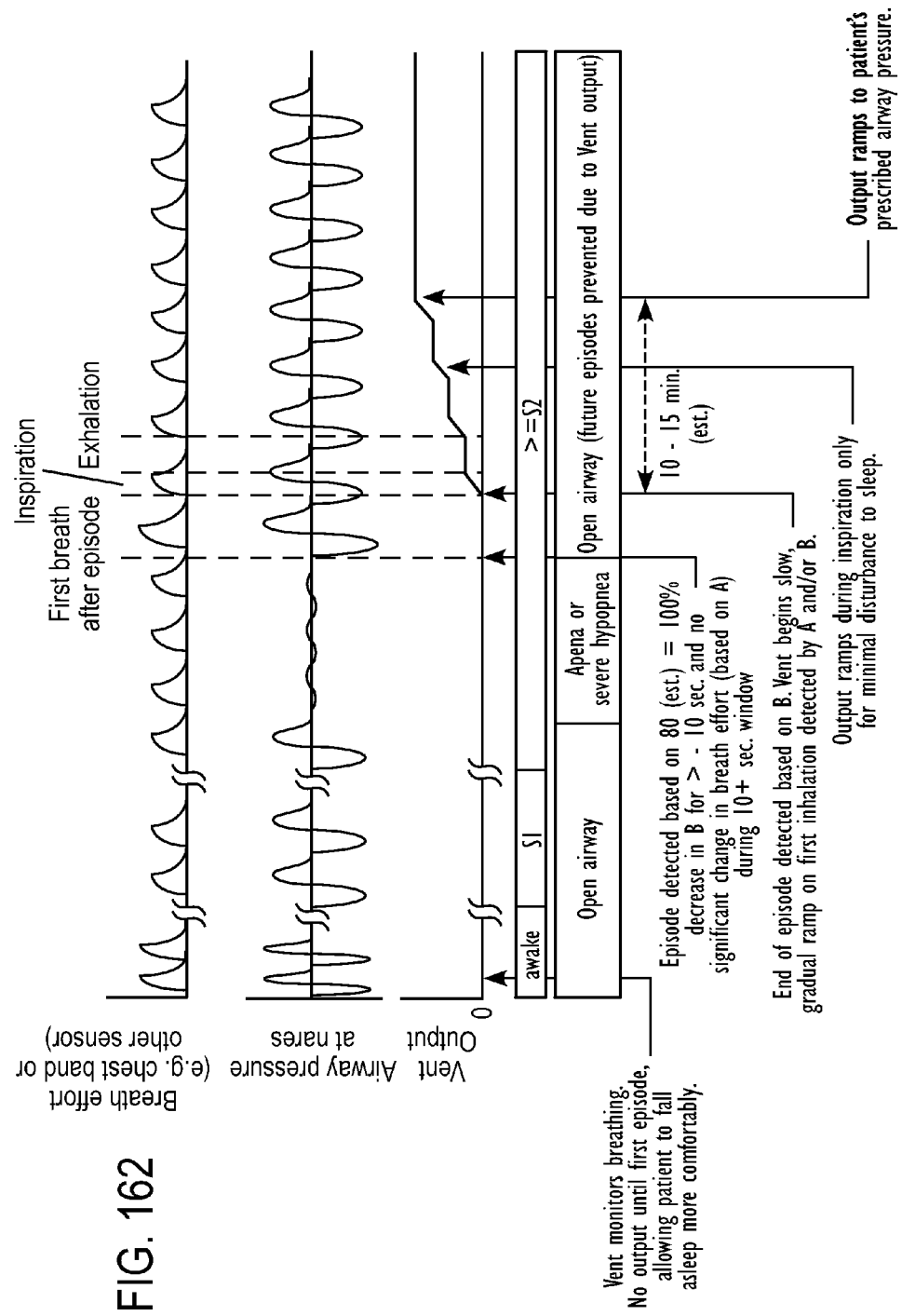

FIG. 162 shows that ramping may be conducted during inspiratory phase only to make the increase more unnoticeable to the patient.

Figure 163:
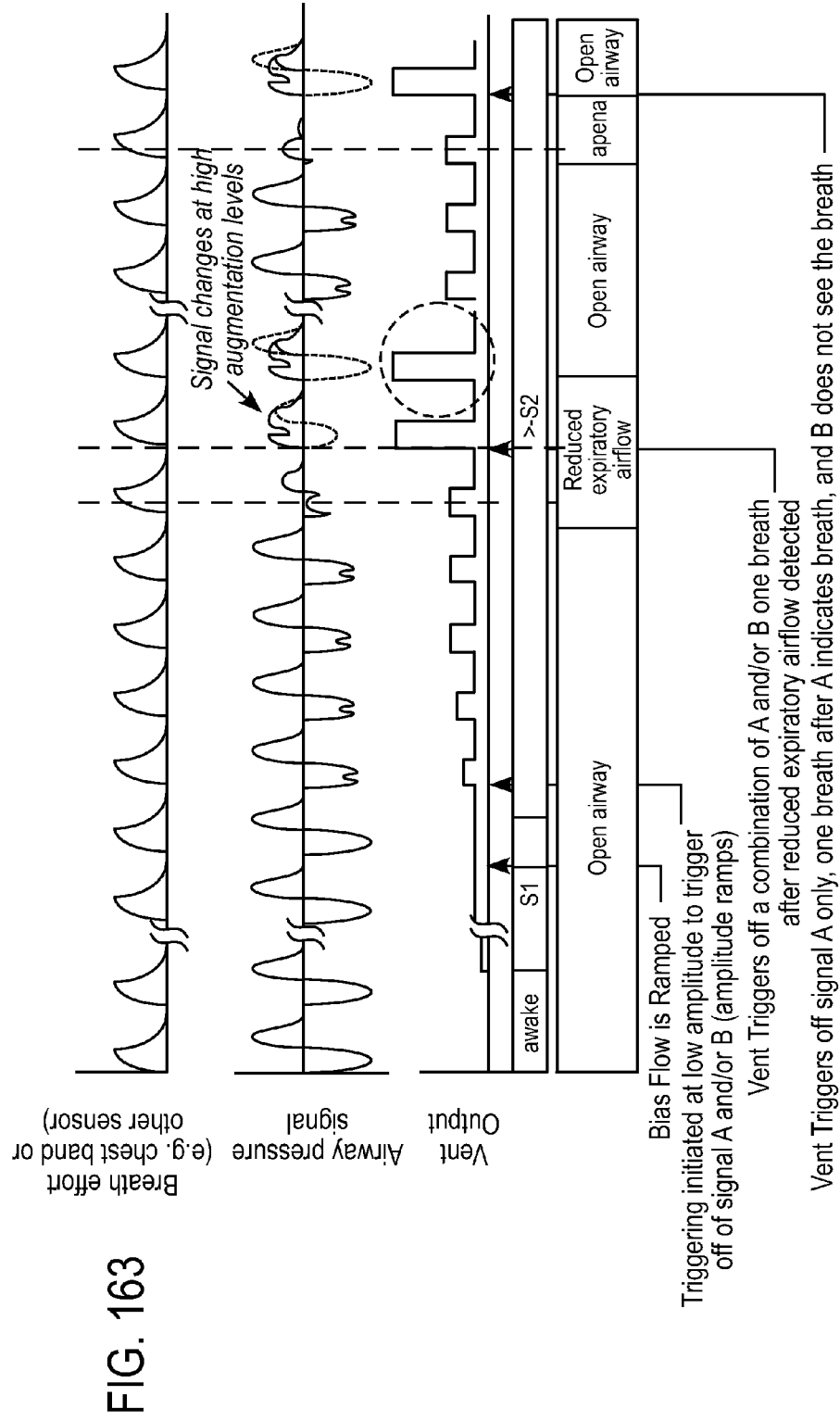

FIG. 163 shows an algorithm in which non-therapeutic pulses of flow are delivered in synchrony with the patient's inspiratory effort, in order to condition or acclimate the patient to the feeling and or sound of the therapy.

Figure 164:
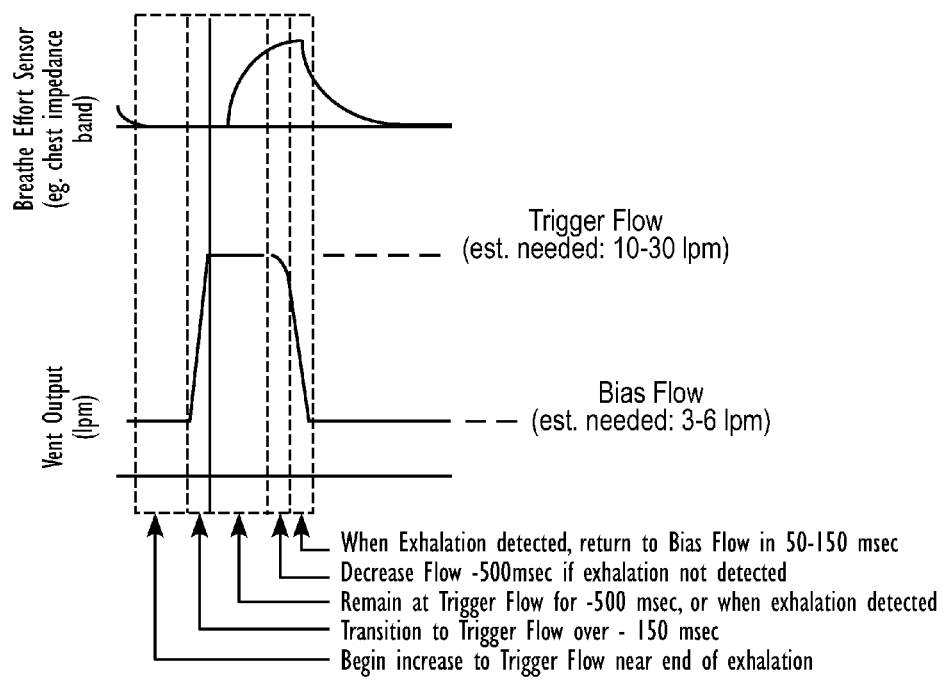

FIG. 164 graphically illustrates in closer detail an optional embodiment of the gas delivery waveform when using an inspiratory effort-synchronized therapy.

Figure 165:
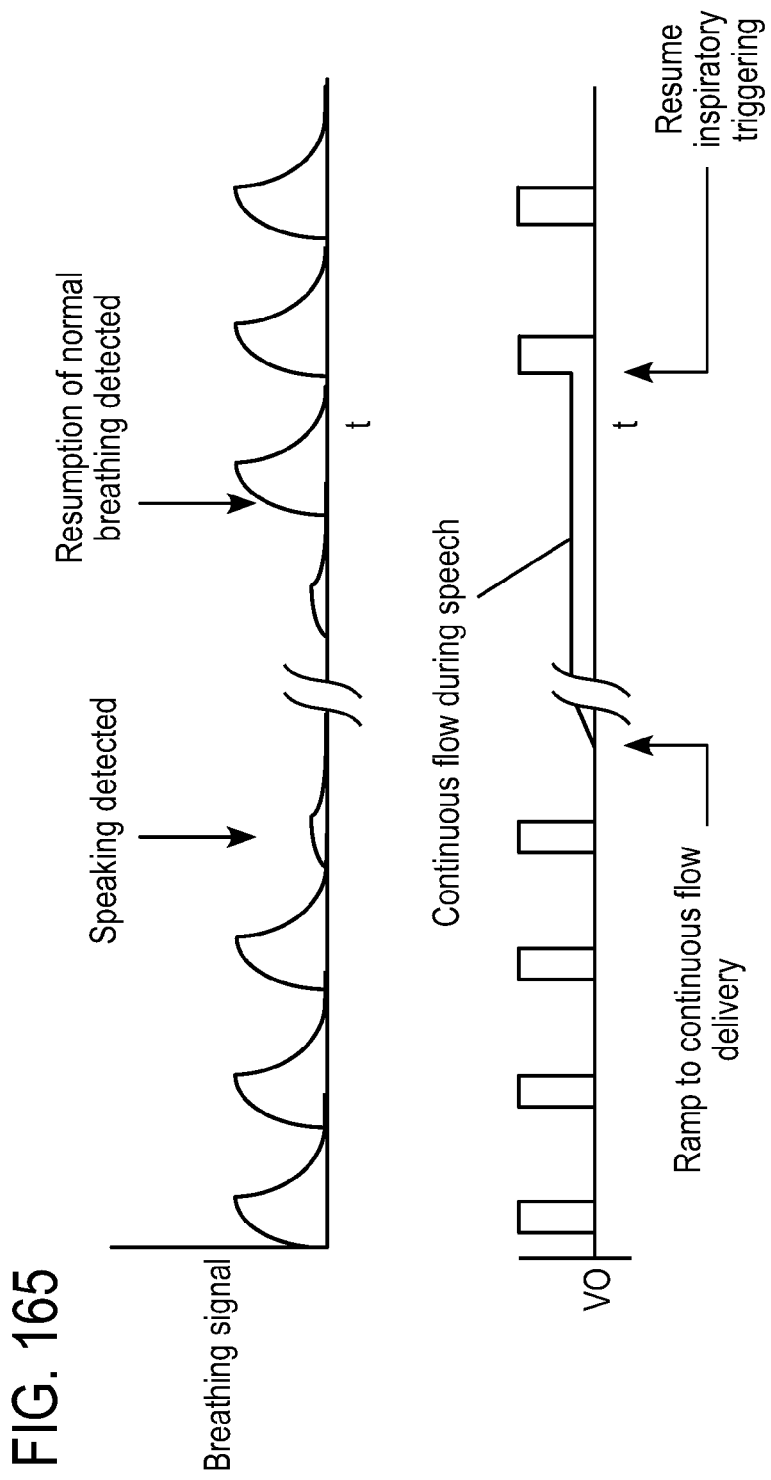

FIG. 165 shows that NIOV can include speaking detection capability, such as using airway pressure signal processing or sound or vibration sensors.

Figure 166:
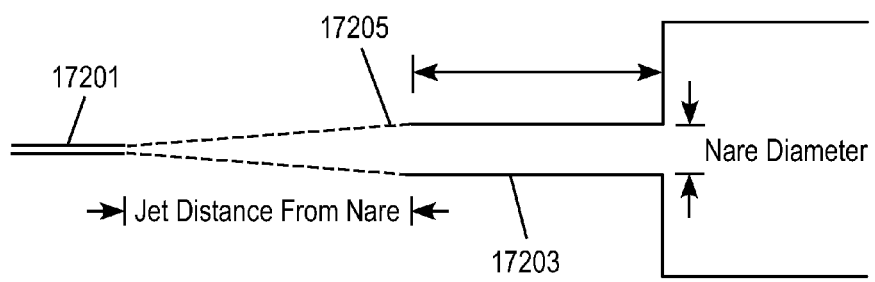

FIG. 166 shows a jet nozzle placed concentric to the nares.

Figure 167:
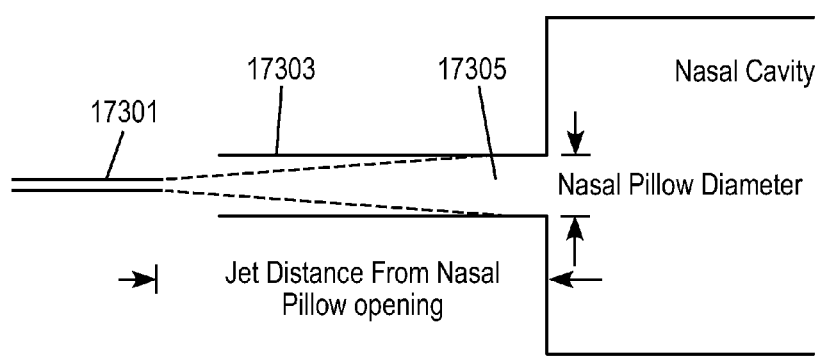

FIG. 167 shows a jet nozzle placed coaxially in nasal pillows.

Figure 168:
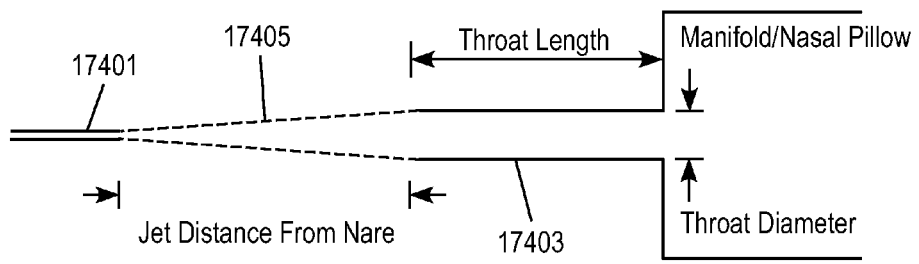

FIG. 168 shows a jet nozzle a distance from an end of a throat section such that a jet profile diameter substantially equals the throat entrance diameter.

Figure 169:
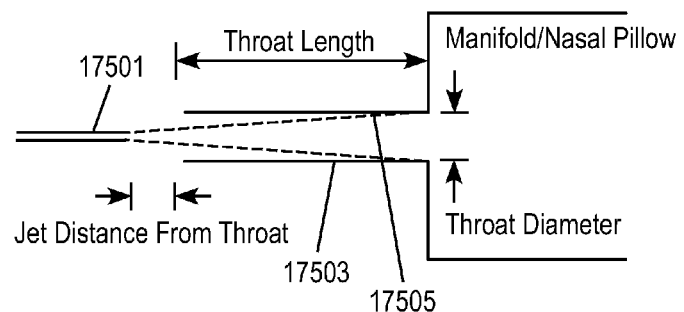

FIG. 169 shows a jet nozzle a distance from an end of a throat section such that a jet profile diameter substantially equals the throat exit diameter.

DETAILED DESCRIPTION OF THE EMBODIMENTS

Figure 1:
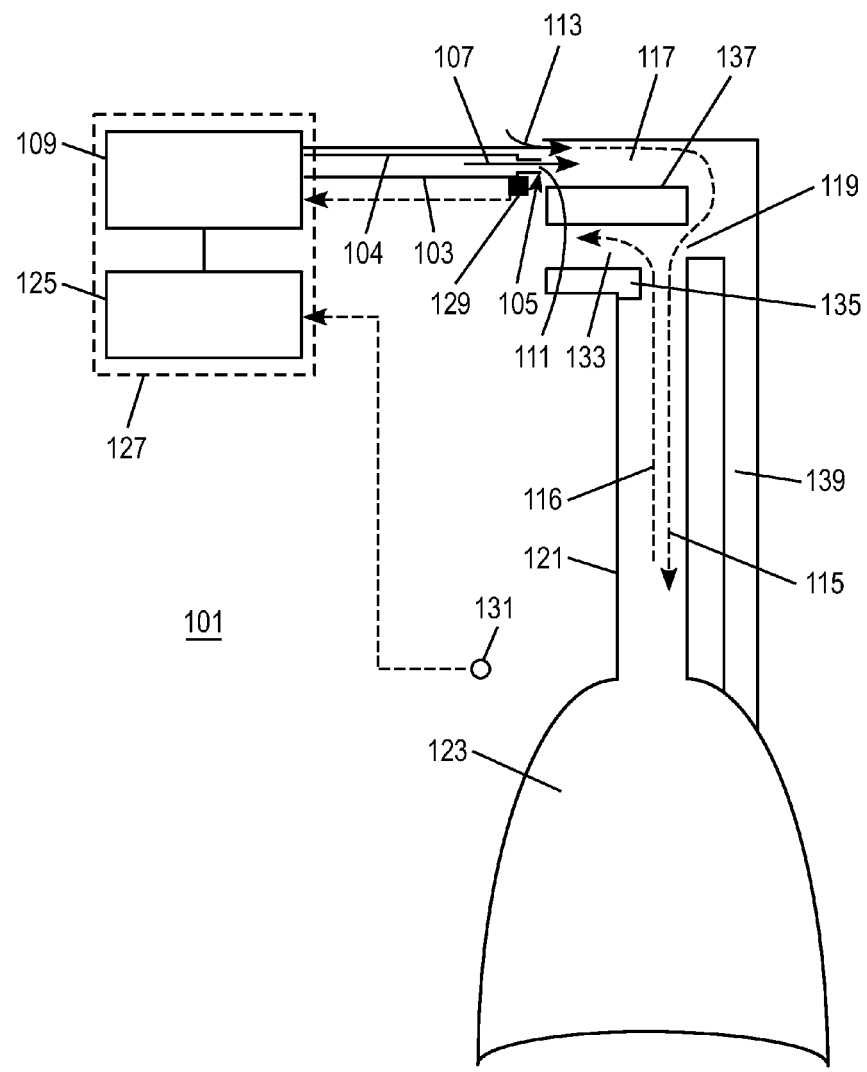
FIG. 1 is a schematic diagram showing an exemplary overall system of an embodiment of the invention.

FIG. 1 is a schematic diagram showing an exemplary overall system 101 of an embodiment of the invention. A patient may be ventilated with non-invasive open ventilation (NIOV) using a ventilation gas delivery circuit 103, an airway pressure sensing line 104, and non-invasive open nasal interface (nasal interface) 105. The nasal interface 105 preferably does not seal against the patient's nose such as is typical with other ventilation interfaces, and rather leaves the nose open for the user to breathe normally and freely from the ambient surroundings. Ventilation gas 107 delivered from a ventilator 109 may travel through the gas delivery circuit 103 and out one or more gas exit ports 111 in the nasal interface 105. The ventilation gas 107 may exit at a speed that entrains ambient air 113, such that the combination of ventilation gas 107, entrained ambient air 113 and spontaneously inhaled air 115, if the patient is spontaneously breathing, is delivered to the patient's airways, such as the nasal cavity 117, oropharyngeal airway 119, trachea 121, lung 123 and others, under power to create a clinically efficacious effect on the lung and airways. Patent may exhale 116 through the nose or mouth.

The nasal interface 105 geometry and dimensions may optimize the physics and fluid dynamics of the system to maximize performance, and user acceptable and tolerability. The performance of the system may create an increase in lung volume, or increase in lung pressure, or reduction in the work-of-breathing of the user, or increase in airway pressure. The invention may be different from oxygen therapy systems that do not provide mechanical ventilatory support or increases in airway pressure, and is different from conventional ventilation systems that work on a closed airway principle with a sealing mask that seals around the nose and/or mouth or cuffed airway tube. In embodiments of the present invention, a patient may exhale completely through ambient air, whereas in existing systems a patient may exhale through a nasal mask and tubing.

The invention may also be different from existing transtracheal systems because embodiments of the present invention perform better than expected. With transtracheal systems, delivered gas must work against resistance in the lower airway to improve airway pressure and assist in work of breathing. For a nasal system to achieve the same result, the delivered gas must work against both the lower airway pressure as in a transtracheal system and upper airway pressure in the nose, oropharyngeal airway, etc. As such, it would not have been expected that a nasal interface could be as effective as a transtracheal system. The inventors, however, have unexpectedly discovered that a nasal interface can provide similar improvements to airway pressure and reductions in work of breathing using a non-invasive, open nasal interface.

The NIOV ventilation system may also include the ventilator 109 in fluid communication with a gas supply or gas generating system 125. The ventilator 109 and/or gas supply or gas generating system 125 may be separate or in a single device 127. Ventilation gas 107 can be oxygen as in the case of respiratory insufficiency applications, air in the ease of sleep apnea or neuromuscular applications, combinations thereof, or any other clinically beneficial gas. The ventilator 109 may have a control unit or system. The ventilator 109 may be powered on and may have a delay of a predetermined time prior to supplying ventilation gas. After a predetermined time, the ventilator 109 may deliver gas as needed, such as in synchrony with a breathing pattern.

A spontaneous breathing respiration sensor 129 may also be used to detect, determine and measure the spontaneous breathing pattern and phases of the patient, as well as apnea or hypopnea events, via communication with the ventilation system 127, and also determine and measure other patient parameters such as respiratory rate or activity level. Using this information, the ventilator 109 may then synchronize and titrate the therapy to the needs of the patient and to match the gas delivery with the patient's breathing for maximal comfort and therapeutic titration.

An additional sensor 131 may be used to detect breathing effort. The invention may be used to support the respiration of the patient, including supporting the work of breathing by increasing pressure and volume in the lung, and can be used for maintaining airway patency of the upper airways such as the oropharyngeal airway 119. When using the invention, the patient breathes normally through their upper airway and through their nose, while receiving mechanical support through the interface. During exhalation, the exhaled gas preferably does not enter the gas delivery circuit but rather exits the nose or mouth directly to ambient air, or through, across or around the nasal interface 105 to ambient air. The patient can keep their mouth closed during use for example during inspiration, to help direct the mechanical support to the lower airways and around the oral cavity 133, base of the tongue 135, palate 137 and esophagus 139, or can use a mouth guard or chin band, if necessary. The gas delivery can be delivered cyclically in synchrony with the patient's breath phases, or continuously, or combinations thereof as will be described in subsequent sections. The patient can use the therapy while stationary, while being transported, while mobile and active, or while resting or sleeping. The therapy has homecare, hospital, subacute care, emergency, military, pandemic and transport applications.

The ventilation control is described in more detail as follows. The ventilation system can be used to provide tidal volume augmentation for spontaneously breathing patients, for example, provide 10-50% of the tidal volume needed by the patient. The ventilation system can also be used to provide significant mechanical support to a spontaneously breathing patient, for example provide 25-75% of the tidal volume needed by the patient. The ventilation system can also be used to provide full support or life support for the patient, for example 75-100% of the patient's tidal volume need. The ventilation system can be a volume ventilator with a volume control or volume assist mode, can have an SIMV mode. The ventilation system can also be a pressure ventilator with a pressure control or pressure support mode. For example, a pressure of 5-20 centimeters of water pressure (cwp) can be generated in the airway of the patient continuously or cyclically. In another example, the system can produce an inspiratory pressure of 5-20 cwp, and an expiratory pressure of 2-10 cwp. Expiratory pressure can be created by increasing the exhalation resistance inherent in the nasal interface, or by the gas delivery jet nozzles delivering the requisite amount of gas flow during expiratory phase, or by the entrainment/spontaneous breathing aperture resistances being adjusted, or any combination of the above approaches. Measuring the pressure in or near the nasal interface, as well as measuring gas flow rate going through the nasal interface, typically in the manifold, is performed to help measure and control the ventilator to emit and produce the desired gas flow, delivered volume, and/or delivered pressure, as well as to monitor and measure exhalation and other respiratory parameters.

Figure 2:
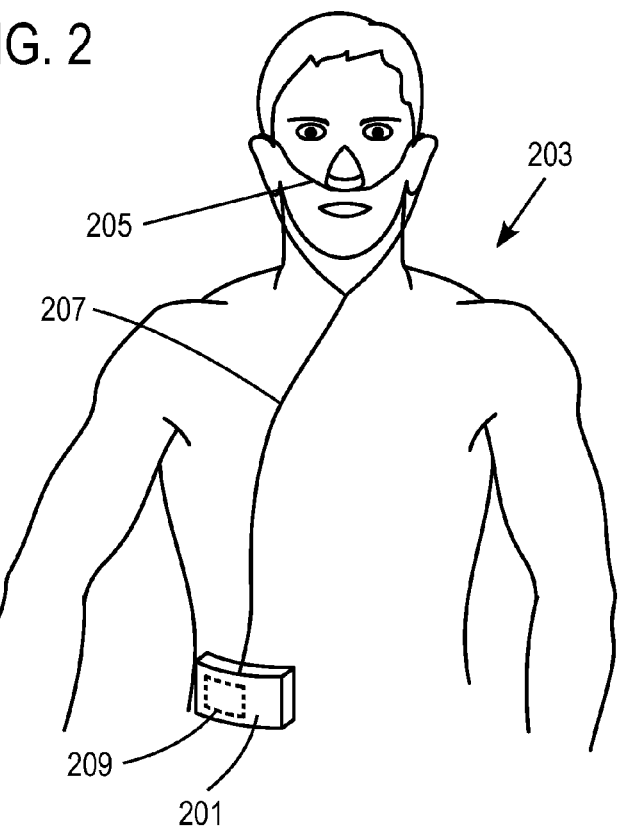
FIG. 2 shows an exemplary embodiment when NIOV is used to treat respiratory insufficiency or neuromuscular disease.

FIG. 2 shows an exemplary embodiment when NIOV is used to treat respiratory insufficiency or neuromuscular disease. A ventilator 201 can be borne or worn by a patient 203. A nasal interface 205 may be placed discretely on the patient's face and a gas delivery circuit 207 can be placed discretely on the user's body. A user may operate the ventilation system through a user interface 209, which may be located on the ventilator 201 or in any suitable location. Because the ventilation system contributes to some of the mechanical work required for a person to breathe, the user can be active without suffering from dyspnea, hypoxemia or hypercapnia. The user can benefit from ambulation, activity, and participate in the routine activities of daily living, such as preparing meals, bathing, chores around the house, and leaving the house for outside activities. Further, the user can communicate, eat, drink and swallow, while receiving mechanical ventilation, as opposed to other ventilation interfaces in which the patient's airway is closed with an external mask, or sealed internally with a cuffed airway tube.

Figure 3:
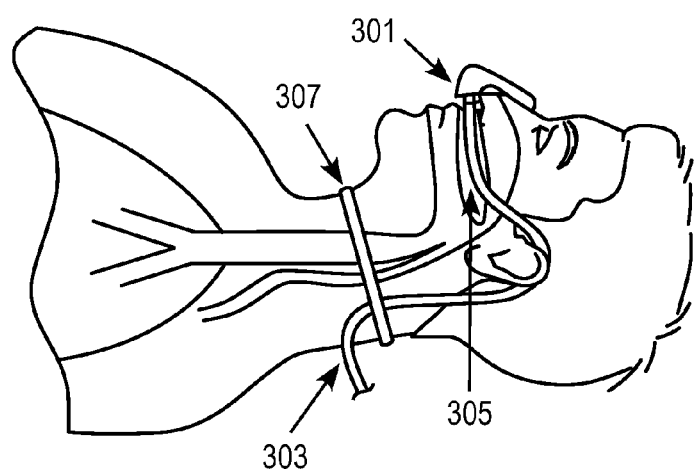
FIG. 3 shows an exemplary embodiment when NIOV is used to treat sleep apnea.

FIG. 3 shows an exemplary embodiment when NIOV is used to treat sleep apnea. The patient can be in a supine position as shown, or can be sleeping on the side or stomach. A nasal interface 301 and a delivery circuit 303 may be significantly less obtrusive than conventional therapies, and the patient may benefit from the sensation of breathing ambient air normally around the nasal interface, since it does not seal the nose. This minimal obtrusiveness and close-to-natural sensation may allow the therapy to be better tolerated by the user, resulting in improved patient adherence and thus a more efficacious therapy. The gas delivery circuit 303 may be coupled to the nasal interface 301 through a cannula 305 and may be secured to the patient with a neck strap 307 or other attachment mechanism.

Figure 4:
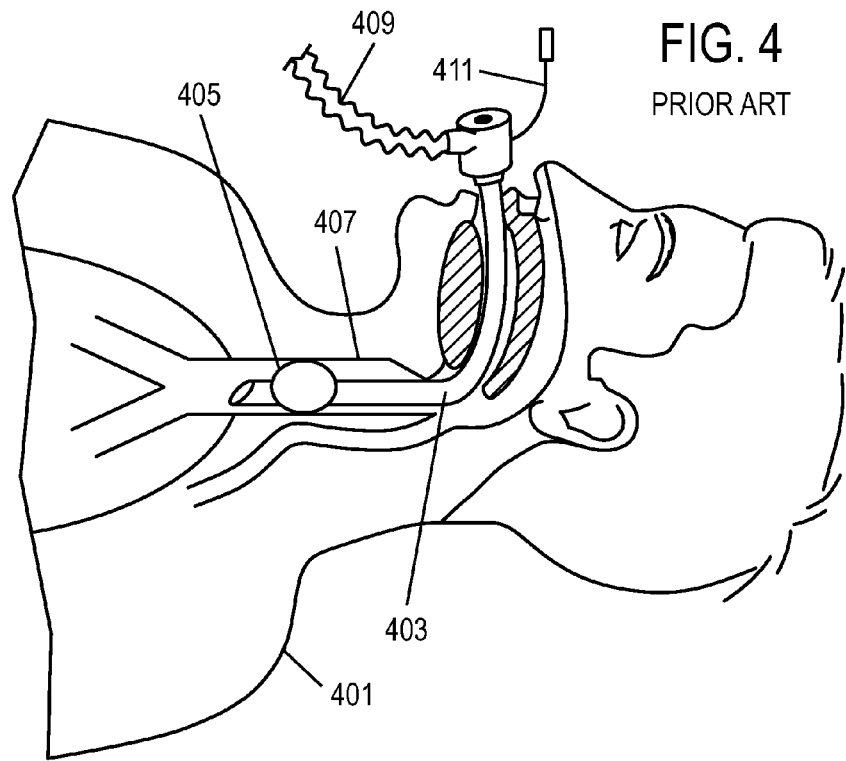
FIG. 4 shows a prior art therapy for mechanical ventilation delivered with an invasive ET tube interface.

FIG. 4 shows a prior art therapy for mechanical ventilation. A patient 401 may be intubated with an endotracheal tube (ETT) 403 and a cuff 405 may be inflated in a trachea 407, thus closing the airway off from ambient air. Ventilation gas may be delivered through a ventilation gas circuit 409 and may be monitored with sensors 411. The patient 401 may be sedated and their lungs are ventilated with gas being delivered and removed through the ET tube. This therapy, while highly effective in providing mechanical support for respiration, is not appropriate for the vast number of patients in whom sedation and complete respiratory support is not needed.

Figure 5:
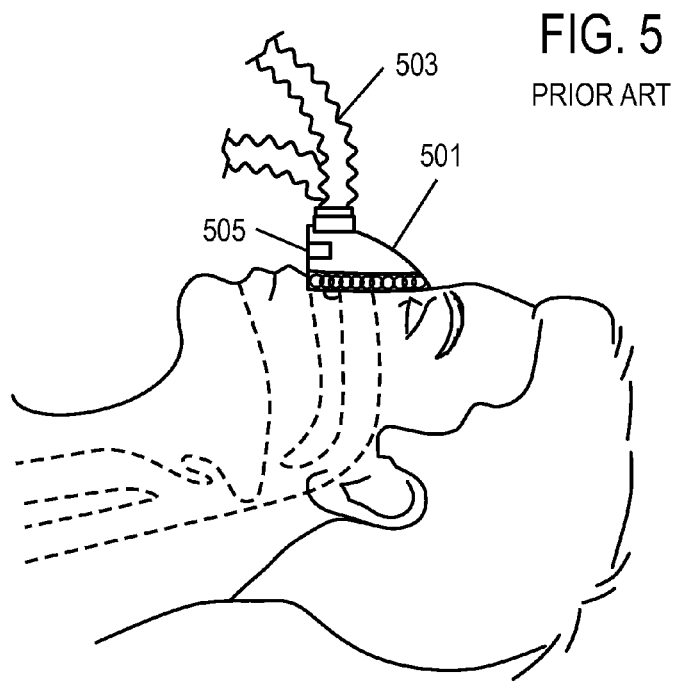
FIG. 5 shows a prior art respiratory support therapy for non-invasive ventilation using a nose mask and using a CPAP or BiPAP ventilation mode.

FIG. 5 shows a prior art respiratory support therapy for non-invasive ventilation, using a nose mask 501 and typically using a BiPAP ventilation mode. NIV is used to breathe for the patient, or can be used to help the breathing of a patient, in which case the patient's spontaneous breathing effort triggers the ventilator to deliver the pressure or volume based MV. All of the volume delivered to and from the lungs may be delivered and removed from a ventilation circuit 503 and the nose mask 501. A similar system can be used for OSA, in which case exhaust vents 505 are included in the nose mask so that a portion of the exhaled gas is exhaled through the vent ports. NIV, CPAP and BiPAP are clinically very effective for spontaneously breathing patients, however, these modes and therapies do not facilitate activities of daily living, the ventilator cannot be borne by the patient, the patient can not breathe room air naturally and freely, and the patient's upper airway cannot function normally and naturally because it is sealed off with the external mask seal.

Figure 6:
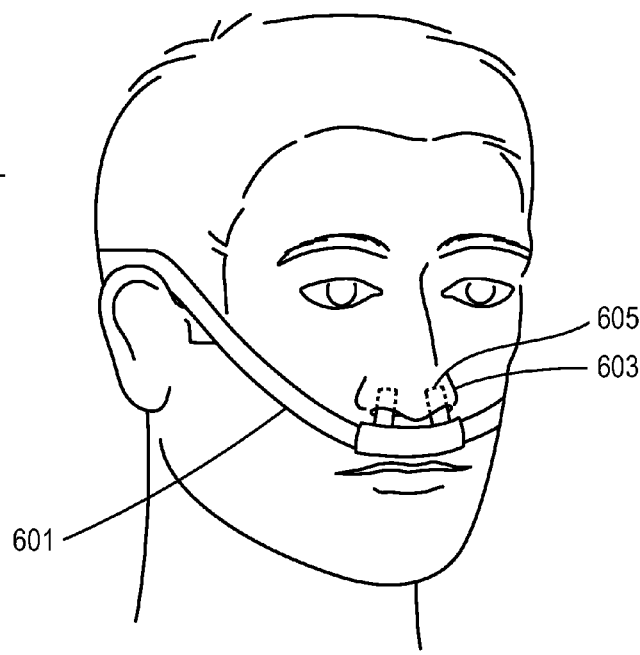
FIG. 6 shows a prior art therapy for treating OSA.

FIG. 6 shows a prior art therapy for treating OSA (Wood, U.S. Pat. No. 6,478,026). This system is used to deliver CPAP or BiPAP to the user, by employing a large bore cannula 601 that seals against the user's nostrils 603. Extensions 605 on the large bore cannula 601 extend into the nostrils to seal the nose. This system has similar drawbacks mentioned associated with NIV, plus has additional drawbacks of comfort and tolerance with the user's face and nose.

Figure 7:
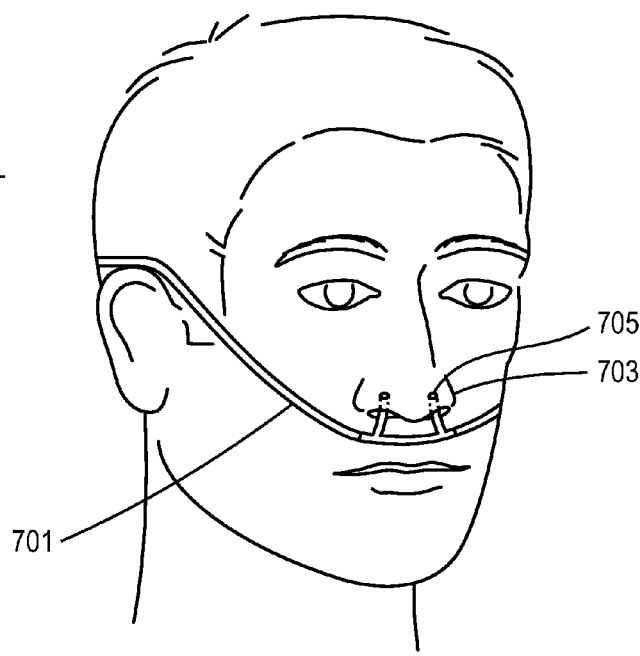
FIG. 7 shows a prior art conventional oxygen delivery cannula for administering oxygen therapy.

FIG. 7 shows a prior art conventional oxygen delivery cannula 701 for administering oxygen therapy. Extensions 705 on the cannula 701 may be configured to enter nares 703. The proximal end of the cannula 701 may be connected to an oxygen delivery device that can deliver continuous flow oxygen at 1-6 LPM to the user's nose, or that delivers a bolus of oxygen upon detection of an inspiratory effort. This system does not mechanically support the work of breathing of the patient, and has not been proven to be effective in preventing moderate to severe forms of OSA. FIG. 7 also describes another oxygen delivery therapy, high flow oxygen therapy (HFOT), in which more than 15 LPM of humidified oxygen is delivered at a continuous flow rate to the user's nose. Because of the high flow required for HFOT, the system may be non-portable and the oxygen must be humidified.

Now referring to FIGS. 8-58, an embodiment of the subject invention is described where a person receives mechanical ventilatory or airway support by gas that is delivered to the nasal airways from gas delivery nozzles positioned below the nose, and in which the nose is free inhale directly from ambient air and exhale directly into ambient air. In FIGS. 8-36, an embodiment of the invention is described in which the gas delivery nozzles are positioned under the nose using a nose support that physically engages with the bridge of the nose. In FIGS. 37-58, an embodiment of the invention is described in which the gas delivery nozzles are positioned under the nose without any physical contact with the bridge of the nose. In the various embodiments described wherein the gas delivery ports are positioned a distance away from the nostrils in free space, while the ports are a distance away from the nostril entrance, a breathing sensor may be placed in closer proximity to the entrance to the nostril, or there is some other breathing sensor placed elsewhere. This may ensure that the gas delivery dynamics provide the power and efficacy needed through proper geometry, but without sacrificing breathing detection and monitoring.

Figure 8:
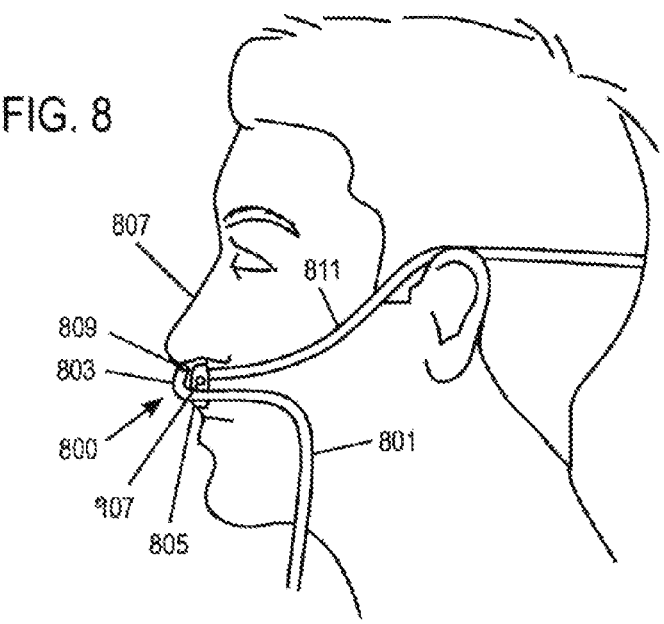
FIG. 8 shows a side view of an exemplary embodiment of a non-invasive open nasal ventilation interface with a cannula tip positioned proximal to the nares or nostril rim opening.
Figure 9:
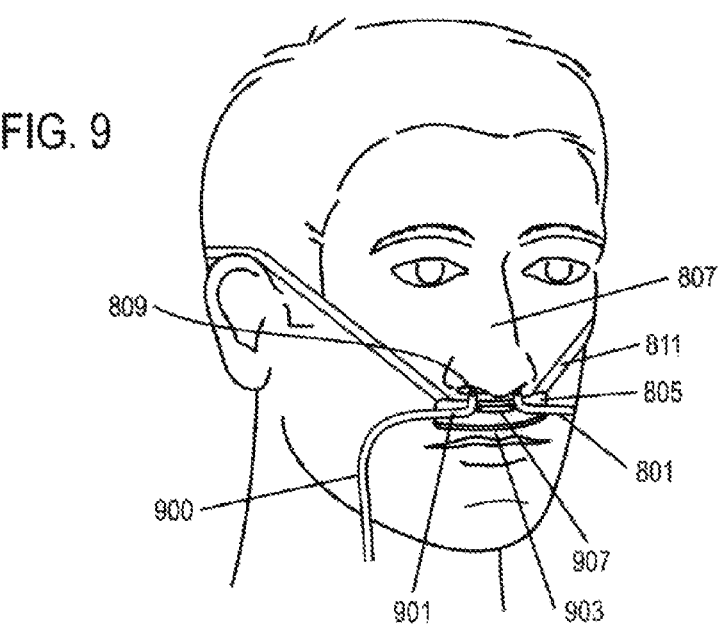
FIG. 9 shows a front view of an exemplary non-invasive open nasal ventilation interface with a cannula tip positioned proximal to the nares or nostril rim opening.

In FIGS. 8 and 9, a side view and front view respectively are shown of a nasal interface 800 of an embodiment of the invention. A left cannula 801 may have a left distal end 803 and a right cannula 900 may have a right distal end 901. As used herein, terms such as left, right, top, bottom and other directional references should be understood to be interchangeable and are not meant as absolute determinations. Generally, directions are given relative to a user, such that a left cannula is located on the user's left side. Similarly, reference to a left or right nostril does not mean that the system cannot be reversed unless indicated otherwise. The left distal end 803 and/or right distal end 901 can optionally be connected with a coupler 907 beneath a nose 807. The coupler 805 can include a breath sensor (not shown). A skin pad 903 can be included on the posterior or skin side of the coupler 805 to set the required distance between the cannula tips 803, 901 and the skin, and to align nozzles 809 at the cannula tips 803, 901 relative to the nostril entrance and nostril foramen.

A head strap 811 may be connected to the cannula 801, coupler 805 or skin pad 903, and may be extended to the back of the head to secure the interface 800 in place. The cannula 801, 900 may be routed bilaterally from the nostrils to below the nostrils, then laterally and posteriorly to the sides of the face, then inferiorly around the corners of the mouth and ultimately to the front of the neck where the cannula are attached to a ventilation gas supply tube. Alternatively, the cannula can be routed bilaterally from the nose to above and around the ears to the front of the neck. The cannula can be preformed in one or more of these compound arcuate shapes to help position the cannula in the most comfortable and least obtrusive part of the patient's anatomy, and to secure the device in place and resist shifting and movement. There may be length adjustment features to adjust the distance between the two cannula nozzles, and cannula tip angle adjustment features to align the angle of the nozzles with the nostril entrance and foramen. Additional details of these features will be described subsequently. Other shapes, adjustment features and fastening features are also included in the invention which will also be described subsequently.

Embodiments of the present invention may have various benefits over standard oxygen therapy nasal cannulae and masks. Existing systems may have limited therapeutic effects. For example, geometries in existing systems may not be optimized and velocity flow dynamics of gas exiting cannula tips may be sub-optimal. Embodiments of the present invention may have improved efficiencies due to optimized jet pump geometries. Additionally, existing systems may be uncomfortable for a patient. The velocity of gas exiting existing cannulae, even though un-optimized, may be extremely uncomfortable for a patient as the gas flow may be turbulent and irritating to the nasal mucosa. A gas profile in embodiments of the present invention may be more organized and/or laminar when the gas enters the nose. Confidential experience with patients indicates that patients with high liter flow oxygen are uncomfortable with their oxygen, but were comfortable with nasal interfaces as described herein. Furthermore, if the cannula tips of existing systems are retracted to be placed outside the nose to improve the geometry and flow profile, the cannula can no longer sense the patient's breathing and the system may not be able to trigger.

As shown in the cross sectional view in FIG. 10, a tip 1005 of a nasal interface 1001 may be reduced in diameter to create a nozzle 1003. The distal tip 1005 of the nozzle 1003 may be positioned proximally relative to the entrance of a nostril foramen 1007 in the nasal septum 1009 so as to create a jet pump. The distal tip 1005 of the nozzle 1003 may be in proximity to the nostril rim and opening 1011 and nostril wall 1013. The jet pump inlet may be defined by the rim of the nostrils, and the vacuum entrainment area of the jet pump 1015 may be proximal to and slightly within the entrance of the nostrils. The jet pump throat area may be the proximal section of the nostril foramen 1007. This jet pump geometry of the invention may facilitate entrainment of ambient air, such that the total gas being delivered into the patient may be of greater volume than the gas exiting the catheter alone, and with sufficient power due to the jet pump configuration, to penetrate airway resistances. This facilitates more effective ventilation of the lung or airways. The parameters of the invention are compared to the prior art therapies in Tables 1 and 2 below.

TABLE 1

Comparison of Embodiments of the Invention with Prior Art Therapies

Lung Volume Augmentation Parameters

| Parameter | INVENTION | | PRIOR ART | | |
|---|---|---|---|---|---|
| | Range | Preferred (Adult*) | OT | HFOT | CPAP |
| Lung Volume Augmentation (%) | 10-150% | 15-65% | 0% | 0-25% | 0-90% |
| WOB reduction (%) | 5-80% | 10-50% | 0% | 0-25% | 0-75% |
| Lung Pressure increase (cwp) | 1-30 | 3-20 | 0 | 0-6 | 3-25 |
| Upper Airway pressure increase (cwp) | 3-34 | 7-25 | 0-2 | 2-10 | 3-25 |
| Lung Waveform | S-R | R | no effect | S-R | S-R |
| Entrained ambient air (%) | 20-200% | 50-100% | 0 | 0 | 0 |
| Gas exit speed out of catheter or patient interface (m/sec) | 25-300 | 50-200 | 10-30 | 40-60 | 5-10 |
| Equipment Output flow rate, ave (LPM) | 5-40 | 10-20 | 1-6 | 10-20 | 40-80 |
| Tubing outer diameter to patient (mm) | 3-7 | 4-6 | 4-6 | 10-18 | 18-22 |
| Equipment Output Pressure (psi) | 10-60 | 20-40 | 5-40 | 5-20 | 0.1-0.5 |
| Equipment Drive Pressure (psi) | 10-60 | 20-40 | 5-40 | 5-20 | ambient |
| Equipment Operating Pressure (psi) | 5-40 | 25-35 | 5-40 | 5-20 | ambient |
| Equipment Output Volume (ml)^ | 10-300 | 25-150 | 16-100 | 167-350 ml | 0-500 |
| Equipment Output Pulse Time (sec.) | 0.100-1.000 | 0.200-0.700 | 0.25-1.0 | Cons't Flow | Cons't Flow |
| Therapy's source gas consumption | 0.25-3.0 | 0.75-1.5 | 1-6 | 10-20 | self generating |
| Equipment Output Synchronization (ms) | variable depending on comfort and need (25-500 ms delay) | variable depending on comfort and need (75-250 ms delay) | 0.1-0.2 | Cons't Flow | Cons't Flow |
| Equipment Output Waveform | S, D, A, Si, O | R, D | S, D | Cons't Flow | Cons't Flow |

NOTES:
*Pediatric and neonatal: Pressure and volume values are 25-75% less (Ped) and 50-90% less (Neo).
^If constant continuous flow system, Output Volume = volume delivered during pt's inspiratory phase Equipment: = ventilator for Invention and CPAP; = oxygen therapy delivery device for OT and HFOT
OT = oxygen therapy;
CPAP = continuous positive airway pressure for NIV or OSA;
HFOT = high flow oxygen therapy CPAP also includes BiPAP
<u>S</u>quare, <u>R</u>ounded, <u>D</u>ecending, <u>A</u>scending, <u>Si</u>nusoidal, <u>O</u>scillating
Cons't Flow = Constant Flow (not synchronized)

TABLE 2

Comparison of Embodiments of the Invention with Prior Art OSA Therapies

Sleep Apnea Therapy Parameters

| Parameter | INVENTION | | PRIOR ART |
|---|---|---|---|
| | Range | Preferred (Adult*) | CPAP |
| Airway Pressure (cwp) | 0-30 | 5-25 | 1-25 |
| Lung Pressure increase (cwp) | 0-20 | 4-20 | 1-25 |
| Upper Airway pressure increase (cwp) | 3-30 | 7-20 | 1-25 |
| Lung Waveform | S-R | R | S-R |
| Tubing outer diameter to patient (mm) | 3-7 | 4-6 | 18-22 |
| Entrained ambient air (%) | 20-200% | 50-100% | 0 |
| Gas exit speed out of patient interface (m/sec) | 25-300 | 50-200 | 5-10 |
| Ventilator Output Pressure (psi) | 5-40 | 25-35 | 0.1-0.5 |
| Ventilator Output flow rate, ave (LPM) | 5-40 | 10-20 | 40-60 |
| Ventilator Operating Pressure (psi) | 10-60 | 20-40 | 0.1-0.5 |
| Ventilator Output Volume per breath (ml)^ | 50-500 | 60-150 | 500-800 |

TABLE 2-continued

Comparison of Embodiments of the Invention with Prior Art OSA Therapies

Sleep Apnea Therapy Parameters

| Parameter | INVENTION | | PRIOR ART |
|---|---|---|---|
| | Range | Preferred (Adult*) | CPAP |
| Ventilator Output Pulse Time (sec.) | 0.250-2.000 | 0.400-1.250 | Contant Flow |
| Ventilator Output Synchronization | SI, SR, SV, CVR | SR | Constant Flow |
| Ventilator Output Waveform | S, D, A, Si, O | R, A | Constant Flow |
| Breathing resistance (cmH2O @ 60 lpm) | 0-3.0 | 0-2.0 | 4.0-6.5 |

NOTES:
*Pediatric and neonatal: Pressure and volume values are 25-75% less (Ped) and 50-90% less (Neo).
^If constant continuous flow system, Output Volume = volume delivered during pt's inspiratory phase
CPAP = continuous positive airway pressure; BiPAP = Bilevel Positive Airway Pressure
SI = syncrhonized intermittent; SR = synchronized ramped; SV = synchronized variable; CVR = continuous variable ramped
Square, Rounded, Decending, Ascending, Sinusoidal, Oscillating FIG. 11 describes a version of a nasal interface 1105 in which a distal tip 1101 of a jet nozzle 1103 may be placed approximately coplanar to the entrance to the nostrils. This placement of the nozzle may entrain more ambient air compared to the nozzle being placed inside the nostrils, depending on other prevailing conditions, such as diameters, delivery pressures and alignment. Jet pump inlet and entrainment zone 1107 is shown. FIG. 12 describes a version of a nasal interface 1205 in which a jet nozzle 1203 may be positioned such that a distal tip 1201 of the nozzle 1203 may penetrate the nostril foramen 1007 to create a jet pump inlet and entrainment zone 1207.

Figure 13A:
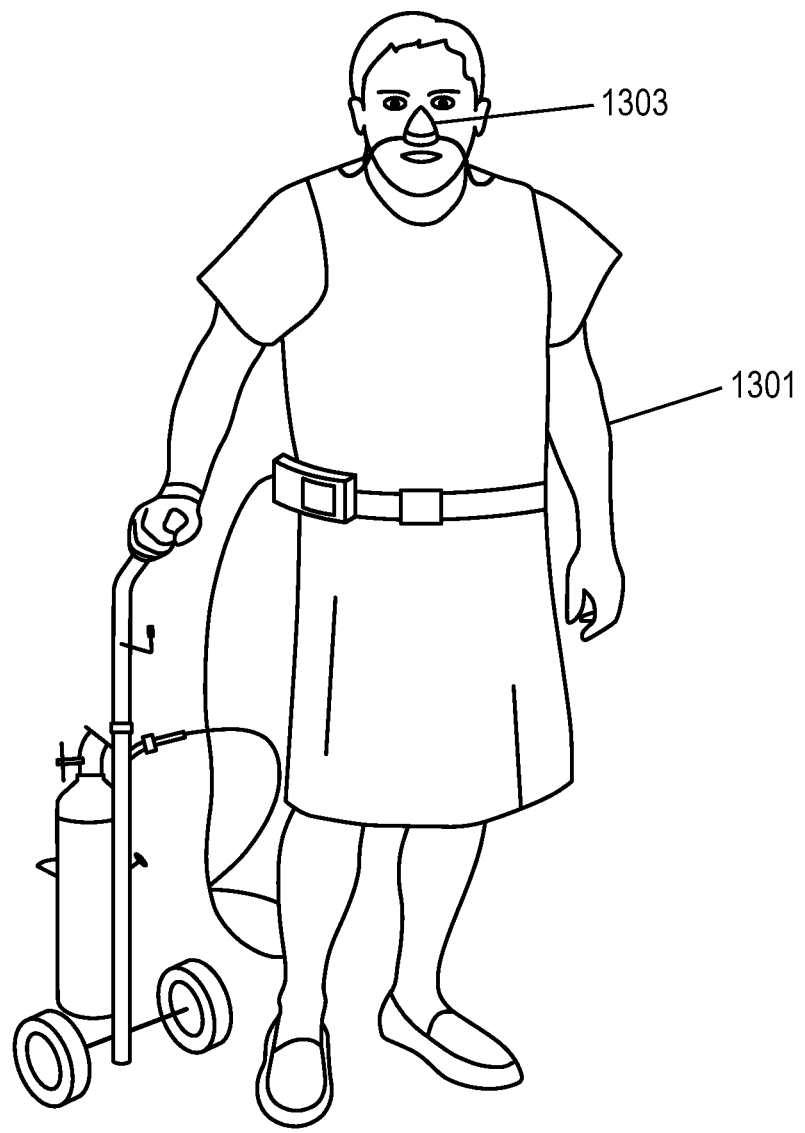
FIG. 13A shows a patient using an embodiment of the invention to provide work of breathing support while ambulating.
Figure 13B:
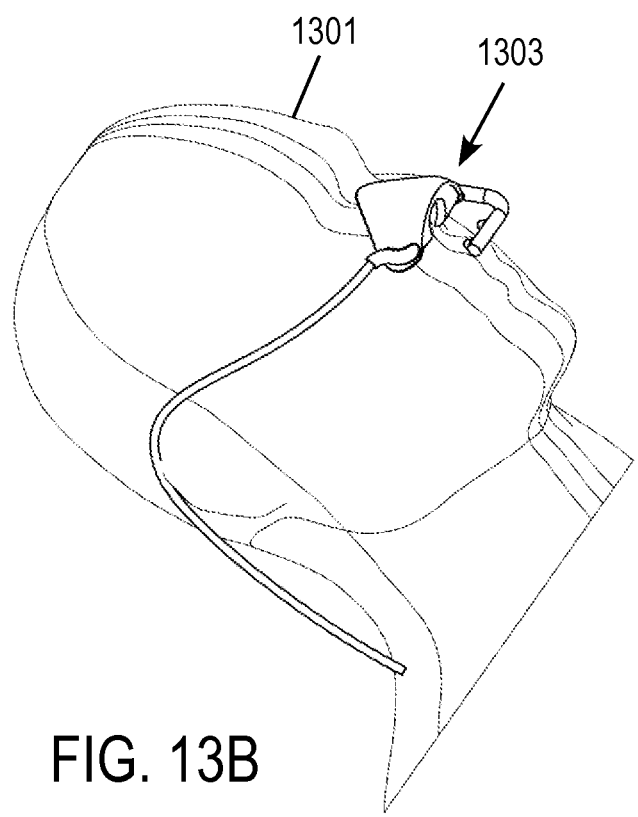
FIG. 13B shows an exemplary embodiment of a nasal interface used on a head of a patient.

FIG. 13A shows a patient 1301 using an embodiment of the invention to provide work of breathing support while ambulating. A nasal interface 1303 may be minimally obtrusive compared to standard masks, so that the patient can feel and act normal while receiving the therapy, see FIG. 2 for details of an exemplary overall system. For example, the patient can talk, swallow, eat or drink with the nasal interface and therapy. The tubing required for the ventilation system may be very small compared to standard ventilator tubing, which makes it much more realistic for the patient to move around with the therapy, and to conceal the equipment and tubing needed for the therapy. FIG. 13B shows the nasal interface 1303 on the head of the patient 1301.

FIG. 14 illustrates an isometric view of a non-invasive open ventilation (NIOV) nasal interface assembly 1401. The assembly 1401 may include a nasal interface 1403, and a ventilation gas attachment 1405 coupled to the nasal interface 1403. Ventilation gas may be delivered from a ventilator through a ventilator attachment 1427, gas delivery circuit 1429 and the ventilation gas attachment 1405. A ventilation gas outlet 1415 may be positioned at a distal end of the ventilation gas attachment 1405. One or more nozzles 1417 may be located at a distal end of the ventilation gas outlet 1415. Preferably, a distal end of the ventilation gas outlet may be positioned approximately 0" to approximately 1.5" outside a nose. More preferably, the distal end of the ventilation gas outlet may be positioned approximately 0.75" to approximately 1.25" outside of a nose.

In addition to the gas delivery circuit 1429, a sensing tube 1431 may be connected between the nasal interface 1403 and the ventilator attachment 1427. The sensing tube 1431 may be a pressure sensing tube. The sensing tube 1431 and/or the gas delivery circuit 1429 may pass through a shell 1433 of the nasal interface 1403. One or more sensors or sensing ports 1435 may be located in various positions on the shell 1433. The one or more sensors 1435 may be airway pressure sensing attachments or flow sensing attachments, but other types of sensors may be used on or near the nasal interface 1403. In certain embodiments, ports 1435 must be in a nostril cavity path to trigger the one or more sensors 1435. Embodiments of the present invention may also include one or more sensors that are carbon dioxide sampling ports. The carbon dioxide sampling ports may be attached to a sampling line on an external surface of the shell 1433.

Embodiments of the present invention may be adjustable or may come in various sizes to accommodate different patient sizes. For example, the shell 1433 may come in various dimensions to accommodate various size noses. A ledge 1411 may be coupled to the shell 1433 for contacting a nostril rim and positioning the nasal interface 1403. The shell 1433 may be self-centering on the nasal bridge. An air knife deflector 1419 may prevent an air knife effect from disturbing the eyes.

During testing, it was determined that the optimal performance was achieved when the nozzles were aimed parallel to the bridge of the nose to align the jets of ventilation gas with the nares. The nozzles of the interface may be aimed parallel to the mask 1433, such that by placing the mask 1433 on the bridge of the nose, the nozzles 1417 may be parallel to the bridge of the nose. If there is some misalignment, performance may degrade. The jets preferably are kept within 10 degrees of being properly aligned with a nasal opening and an axis of the nares.

As such, when a patient moves their nose to the left or right (e.g. by moving your jaw in an exaggerated manner), the nasal interface 1403 may follow the nose, ensuring that the nozzles remain aligned with the centerline of the nose, and therefore the nostrils.

Figure 15:
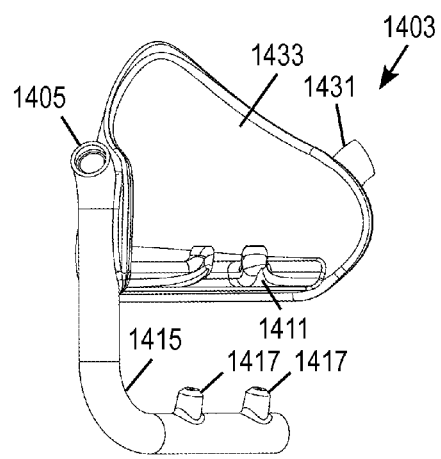
FIG. 15 is a close up rear view of the distal end of the nasal interface of FIG. 14.
Figure 16:
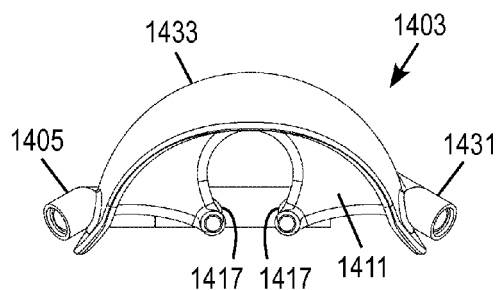
FIG. 16 illustrates a close up front view of the nasal interface of FIG. 14.
Figure 17:
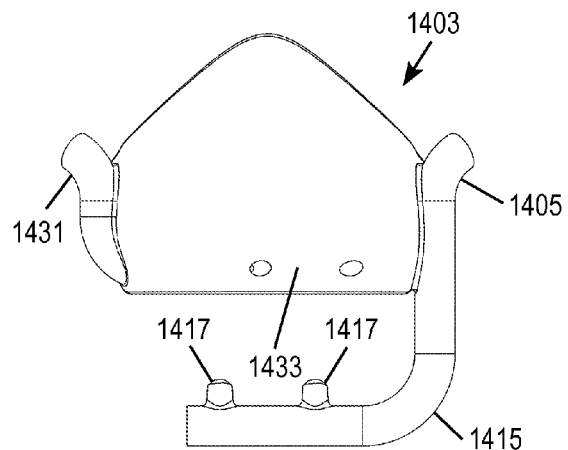
FIG. 17 illustrates a close up top view of the nasal interface of FIG. 14.

FIG. 15 is a close up rear view of the distal end of the nasal interface 1403 of FIG. 14. FIG. 16 illustrates a close up front view of the nasal interface 1403 of FIG. 14. FIG. 17 illustrates a close up top view of the nasal interface 1403 of FIG. 14.

Figure 18:
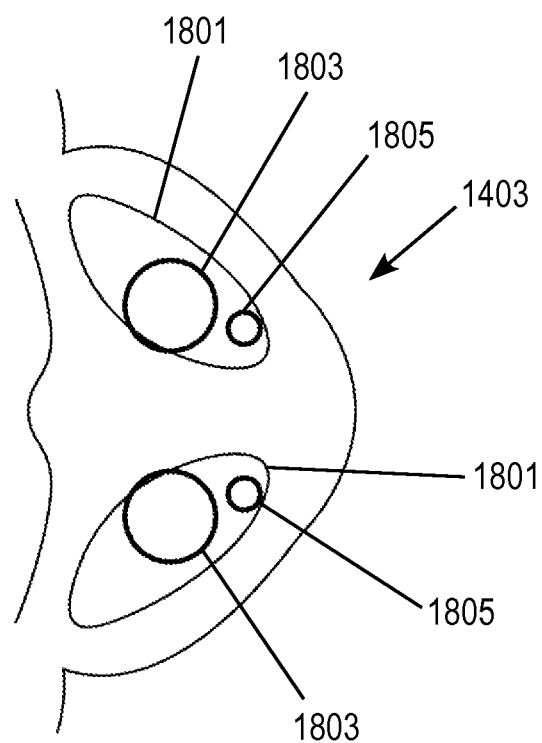
FIG. 18 illustrates a bottom view of the nasal interface of FIG. 14 on a patient with a gas delivery pattern and nasal air pressure sensor.

FIG. 18 illustrates a bottom view of how the nasal interface 1403 of FIG. 14 may communicate with a nasal airway 1801 of the patient. The nasal airway 1801 is represented by the oval patterns. Gas delivery nozzles 1803 and nasal air pressure sensing locations 1805 are indicated by the large and small circles, respectively. The nasal air pressure sensing ports may be protrusions to help achieve a positive location of the sensing ports in the breath path in the nares. The gas delivery ports may be positioned such that the gas delivery path has a clear path to the nostril airway. There may be two or more sizes of masks, and or adjustment features in the mask, so that the sensing ports and gas delivery zones are properly aligned with the nasal airway path. The previous figures describe that the sensing locations must be in proximity to the entrance of the nostril, either inside, coplanar to the entrance, or slightly outside but if outside no more than 5 mm away from the entrance, whereas the jet nozzle tips are located a distance from the entrance to the nostrils, for example 10-25 mm away. This configuration may allow the mask to take advantage of the jet pump geometry, while not sacrificing sensing accuracy, so that the ventilator is in proper synchrony with the patient. Also, the gas flow profile may become more organized before entering the patient's nostril, rather than a turbulent jet entering the nostril, which would be quite uncomfortable and intolerant to the patient.

Figure 19:
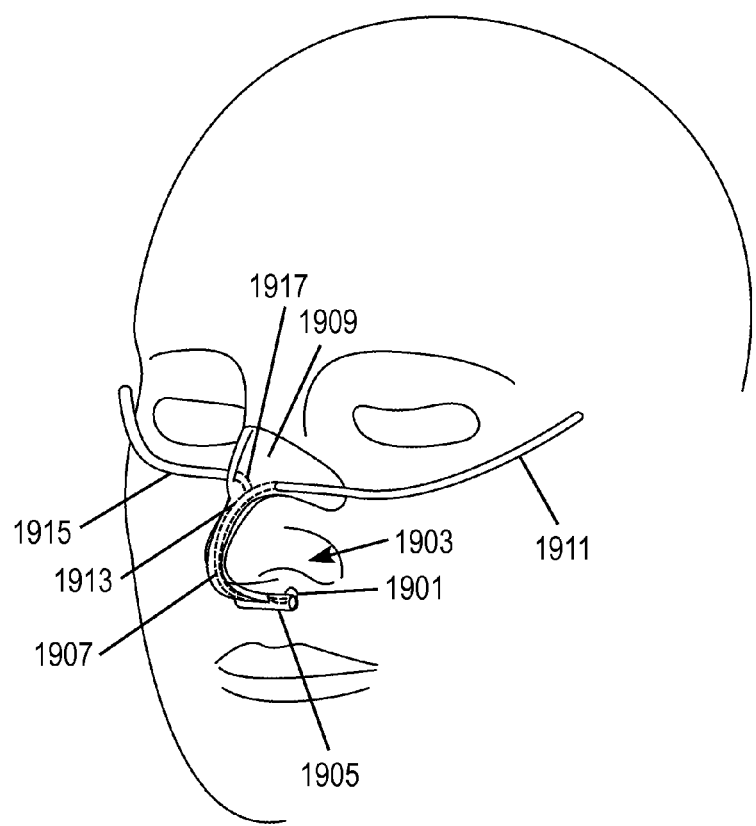
FIG. 19 shows a variation of the above embodiment in which gas delivery ports may be positioned and aligned below a nose by being coupled to a manifold that is coupled to the end of a nose bridge piece.

FIG. 19 shows a variation of the above embodiment in which gas delivery ports 1901 may be positioned and aligned below a nose 1903 by being coupled to a manifold 1905 that is coupled to the end of a nose bridge piece 1907. The nose bridge piece 1907 may be coupled to a nose bridge support 1909. The nose bridge support 1909 may secure the system in place. The nose bridge piece 1907 may be narrow providing for an aesthetically appealing design, but also may be functional in that the nose bridge piece 1907 precisely locates the gas delivery nozzles 1901. The gas delivery tubes 1911 may be coupled to the nose bridge support 1909. Ventilation gas may be channeled to the gas delivery nozzles 1901 through at least one channel 1913 in the nose bridge support 1909 and/or nose bridge piece 1907. A nasal air pressure sensing line 1915 may also be attached to the nose bridge support 1909. The nasal air pressure sensing line 1915 may communicate with a pressure sensing conduit 1917 in the nose bridge support 1909 and/or the nose bridge piece 1907. The nasal air pressure sensing line 1915 may terminate at or near the manifold 1905, typically closer to the nasal entrance than the nozzles.

The nose bridge support 1909 may be made of malleable material so that it can be conformed ideally to the user's nose, and the bridge piece can be adjustable to help align the nozzles correctly, or to adjust the strength of the therapy by changing the distance of the nozzles to the nose. The support and bridge piece can be padded on the skin side to optimize the comfort of the fit, and/or can include a pressure-sensitive adhesive that helps secure it to the skin. The support can also posses shape memory properties such as nitinol, spring steel or a thermoplastic, such that it compresses to lightly pinch the nose. The support and bridge piece can also be used to prevent distension of the nostrils when the nasal cavity is pressurized by the delivery of the ventilation gas. The gas delivery and nasal airway pressure sensing lines can be preformed into a shape to keep the tubing away from the user's eyes. The tubing is shown as typically be routed above and around the ears, however it can be routed around the corners of the mouth to the front of the neck, in which case a strap would attach the mask to the face. As in other embodiments described herein, the gas delivery channel and nasal airway pressure sensing channel can be separate lumens in the same tubing, or can be separate tubes.

Figure 20:
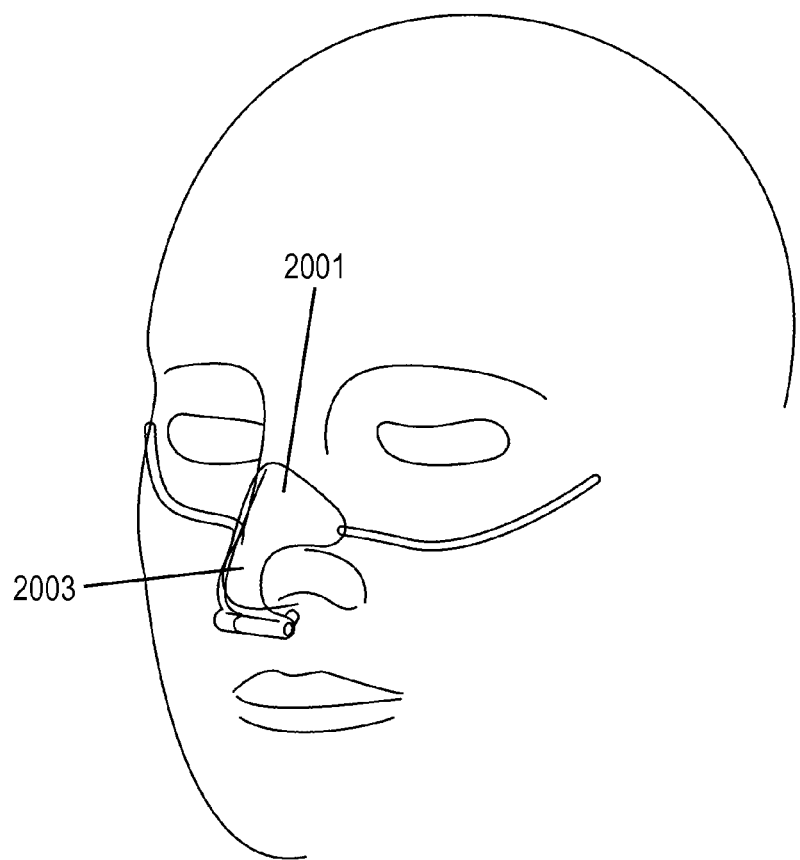
FIG. 20 describes a similar version to FIG. 19 in which a nose bridge support and a nose bridge piece are more substantial.

FIG. 20 describes a similar version to FIG. 19 in which a nose bridge support 2001 and a nose bridge piece 2003 are more substantial, which could be more useful in more critical applications in which aesthetics are less important, for example emergency or critical care.

Figure 21:
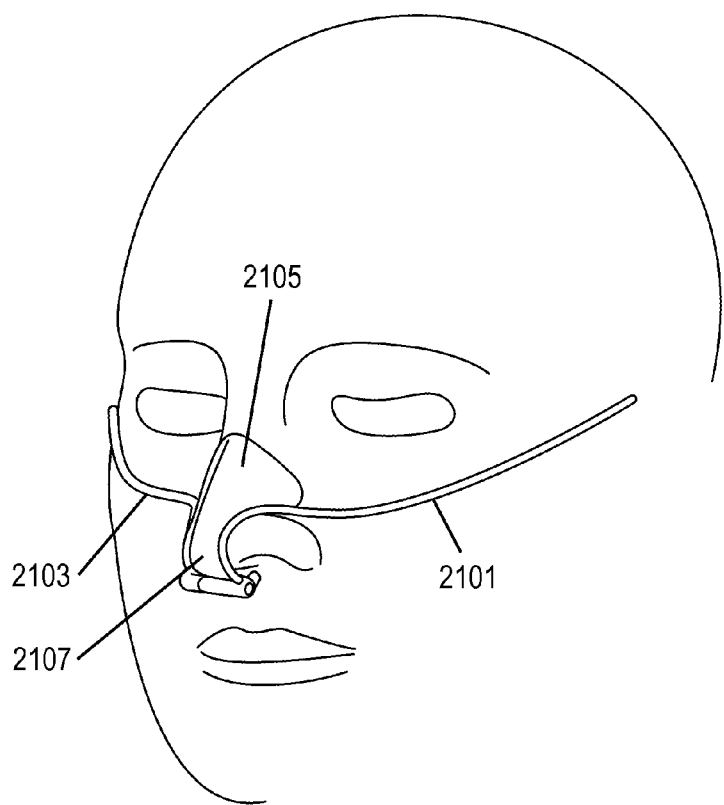
FIG. 21 shows a gas delivery circuit and a sensing tube external to a nose bridge support and a nose bridge piece.
Figure 22:
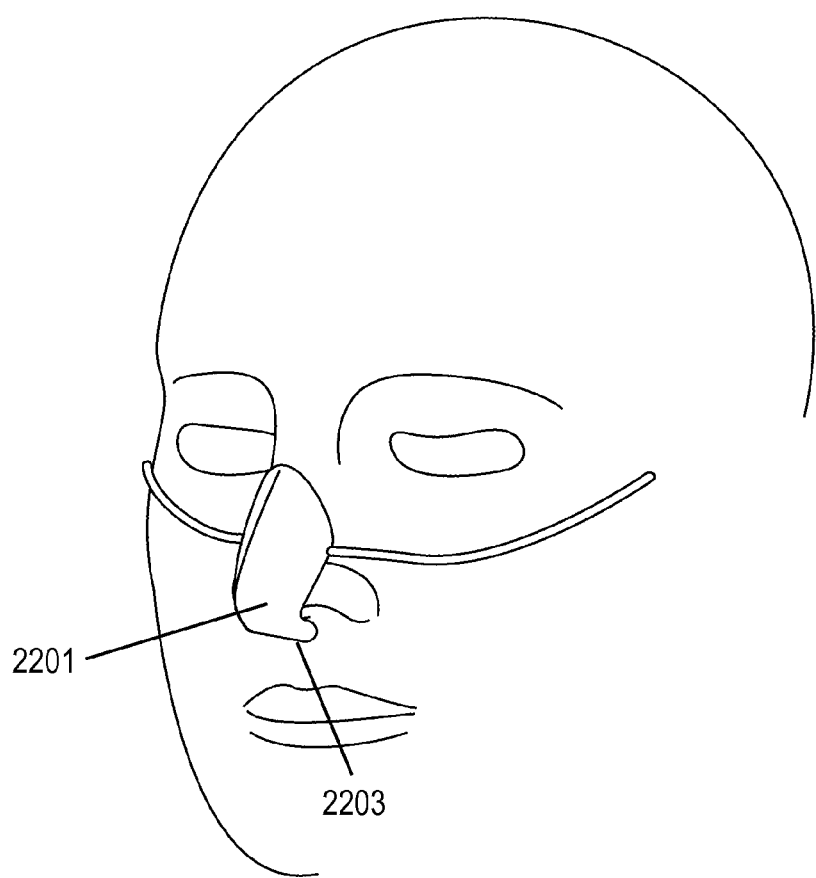
FIG. 22 shows a more substantial connection between a nose bridge piece and a manifold, such that they are a unified piece.
Figure 23:
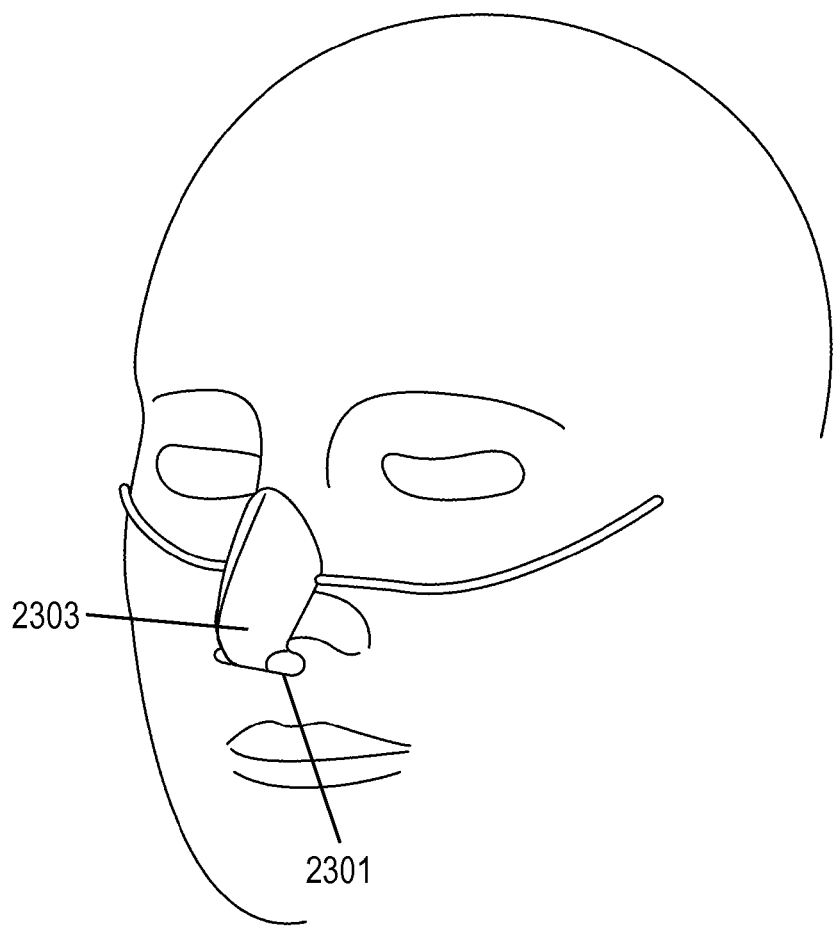
FIG. 23 shows a similar configuration to FIG. 22 except a manifold is separate from the nose bridge piece.
Figure 24:
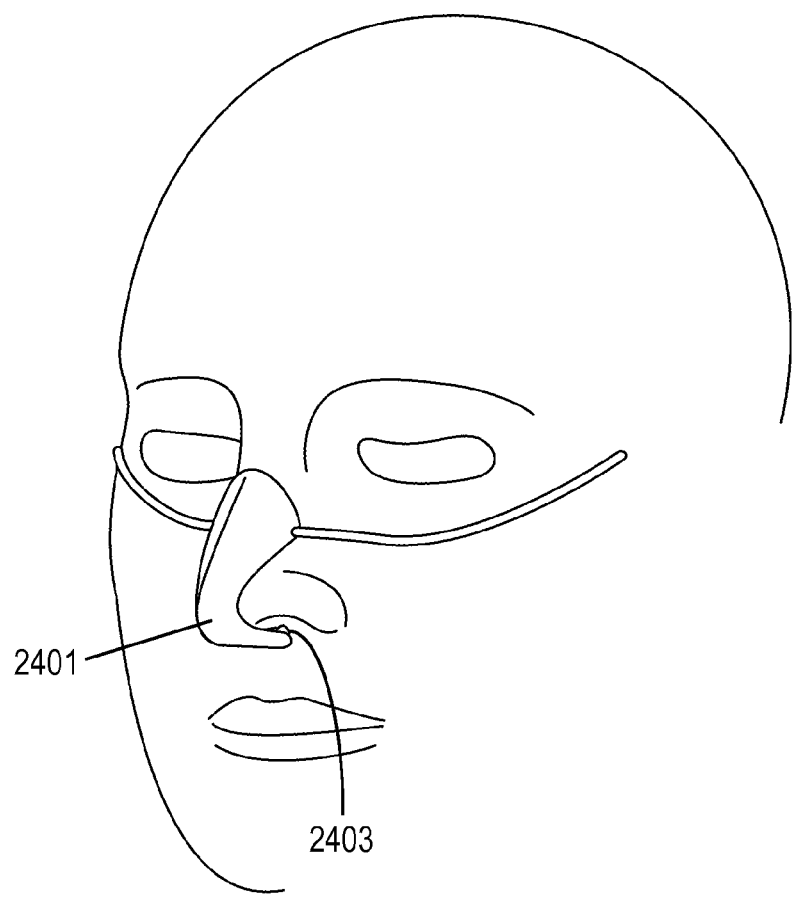
FIG. 24 shows a configuration with a nose bridge piece surrounding nozzles.
Figure 25:
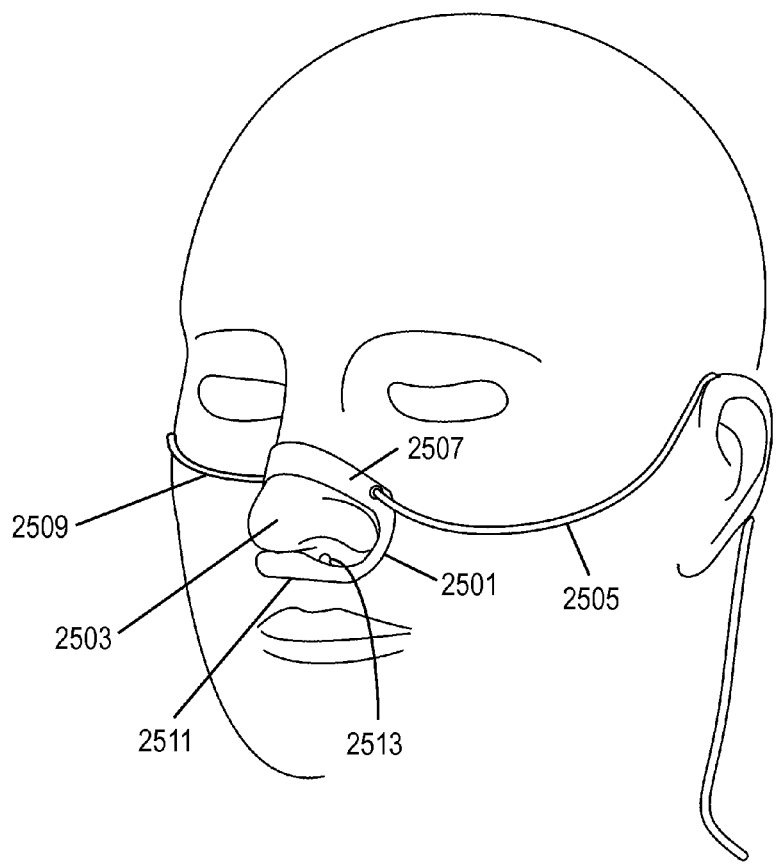
FIG. 25 shows an embodiment where a nose bridge piece is located to one side of a nose, rather than along the midline of the nose.

FIGS. 21-24 illustrate various different configurations of the above elements. For example, FIG. 21 shows a gas delivery circuit 2101 and a sensing tube 2103 external to a nose bridge support 2105 and a nose bridge piece 2107. FIG. 22 shows a more substantial connection between a nose bridge piece 2201 and a manifold 2203, such that they are a unified piece. FIG. 23 shows a similar configuration to FIG. 22 except a manifold 2301 is separate from the nose bridge piece 2303. FIG. 24 shows a configuration with a nose bridge piece 2401 surrounding nozzles 2403.

Figure 26:
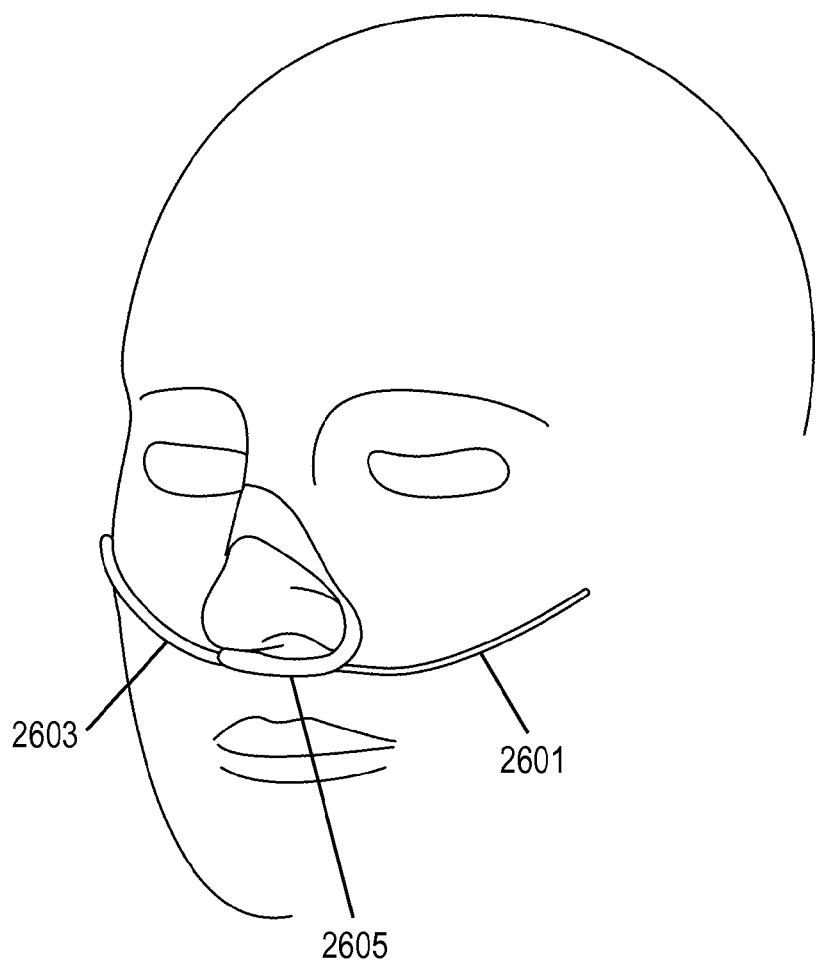
FIG. 26 shows a gas delivery circuit and nasal airway pressure sensing line may attach to a manifold to help secure the system in place.
Figure 27:
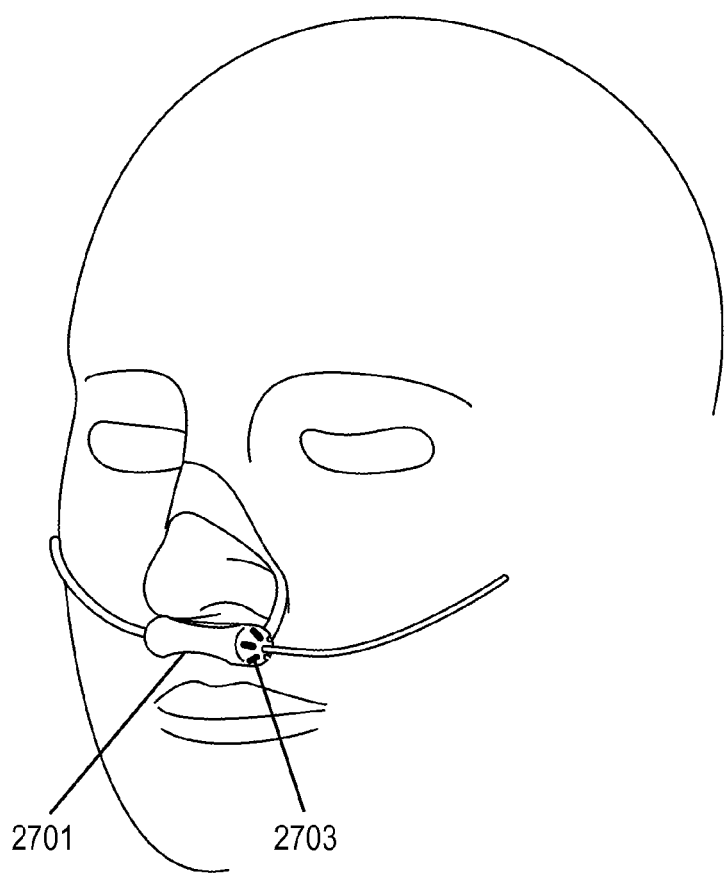
FIG. 27 shows a gas delivery nozzle within a manifold, so that the manifold can diffuse and dampen the noise generated by the gas exiting the nozzles.
Figure 28:
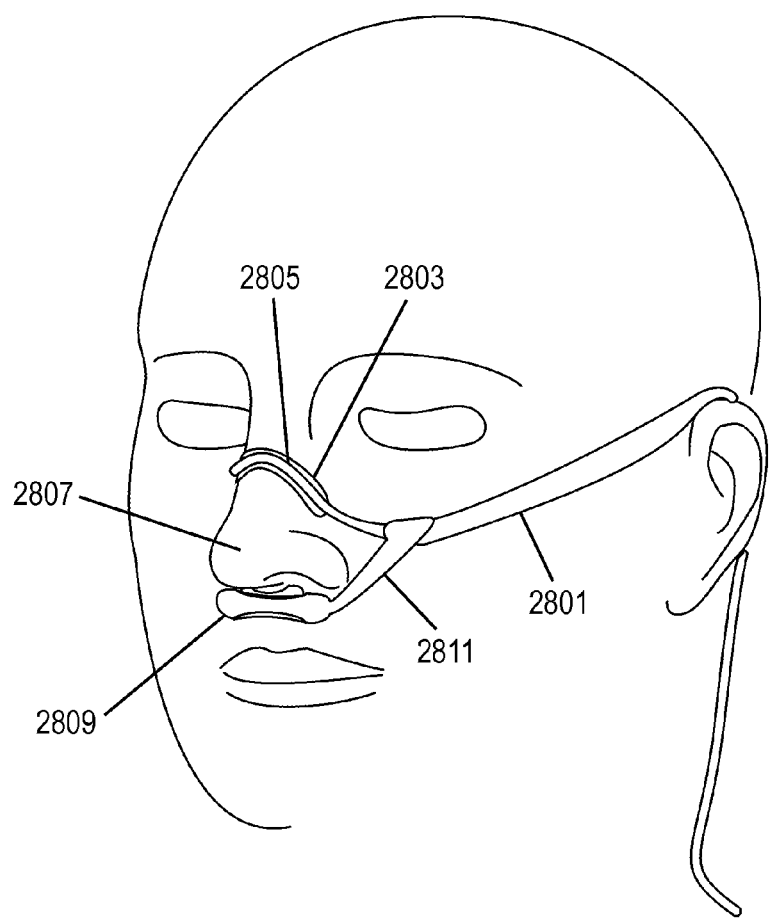
FIG. 28 shows a gas delivery conduit routed unilaterally to one side of the face to free the opposite side from any objects.
Figure 29:
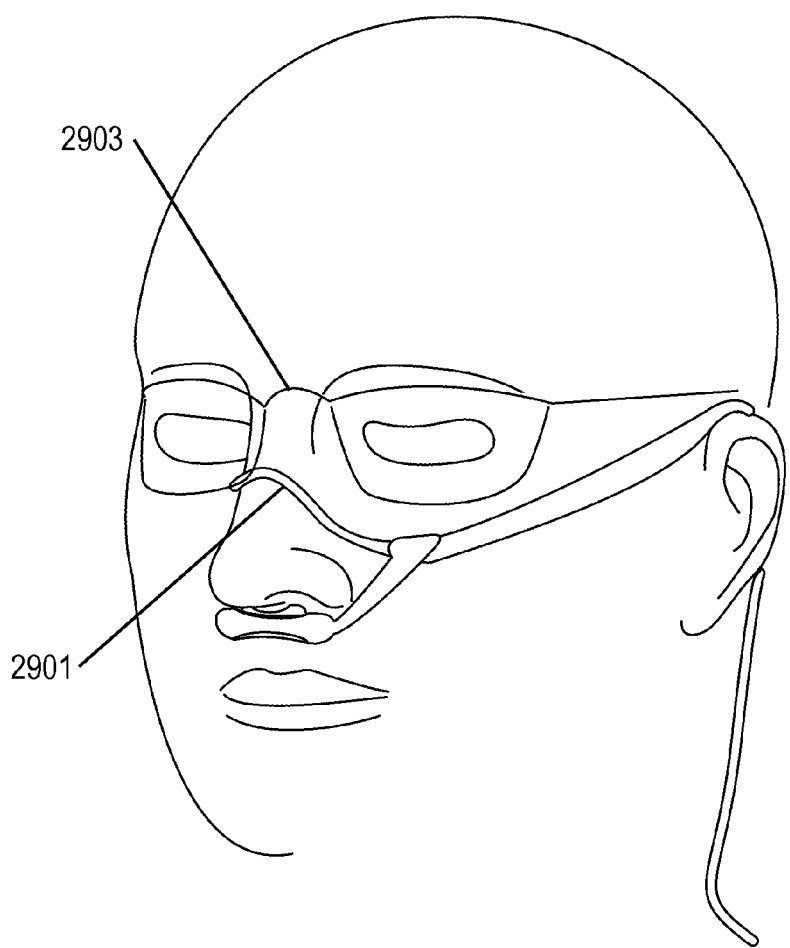
FIG. 29 shows an embodiment similar to FIG. 28 where a nose bridge support is held in place by or coupled to glasses.
Figure 30:
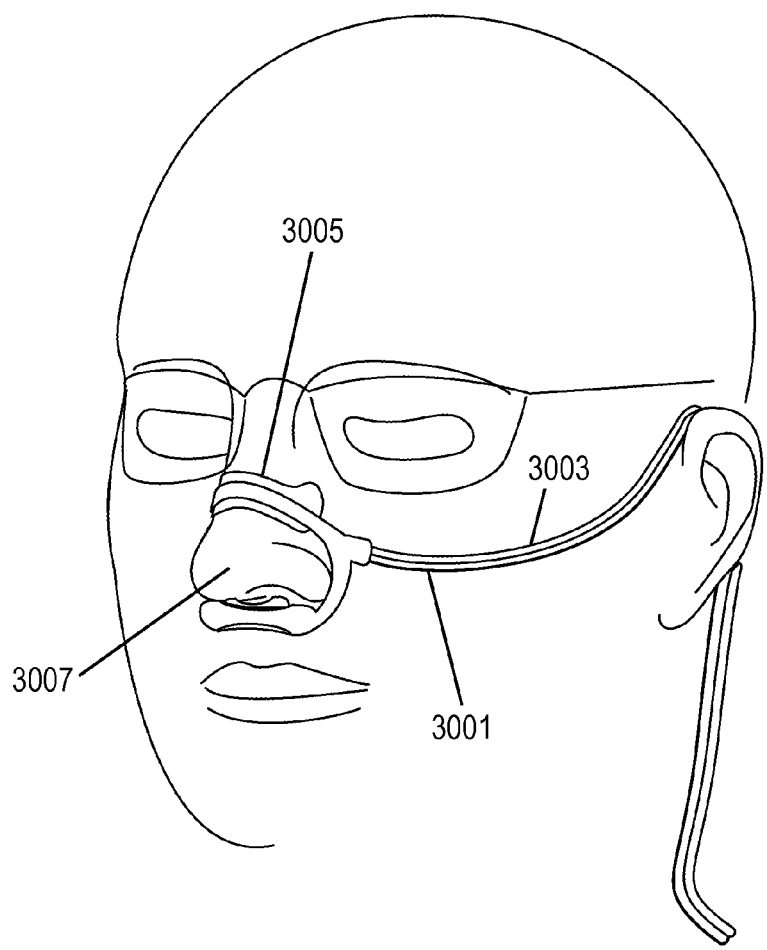
FIG. 30 shows a unilateral configuration with a sensing tube following the path of a gas delivery circuit and held in place with a skin cushion on a nose.
Figure 31:
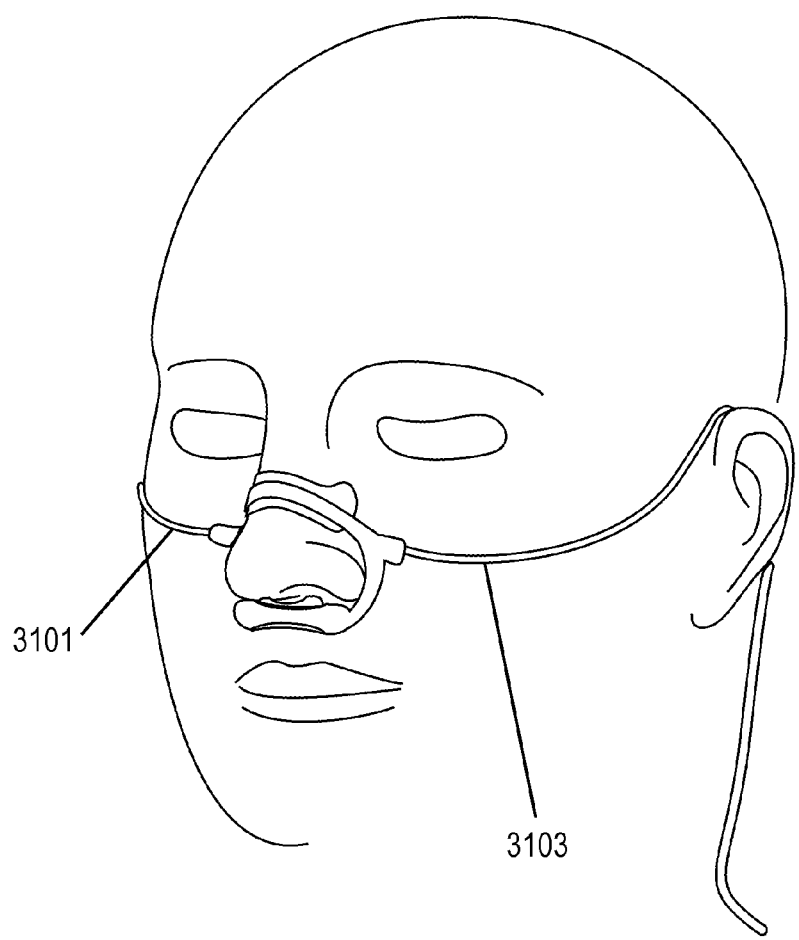
FIG. 31 shows a sensing tube on an opposite side of a face from a gas delivery circuit.
Figure 32:
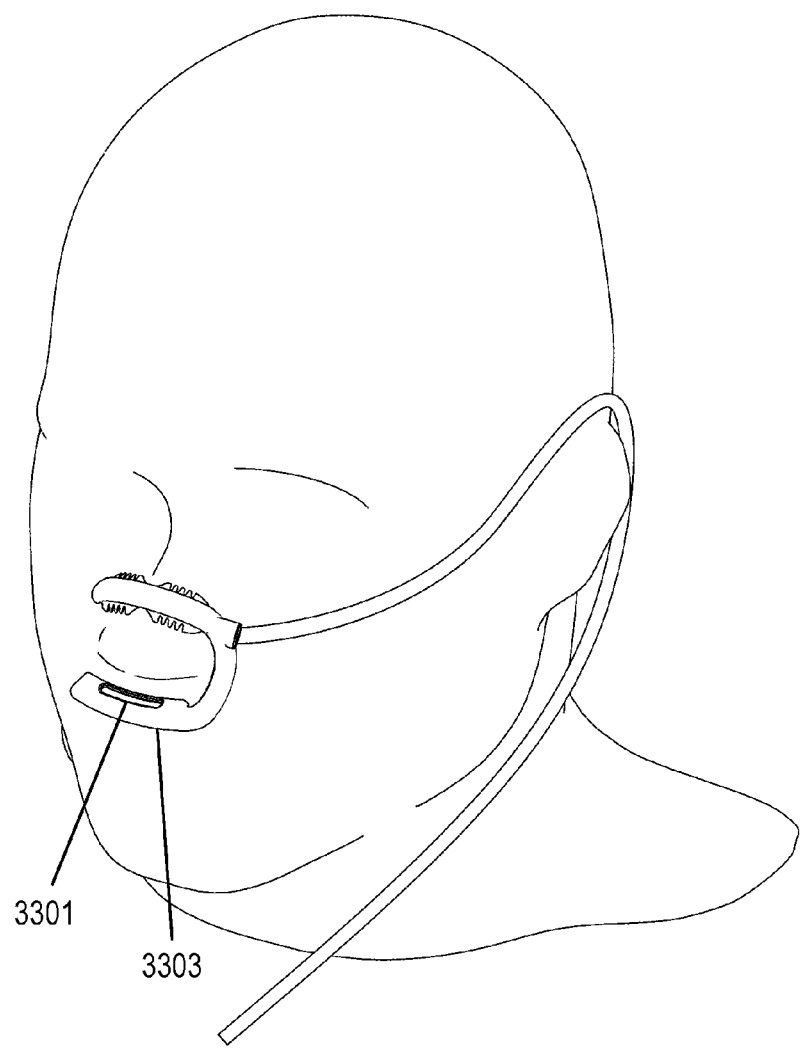
FIG. 32 shows a sound muffler incorporated into a manifold.
Figure 33:
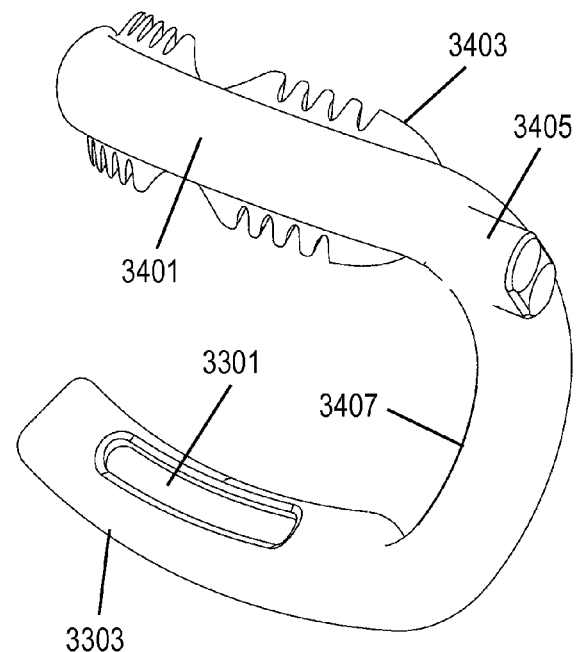
FIG. 33 is a close up anterior view of the embodiment of FIG. 33.
Figure 34:
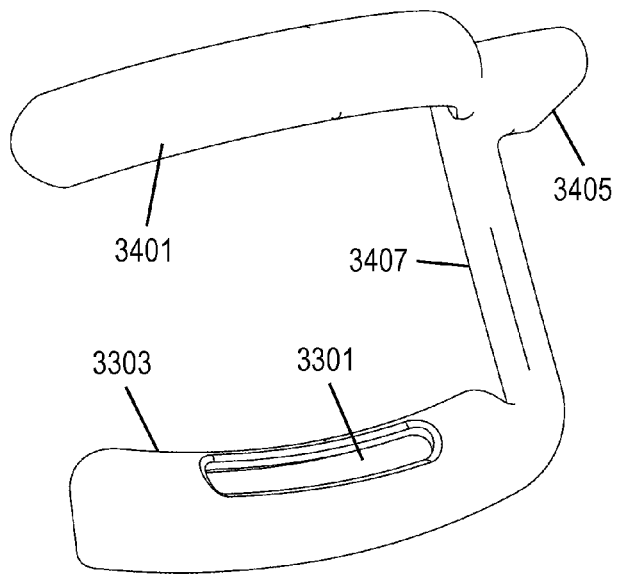
FIG. 34 is a close up posterior view of the embodiment of FIG. 33.

FIGS. 25-34 describe an embodiment where a nose bridge piece 2501 is located to one side of a nose 2503, rather than along the midline of the nose 2503. A gas delivery circuit 2505 may supply ventilation gas to a nose bridge support 2507. A sensing tube 2509 may also be coupled to the nose bridge support 2507. The nose bridge piece 2501 may be coupled to a manifold 2511 with one or more nozzles 2513. In FIG. 26, a gas delivery circuit 2601 and nasal airway pressure sensing line 2603 may attach to a manifold 2605 to help secure the system in place. FIG. 27 shows a gas delivery nozzle within a manifold 2701, so that the manifold can diffuse and dampen the noise generated by the gas exiting the nozzles. Ports 2703 may allow passage of ventilation gas. FIG. 28 shows a gas delivery conduit 2801 routed unilaterally to one side of the face to free the opposite side from any objects. A skin cushion 2803 may hold a nose bridge support 2805 on a nose 2807. A manifold 2809 may be coupled to a side nose bridge piece 2811. FIG. 29 shows an embodiment similar to FIG. 28 where a nose bridge support 2901 is held in place by or coupled to glasses 2903. FIG. 30 shows a unilateral configuration with a sensing tube 3001 following the path of a gas delivery circuit 3003 and held in place with a skin cushion 3005 on a nose 3007. Tubes may be combined in a multi-lumen system or may remain separate. Tubes may be held in place with bendable wires. Tubing may be integrated into a strap. FIG. 31 shows a sensing tube 3101 on an opposite side of a face from a gas delivery circuit 3103. FIG. 32 shows a sound muffler 3301 incorporated into a manifold 3303. Jet nozzles may be located below within or below the manifold 3303. FIG. 33 is a close up anterior view of the embodiment of FIG. 32. A nose support piece 3401 may have a nose coupler 3403 and an inlet 3405 for gas from a gas delivery circuit (not shown). An arm 3407 may couple the nose support piece 3401 to the manifold 3303. FIG. 34 is a close up posterior view of the embodiment of FIG. 32.

Figure 35:
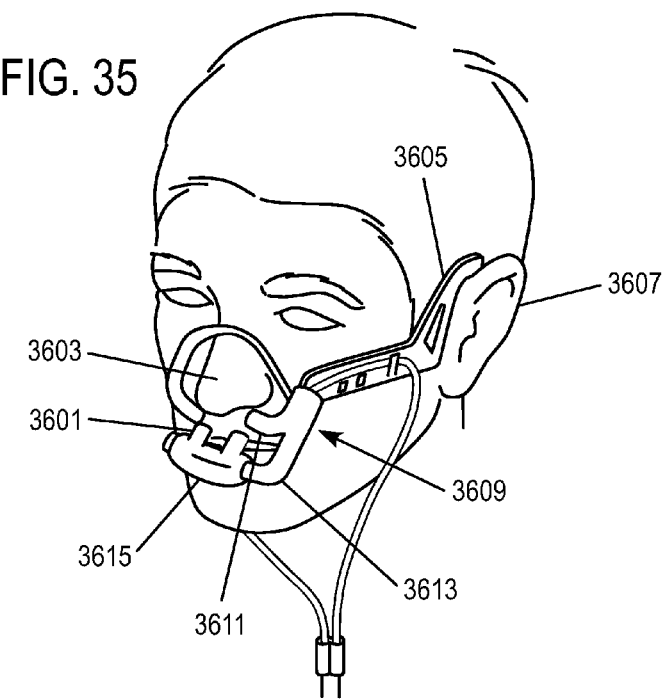
FIG. 35 shows an alternative embodiment of positioning gas delivery nozzles below a nose.

FIG. 35 shows an alternative embodiment of positioning gas delivery nozzles 3601 below a nose 3603. A bracket 3605 may extend from the nose 3603 to one or both ears 3607. At an anterior end of the bracket 3605, a ducting system 3609 may be attached, which may include the nasal airway pressure sensing limbs 3611 that terminate close to and under the nose 3603. The anterior end of the bracket 3605 may also include a gas delivery limb 3613 that may include a gas delivery manifold 3615 to which the gas delivery nozzles 3601 may be mounted. The system may include adjustment features to align the sending and delivery nozzles correctly.

Figure 36:
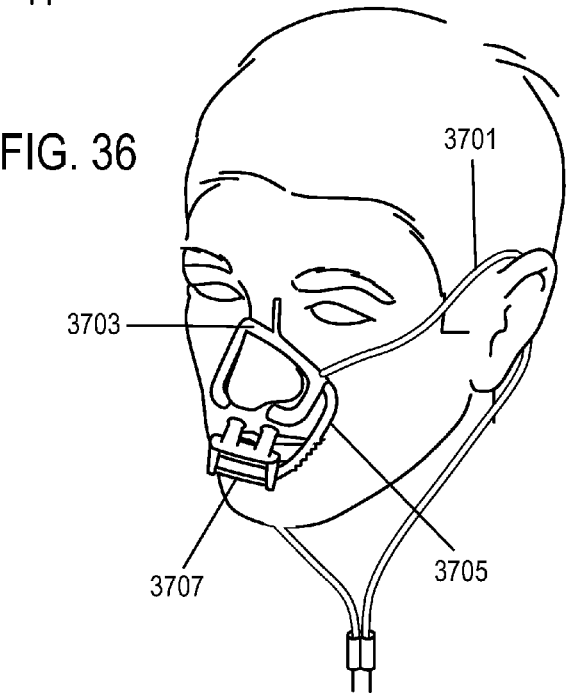
FIG. 36 shows gas delivery tubing and a nose support.

FIG. 36 shows gas delivery tubing 3701 and a nose support 3703. The nose support 3703 may hold the nasal interface in place on the face. A bracket 3705 may extend from the nose support 3703 to a gas delivery manifold 3707. The bracket 3705 can be flexible or adjustable so that the user can adjust as desired.

FIGS. 37-53 describe certain embodiments of the invention in which the gas delivery nozzles are positioned under the nose without the use of brackets or nose supports, but with the use of tubing or head straps.

Figure 37:
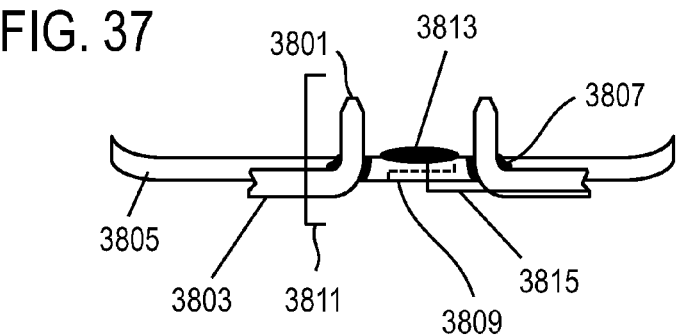
FIG. 37 describes a front view of an embodiment of a distal end of a patient interface.

FIG. 37 describes a front view of an embodiment of a distal end of a patient interface. Gas delivery jet nozzles 3801 may be located at an end of a cannula 3803, wherein the cannula 3803 and/or nozzles 3801 are attached to a head fastener 3805 via one or more cannula connectors 3807. In this embodiment, the patient's nostrils serve the role of the outer tube and jet pump inlet, throat and diffuser. Optionally, outer tubes, which are separate components, can be independently placed in the nose, and the interface shown in FIG. 37 can then be fastened to the face so that the nozzles are aligned and positioned correctly with the outer tubes. In FIG. 37, left and right cannula may be connected together by an extension of the fastener or by a coupler 3809. The coupler 3809 can include length and angle adjustment features. The jet pump nozzles 3801 may create a jet pump inlet and entrainment area 3811. A sensor 3813 may be coupled to a controller (not shown) via a sensor wire 3815.

Figure 38:
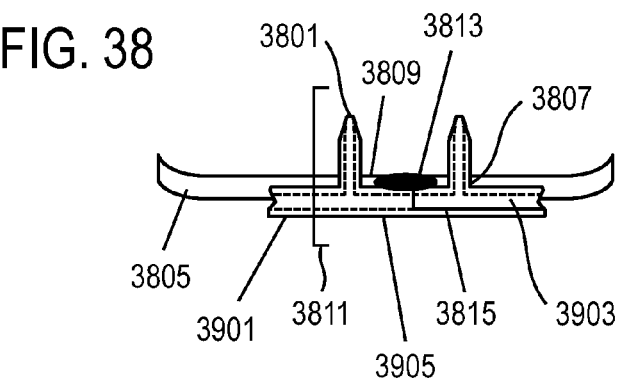
FIG. 38 shows an embodiment where a left and right cannula may be interconnected with an air flow path, such as a manifold, and the portion of the nasal interface that includes the distal tip jet nozzle can extend upward from the manifold.

FIG. 38 shows an embodiment where a left and right cannula 3901 may be interconnected with an air flow path 3903, such as a manifold 3905, and the portion of the nasal interface that includes the distal tip jet nozzle 3801 can extend upward from the manifold 3905.

Figure 39:
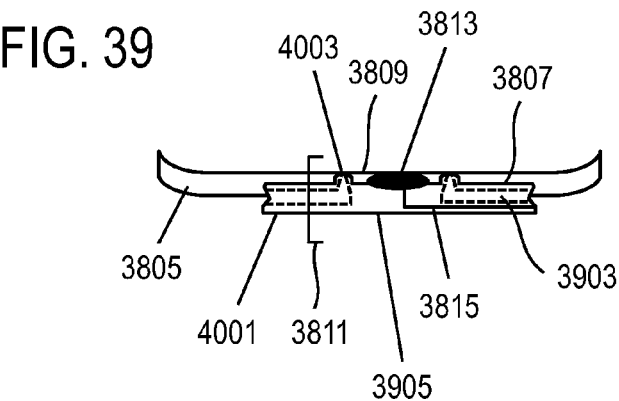
FIG. 39 shows an alternative embodiment in which the jet nozzles at a distal end of a cannula may be apertures in a superior wall of the cannula, and wherein the cannula is curved laterally to one or both sides of the nose.

FIG. 39 shows an alternative embodiment in which the jet nozzles 4003 at a distal end of a cannula 4001 may be apertures in a superior wall of the cannula 4001, and wherein the cannula 4001 is curved laterally to one or both sides of the nose. The low profile nozzles 4003 may allow the cannula 4001 extending away from the nozzles 4003 to be located close to the nose and away from the mouth, to create an unobtrusive design. As shown in FIG. 39, the gas flow paths of the left and right cannula may not connect in the manifold 3905 but end at the nozzles 4003. As the gas enters the nozzle 4003 from the cannula gas flow path 3903, the gas flow path 3903 may be curved to help create a uniform and consistent gas flow profile in the nozzle. Optionally, the gas flow paths can connect in the manifold 3905.

The embodiments shown in FIGS. 37-39 may or may not include outer concentric tubes around the outside of the nozzle. These embodiments can be combined with a length adjustment coupler in between the nozzles or outer tubes, angle swivel connections between the nozzles and manifold or between the outer tubes and the coupler.

Figure 40:
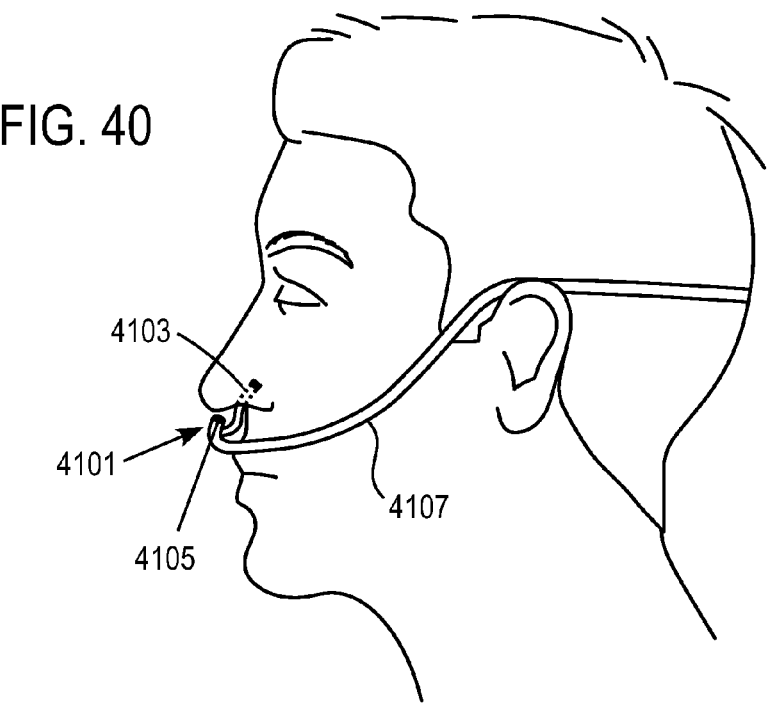
FIG. 40 shows a side view of an embodiment of the invention in which the nasal interface includes a locating device to align and position a tip of the nasal interface correctly, in relation to the nostril foramen.
Figure 41:
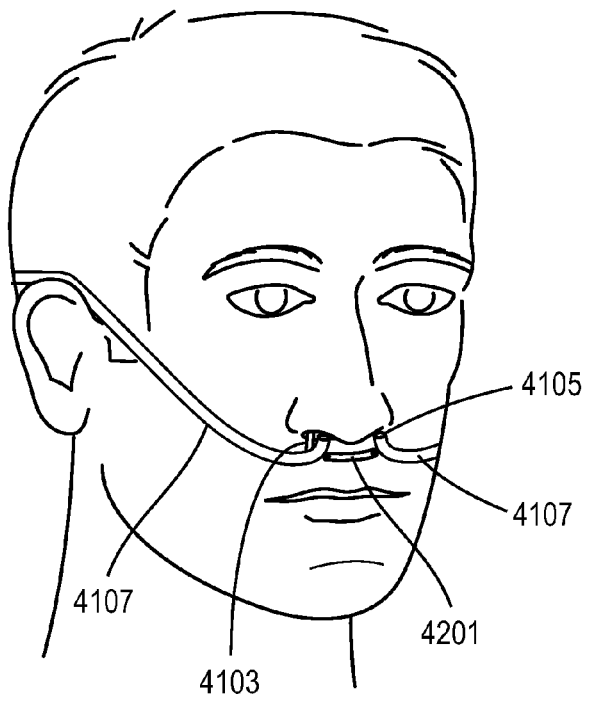
FIG. 41 shows a front view of this embodiment with a connector between opposite sides of the gas delivery circuit.

FIG. 40 shows a side view of an embodiment of the invention in which the nasal interface 4101 includes a locating device 4103 to align and position a tip 4105 of the nasal interface 4101 correctly, in relation to the nostril foramen. The locating device 4103 can be a soft but semi-rigid arm that impinges on the nostril wall or nostril septum. For example, the locating device 4103 can lightly pinch the nostril septum by two arms that press inward on the left and right wall of the nostril septum. There can be one or more arms for each nostril, or just one arm for both nostrils. The arms can contact the posterior, anterior, lateral or medial wall of the nostril, or optionally can contact an outside wall of the nostril. The locating device 4103 may be attached to the gas delivery circuit 4107 such that the distal tip and gas exit port of the nozzle is directed as desired toward the nostril foramen. FIG. 41 shows a front view of this embodiment with a connector 4201 between opposite sides of the gas delivery circuit 4107.

Figure 42:
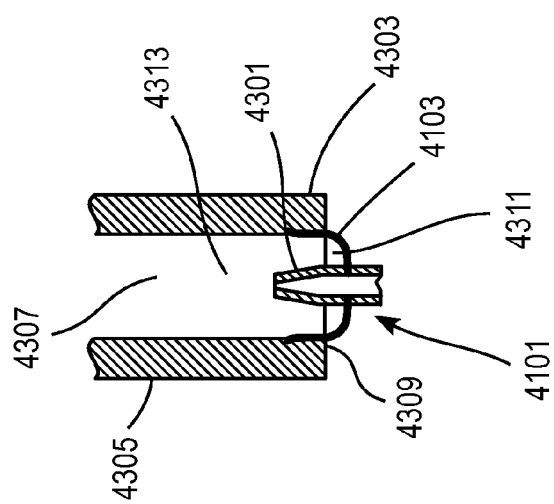
FIG. 42 shows a cross sectional schematic of the embodiment shown in FIGS. 40 and 41.

FIG. 42 shows a cross sectional schematic of the embodiment shown in FIGS. 40 and 41. A jet pump nozzle 4301 may be positioned within the nasal septum 4303, nostril wall 4305, nostril foramen 4307, nostril rim and opening 4309, and/or jet pump throat 4313 to create a jet pump inlet and entrainment zone 4311.

Figure 43:
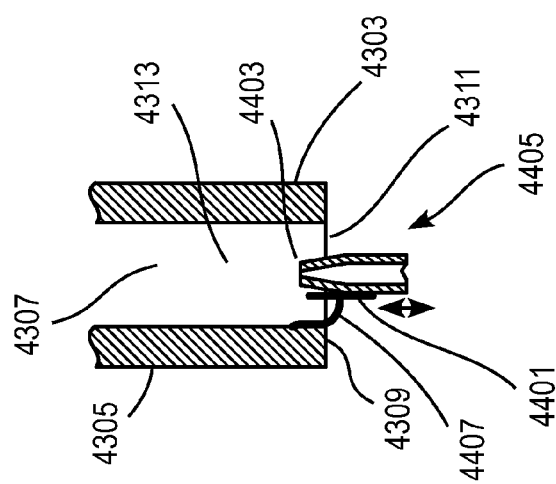
FIG. 43 shows a cross sectional schematic view of an embodiment of a nasal interface that may include an adjustment feature coupled to an adjustment arm that is used to adjust the position of a nozzle relative to the nostril.

FIG. 43 shows a cross sectional schematic view of an embodiment of a nasal interface 4405 that may include an adjustment feature 4401 coupled to an adjustment arm 4407 that is used to adjust the position of a nozzle 4403 relative to the nostril. Primarily, the depth of insertion of the nozzle 4403 into the nose may be adjusted by this adjustment feature 4401; however, the alignment and centering of the nozzle 4403 can also be adjusted, relative to the nostril opening and nostril foramen.

Figure 44:
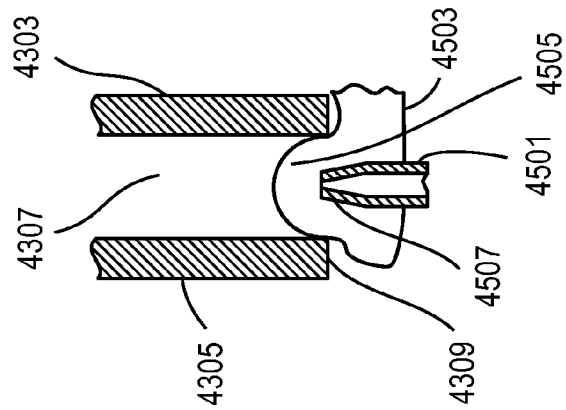
FIG. 44 shows a cross sectional front view of a right nostril in which an attachment and positioning pad may be included with the system.

FIG. 44 shows a cross sectional front view of a right nostril and an alternate embodiment of a nasal interface 4501, in which an attachment and positioning pad 4503 may be included with the system. The nasal interface 4501 may be attachable to the attachment and positioning pad 4503, and the attachment and positioning pad 4503 may also include an extension or locating tab 4505 in the superior direction configured and dimensioned for it to be inserted slightly into the nostril and placed against a posterior wall of the nostril. The locating tab 4505 may locate the attachment and positioning pad 4503 in a known orientation and location, and a cannula (not shown) that may be attached to the attachment and positioning pad 4503, and nozzle 4507, may be, as a result, positioned, oriented, and angled optimally toward the nostril opening and nostril foramen. The attachment and positioning pad 4503 may also be used to position the distance of the cannula tip relative to the nostril opening to the optimal distance. The attachment of the cannula to the attachment and positioning pad 4503 can be a removable and adjustable attachment, so that the cannula position can be adjusted to meet the needs and goals of the therapy, and to adjust the fit to match the anatomy of each individual.

FIGS. 45-59 describe a version of the above embodiment in which the gas delivery nozzles are integral to a manifold that is positioned under the nose without the aid of nose supports or brackets.

Figure 45:
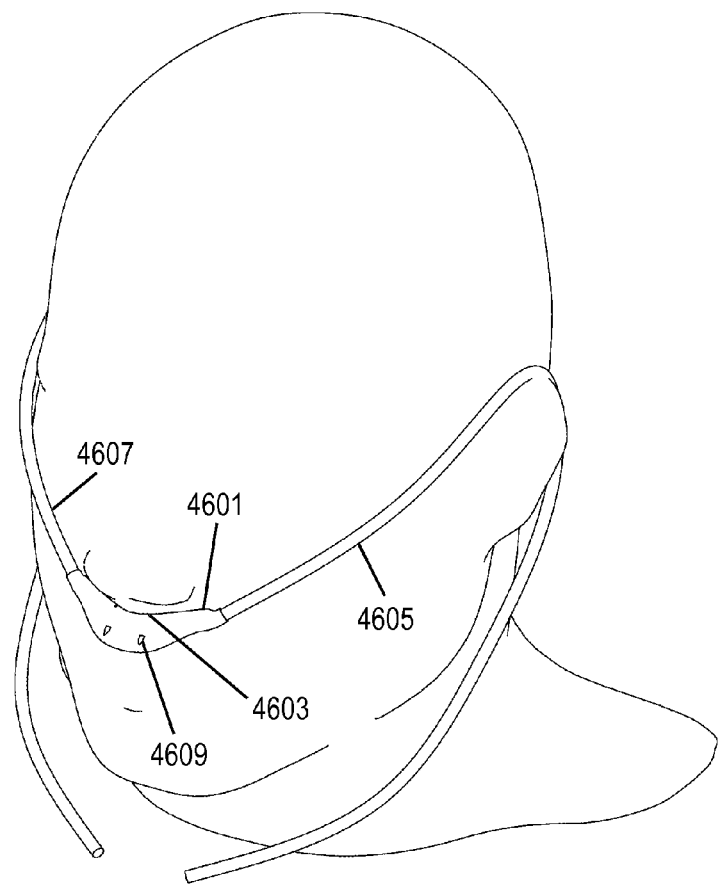
FIG. 45 shows a manifold with anatomically matching curves is described.
Figure 46:
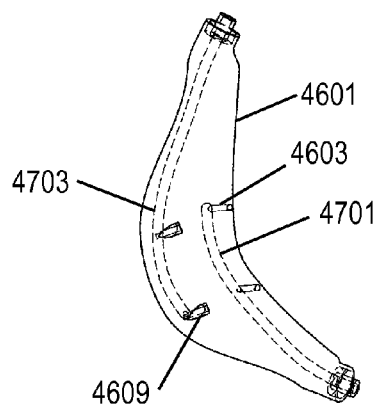
FIG. 46 is a close up side-front view of the manifold described in FIG. 46, showing the gas delivery nozzles with gas delivery routing, and nasal airway pressure sensing ports with pressure sensing lumens.

In FIG. 45, a manifold 4601 with anatomically matching curves is described. Gas delivery nozzles 4603 may be positioned on a superior-posterior side of the manifold 4601, so that gas delivery is aligned with the nostrils. Gas delivery tubing 4605 and nasal airway pressure sensing tubing 4607 may attach to lateral ends of the manifold 4601, and the tubing 4605, 4607 may be used to secure the manifold 4601 under the nose. As in other embodiments described herein, the gas delivery channel 4605 and nasal airway pressure sensing tube 4607 can be separate lumens in the same tubing, or can be separate tubes. Sensors 4609 may be located on a superior-anterior side of the manifold 4601 or any other appropriate location. FIG. 46 is a close up side-front view of the manifold 4601 described in FIG. 45, showing the gas delivery nozzles 4603 with gas delivery routing 4701, and nasal airway pressure sensing ports 4609 with pressure sensing lumens 4703. FIG. 46 is a top view of the manifold 4601 shown in FIG. 46.

Figure 47:
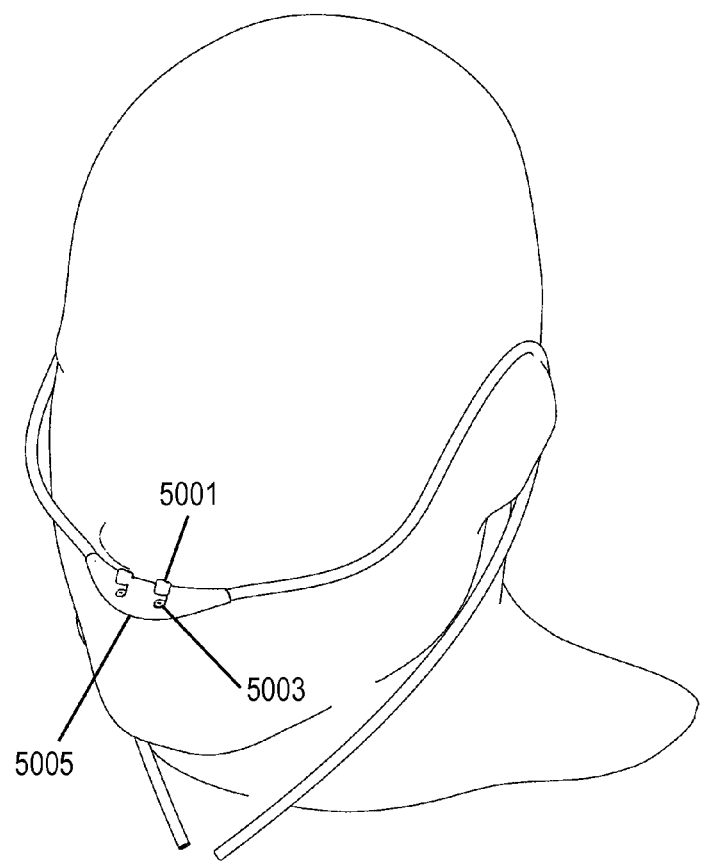
FIG. 47 describes an embodiment in which a sound baffle is provided above gas delivery nozzles on a manifold, so that the sound generated by the gas exiting the nozzles is muted.
Figure 48:
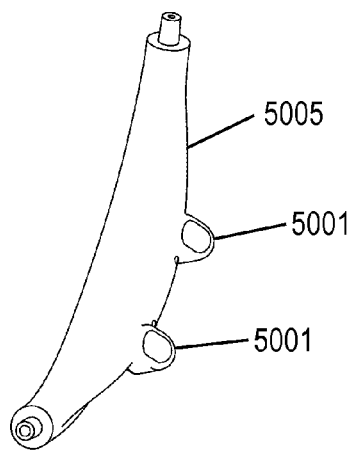
FIGS. 48 and 49 describe rear and front views, respectively, of the manifold shown in FIG. 47.
Figure 49:
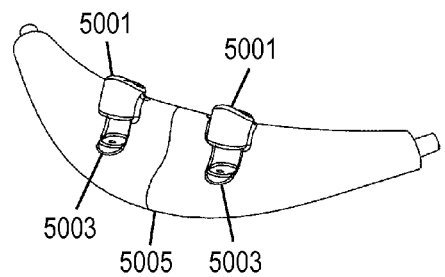

FIG. 47 describes an embodiment in which a sound baffle 5001 is provided above gas delivery nozzles 5003 on a manifold 5005, so that the sound generated by the gas exiting the nozzles 5003 is muted. FIGS. 48 and 49 describe rear and front views, respectively, of the manifold shown in FIG. 47. The baffles can also be used as flow organizers to adjust the flow velocity profile and dynamics as necessary. For example, the baffles can take the incoming velocity profile and shape it to a more uniform velocity profile on the outlet side, so that when the gas and entrained air enter the nose of the user, it feels more comfortable yet still has the power to penetrate the respiratory system. The sound baffles can also be used as cushions to impinge on the nostril in which case the baffles are comprised of a soft material.

Figure 50A:
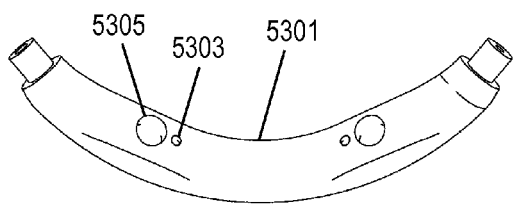
FIG. 50A describes an embodiment in which a manifold includes gas delivery nozzles as well as entrainment apertures.
Figure 50B:
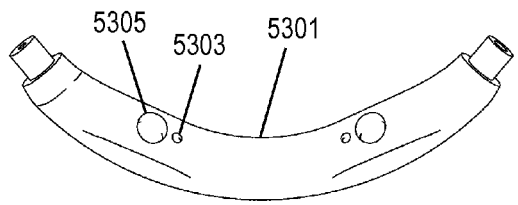
FIG. 50B shows an anterior view of the embodiment shown in FIG. 53A.

FIG. 50A describes an embodiment in which a manifold 5301 includes gas delivery nozzles 5303 as well as entrainment apertures 5305. FIG. 50B describes an anterior view of this embodiment.

Figure 51A:
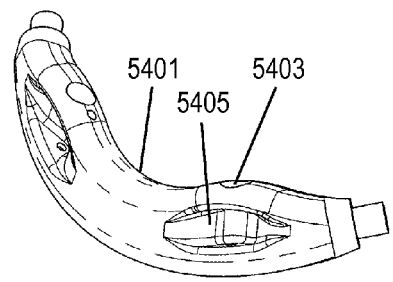
FIG. 51A shows describes an embodiment in which a manifold includes gas delivery nozzles as well as entrainment ports.
Figure 51B:
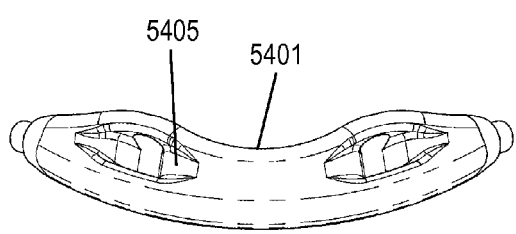
FIG. 51B describes an anterior view of the embodiment shown in FIG. 51A.

FIG. 51A shows describes an embodiment in which a manifold 5401 includes gas delivery nozzles 5403 as well as entrainment ports 5405. FIG. 51B describes an anterior view of this embodiment.

Figure 52:
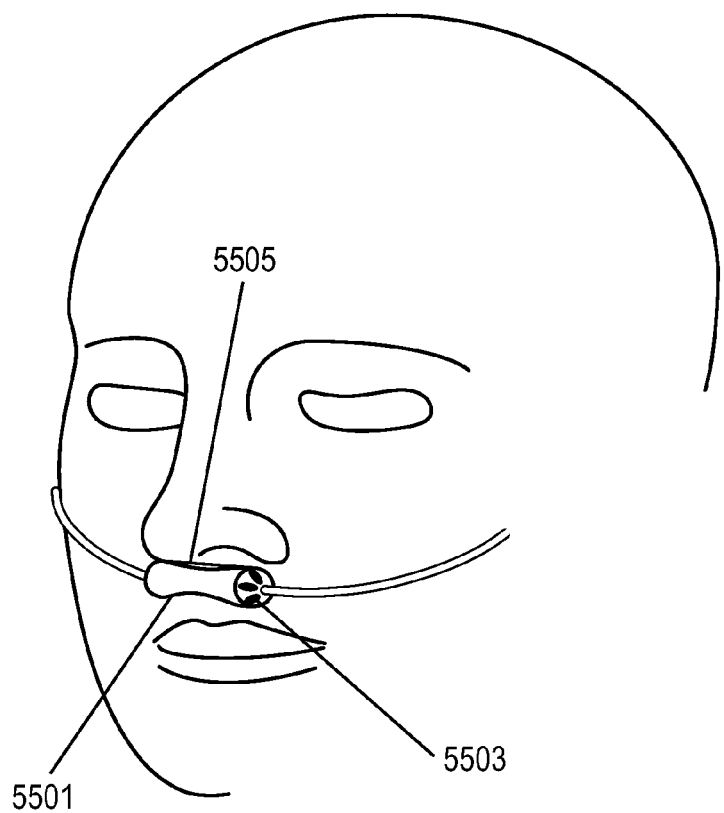
FIG. 52 shows an embodiment in which a manifold includes gas delivery nozzles recessed in the manifold to help dampen the sound that is generated and to position the manifold closer to the nose to reduce the profile of the nasal interface.

FIG. 52 shows an embodiment in which a manifold 5501 includes gas delivery nozzles 5503 recessed in the manifold 5501 to help dampen the sound that is generated and to position the manifold 5501 closer to the nose to reduce the profile of the nasal interface. An opening 5505 may allow passage of ventilation gas.

Figure 53:
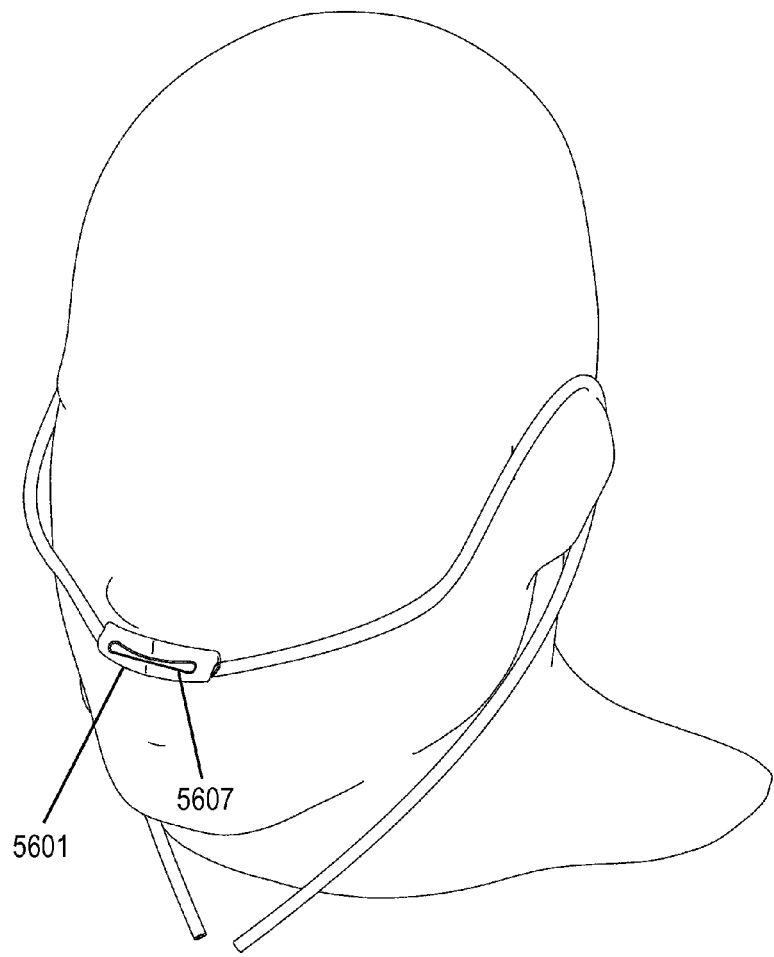
FIG. 53 shows an embodiment in which a manifold includes a pad on the posterior skin side of the manifold to help position and cushion the manifold against the skin and apertures.

FIG. 53 shows an embodiment in which a manifold 5601 includes a single aperture 5607.

Figure 54:
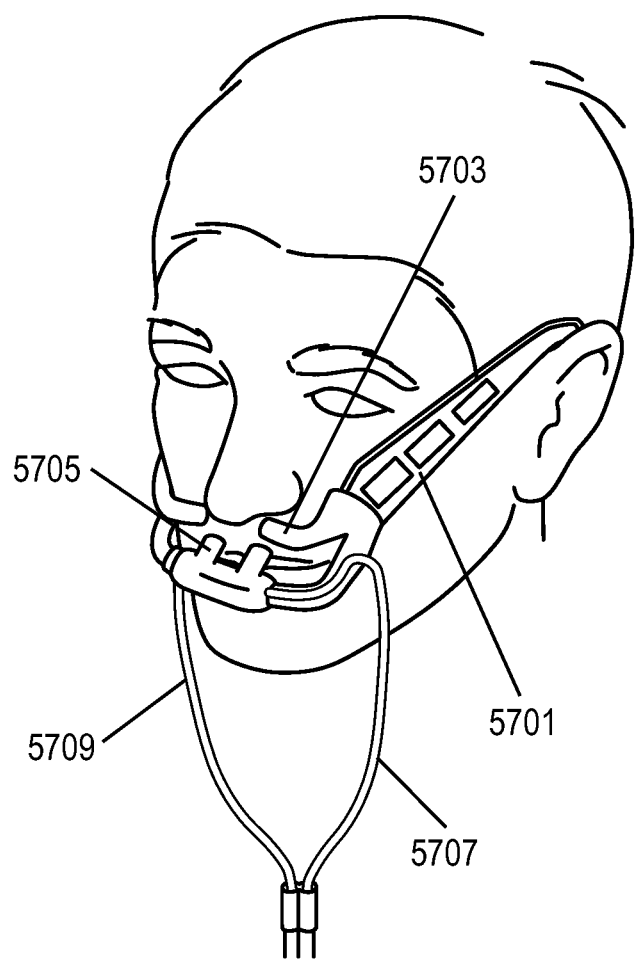
FIG. 54 shows an embodiment in which a bracket worn on the user's face may position nasal airway pressure sensing ports below the nose and gas delivery nozzles below the nose.

FIG. 54 shows an embodiment in which a bracket 5701 worn on the user's face may position nasal airway pressure sensing ports 5703 below the nose and gas delivery nozzles 5705 below the nose. Gas delivery tubing 5707 and pressure sensing tubing 5709 can be routed around the corners of the mouth to the front of the neck or can be routed to above and around the ears.

Figure 55:
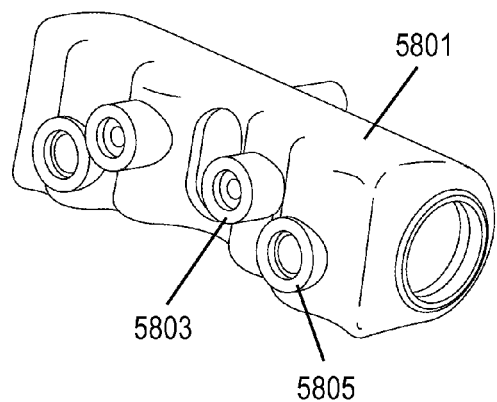
FIG. 55 shows a top view of a manifold of a nasal interface that is positioned under the nose, and shows gas delivery nozzles and nasal airway pressure sensing ports.

FIG. 55 describes a top view of a manifold 5801 of a nasal interface that is positioned under the nose, and shows gas delivery nozzles 5803 and nasal airway pressure sensing ports 5805.

Figure 56:
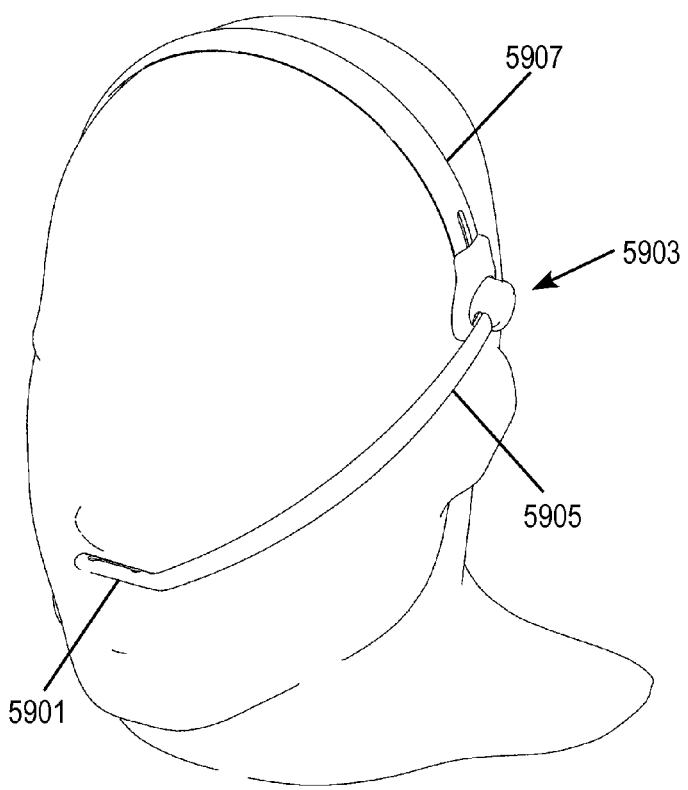
FIG. 56 shows a nasal interface in which a manifold is positioned under the nose using a head set similar to a hands free microphone.
Figure 57:
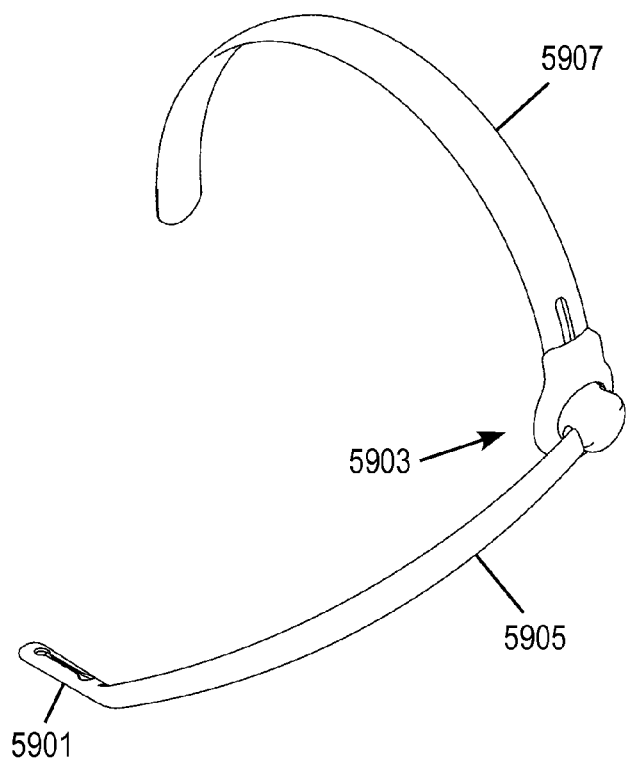
FIG. 57 shows a posterior view of the embodiment of FIG. 59 off of the user's head.
Figure 58:
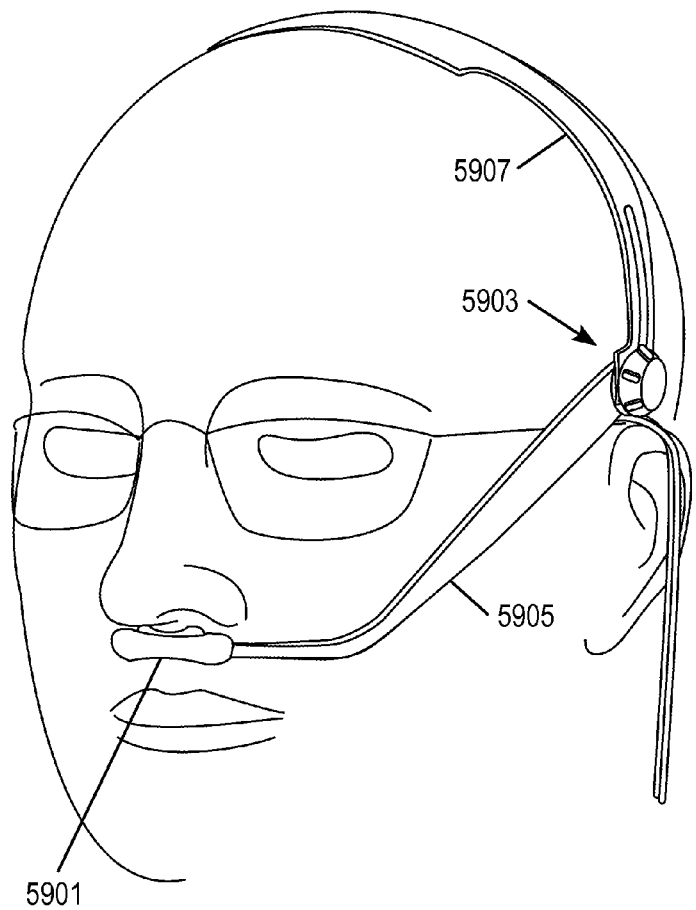
FIG. 58 shows an alternative to the embodiment of FIG. 56.

FIG. 56 describes a nasal interface in which a manifold 5901 is positioned under the nose using a head set 5903 similar to a hands free microphone. A gas delivery channel may be integrated into a bracket 5905 extending from above the ear to the manifold 5901 under the nose. The bracket 5905 may be attached and secured to the head using a head band or head brace 5907. The connection of the bracket 5905 to the head brace 5907 may be disconnectable or a may be a swivel. For example, if the user wants to sneeze or blow their nose, or discontinue or pause therapy, the bracket 5905 may be swiveled upward, which can shut off the gas flow to the manifold 5901. FIG. 57 shows a posterior view of the embodiment of FIG. 56 off of the user's head. FIG. 58 shows an alternative to the embodiment of FIG. 56.

The nasal interface distal end designs shown in foregoing features may include features and components that can be mixed in every possible combination to meet the needs of the particular clinical application, and to achieve a design that maximizes user ergonomics, and to achieve desired performance. The interface cannula can be routed to both sides of the face, or to one side of the face. The cannula can be routed over the ears, or up the center of the face between the eyes, or around the corners of the mouth to the front or back of the neck. The strap or fastener used to fasten the interface to the head can be routed to the back of the head above the ears, or can be fastened around the neck. The interface can include length adjustment features to set the distance between the two nozzles, or angle adjustment pivot or swivel joints to set the angle between the nozzles or the angle in the sagittal plane in order to align the nozzles with the nostril foramen. The interface can deliver gas in one nostril or both nostrils. Other routes of entry of the ventilation gas into the patient's airway are also included in the invention, as will be described, with requisite modifications to make the configuration compatible with outer entry points.

FIGS. 59-78 describe an embodiment of the invention in which gas may be delivered to the nasal airway using a nasal interface that includes a manifold. The manifold may (a) engage with the nostrils, and/or (b) extend bi-laterally from the nostrils to the sides of the nose, and/or (c) include gas delivery nozzles placed in the manifold, typically at a lateral end of the manifold.

Figure 59:
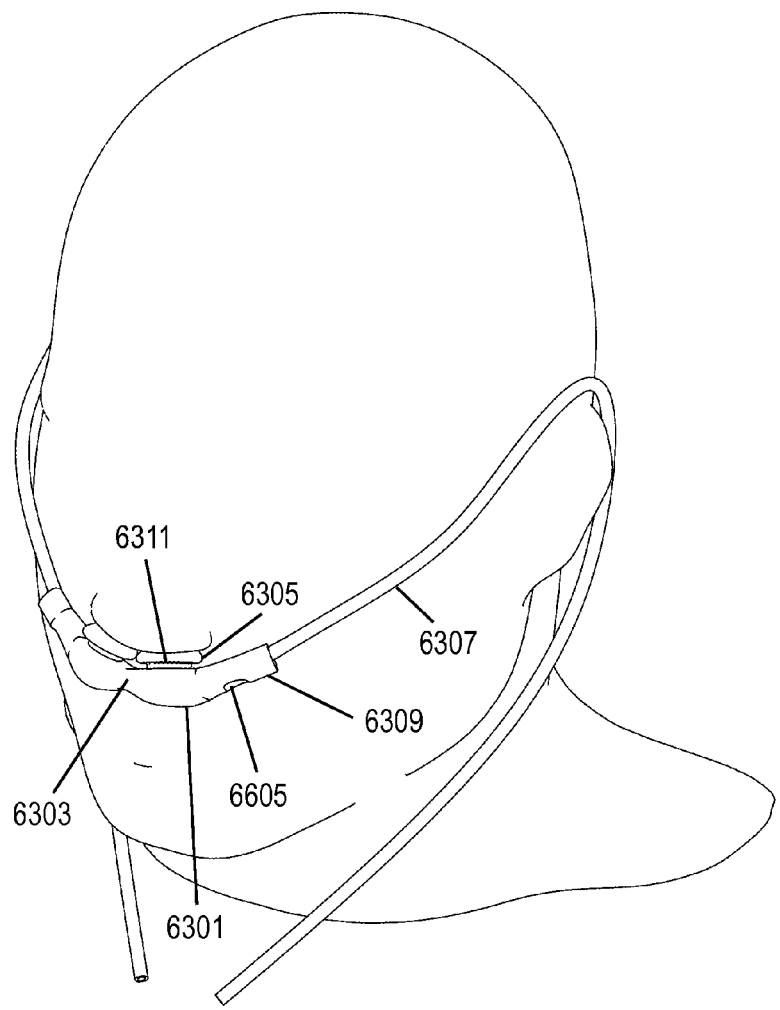
FIG. 59 shows an exemplary embodiment where a manifold may be curved and configured to be placed under the nose of the user, and which may extend bilaterally from the midline of the face to the sides of the nose.
Figure 60:
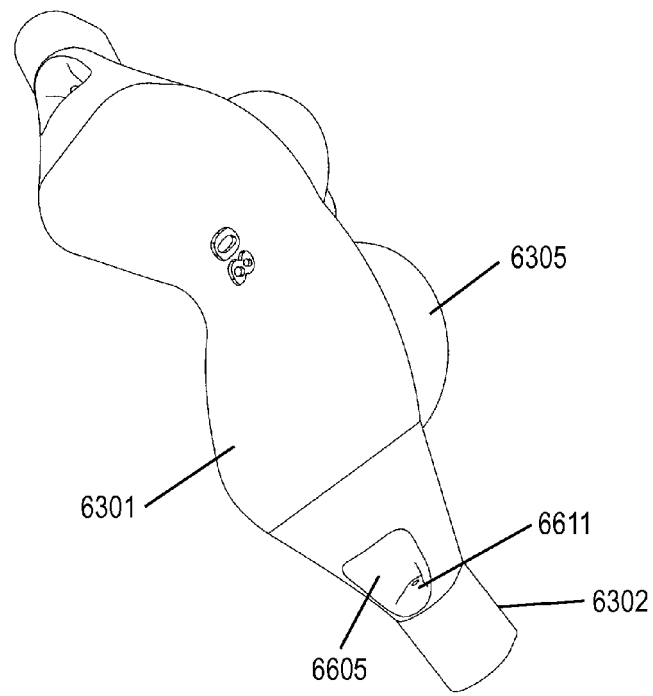
FIG. 60 shows a front-bottom view of the manifold of FIG. 59.
Figure 61A:
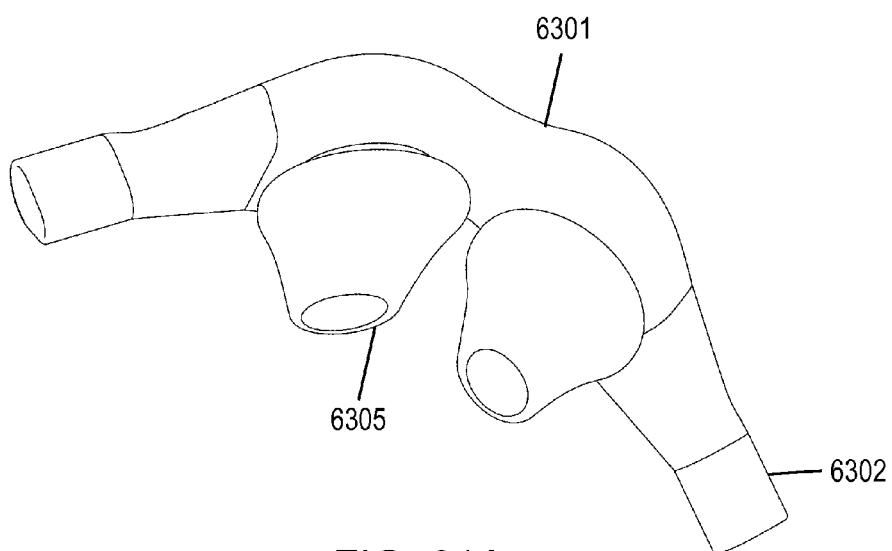
FIG. 61A shows a top-front-side view of the manifold of FIG. 59.
Figures 63A, 63B:
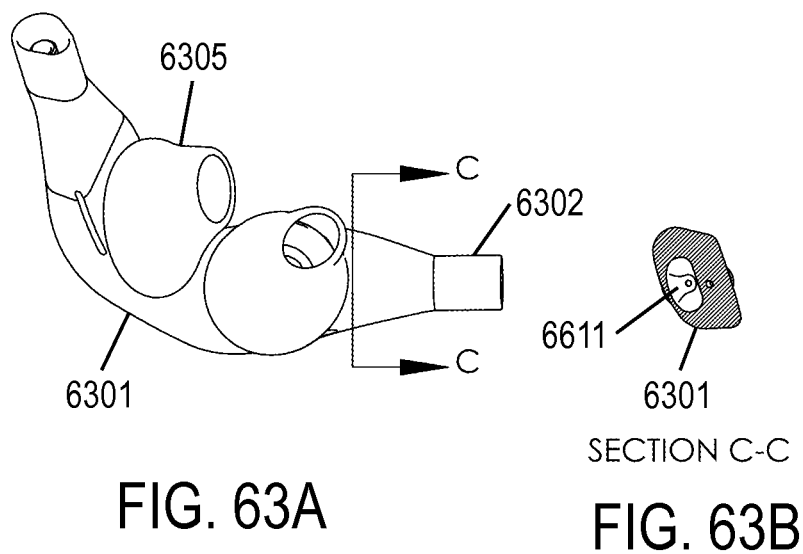
FIG. 63A shows a rear-side view of the manifold of FIG. 59.
FIG. 63B shows a sectional view of the manifold of FIG. 63A along a line B-B showing an end view of a gas delivery nozzle.

FIG. 59 shows an exemplary embodiment where a manifold 6301 may be curved and configured to be placed under the nose of the user, and which may extend bilaterally from the midline of the face to the sides of the nose. FIG. 60 shows a front-bottom view of the manifold 6301 of FIG. 59. FIG. 61A shows a top-front-side view of the manifold 6301 of FIG. 59. FIG. 61B shows a front-side view of the manifold of FIG. 59. A sound reducing aperture or slit 6621 may be provided. FIG. 62A shows a rear view of the manifold 6301 of FIG. 59. FIG. 62B shows a sectional view of the manifold 6301 of FIG. 62A along a mid-line A-A showing a gas flow path 6601. FIG. 63A shows a rear-side view of the manifold 6301 of FIG. 59. FIG. 63B shows a sectional view of the manifold 6301 of FIG. 63A along a line B-B showing an end view of a gas delivery nozzle.

The manifold 6301 may include a gas flow path 6601 inside the manifold 6301 and a gas delivery tube attachment 6302. The gas flow path 6601 may terminate at a distal end at gas flow openings 6003 at a superior side of the manifold 6301 positioned just lateral to a midline 6303 of the manifold 6301 on both sides of the midline 6303. Typically, there may be pneumatically separate left and right gas flow paths 6601; however, the two gas flow paths can alternatively be pneumatically joined together with a channel. A channel may be useful in providing balanced flow delivery to both nostrils in the event one nostril is congested. The ventilation system may include an alarm that may detect high levels of pressure in the manifold, for example, if one of the apertures is occluded. The manifold 6301 may be typically shaped in a compound arcuate shape to match the contours of the lace under and to the side of the nose. The manifold 6301 may typically curve bilaterally and posteriorly. It can in addition curve superiorly or inferiorly as it is curving laterally and posteriorly. The overall manifold assembly can be a bilateral assembly meaning the gas delivery is attached to both the left and right side, or it can be unilateral meaning that the gas delivery is attached to only one side. The later configuration may be useful for side sleeping or to reduce the obtrusiveness on one side of the face. The manifold cross sectional geometry is typically variable, and can be generally round or semi-round, or can be D-shaped or oval in order to optimize performance and ergonomics. Flatter cross sectional geometries that do not protrude far from the user's skin may be preferred ergonomically. The internal structure of the manifold may be devoid of corners and abrupt bends and angles to facilitate efficient gas flow fluid dynamics and sound generation. The manifold may be typically made of a semi-rigid material, either a thermoplastic or elastomeric material, typically of 30-90 Shore A hardness. The manifold can also be constructed to be malleable or moldable by the user for the user to make minor adjustments to allow the manifold to fit ideally to that individual. The overall assembly can be disassemble-able, so the user can take the assembly apart for cleaning, or to assemble correct sizes of the different parts together to customize the fit. The manifold and cushions, if included, may typically be translucent, but also can be transparent or opaque. Humidification can be added to the gas delivery circuit, either by active heated humidification or by aerosolizing moisture particles into the gas delivery system, typically into or from the manifold or a heat moisture exchange (HME) or combinations of the above. To prevent rainout from occurring in the manifold, the manifold may have a drainage line to scavenge any moisture that is collecting.

Two tubular extensions 6305 may be coupled with and extend superiorly from the distal end gas flow openings 6603. The tubular extensions 6305 may be configured to impinge with the nostrils and optionally seal against the nostrils by engaging the rim of the nostril. The extensions 6305 are typically soft and compliant to allow for comfortable contact with the nostril and, if a seal is intended, compress against the nostril in a comfortable manner. The extensions 6305 may be fit on stems 6311. The gas flow path 6601 in the manifold 6301 may be dimensioned such that the patient can breathe freely through the gas flow path without feeling restricted. The gas flow path 6601 may be curved and devoid of abrupt angles and corners in order to channel the gas with as little resistance and disturbance as possible. Gas delivery jet nozzles 6607 that may deliver the supplemental ventilation gas into the manifold 6301 may be positioned at the lateral proximal ends of the manifold 6301. Gas exiting the nozzles 6607 may entrain ambient air from the nearby manifold apertures 6605. The gas delivery jet nozzles can be positioned in the manifold near the base of the nasal cushions, or inside the nasal cushions, or can be positioned in the manifold at a distance proximal to the nasal cushions. The nozzles can be positioned near the lateral ends of the manifold in which case the manifold internal geometry is devoid of abrupt angles and corners, so that the gas being delivered by the nozzles flows in an organized flow profile with minimal turbulence. The nozzle exit vector or directional alignment preferably is aligned with the average centerline arc of the manifold internal geometry. This may be important to make the system more efficient and to produce less sound. Typically the nozzle may be centered with respect to the manifold internal geometry at the location of the nozzle; however, it can also be off-center, for example, in situations in which minimal sound generation is desired. The manifold internal geometry can be round in cross section or can be non-round, such as D-shaped, oval, or elliptical, in order to optimize both flow dynamics, sound and ergonomics. The jet nozzle tip inner diameter can range from approximately 0.010" to approximately 0.080" in diameter or effective diameter, and may be preferably approximately 0.020"-approximately 0.060" in diameter or effective diameter. Other dimensions are possible depending on certain uses. The position of the nozzle relative to the manifold and the apertures can be adjustable such that the adjustment can change the level of ventilatory support provided if so desired. Typically the jet ports are positioned bilaterally; however a single jet port is also contemplated.

The inspired gas may be a combination of (1) supplemental ventilation gas being delivered from the ventilator through the nozzles, (2) entrained air drawn through the apertures by the ventilation gas exiting the nozzles, and (3) air drawn through the apertures from the user's own spontaneous breathing effort. Exhaled gas may be exhaled entirely through the apertures 6605.

In addition, the pressure inside the manifold 6301 may be measured by a pressure tap 6611, and this pressure may be continuously measured by a transducer in the ventilator by a conduit connecting the pressure tap 6611 to the transducer. The measured pressure inside the manifold 6301 may be used to detect the phases of the breathing cycle, and to measure the delivered ventilation pressure. Ideally, the pressure tap 6611 may terminate at a point in the manifold gas flow path 6601 that has as few artifacts as possible, typically as close to the distal end of the gas flow path 6601 in the manifold 6301. There may be multiple pressure taps in the manifold 6301 to measure pressure in multiple locations in the manifold 6301, for example to determine flow by measuring the pressure difference between two pressure tap locations, or for example to measure at one location during inspiratory phase and a second location during expiratory phase, or for example one pressure tap to be used to detect spontaneous breathing signals and one pressure tap to be used to measure the ventilation pressure being delivered.

The supplemental ventilation gas from the ventilator may be delivered to the manifold 6301 from the ventilator via tubing 6307, which may be coupled to proximal ends 6309 of the manifold 6301. This tubing 6307 may include both the ventilator gas delivery channel and the pressure tap conduit. The tubing 6307 may typically extend around the ear to secure the nasal interface to the patient, or may be routed in other positions on the user's face, for example, around the corners of the mouth to the front of the neck, in which case a strap may be included to strap the manifold to the face and head.

For the purpose of these descriptions, the terms tubular extensions, nasal pillows, nasal cushions may be used interchangeably to describe the tubular bodies that impinge on the nose. These bodies may impinge on the rim of the nostril, seal on the rim of the nostril, seal inside the nostril, impinge on the tissue underneath the nose, or various combinations of the above. The tubular extensions 6305 may typically include convolutions in the shape to allow the extension to flex in multiple planes, and to compresses along a centerline axis, to conform to the user's nose. The extensions 6305 can be permanently affixed to the manifold 6301 or can be removably attached. The extensions 6305 or nasal cushions are described in more detail as follows. The nasal cushions can be positioned on the superior surface of the manifold, or the superior-posterior surface. The cushions can seal against the nostril rim or other part of the nostril so that there is not inadvertent leakage between the cushion and nose and so that the majority of the breathing gas flows through the cushion. However, this seal does not need to be leak free, and in some embodiments the may be a desired gas flow between the cushion and the nostril. The cushions can be attached to the manifold with a flex joint or corrugation in order to allow the cushions to flex, bend, or angulate under slight pressure so that they self-align with the nostril openings. The cushions can also compress inward toward the manifold so that the contact force at the contact point between the cushion and the nostril is dampened and absorbed. These features may make the cushion a flexible seal or flexible quasi-seal and may make the assembly more forgiving to mate with different facial structures and inadvertent movement of the assembly while being worn. The cushions are typically a compliant material such as silicone or elastomeric or thermoplastic material of Shore 10-60 A, but other materials may be used. The cushions can also be removably attachable from the manifold and available in different sizes so that the user can select a size that matches their anatomy.

The gas flow path 6601 in the manifold 6301 can be defined by two separate paths; a left path and right path that are separated by a septum 6609 at the midline 6303 of the manifold 6301. Alternatively the left path and right path can be interconnected at the midline of the manifold 6301, for example, to balance out the gas flow if one side of the nasal airway is more resistive than the other. Materials and dimensions of this embodiment are further explained in Table 3. In addition, FIG. 61B shows a sound reducing aperture 6621 communicating with the gas flow path 6601 is shown, which allows for an exit pathway for gas venting to reduce gas-gas shearing and resultant sound The apertures 6605 may address two functions: (1) the apertures may allow ambient air to be entrained by the jet ports, and (2) the apertures may allow for the patient to spontaneously breathe through the manifold. The aperture can be a single aperture, or multiple apertures. The entrainment aperture can be the different from the spontaneous breathing aperture, or the apertures can be separate. The spontaneous breathing apertures can be roughly or substantially in-line with the gas flow openings of the nasal cushion or manifold, or can be on the superior surface of the manifold, the inferior surface, the anterior surface, or a combination of these surfaces. In general, the spontaneous breathing apertures are preferably placed so that the exhaled gas from the patient is directed in a natural vector or direction. The entrainment aperture is preferably near the jet exit ports however can be placed in other locations on the manifold as well. The entrainment apertures can be positioned near the lateral proximal ends of the manifold and can be on the superior, anterior, inferior surfaces of the manifold or combinations thereof. The apertures can be variably adjusting for example can be adjusted between fully open and fully closed. The adjustment can help adjust and control the level of ventilatory support to the desired level that the overall system is intended to provide for the prevailing situation. The adjustment can be manual, but is preferably automatic with the use of valves, for example a valve that is controlled by a pressure signal delivered from the ventilator though a small bore conduit to the valve. The level of support can range from partial support to full ventilator support.

Sound generated by the jet nozzles and resultant entrainment, gas-gas shearing, and gas-surface shearing, can be abated by shrouding the nozzles, by covering the apertures with a sound filter media, by covering the apertures with low resistance mufflers, by treating and contouring the surfaces, or by optimizing the flow path geometry to permit a highly organized gas flow profile. The nozzle exit port can also be rounded to reduce noise generation. The inner wall of the manifold can be treated or textured to create additional sound barrier. The manifold material itself can be sound retardant to absorb and reflect sound, so that sound generated by the jet nozzles does not escape the manifold, for example, but not limited to, by using a porous but antimicrobial material. The inner manifold surface can also include a helical rib or ribs or helical groove or grooves to help organize the gas flow profile into a dynamic that produces less sound as a function of total volumetric flow rate.

The breathing of the user may be sensed by one or more respiration sensors. The sensors may be positioned inside the manifold 6301, or on the surface of the manifold 6301. The sensors may be positioned in a location that is minimally affected by artifacts caused by the jet, such as a vacuum signal. The sensor may typically be a pressure sensing port and sensing lumen that extends back to the ventilator and is in communication with the ventilator control system. However, the sensor can be other types as well, such as thermal, sound, vibration, gas composition, humidity, and force, or any combination thereof. The sensor can be used to measure breathing pressures, but can also be used to measure breathing gas flows, or other breath-related parameters, such as sound or gas composition. There may be a combination of breath sensors inside the manifold and a breath sensor on the outside of the manifold. The sensing element can be integral to the manifold, or in the ventilator. There may be two breath sensors, one for each nostril, or a single breath sensor. There may be multiple breath sensors for a nostril, for example an inspiratory breath sensor, and an expiratory breath sensor. The breath sensors can also be used to measure gas flow and gas volume, for example inspired and expired flow rate and inspired and expired tidal volume, of both the ventilator delivered gas and the spontaneously breathed gas. In addition to breath sensing, the apparatus may also include gas composition sensors, such as end-tidal $CO_2$ sensors, and oxygen sensors. $CO_2$ is a useful clinical parameter to measure and respond to, and can also be used as an additional breath detector, apnea detector, leak detector, and interface fitting detector (a certain characteristic $CO_2$ signal may indicate proper or improper fitting and placement of the interface). Oxygen sensing may be a useful parameter to measure and can be used to determine the FIO2 being delivered by the system to the patient and therefore can be used as a measured parameter and to make ventilator adjustments to achieve the desired FIO2.

Unfortunately, without the embodiments described above, the nasal interfaces may generate an undesirable amount of noise because of the jet pump principle. Jet pumps are known to create noise from the gas velocity exiting the jet nozzle, and the surrounding air being entrained by the jet. In some applications of the invention, such as when the user is in public, or desires quite surroundings, or when being used during sleep, it may be desired to have as little sound as possible. Placing the jet inside an outer tube or manifold may help reduce the noise of the jet, for example from 25-35 db to 15-25 db. There are, however, additional ways to further reduce the noise generated by the nasal interfaces of this invention, as shown in FIGS. 64A-65.

Figure 64A:
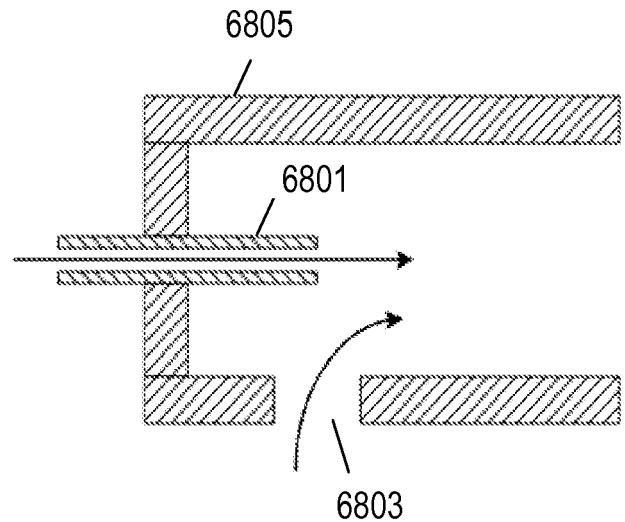
FIG. 64A shows a cross sectional schematic view of an embodiment for further reducing noise.
Figure 65:
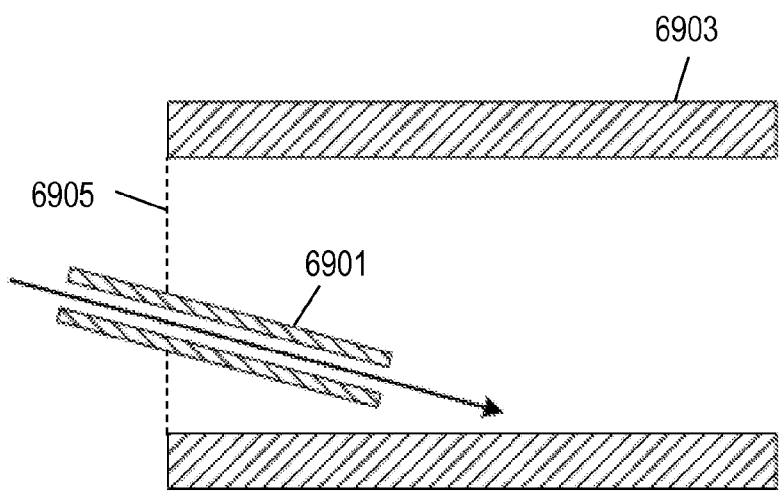
FIG. 65 describes an alternative embodiment of the invention in which a nozzle may be angulated with respect to the axial centerline of an outer tube or manifold.

FIG. 64A shows a cross sectional schematic view of an embodiment for further reducing noise. One half of the nasal interface is shown, for example, the left side or the right side. A gas delivery nozzle 6801 is shown positioned in parallel with a breathing aperture 6803, rather than coaxial. For purposes of this disclosure, parallel refers to gas flow direction. As such, the parallel position of FIG. 64A refers to the parallel flow of the ventilation gas delivered from the nozzle 6801 and the flow of entrained ambient air through the breathing aperture 6803. This configuration may allow the device to accomplish three important things. First, it allows the nasal interface to be as small as possible because the jet nozzle is not in the way of the spontaneous breathing path. If the jet nozzle is in the spontaneous breathing path, the area around the jet nozzle likely must be bigger to compensate for the nozzle so that the flow path is not made too resistive. Second, the parallel aperture may allow the device to channel the gas flow away from the mouth. Third, locating the aperture parallel to the nozzle may reduce the sound created by the nozzle 6801. An outer tube 6805 can be a nasal cushion or can be a manifold. The outer tube 6805 in the schematic is shown straight, but it could be straight or curved.

Figure 64B:
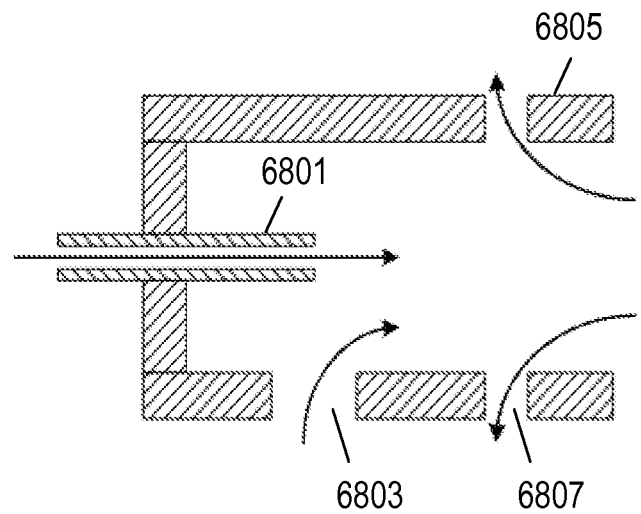
FIG. 64B shows a secondary gas flow aperture is shown.

In FIG. 64B, a secondary gas flow aperture 6807 is shown. This secondary aperture 6807 may allow for a second gas exit pathway during exhalation or when flow is traveling in both directions in the tube or manifold.

Figure 64C:
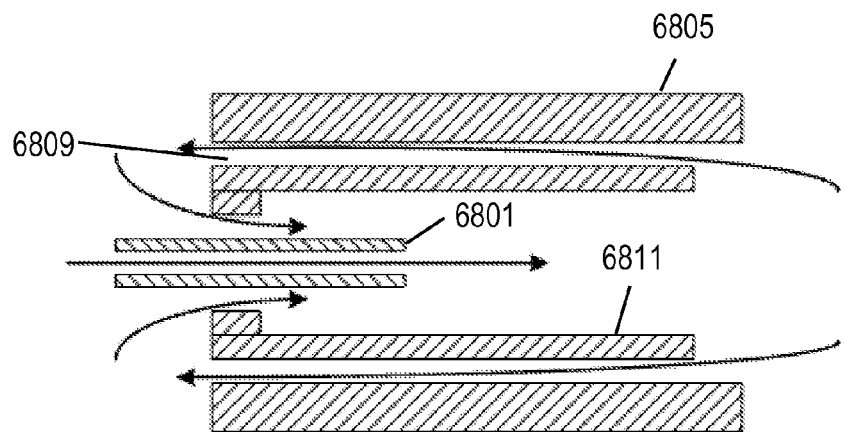
FIG. 64C shows an alternative secondary gas flow aperture with an inner tube, in which the gas pathway is co-axial to the primary gas flow pathway.

FIG. 64C shows an alternative secondary gas flow aperture 6809 with an inner tube 6811, in which the gas pathway is co-axial to the primary gas flow pathway. This embodiment is especially useful when the invention is used to delivery gas continuously to the patient, or when gas is being delivered during exhalation for example to create PEEP. In these situations, gas can be flowing in the manifold or outer tube in both directions simultaneously, in the inspired direction and the exhaled direction, which increases the sound generated by the jet pump due to mixing. The secondary gas path may allow a significant amount of gas moving in the exhaled direction to travel through the secondary path which can reduce the noise considerably, for example from 30 db at 1 meter to 15 db at 1 meter. The secondary gas flow path can be a slit, a pattern of holes, or a channel. In addition to the embodiments shown, a low profile muffler can shroud portions of the manifold, as described earlier.

Figure 64D:
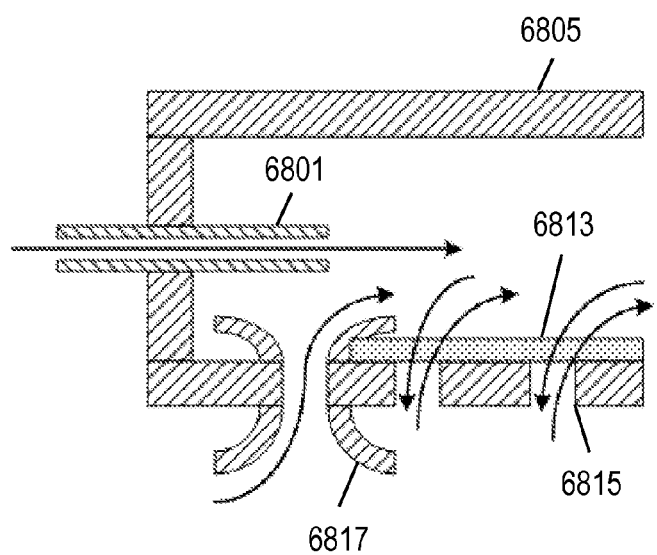
FIG. 64D shows an embodiment a filter at an aperture, and optionally inside the outer tube or manifold.

FIG. 64D shows an embodiment with a filter 6813 at an aperture 6815, and optionally inside the outer tube 6805 or manifold. A portion of the exhaled airflow may flow through the filter 6813 that may collect some of the moisture in the exhaled air. The collected moisture may be entrained with the jet when the jet nozzle is delivering air in the inspired direction. The configuration, therefore, may help recycle the humidity for the patient to help ensure that the patient's airway remains moist. The filter 6813 can also be used as a sound reducing material, in which case the filter 6813 may cover the entire aperture, and may be less resistive than a humidity collecting filter. In addition, the filter 6813 can be used as a particulate filter, to prevent entrainment from introducing environmental dust and particulate into the manifold and airways of the user. A fluted entrance 6817 of the breathing/entrainment aperture may also be used, which may further reduce the noise generated by the nasal interface. The flute dimensions may help reduce the sound generated by entrained air by creating a low friction boundary layer. In addition, a surface at the aperture may be dimpled to further create a low friction boundary layer to reduce sound.

FIG. 65 describes an alternative embodiment of the invention in which a nozzle 6901 may be angulated with respect to the axial centerline of an outer tube 6903 or manifold. In this case, the entrainment/breathing aperture 6905 may be co-axial with the jet nozzle 6901, rather than in parallel; however, it could also be in parallel or both. Angulating the nozzle 6901 into the wall of the outer tube or manifold may reduce the sound generated by the jet pump at a greater ratio than the loss of entrainment performance. For example, a 30-degree angle may reduce downstream pressure creation by approximately 10-25%, but may reduce sound generated by the system by approximately 25-75%, which is a preferred tradeoff in many situations.

Figure 66:
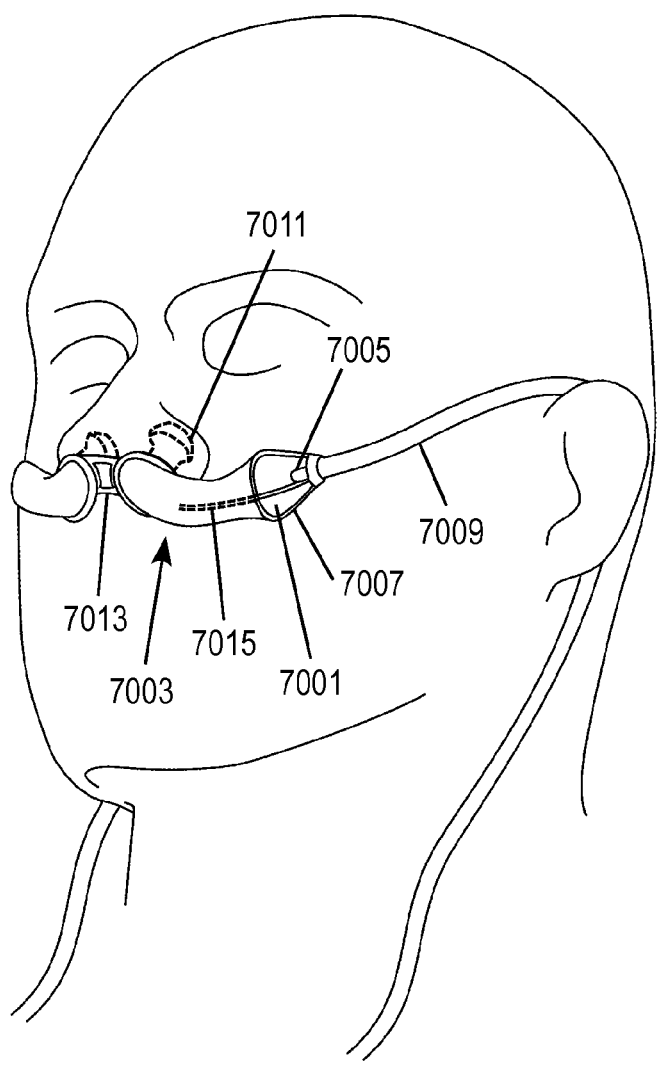
FIG. 66 describes an embodiment in which a manifold entrainment/breathing aperture may be located at a lateral end of a manifold.
Figure 67:
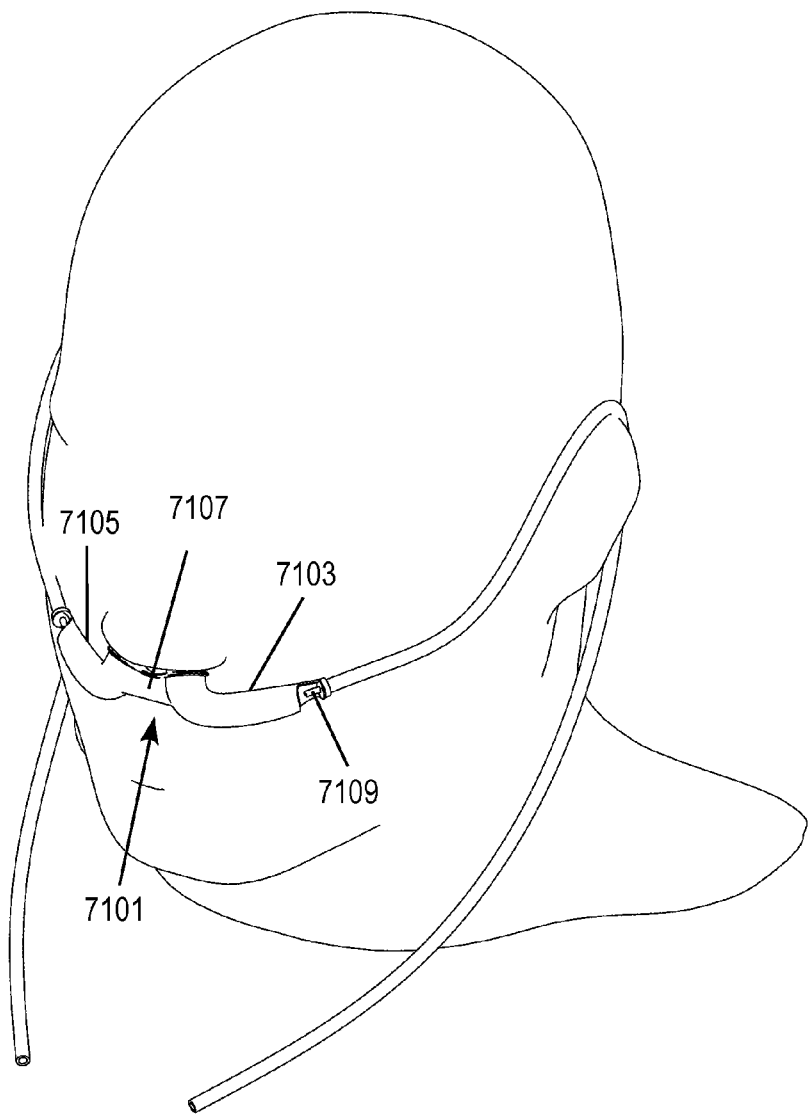
FIG. 67 shows an embodiment in which a manifold may include a left curved cannula and a right curved cannula.
Figure 68:
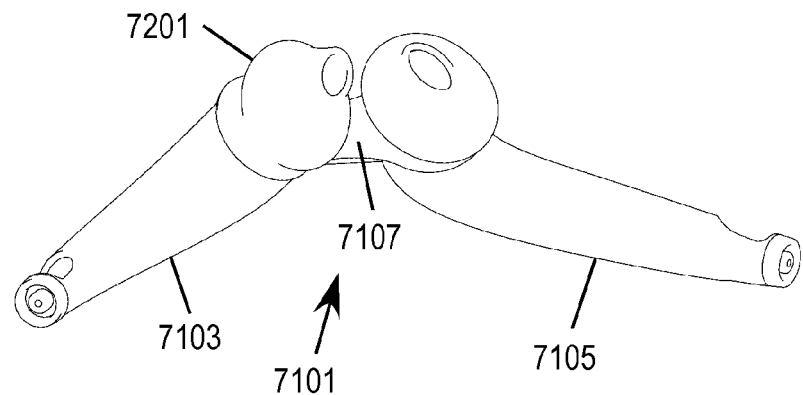
FIG. 68 shows a posterior view of the manifold of FIG. 67 with nasal pillows.

FIGS. 66-68 describe versions of the embodiment described in FIG. 59.

FIG. 66 describes an embodiment in which a manifold entrainment/breathing aperture 7001 may be located at a lateral end of a manifold 7003. A jet nozzle 7005 may be located lateral to the aperture 7001. The jet nozzle 7005 may or may not be located within an outer tube 7007. The jet nozzle 7005 may receive ventilation gas from a ventilator via a gas delivery circuit 7009. The manifold 7003 may interface with the patient's nostrils using soft nasal pillows 7011. The manifold 7003 may be split into left and right sides connected by a rigid, semi-rigid or flexible member 7013. One or more sensing lumens 7015 may measure the patient's breathing. The one or more sensing lumens 7015 may be inside the nasal pillows to improve signals.

Figure 69:
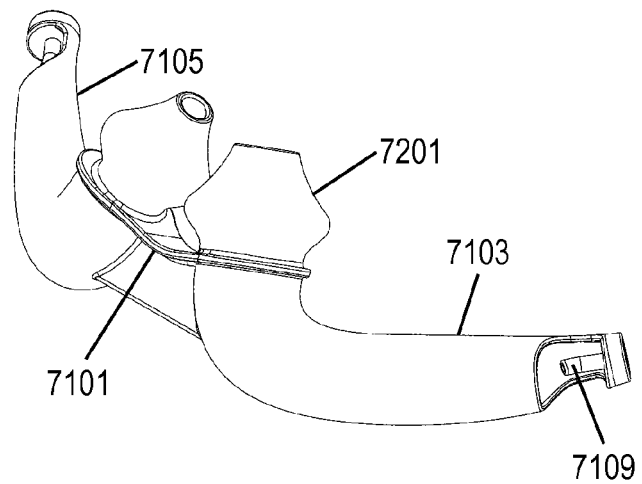
FIG. 69 shows an anterior view of the manifold of FIG. 67.

FIG. 67 shows an embodiment in which a manifold 7101 may include a left curved cannula 7103 and a right curved cannula 7105. The cannula 7103, 7105 can be connected to each other with an adjustable inter-connector 7107, which can allow for spacing adjustment between the two cannulae and allow pivoting or swiveling of the distal ends of the cannula to help align the cushions at the distal end of the cannula with the user's nostril. Nozzles 7109 may be open to ambient. FIG. 68 shows a posterior view of the manifold 7101 of FIG. 67 with nasal pillows 7201. FIG. 69 shows an anterior view of the manifold 7101 of FIG. 67.

Figure 70:
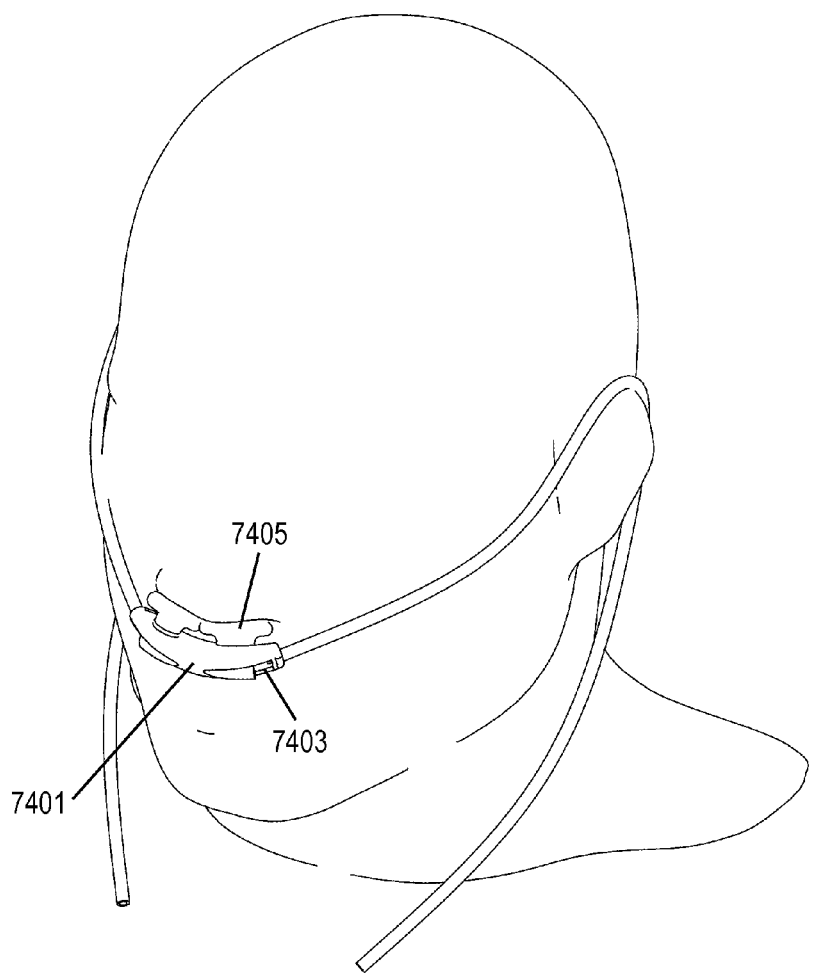
FIG. 70 shows an embodiment in which a manifold may be shorter in left to right length to reduce the size and profile of the nasal interface.
Figure 71:
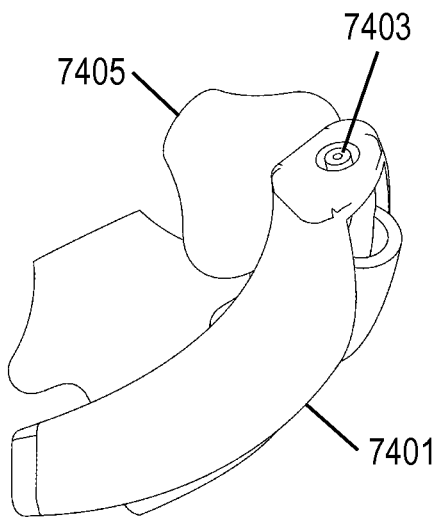
FIG. 71 shows a posterior view of the manifold of FIG. 70.
Figure 72:
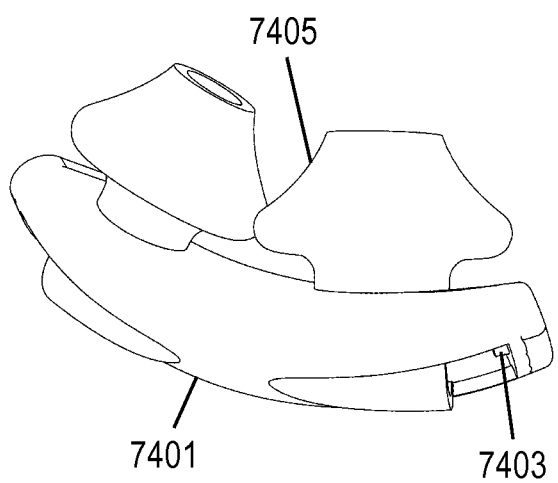
FIG. 72 shows an anterior view of the manifold of FIG. 70.

FIG. 70 shows an embodiment in which a manifold 7401 may be shorter in left to right length to reduce the size and profile of the nasal interface. Nozzles 7403 are positioned laterally to the nose and nasal pillows 7405 engage the nostrils. FIG. 71 shows a posterior view of the manifold 7401 of FIG. 70. FIG. 72 shows an anterior view of the manifold 7401 of FIG. 72.

Figure 73:
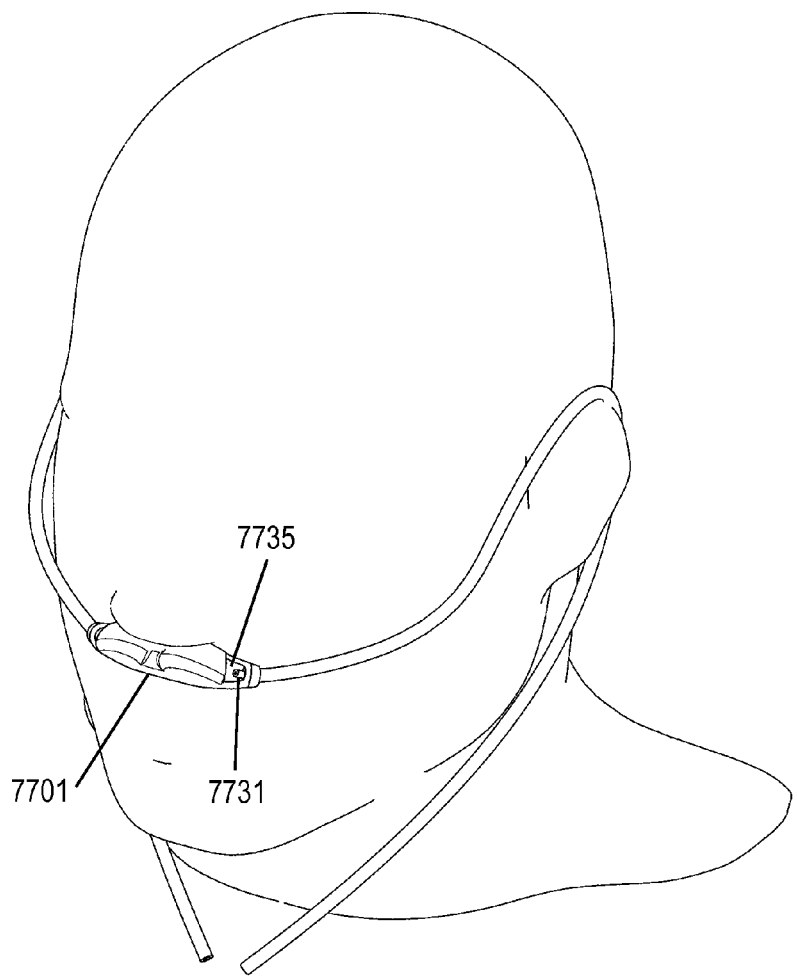
FIG. 73 shows an embodiment in which a manifold has at least one flattened section on a posterior side of the manifold so that the manifold lays flat against the surface of the skin to help stabilize the manifold in place on the user.

FIG. 73 shows an embodiment in which a manifold 7701 has at least one flattened section 7703 on a posterior side of the manifold 7701 so that the manifold 7701 lays flat against the surface of the skin to help stabilize the manifold 7701 in place on the user. In addition, gas flow openings 7705 at a superior side of the manifold 7701 may not include tubular extensions. In this embodiment, the gas flow openings 7705 may communicate with or impinge directly on the nostrils.

Figure 74:
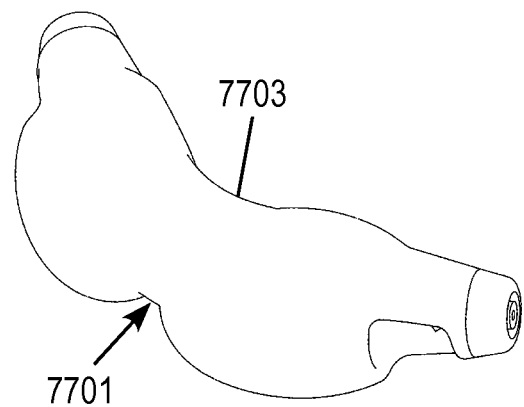
FIG. 74 shows a posterior view of the manifold of FIG. 73.
Figure 75:
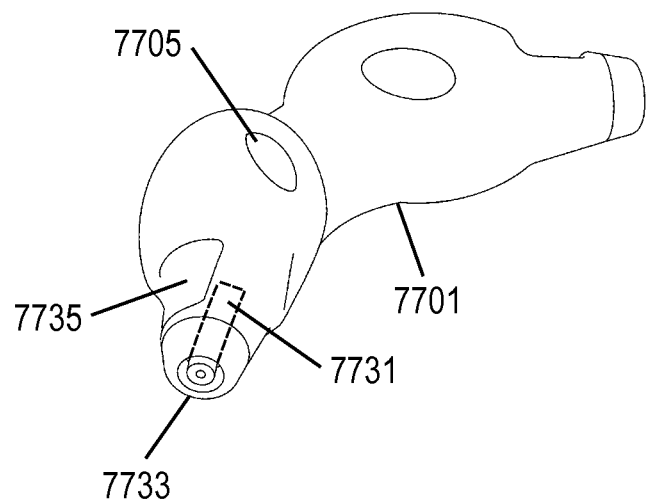
FIG. 75 shows an anterior view of the manifold of FIG. 73.

FIG. 74 shows a posterior view of the manifold 7701 of FIG. 73. FIG. 75 shows an anterior view of the manifold 7701 of FIG. 73 with a jet nozzle 7731, gas delivery tube attachment 7733 and breathing aperture 7735.

Figure 76:
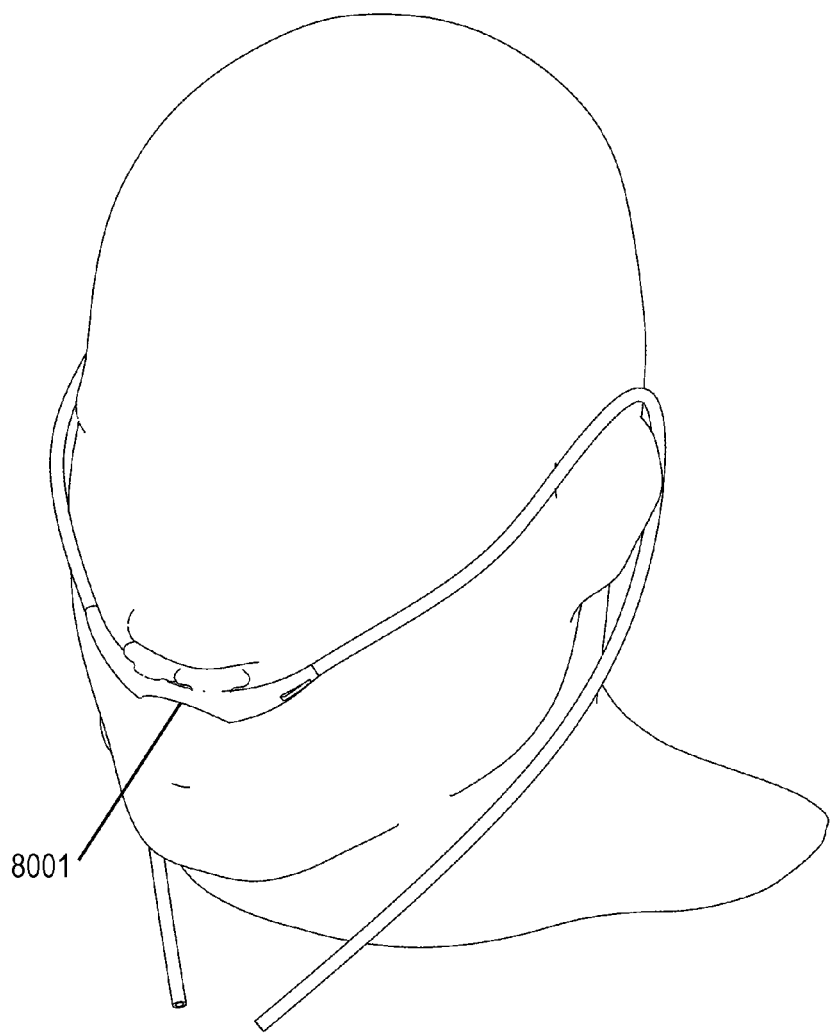
FIG. 76 shows an embodiment in which a manifold is narrower in the top to bottom dimension to space the manifold away from the mouth as much as possible.
Figure 77:
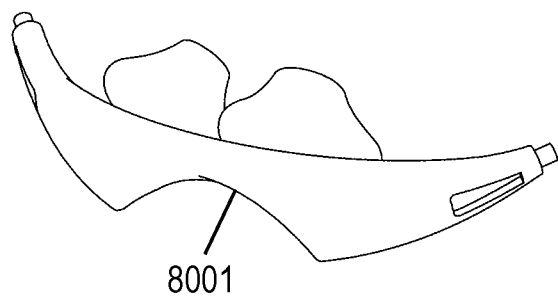
FIG. 77 shows a posterior view of the manifold of FIG. 76.
Figure 78:
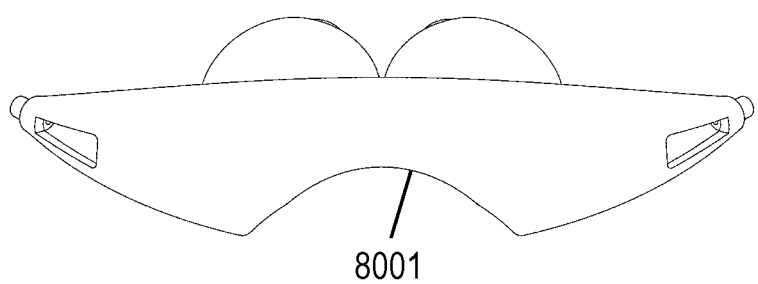
FIG. 78 shows an anterior view of the manifold of FIG. 76.

FIG. 76 shows an embodiment in which a manifold 8001 is narrower in the top to bottom dimension to space the manifold 8001 away from the mouth as much as possible. FIG. 77 shows a posterior view of the manifold 8001 of FIG. 76. FIG. 78 shows an anterior view of the manifold 8001 of FIG. 76.

Figure 79:
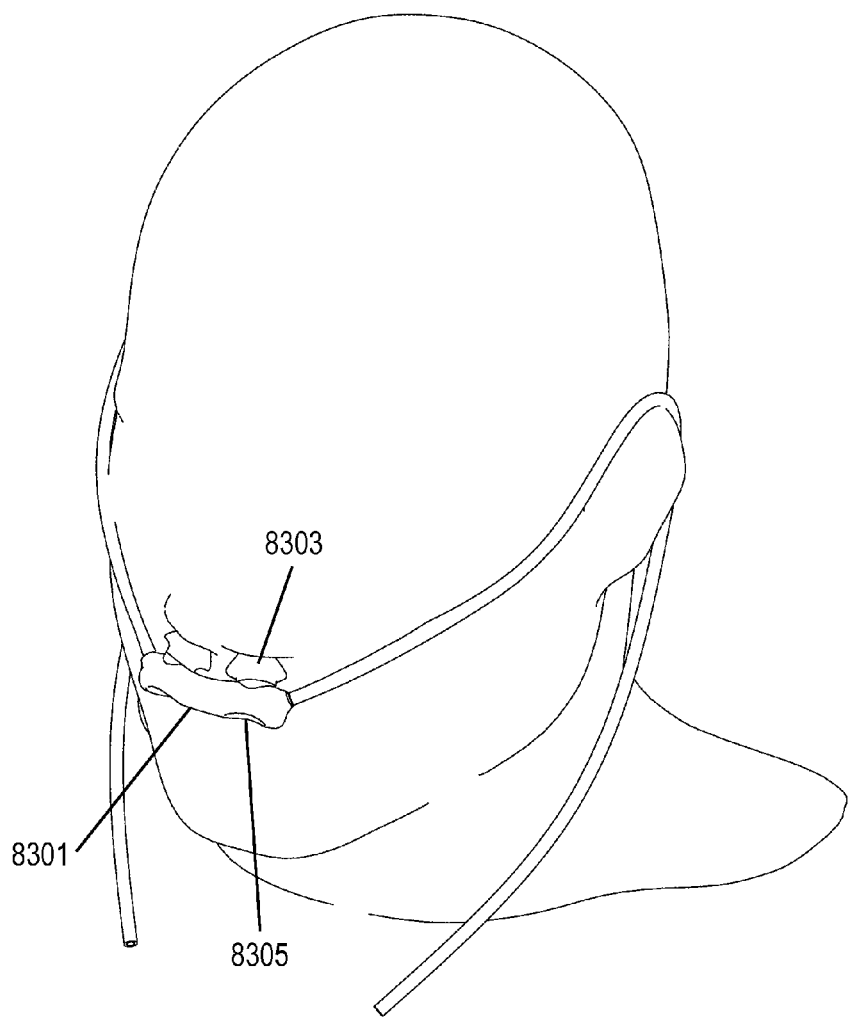
FIG. 79 shows an embodiment including a manifold, tubular extensions on the superior side of the manifold to impinge with the nostrils, and entrainment/breathing ports on the inferior side of the manifold in alignment with the nostrils and tubular extensions.
Figure 80:
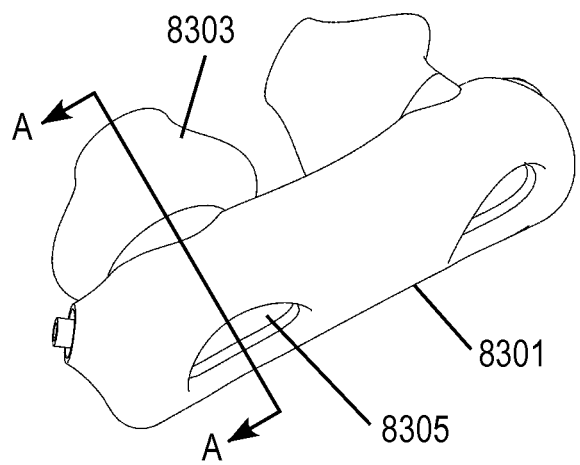
FIG. 80 shows an anterior view of the manifold of FIG. 79.
Figure 81:
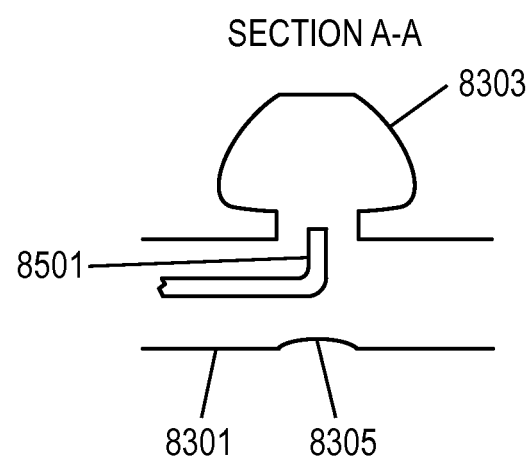
FIG. 81 shows a cross section through line A-A of the manifold of FIG. 80.

FIG. 79 shows an embodiment including a manifold 8301, tubular extensions 8303 on the superior side of the manifold 8301 to impinge with the nostrils, and entrainment/breathing ports 8305 on the inferior side of the manifold 8301 in alignment with the nostrils and tubular extensions. The entrainment/breathing ports 8305 can also be located on the anterior side, or anterior-inferior side of the manifold 8301. Gas delivery nozzles 8501, as shown in FIG. 81, may be positioned somewhere below the tubular extensions inside the manifold. FIG. 80 shows an anterior view of the manifold 8301 of FIG. 79. FIG. 81 shows a cross section through line A-A of the manifold 8301 of FIG. 80.

FIGS. 82-99 describe another embodiment of the invention in which gas from gas delivery jet nozzles is directed to the nostrils through an outer tube, such that the combination of the nozzle and outer tube define a jet pump configuration.

Figure 82:
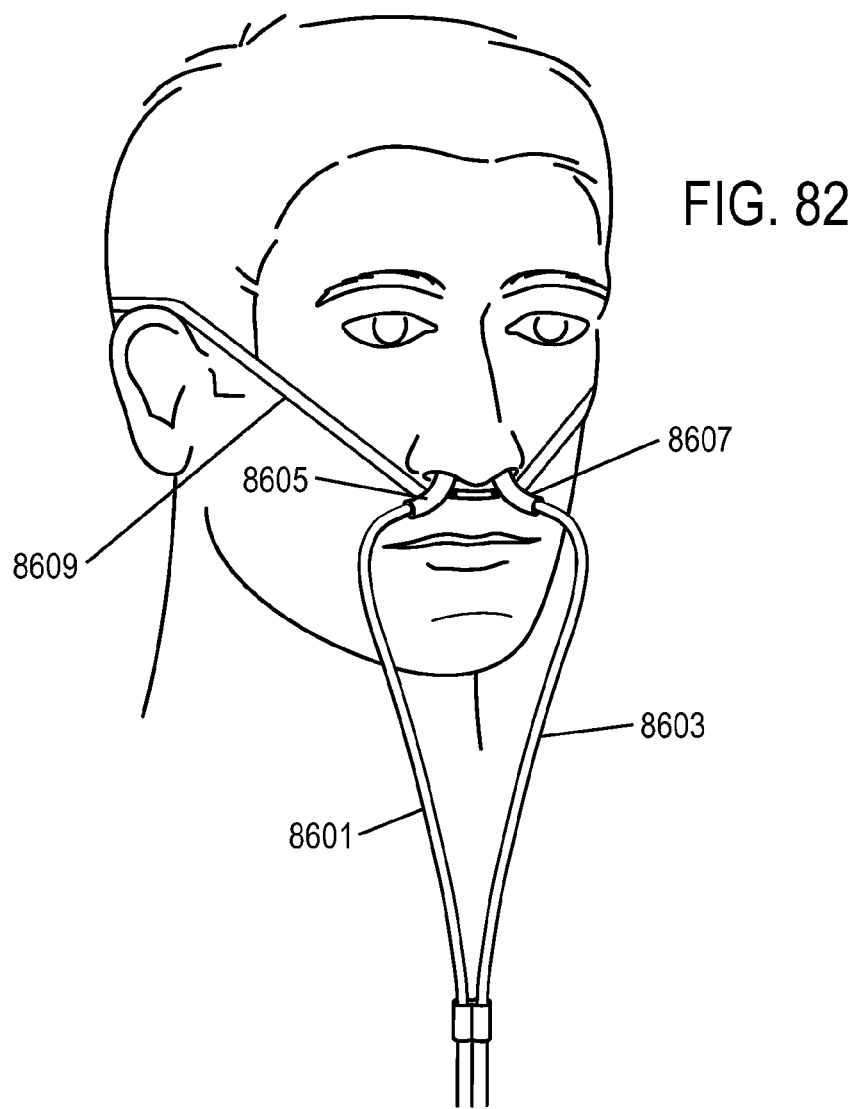
FIG. 82 shows an embodiment in which two tubes impinge with the nostrils at their distal ends and curve laterally and inferiorly away from the nostrils.

FIG. 82 shows an embodiment in which two tubes 8601, 8603 impinge with the nostrils at their distal ends 8605, 8607 and curve laterally and inferiorly away from the nostrils. Gas delivery nozzles may be positioned so that the nozzle is at, near or inside the proximal opening in the tubes. The nozzles can enter the tubes at the proximal opening, as shown, or can enter the tubes through the lateral wall of the tube. The gas delivery nozzles may be attached to a small cannula which extends to the ventilator. The inner diameter of the tubes and the annular space between the nozzles and tubes may be dimensioned to match the airflow resistance of the nose, or to increase the resistance a maximum of 10%. This may be done by widening the area of the tube where the nozzle is located, and by minimizing the length of sections of the tube that are less than the effective inner diameter of the nasal passage. The cannula can also include a lumen for pressure sensing within the tubes, so that the nasal breathing pressure can be measured, and this sensing lumen can extend closer to the nostril entrance compared to the gas delivery nozzle tips. The two tubes 8601, 8603 may be curved to direct the proximal opening and the gas delivery nozzle to the side of the nose away from the center of the mouth. Therefore, the user may be able to use their mouth for normal functions while the therapy is being used because the airflow going in and out of the tubes is not in the way of the mouth. The tubes may typically be joined together with an interconnecting member that can allow for spacing adjustment of the tubes or angular adjustment of the tubes. The tubes and or the interconnecting member may have a cushion attached to the posterior side to space and align the tubes correctly with respect to the nostrils as will be explained subsequently. The tube curvature may be shaped to optimize the convenience to the user and to stabilize the apparatus to the face of the user to avoid inadvertent shifting. The apparatus may be secured to the face by straps 8609 that are connected to either the interconnecting member or the tubes. Alternatively, the cannula attached to the gas delivery nozzle can be used to secure the apparatus to the face. The proximal opening of the tubes may alternatively may include a muffler to reduce dampen sound, and the nozzle-tube relationships can include geometries, materials and surface characteristics to reduce sound generation as described previously.

The outer tubes 8601, 8603 may be sized to contact the inner wall of the nostril. The outer tubes can be radially expanding to allow it mate with a range of nasal dimensions, or can be tapered to mate with a range of dimensions, or can be of a fixed dimension. The outer tube can also be provided in multiple sizes for it to be compatible with a range of anatomical sizes. The outer tube can optionally be surrounded with a compliant compressible material that compresses when inserted into the nostril so that the outer tube is held in place in the nostril with a light amount of interference tension, for example less than 0.5 lbs of tension.

In the example shown in FIG. 82, the outer tube is shown curved to direct the exiting gas in an anatomically correct pathway. For simplicity, the figures throughout may be shown with the jet nozzle and outer tube with straight centerlines, or in a view in which the centerline is straight, however, it should be noted that a straight depiction is exemplary only, and that the jet nozzles and outer tube can be straight, angled or curved, or combinations thereof, to optimize fit and gas flow dynamics. Additional details of the jet pump features, shapes and dimensions are described in subsequent descriptions.

Figure 85:
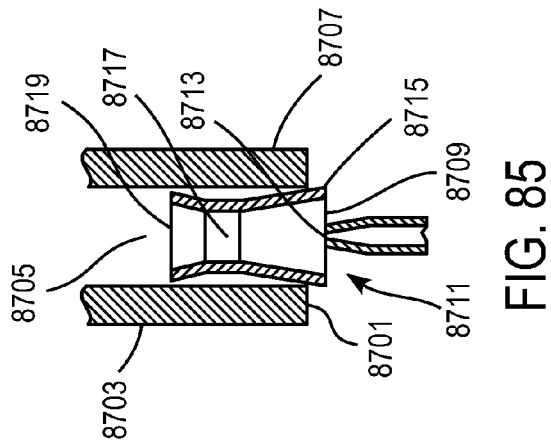
FIG. 85 shows that the tip of the nozzle may be substantially flush with the proximal end of the outer tube.
Figure 84:
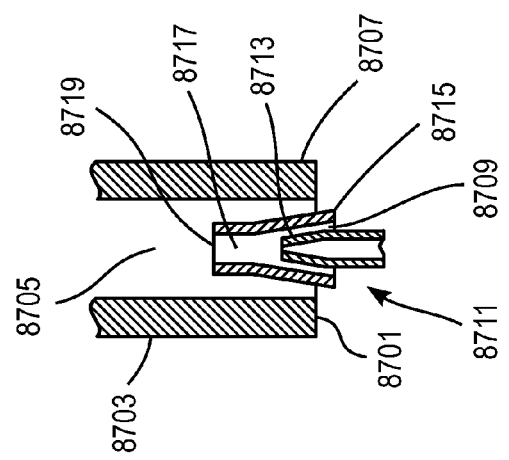
FIG. 84 shows an entrainment chamber that may form between the nozzle and the outer tube when the nozzle is partially inserted into the outer tube.
Figure 83:
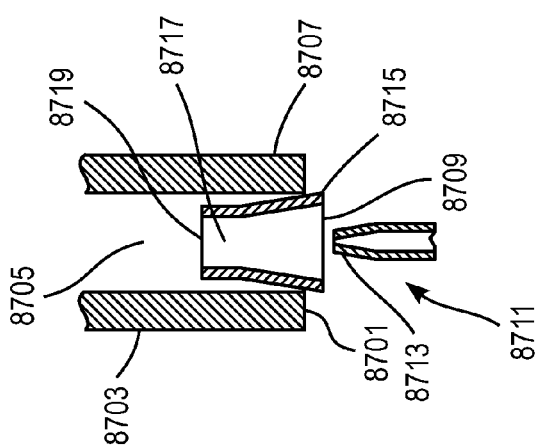
FIG. 83 shows a jet pump inlet and entrainment zone that may be formed in a nostril rim and opening, nostril wall, nostril foramen, and/or nasal septum.

FIGS. 83-85 show various embodiments of a schematic cross section through the nasal interface described in FIG. 82, indicating the nozzle proximal to, distal to, or coplanar with the proximal opening of the tube, respectively. For simplicity the cross sections are shown straight, however, the structure is preferably curved as shown in the isometric view in FIG. 82. In addition, the outer tubes can be curved or angled from front to back to match the angle of the nostril.

FIG. 83 shows a jet pump inlet and entrainment zone 8709 that may be formed in a nostril rim and opening 8701, nostril wall 8703, nostril foramen 8705, and/or nasal septum 8707. In FIG. 83, a nasal interface 8711 may include a jet pump nozzle 8713 outside an outer tube 8715. The outer tube 8715 may have a jet pump throat 8717 and a jet pump diffuser 8719.

In FIG. 84, an entrainment chamber 8709 may form between the nozzle 8713 and the outer tube 8715 when the nozzle 8713 is partially inserted into the outer tube 8715. As shown in FIG. 84, the outer tube 8715 may be dimensioned such that it is smaller than the nostril, enabling the patient to breathe spontaneous air around the outside of the outer tube, as well as through the inside of the tube. In the example shown, the jet nozzle distal tip may be positioned inside the outer tube, in the transition zone region where the outer tube transitions in diameter from the inlet to the throat. The nozzle tip location can be located anywhere within this transition region, including coplanar with the inlet, and coplanar with the start of the throat area, and alternatively, the nozzle tip can be proximal to the inlet.

In FIG. 85, the tip of the nozzle 8713 may be substantially flush with the proximal end of the outer tube 8715. As seen in the cross sectional schematics in FIGS. 83-85, the outer tube 8715 may include a jet pump inlet and throat. The patient may be permitted to breathe room air spontaneously through the outer tube. The entrainment area 8709 of the jet pump may be the area proximal to the outer tube proximal end. The outer tube can be whole or partly inserted into the nostrils. The outer tube may also serve to align the jet nozzle and overall jet pump relative to the nostrils, and may also serve to position and secure the interface to the patient's nose and face. As described in FIG. 85 the outer tube may include a widening at its distal end to serve the function of a jet pump diffuser. The diffuser may help create a laminar gas flow exit profile, and improves the efficiency and overall power of the jet pump. In the example shown, the nozzle distal tip may be coplanar with the outer tube inlet, however, the distal tip can be placed in other locations, including proximal to the inlet, and recessed inside the outer tube.

FIGS. 86-93 show another embodiment of the invention.

FIG. 86 shows an overall view of a nasal ventilation interface 9000. The interface 9000 may include a ventilator connector 9001, a gas delivery circuit portion 9003, a cannula portion 9005, a distal end portion 9007 designed to be placed at, in or proximal to the entrance to the nostrils, a cannula jet nozzle 9009 at or near the distal tip of the overall assembly, optionally an outer tube 9011 concentric about the distal tips of the cannula jet nozzle as shown, or alternatively a manifold, an attachment and positioning pad 9015 at the distal end, an adjustment member 9013 at the distal end to adjust the position and angulation of the distal end cannula nozzles 9009, and to adjust the location relative to the nostril opening, and a spontaneous respiration sensor 9017.

FIG. 88 describe a more detailed side view of the distal end of the nasal interface 9000 shown in FIG. 86. The cannula jet nozzle 9009 may or may not be located within or concentric to an outer tube 9011 as previously described. Pressure or flow sensing ports 9201 may be located on the distal end 9007 of the cannula 9005 near the nozzle 9009, and an airflow or pressure sensor 9017 may be located on the outer tube 9011, either on the inner or outer wall of the outer tube. The flow sensing ports 9201 may be in communication with one or more sensing lumens 9203. A diffuser 9205 may be located at a distal end of the outer tube 9011. The cannula 9005 and/or outer tube 9011 may be attached to the attachment and positioning pad 9015 and the attachment and positioning pad 9015 may include a nostril locating tab extension 9019 that extends superiorly and which is used to position the distal end of the assembly properly below and optionally slightly inside the nose. A head strap 9021 may be provided to secure the overall assembly to the head and face, and is typically connected to the attachment and positioning pad, although it can be attached to the cannula or outer tubes as well.

FIG. 87 describes an exemplary cross section of the cannula of the nasal interface at line A-A indicated in FIGS. 86 and 88. Optional features are shown, such as a second sensing lumen 9101 (in the case two sensing lumens are used to derive airflow, or in the case that two sensing lumens are used to correct for the effects of the Venturi or as a redundancy), a humidity delivery lumen 9103, a drug delivery channel 9105, an external sensing tube 9107 positioned on the outside of the cannula in the case that breath sensing is performed with a separate tube, and a transmission wire 9109 for an additional breath sensing element such as a piezoelectric, a thermal sensor, or other types of sensing elements. A ventilation gas delivery lumen 9111 may be within the outer tube 9011.

Figure 89:
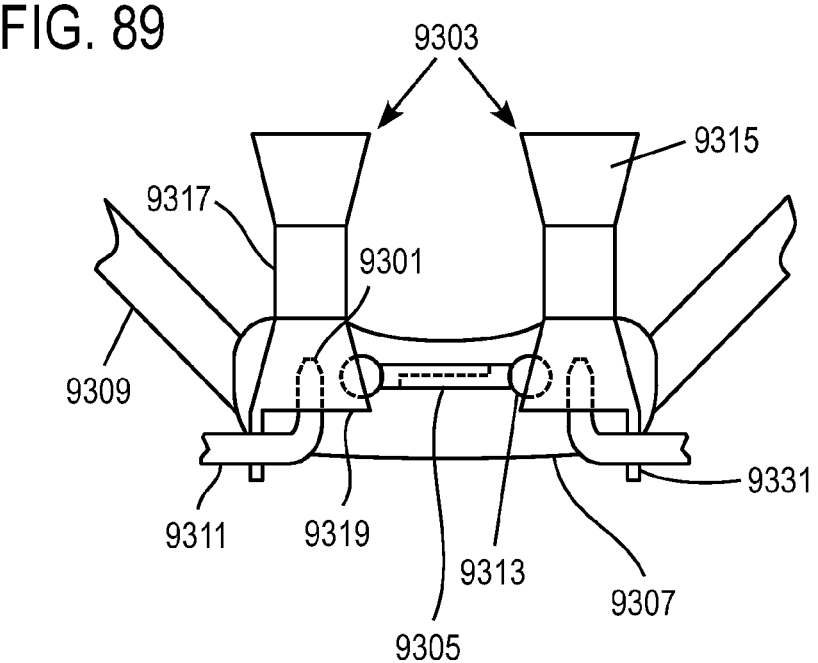
FIG. 89 shows a front view of an alternate embodiment of a distal end of a nasal interface.

FIG. 89 shows a front view of an alternate embodiment of a distal end of a nasal interface. The distal ends of the cannula or nozzles 9301 may be connected to outer concentric tubes 9303 with a slot or bracket to align the nozzles 9301 with the outer concentric tubes 9303. The nozzle distal tips 9301 are shown concentrically inside the outer tubes, however, could be coplanar with the outer tubes entrance or proximal to the outer tubes. An interconnecting length adjustment coupler 9305 may attach the two outer tubes together. The coupler 9305 can be adjusted to set the spacing between the outer tubes to the desired dimension, to fit the anatomy of the individual user. A connecting pad 9307 may be attached to the cannula-outer tube-coupler assembly. The attachment between the coupler and the outer tubes can include a swivel connection 9313 to rotate or adjust the angle of the outer tube in at least one plane, so that the outer tubes can be aligned properly with the individual's anatomy, to optimize fit, comfort and function. The angle of the outer tubes can also be adjusted to lightly pinch the nasal septum to help secure the assembly in place in the user's nose. A head strap or head fastener 9309 may fasten the assembly's distal end to the user's head and face. The strap or fastener 9309 can be a fabric, plastic or metal material, or combinations thereof. In this as well as the other embodiments, a cannula 9311 can optionally be comprised of a rigid or semi-rigid tubular material, which can also serve the role of the head fastener. The rigid or semi-rigid material can be attached to the outer tubes such that the nozzle is positioned relative to the outer tubes as desired. The semi-rigid tubular material can be for example a rigid plastic such as nylon, or a metal alloy which extends from the ventilation gas delivery hose to the distal tip of the nozzle. Portions of the cannula can be backed with a soft material such as a fabric or foam to make it comfortable against the skin. A cannula connection slot 9331 may couple the cannula 9311 to the outer tubes 9303 or connecting pad 9307. The outer tubes 9303 may include a jet pump diffuser 9315, a jet pump throat 9317 and a jet pump inlet chamber 9319.

Figure 90:
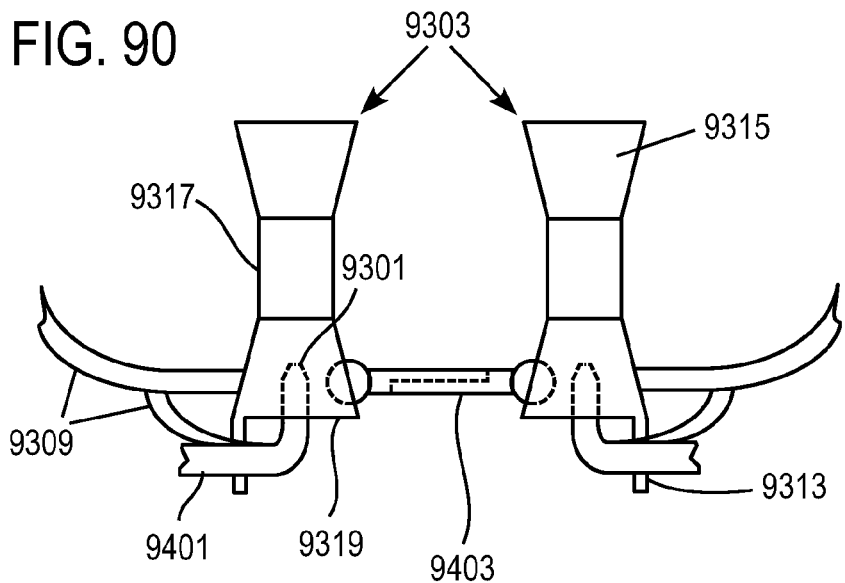
FIG. 90 shows a front view of an alternate embodiment of the distal end of the nasal interface.

FIG. 90 shows a front view of an alternate embodiment of the distal end of the nasal interface. A cannula 9401 may be connected to outer concentric tubes 9303 with a slot or bracket, and nozzles 9301 may be included at the distal tip of the cannula 9401. The nozzle distal tips 9301 are shown concentrically inside the outer tubes 9303, however, could be coplanar with the outer tubes entrance or proximal to the outer tubes. An interconnecting length adjustment coupler 9403 may attach the two outer tubes together. The coupler 9403 can be adjusted to set the spacing between the outer tubes to the desired dimension, to fit the anatomy of the individual user. A head fastener 9309, which can optionally be an extension of the coupler, attaches to the outer tubes and may be used to attach the assembly to the head and face. The head fastener 9309 also optionally includes a portion that connects to the cannula 9401.

Figure 91:
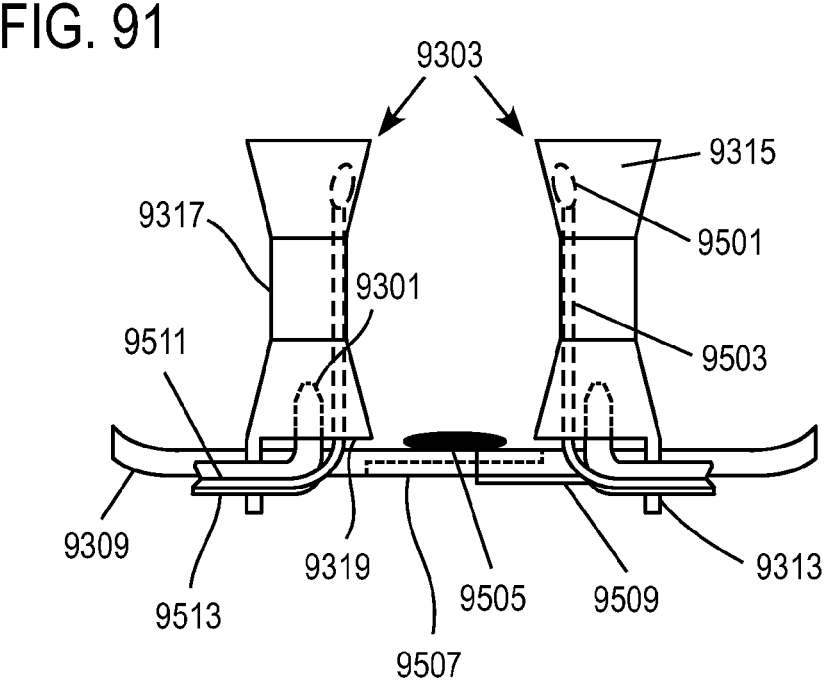
FIG. 91 describes a front view of an alternate embodiment of the distal end of the nasal interface, similar to the embodiments described in FIGS. 89 and 90.

FIG. 91 describes a front view of an alternate embodiment of the distal end of the nasal interface, similar to the embodiments described in FIGS. 89 and 90. Breath sensing ports 9501 and lumens 9503 may be included in the outer concentric tubes 9303. The lumens 9503 can be integral to the construction of the outer tubes, or can be coupled to the outer tubes, or can be a separate tube. The sensing lumens 9503 may be used to measure the pressure or flow signal generated by the patient's spontaneous breathing. Additionally or optionally, a sensor 9505 can be placed somewhere outside of the outer tubes, for example on a coupler 9507 as in the example shown. The sensor can be a thermal sensor, or some other type of sensing element as described subsequently. In the example shown the sensor would be positioned outside of and inferior to the nostrils, however, the sensor could be located inside the nostril or directly at the entrance to the nostril. Alternatively, one nostril could be used for sensing while the other nostril is used for gas delivery. Sensors may communicate reading through a sensor wire 9509 and/or a sensor tube 9511. A cannula 9513 may deliver ventilation gas.

Figure 92:
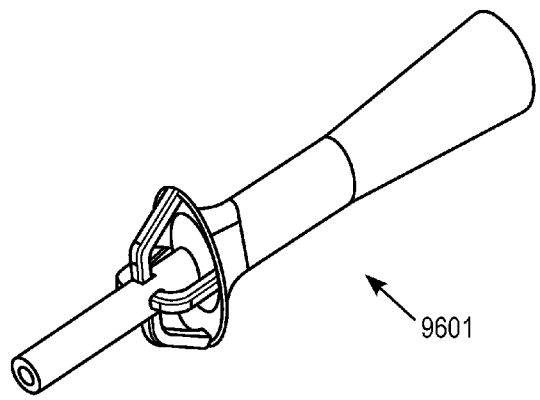
FIGS. 92 and 93 describe an alternate embodiment of a jet pump portion of the distal end of the nasal interface.
Figure 93:
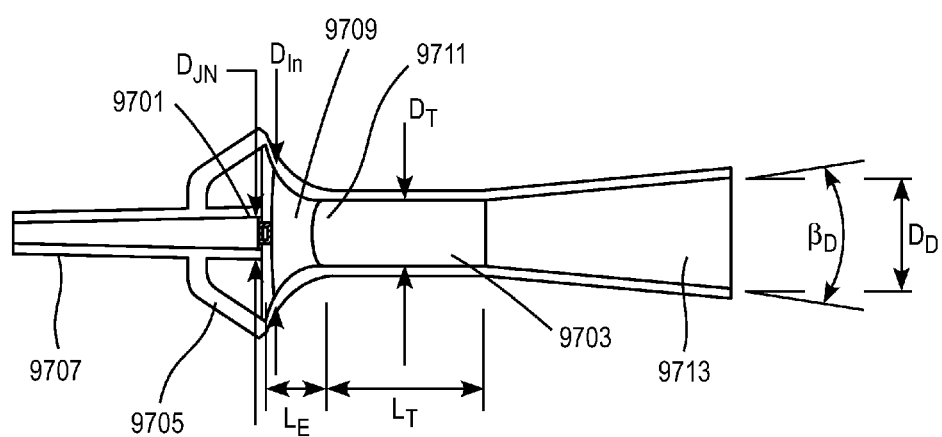

FIGS. 92 and 93 describe an alternate embodiment of a jet pump 9601 portion of the distal end of the nasal interface. In FIG. 92, a full isometric view of the jet pump is shown and FIG. 93 describes the various sections of the jet pump. In this embodiment a jet nozzle 9701 can be physically coupled to an outer tube or throat 9703 by a connection and alignment bracket 9705 as shown, or by a direct connection, or by another component such as an attachment pad as previously described. A cannula 9707 may lead to an entrance 9709. The entrance 9709 may lead to a throat inlet 9711, the throat 9703, and a diffuser 9713. The jet nozzle tip internal diameter may have a variety of geometries. For example, it may have a restricted diameter to increase gas flow linear velocity at the very tip, or can include a uniform inner diameter for a distance of at least 3-5 times the internal diameter, or can be flared. The assembly of the nozzle and outer tube or throat can be fastened to the nose and face by a variety of methods; for example, the throat can be inserted into the nose with an interference fit or with a frictional fit, and the nozzle is positioned and aligned by the position of the throat. Alternatively, the throat can be held in place by the attachment pad as previously described, or can be held in place by a face or head strap, for example a strap that attaches to the pad or throat, and extends to the back and/or top of the head. Or, alternatively the cannula leading to the nozzle can be held in place and fastened to the user by a head strap fastened to either the cannula or attachment pad with a strap or fastener that extends to the back and/or top of the head. Other attachment configurations described elsewhere can also be used. Dimensional values of the jet pump features may vary depending on the patient size, the selected ventilator flow and pressure output, the patient type, the disease, and the level of the therapy desired.

Figures 94, 95:
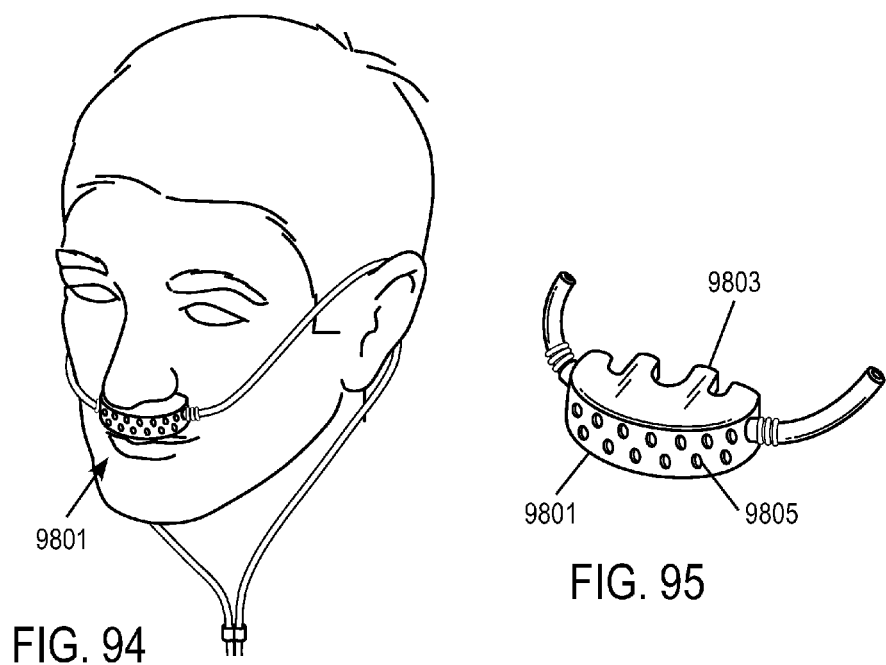
FIGS. 94 and 95 show an alternative embodiment in which the gas delivery nozzles are provided in a manifold that includes compliant nostril inserts.

FIGS. 94 and 95 show an alternative embodiment in which the gas delivery nozzles are provided in a manifold 9801 that includes compliant nostril inserts 9803. The manifold 9801 may include multiple entrainment/breathing apertures 9805. A gas delivery nozzle can be positioned to direct the gas directly through the nostril inserts into the nostril, or can be positioned lateral to the nostril inserts in which case the manifold that may include a curved gas flow path curving from the gas delivery nozzle to the nostril inserts.

Figures 96, 97:
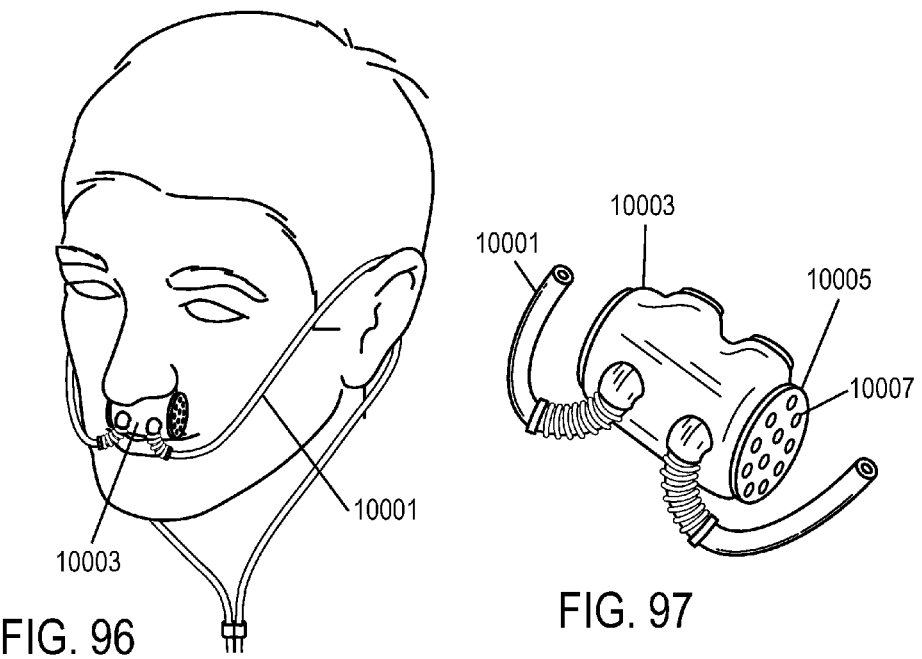
FIGS. 96 and 97 show another embodiment in which the gas delivery tubes may attach to a manifold in a mid-section of the manifold, to generally align the gas delivery nozzles with the nostril inserts, rather than the gas delivery tubes attaching to the sides of the manifold.

FIGS. 96 and 97 show another embodiment in which the gas delivery tubes 10001 may attach to a manifold 10003 in a mid-section of the manifold 10003, to generally align the gas delivery nozzles with the nostril inserts, rather than the gas delivery tubes attaching to the sides of the manifold. Sides 10005 of the manifold 10003 may include openings 10007 to ambient air.

Figure 98:
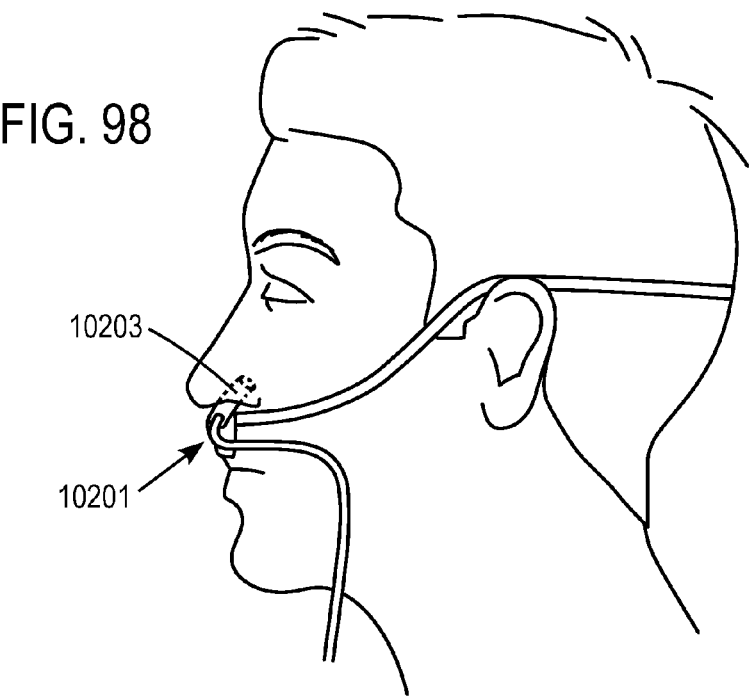
FIGS. 98 and 99 show an embodiment where a distal tip of the interface includes an inner nozzle and concentric outer tube jet pump configuration.
Figure 99:
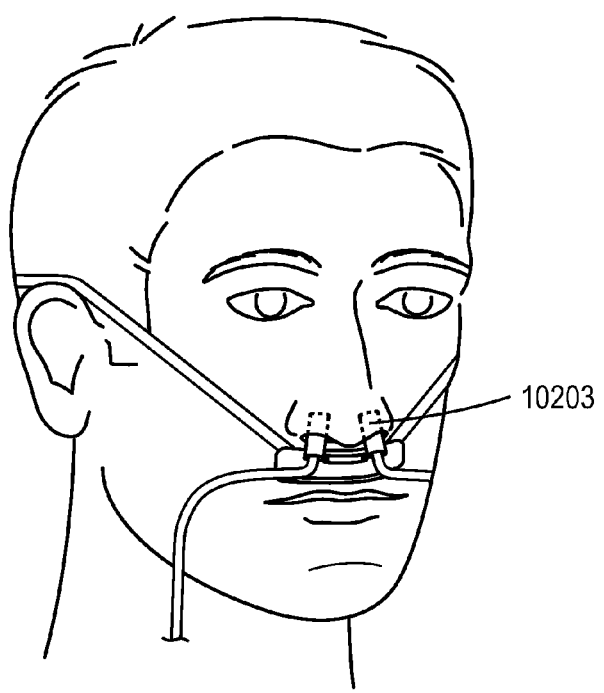

FIGS. 98 and 99 show an embodiment where a distal tip of the interface includes an inner nozzle and concentric outer tube jet pump configuration. FIG. 98 shows a side view of this embodiment in which the nasal interface 10201 comprises concentric inner and outer tubes 10203, in which case the outer tube may be sized to contact the inner wall of the nostril. The outer tube can be radially expanding to allow it to mate with a range of nasal dimensions, or can be tapered to mate with a range of dimensions, or can be of a fixed dimension. In FIG. 99, the outer tube 10203 is shown curved to direct the exiting gas in an anatomically correct pathway. Other configurations are possible.

The outer tube can also be provided in multiple sizes for it to be compatible with a range of anatomical sizes. The outer tube can optionally be surrounded with a compliant compressible material that compresses when inserted into the nostril so that the outer tube is held in place in the nostril with a light amount of interference tension, for example, less than 0.5 lbs of tension.

Figure 100:
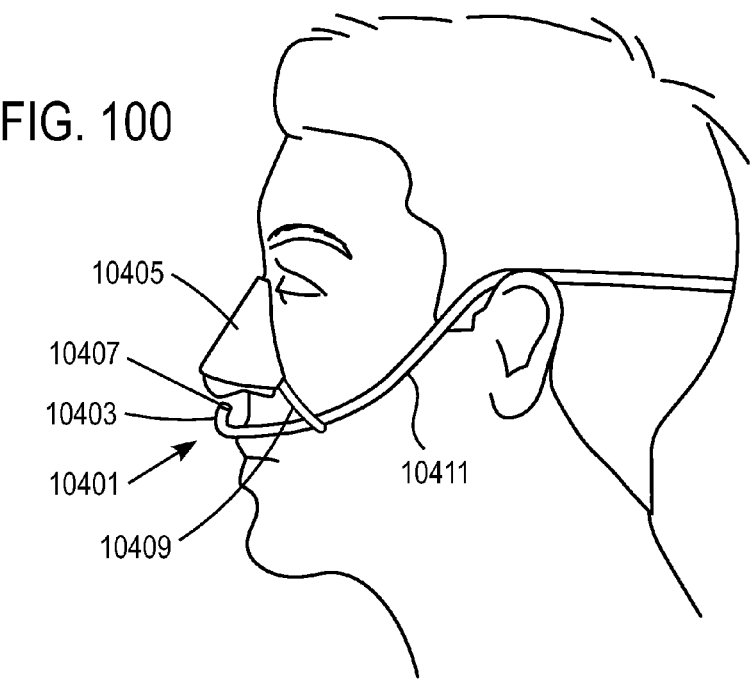
FIGS. 100 and 101 show an embodiment where a low profile nasal interface 10401 may be attached to the exterior of the nose.
Figure 101:
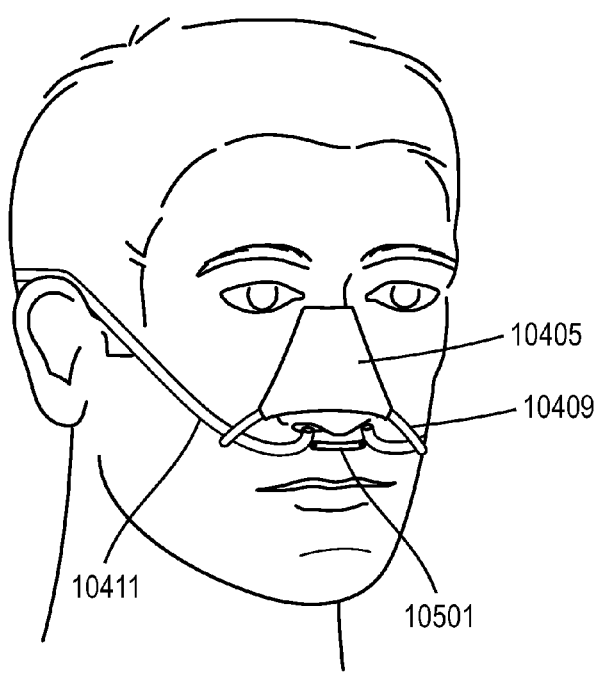

FIGS. 100 and 101 show an embodiment where a low profile nasal interface 10401 may be attached to the exterior of the nose. The nasal interface 10401 may serve two functions: first, the nasal interface 10401 can be used to connect the nasal interface 10401 to the face, and position and locate a cannula 10403 correctly, and second, the nasal interface can be used to prevent distention of the nostril wall when the ventilation gas is delivered, in the cases in which a high level of therapy is being delivered. In addition to the nasal interface, a mouth seal can be used with the invention, or a head band to keep the mouth closed, for example, when a mouth breather uses the therapy when sleeping (not shown). The nasal interface 10401 may have a shell 10405, a nozzle 10407, a coupler 10409, a gas delivery circuit 10411, and/or a connector 10501.

Table 3 provides exemplary dimensions and materials for various embodiments of the present invention. These are only exemplary and other dimensions and materials may be used for various situations.

The various embodiments of the present invention may have variable technical details and parameters. The following are exemplary technical details and parameters that may be use. These are not meant to be limited, but are merely for illustrative purposes.

For jet nozzles located in free space, such as those of FIGS. 8-58, the following may apply:

1) Dimensions/Relationships a. A jet nozzle diameter 17201 and distance from a nare opening 17203 may provide that a jet profile 17205 is substantially the same diameter as the nare 17203 when entering the nare 17203, see FIG. 166.

TABLE 3

Exemplary Dimensions, Values and Materials of the Invention

| Dimensions | Feature Range | Preferred Range |
|---|---|---|
| Gas delivery hose, ID (mm) | 2.0-7.0 | 2.5-4.5 |
| Gas delivery hose, Length (ft), ambulating with wearable system | 2-6 | 2.5-4 |
| Gas delivery hose, Length (ft), ambulating with stationary system | 20-75 | 40-60 |
| Gas delivery hose, Length (ft), sleeping | 4-15 | 6-10 |
| Cannula, ID (mm) | 0.5-5.0 | 2.0-3.0 |
| Cannula Length (in) | 5-20" | 8-12" |
| Jet Nozzle, ID (mm) | 0.25-2.0 | 0.05-1.75 |
| Jet Nozzle, Length (mm) | 1.0-30 | 4-12 |
| Jet Nozzle distance to nose, Nozzle inside manifold design (mm) | 5-60 mm | 15-40 mm |
| Jet Nozzle distance to nose, Nozzle inside outer tube design | ⁻5-60 mm | 5-50 mm |
| Jet Nozzle distance to nose, Nozzle in free space design (mm) | ⁻2-40 mm | 5-30 mm |
| Manifold Length (mm) | 20-160 mm | 30-80 mm |
| Manifold throat cross sectional area (in 2) | .015-.080 | .025-.050 |
| Manifold Pillow opening CSA (in 2) | .040-.120 | .065-.105 |
| Manifold pressure sensing line diameter (in) | .015-.055 | .025-.045 |
| Manifold Breathing Aperture CSA (in 2) Should be 1.125 to 3.0 times the size of the Manifold throat cross sectional area, preferably 1.75-2.25 times the size | .035-.095 | .050-.080 |
| Manifold sound reducing return vent CSA (in 2) Should be $1/10^{th}$ to $1/4^{th}$ the size of the manifold breathing aperture | .002-.050 | .005-.020 |
| Manifold breathing resistance (cmH2O @ 60 lpm) | 1-4 | 1.5-2.5 |
| Breathing resistance, outer tube design (cmH2O @ 60 lpm) | 1-4 | 1.5-2.5 |
| Breathing resistance, free space design, distance to nose (cmH2O @ 60 lpm) | 0-2 | 0-1 |
| Breathing sensing port, free space design, distance to nose (mm) | ⁻5-10 | ⁻2-5 |
| Breathing sensing port, manifold or outer tube design, distance to nose (mm) | ⁻5-30 | 0-20 |
| Outer Concentric Tube, OD (mm) | 5-20 | 8-14 |
| Outer Concentric Tube, Inlet max ID (mm) | 3-12 | 5-8 |
| Outer Concentric Tube, Inlet length (mm) | 4-15 | 6-12 |
| Outer Concentric Tube, Throat ID (mm) | 3-12 | 5-9 |
| Outer Concentric Tube, Throat Length (mm) | 3-20 | 8-12 |
| Outer Concentric Tube, Diffuser outlet ID (mm) | 3-12 | 7-11 |
| Outer Concentric Tube, Diffuser length (mm) | 2-10 | 6-10 |
| Spacing between jet nozzle tip and pump inlet (+value = proximal to; −value = recessed. Pump inlet may be outer tube, or may be nostril rim) | 30 mm to −15 mm | 10 mm to −5 mm |
| Attachment and Positioning Pad; L x D x H (mm) | 20-80 x 1.0-10.0 x 6-35 | 40-60 x 3.0-6.0 x 12-24 |
| Coupler, L | 5-25 mm | 7-10 mm |
| Coupler adjustment range | 6-25 mm | 8-10 mm |
| Angle adjustment in front plane between nozzles and/or outer tubes | Parallel to 45 degree included angle | 5-20 degree included angle |

| Materials | Types | Preferred |
|---|---|---|
| Gas delivery hose | PP, PE, PS, PVC | PE |
| Cannula | PU, PVC, Silicone | PVC, Silicone |
| Manifold | PVC, Silicone, PU, PE, Polysolfone | PVC, Silicone |
| Jet Nozzle | Metal, Ultem, Nylon, LCP, PVC, PC, ABS, PEEK | PVC |
| Outer Concentric Tube or Pillows | PVC, Silicone, PS | Silicone |
| Attachment and Positioning Pad | Silicone, Foam | Silicone |
| Coupler | Metal, Nylon, PVC, Silicone | Metal and Silicone |
| Manifold gas volume (cubic inches) | .050-.400 | .075-.200: |

Dimensions listed are exemplary and for average sized adults; pediatric sizes 20% less, neonatal sizes 50% less.
Diameters listed are effective diameters (average cross sectional dimension)

b. The jet nozzle 17201 preferably may be placed concentric to the nare 17203 for maximum performance, although this configuraiton may increase noise in some situations.

2) Materials
   a. A simi-rigid elastomer may be used for patient comfort.
   b. A majority of the sound generated by these configurations may be from the mixing of the high velocity jet with the low velocity entrained air at the nare opening. Material selection most likely does not have an affect on sound.

3) Exit Velocity
   a. Exit velocity perferably is maximized sonic flow to create as large of a jet flow rate as possible. Limitations may include ventilator source pressure limitations and peak delivered flow requirements.

4) Entrainment/Flow Amplification
   a. In these configurations, total flow can be up to four times or more the augmented flow.

5) Pressure Generation
   a. Values of approximately 17 cmH2O (@0 inspiratory flow) have been observed.

6) Sense Ports
   a. The sense ports may be as proximal to the nare opening as possible. Preferably the mask may slightly occlude the nare opening so that a sense port located between the occlusion and the nare opening may sense the pressure drop due to the occlusion during an inspiratory effort.

For jet nozzles coaxially located in nasal pillows, such as those of FIGS. 59-81, FIG. 167 illustrates one potential positioning of a jet nozzle 17301 relative to a nasal pillow diameter 17303. A jet profile 17305 may be substantially the same diameter as the nasal pillow 17303 when entering the nasal pillow 17303.

For jet nozzles coaxially inside a manifold lateral to the nose, such as those of FIGS. 82-99, the following may apply:

1) Dimensions/Relationships
   a. A jet diameter 17401 and a distance from the jet to an end of a throat section 17403 may be configured such that a jet profile 17405 substantially equals the throat diameter at the entrance to the throat section, as shown in FIG. 168. Another acceptable extreme may be when a jet diameter 17501 and a distance from the jet to an end of a throat section 17503 may be configured such that a jet profile 17505 is substantially the same diameter as the throat when entering just before exiting the throat section, as shown in FIG. 169.
   b. Jet may be placed concentric to the throat for maximum performance, although this configuration may be louder than other configurations.
   c. Jet may be placed near tangent and at a slight angle for maximum noise attenuation without significant reduction in performance.
   d. The path of the throat section may be fairly straight without significant changes in area and direction. This may apply up to a location where the jet profile area equals the throat diameter. Beyond this critical point the geometry may be more organic.

2) Materials
   a. A simi-rigid elastomer may be used for patient comfort.
   b. A simi-rigid elastomer may also be helpful in attenuating any noise generated in the manifold section of the nasal interface.

3) Exit Velocity
   a. Exit velocity preferably may be maximized sonic flow to create as large of a jet flow rate as possible. Limitations to this rule may be ventilator source pressure limitations and peak delivered flow requirements.

4) Entrainment/Flow Amplification
   a. In these configurations, total flow can be up to four times the augmented flow.

5) Pressure Generation
   a. Values of 25 cmH2O (@0 inspiratory flow) have been observed, but values of 30 cmH2O or more may be possible.

6) Sense Ports
   a. The sense ports may be located between the entrainment opening in the mask and the nasal pillow. The entrainment opening may provide a differential pressure for the sense ports to measure.
   b. If the throat section is configured to neck down for increased pressure capacity, then it may be preferable to place the sense port between this necking and the nasal pillow. This may increase the differential pressure available for the sense port.

In various embodiments of the present invention, a nasal interface may have ventilation gas jet nozzles that are substantially further from the nose than breathing sensors. Jet nozzles more distant than breath sensors may allow for improved gas flow profiles entering the nose, while still allowing for accurate and sensitive breath measurements because the sensors are close to the inlet and outlet of the nose.

The nasal interface may typically be provided in a kit. For example, two lengths of gas delivery hoses, 3-5 sizes of outer tubes, and 2-3 sizes of manifold assemblies may be provided so that the user can select the sizes appropriate for his or her anatomy, and assemble the components together into a complete assembly.

Figure 102:
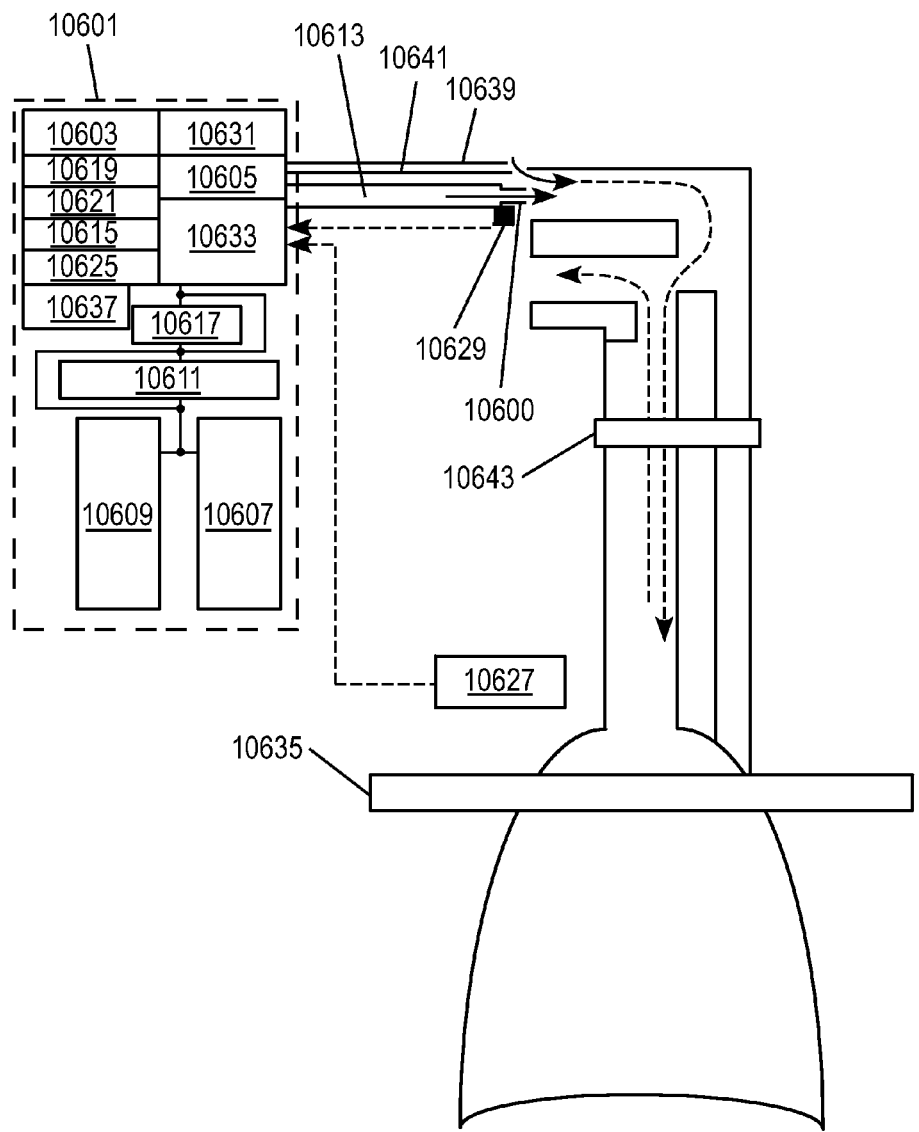
FIG. 102 is a block diagram describing an exemplary system of the invention.

FIG. 102 is a block diagram describing an exemplary system of the invention with a non-invasive open nasal interface 10600. A ventilator module 10601 may include or is in communication with several other accessories or functional modules. A transmitter 10603 may be included to transmit information regarding the patient, the patient's therapy, and the ventilator performance to a remote location for review, analysis, remote intervention, two way communication, and archival. For example, the patient's compliance to the therapy or utilization of the therapy can be monitored and assessed. Important information can be trended, for example the patient's breath rate, I:E ratio or depth of breathing. Also, information can be sent to the ventilator, for example programming of settings to titrate the ventilator output to meet the needs of the patient.

An internal or external humidifier 10605 can be included for extended uses of the therapy, or if using in dry climates. In addition to an oxygen source 10607, a compressed air source 10609 can be included, typically external attached to the ventilator module 10601, however optionally internal to the ventilator module 10601 if the therapy is being used for stationary use, for example in the home. A blender 10611 can be included to control the fractional delivered O2 in a gas delivery circuit 10613, and a pulse oximeter 10615 can be used in order to determine the correct blender setting in order to achieve the proper oxygen saturation. The pulse oximeter can also be used to titrate the other settings of the ventilator system to meet the physiological needs of the patient. In addition to compressed supplies of oxygen and air gas, the ventilator can include internal or external air and oxygen generating systems 10617, such as a compressor, pump or blower to create pressurized air, and an oxygen generator and/or pump to create pressurized oxygen gas, and a compressed gas accumulator. The oxygen source can also be liquid oxygen, or a liquid oxygen generating system. Because the therapy is frequently used to help activities of daily living, and to promote activity, a pedometer 10619 and/or actigraphy sensor 10621 can be included internal to or external to a ventilator module 10601. A CO2 sensor 10625 may also be included and/or another external sensor 10637 an/or a breathing sensor 10643. A CO2 sensing line 10639 and/or an airway pressure sensing line 10641 may be present. An external respiration sensor or respiration effort sensor 10627 can be included, such as a respiratory muscle effort sensor, a chest impedance sensor 10635, or other types of sensors, such as a tracheal or other microphone or vibration or acoustical or ultrasonic sensor. The external sensor is used either as a redundant sensor to the nasal airflow or nasal pressure sensor 10629, or to complement the information obtained from the nasal airflow sensor, or in place of the nasal airflow sensor. A drug delivery module 10631 can be incorporated internally or externally to a ventilator 10633. Because of the challenges with current aerosolized drug delivery inhalers, the system can be used to propel and deposit medication particles deep in the respiratory system without a carrier propellant. Because the patient's using the therapy often may also require prescription medication, this may be a convenient and efficient way to administer the medication.

When the therapy is being used for respiratory support, the user may have two options: (1) wearing or toting the ventilator so that the user can be ambulatory or enjoy the activities of daily living, or (2) stationary use, in the event the patient plans on being stationary or does not have the ability to ambulate. For the later, the delivery circuit can optionally be provided in a 25-100 foot length, such that the gas source and ventilator can be stationary in the patient's home, while the patient can move around their home while wearing the interface and receiving the therapy. Or, the gas source can be stationary, and connected to the ventilator with a 25-100 foot hose, so that the patient can wear or tote the ventilator and be mobile within the range of the hose.

Figure 103:
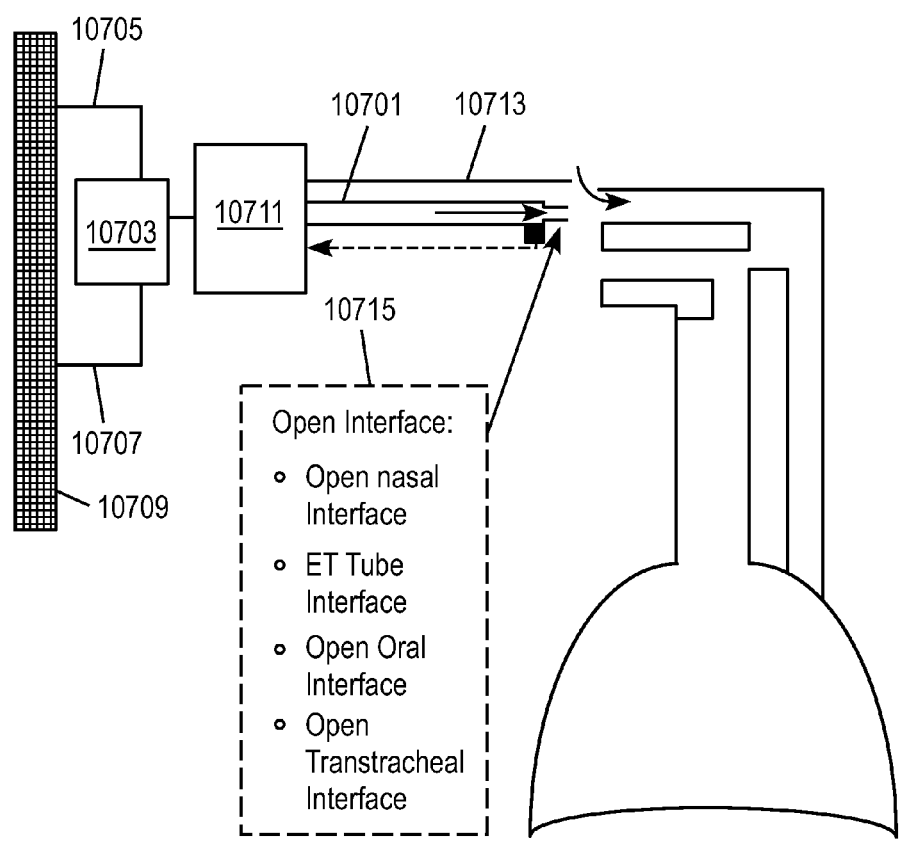
FIG. 103 describes an optional embodiment when the invention is intended for hospital or institutional use, in which a gas delivery circuit may be connected to a blender, which receives pressurized oxygen and pressurized air from the hospital pressurized gas supplies.

FIG. 103 describes an optional embodiment when the invention is intended for hospital or institutional use, in which a gas delivery circuit 10701 may be connected to a blender 10703, which receives pressurized oxygen and pressurized air from the hospital pressurized gas supplies, such as compressed O2 10705 and compressed air 10707 from systems that may be attached to a wall 10709. The gas supply may pass from the blender 10703 to a flow control 10711. An airway pressure sensing line 10713 may be present. An open interface 10715 may include an open nasal interface, an ET tube interface, an open oral interface and/or an open transtracheal interface. In this application, in which mobility may be less important, the system can be attached to the house gas supply, and higher levels of therapy can be delivered, as well as PEEP therapy during exhalation. All of these different options of stationary use and mobile use apply to the various different interface techniques described in the foregoing.

Delivering humidity can sometimes be useful when using the therapy described in this invention. The humidity can be delivered using a humidification generator that is integral or coupled with the ventilator, or using a stand alone humidifier. The humidified air or oxygen can be delivered through the gas delivery channel of the gas delivery circuit, or through another lumen in the gas delivery circuit as previously described, or through a separate cannula or tubing. For extended use, when the patient is likely to be stationary, the humidification system can be a stationary system and capable of delivering a relative high amount of humidity, and for periods of mobility, the patient can either not receive humidification, or use a portable humidification system that is capable of delivering relatively a small amount of humidity, due to size and energy consumption constraints.

The therapy described in this invention can be used with a variety of gas sources. For example, when treating respiratory insufficiency such as COPD, the gas source of choice is oxygen-rich gas, for example from a compressed oxygen cylinder or wall source, a LOX dispensing device, or an oxygen concentrator. In the event the patient requires some, but less, O2, both an oxygen and air source can be used as input into the ventilator, and a blender used as previously described to titrate the amount of O2 needed, either based on a clinical determination, or by pulse oximetry or other biofeedback signals. Alternatively, the ventilator can receive a compressed supply of one of either oxygen or air, and the other gas can be entrained into the gas delivery circuit or ventilator. If air is entrained in, it can be entrained in from room air. If oxygen is entrained in, it can be entrained in from for example an oxygen concentrator or LOX dispenser or oxygen liquefaction system. For sleep apnea applications, however, supplemental oxygen may not be needed, and hence the ventilation system uses a source of compressed air, or an air generating source. Also, neuromuscular diseases may similarly require only air. As described previously, combinations of gas delivery can be used, for example, a continuous delivery of oxygen can be administered, for example 2 LPM to provide proper oxygenation, and a synchronized volume delivery of gas can be delivered during inspiration to provide the mechanical support. This modality can be used to titrate the FIO2 and oxygen saturation needed. For treating other diseases and applications, other therapeutic gases can also be delivered by blending into the delivered gas, such as helium-oxygen mixtures, nitric oxide, or combinations of air, oxygen, helium and nitric oxide.

To facilitate integration of this new ventilation therapy into the existing therapeutic paradigms, a convertible system may be used. Specifically, the patient interface can be modular, such that a patient can be administered conventional oxygen therapy with a typical or slightly modified oxygen nasal cannula. Then, when it is desired to switch the patient to this new ventilation therapy, an additional component such as the outer concentric tube, or manifold, or breath sensing port, may be added to the nasal cannula to create the jet pump design and to position the distal tips of the cannula properly to achieve the function of this invention, while still maintaining breath sensing. Or for example, a switch on the gas delivery equipment can be switched to change the output of the equipment from oxygen therapy, to this therapy, by for example, enabling additional breath sensing functions, timing functions, waveform functions, and switching to the output amplitude necessary. Modular features such the portions of the equipment can be used for both COPD during daytime use, and sleep apnea during sleeping, are contemplated in the invention with the appropriate modularity and docking stations.

Figure 104:
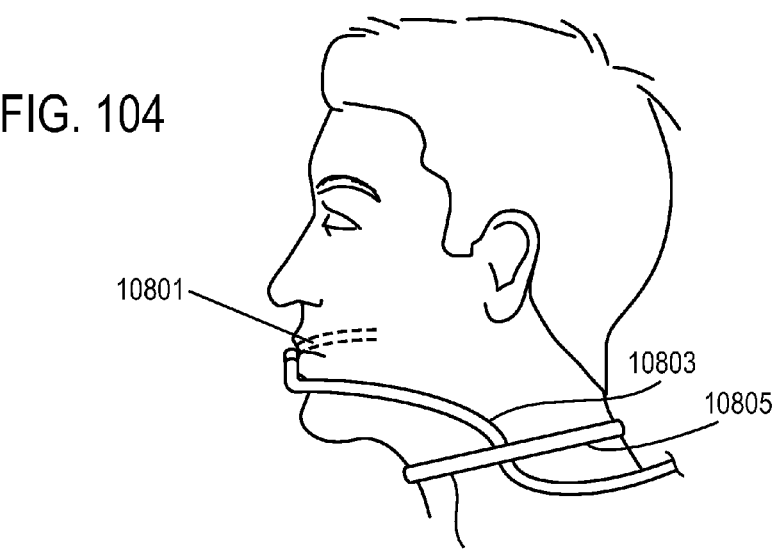
FIG. 104 shows that the therapy may use a trans-oral interface.

While the foregoing has described the therapy of this invention using a nasal interface, other interfaces may also be included in the invention. In FIG. 104, the therapy is described using a trans-oral interface 10801. A cannula 10803 may be secured to the patient with a neck strap 10805. The tip of the catheter can be proximal to the mouth entrance, coplanar with the mouth entrance, or recessed inside the mouth between the lips and the awe line. The catheter can be shaped to be routed along the teeth, either on the buccal side or lingual side of the teeth, or through the center of the mouth. The catheter can be positioned so that a portion of the catheter rests on the superior surface of the tongue, or can be positioned so that a portion of the catheter rests against the inferior surface of the hard palate, in which case the distal tip of the catheter may be angled or curved inferiorly away from the palate and towards the oropharyngeal airway. The catheter can be bifurcated so that there is a left and right catheter positioned on both the right and left side of the mouth. The catheter can be integral to a bite block or mouth guard. The catheter is easily inserted and removed from the patient's mouth. All of the appropriate details described previously in conjunction with the nasal interface may apply to the oral catheter used in this version of the invention. While an intra-oral catheter or mouthpiece is shown in FIG. 104, the invention can also be a mouthpiece that barely enters the mouth, or a nasal-oral mask that can provide the therapy to both the nasal airway and the oral airway, with the appropriate breath sensors determining if the patient's month is open to adjust the therapy as needed.

Figure 105:
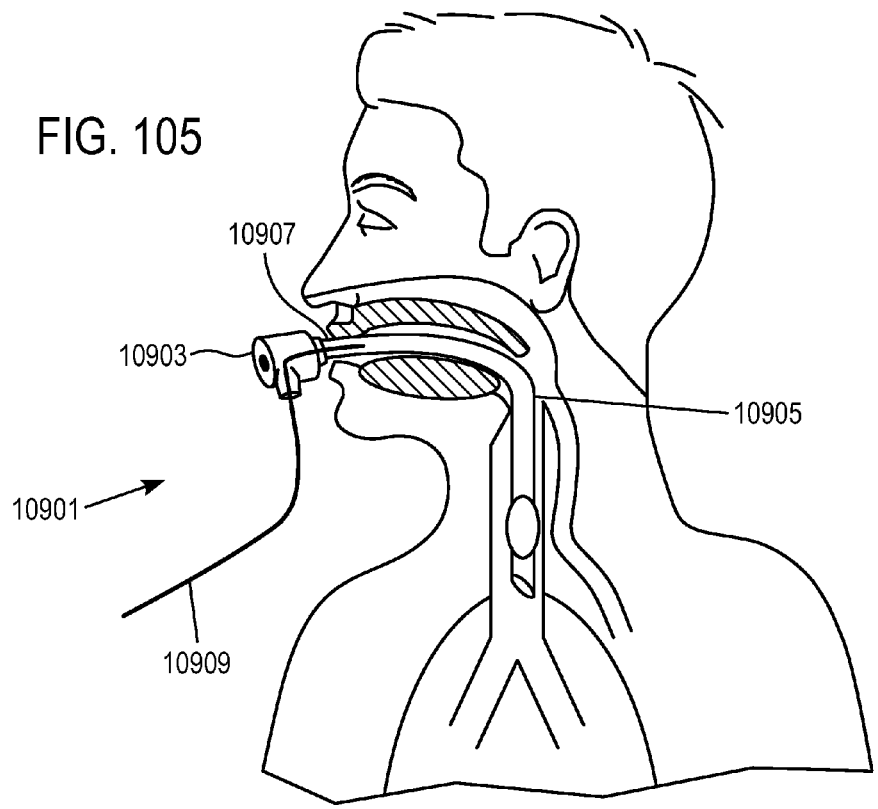
FIG. 105 shows an embodiment used with an ET tube interface.

FIG. 105 shows an embodiment used with an ET tube interface 10901. This version of the interface can be helpful to institutions which walk their patients during the weaning stages off of invasive mechanical ventilation. Walking patients whom are on ICU ventilators is typically very onerous because the patient must have the assistance of a number of medical staff to move the large and complex ICU ventilator along side the patient. In FIG. 105, the present invention may be used to help a patient walk, while receiving adequate ventilatory support form the ventilation system and interface described in this invention. In this embodiment, the ET tube connector may include an attachment for the ventilation interface. The patient can breathe ambient air spontaneously through the proximal end of the ET tube proximal connector which is left open, while the patient's spontaneous breaths are efficaciously augmented by the ventilation system, gas delivery circuit 10909 and catheter interface 10901. Optionally, in addition if it is desired to apply PEEP, a special PEEP valve 10903 may be included for attachment to the end of an ET tube 10905. The special PEEP valve may include a one way valve so that ambient air is easily entrained into the ET tube toward the patient's lung by a jet nozzle 10907, but also allows exhalation through the PEEP valve 10903, while maintaining the desired PEEP level. The patient can still also breathe room air spontaneously through the PEEP valve through an inspiratory valve integral to or in parallel with the PEEP valve. For PEEP application, alternatively the ventilator used in the present invention can provide PEEP as previously described by delivering gas with the appropriate waveform during the patient's expiratory phase. The catheter tip can be slightly proximal to the proximal end opening of the ET tube proximal connector, or can be coplanar with the proximal end opening, or can be inserted into the ET tube to the appropriate depth, typically at around the mid-point however which will depend on other variables of the system. The depth can be adjustable to optimize the entrainment and performance or function for individual situations, as required clinically or for patient tolerance. The ET tube connector used in this embodiment of the invention may be of a special unique configuration that provides the necessary jet pump geometry as previously described in conjunction with the nasal cannula outer concentric tube. The connector can include a jet inlet, jet throat and diffuser section. Or, alternatively, the ET tube can be of a special configuration, which incorporates dimensions and geometries advantageous to the jet pump performance. All of the appropriate details described previously with the nasal interface, apply to the ET tube catheter interface used in this version of the invention. In addition, PEEP can be included in the other patient interfaces described in the invention by including a similar special PEEP valve designed for each of the different patient interfaces.

Figure 106:
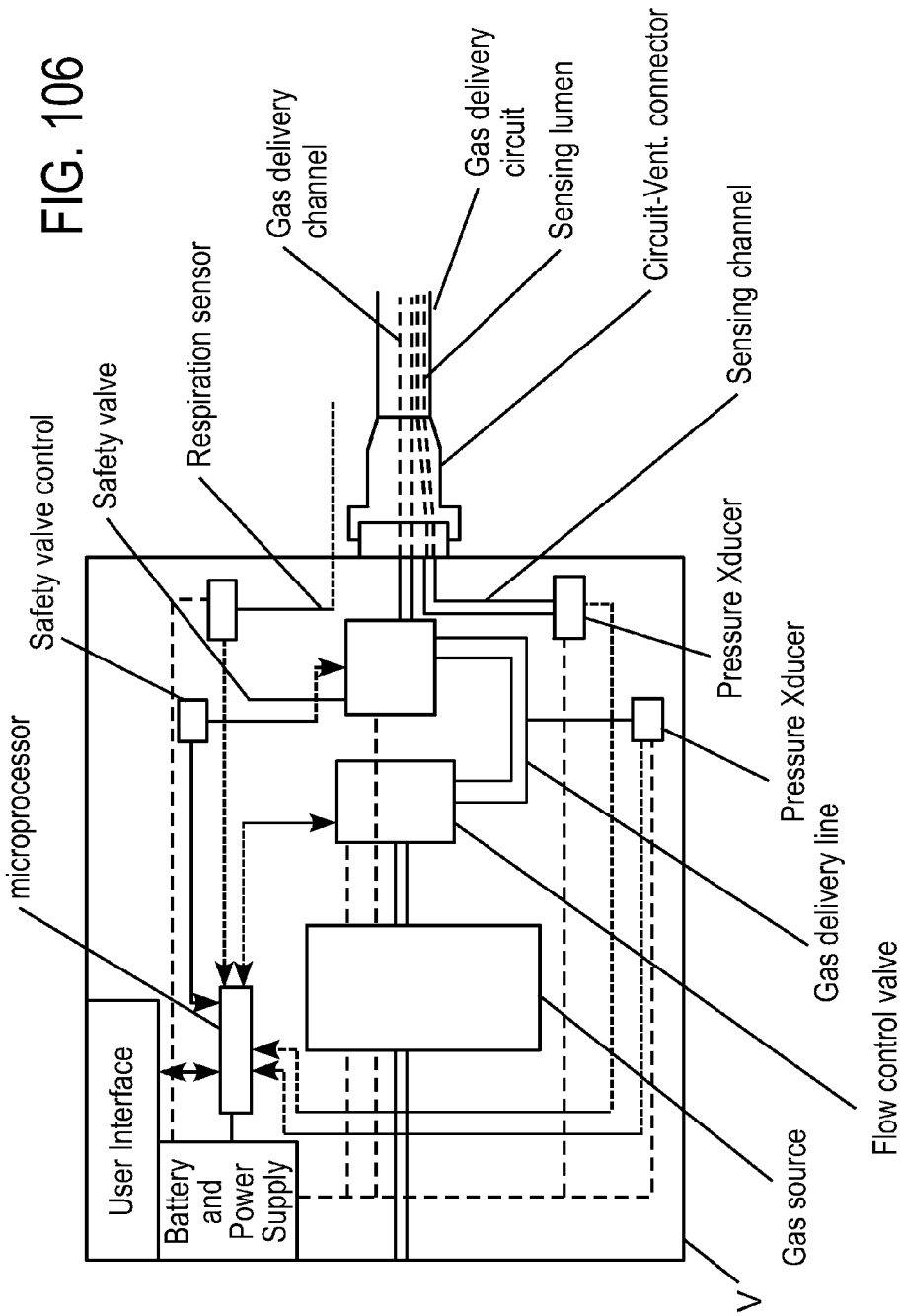
FIG. 106 is a system block diagram of the components of a ventilator V.

FIG. 106 is a system block diagram of the components of a ventilator V, minus the optional modules and accessories described earlier. The ventilator can be self contained with a battery and gas supply to enable it to be borne by the patient, so that the patient can ambulate and participate in activities of daily living, which is made possible by the respiratory support they are receiving from the ventilator, but in a package that can easily be borne.

Figure 107:
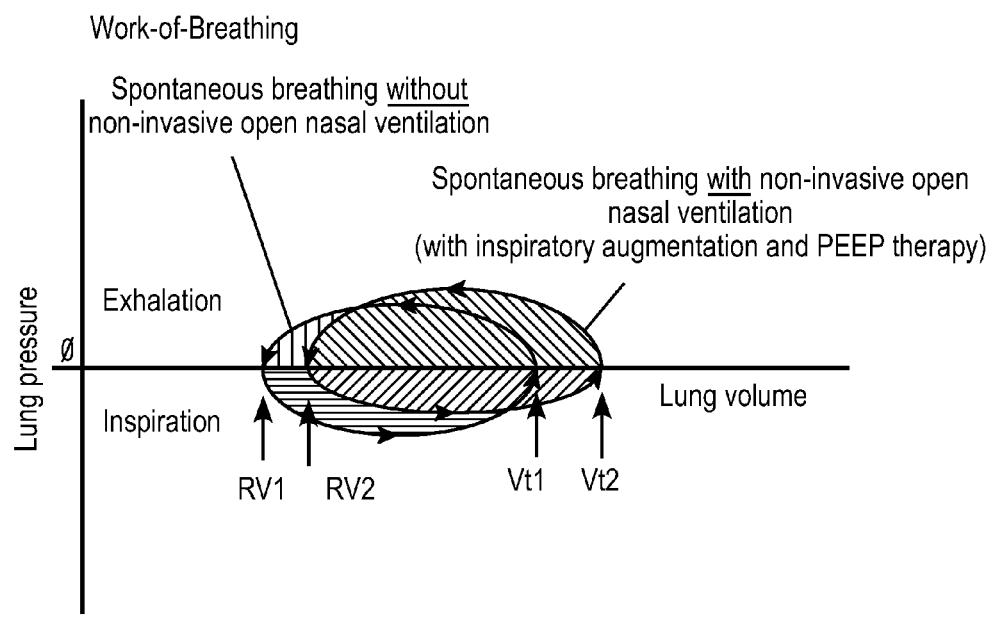
FIG. 107 describes how the patient's work of breathing may be beneficially affected by the invention, when the invention is used for lung disease or neuromuscular disease applications.

FIGS. 107-164 show various therapeutic aspects of the present invention in more detail. For the therapy described in this invention to be more effectively titrated to the needs of the patient, the ventilator system can perform an analysis to determine the level of respiratory support needed. To accomplish this, the ventilator can titrate the output to the needs of the patient, for example during ambulation or activity, the output can increase. Alternatively, during higher respiratory rates as measured by the spontaneous breath sensor, the output can increase. Alternatively, during higher breath effort as measured by the breath sensor, the output can increase. Other biofeedback signals can be used. In addition to the output increasing or changing to meet the respiratory needs of the patient, the timing of the ventilator output relative to the patient's spontaneous inspiratory phase, and the output waveform, can change to meet the comfort and physiological needs of the patient. For example, during exercise, the output can change from an early delivery at 75 ml with an ascending waveform, to being triggered with a delay to start for example 100 msec after the start of inspiration, and with a decelerating waveform.

When the patient is attaching the patient interface when starting a therapeutic session, the breath sensors can be used to determine proper positioning of the distal tip of the interface relative to the patient's nostrils. For example, if the jet nozzles and or outer concentric tubes are not aligned properly, the sensor may detect less entrainment than expected, or detect that a certain pressure signal characteristic is missing, and the signal may initiate an alert to be communicated to the patient, caregiver or clinician through the ventilator user interface, or through remote monitoring. Once the alignment and positioning is proper, the alert may disable and the ventilator may inform the patient, caregiver or clinician that the interface is positioned properly. Similarly, during a therapeutic session, if at any time the interface is improperly positioned, the sensors can detect the low entrainment values or the wrong characteristic signal, and using that signal the system can send the notification or alert to the patient, caregiver or clinician that a repositioning is required. The detection of entrainment values can be accomplished by including flow or pressure sensors near the tips of the jet nozzles or coupled with the concentric outer tubes, which may register entrained ambient airflow movement past the sensing elements or sensing ports, as previously described. Special configurations of the interface assembly can include sensor locations in which at least one sensor is biased toward registering spontaneous breathing by the patient, while at least one other sensor is biased toward registering entrained ambient airflow. This configuration allows the system to distinguish between spontaneous breathing and entrainment, such that entrainment does not mask the breathing signal. Alternatively, the sensor can register predominantly entrainment during the time when ventilator output is active, and register predominantly spontaneous breathing when the ventilator output is off FIG. 107 describes how the patient's work of breathing may be beneficially affected by the invention, when the invention is used for lung disease or neuromuscular disease applications. The patient's lung volume may be graphed as a function of lung pressure, the area inside the curve representing work, typically expressed in Joules per Liter (J/L), and for a normal healthy adult can be 0.3-0.6 J/L. For a respiratory compromised patient, 4-10 times more work can be required to breathe during rest, and even more during exertion, to overcome the diseased state of the tissue, for example to overcome static and dynamic hyperinflation as in the case of COPD, or to overcome high airways resistance as in the case of fibrosis or ARDS. In the graph shown, the area inside the curve below the pressure axis is the inspiratory WOB, and the area defined by the area inside the curve above the pressure axis is the expiratory WOB. The arrows show the cycle of a single breathe over time, starting from RV to VT then returning from VT to RV. RV1 and VT1 are the residual volume and tidal volume without the therapy. RV2 and VT2 are the residual volume and tidal volume with the therapy. As can be seen, RV increases with the therapy because in this example, expiratory flow is provided as part of the therapy, which may increase residual volume. Importantly, VT is increased with the therapy and is increased more that the RV is increased, indicating that more volume is entering and leaving the lung as a result of the therapy. The increase in tidal volume is considered clinically efficacious, however is technically challenging to achieve in an open ventilation, non-invasive and minimally obtrusive system. As is shown in the graph, the patient's inspiratory WOB with the invention ON may be about 25% less than the patient's inspiratory WOB with the invention OFF. Also, inspiratory lung pressure increases (is less negative) and tidal volume increases, and optionally exhaled pressure increases if the therapy is provided during exhalation. While residual volume increases in the example shown because the ventilator is providing gas in this example during the expiratory phase, the ventilation parameters can be titrated to not effect residual volume, and because of the ability of the patient to exercise their lung muscles when receiving the therapy, the patient's lung mechanics may remodel in the case of COPD, actually causing a reduction of residual volume to a more normal value. In the graph shown, the waveform with therapy assumes an early inspiratory trigger time for the ventilator inspiratory phase therapy output, and that the volume output is delivered within the patient's inspiratory time. Optionally, however, different delivery waveforms and delivery synchronizations can be performed, which may adjust the WOB curve. For example, the ventilator inspiratory phase therapy can be delivered late in the person's inspiratory cycle, with delivery completing at the end of inspiration, and delivered with a square or ascending waveform profile. In this case the WOB curve with therapy will be tilted upward to the right of the curve, such that Inspiration ends and transitions to Exhalation at a point above the lung pressure zero axis.

Figure 108:
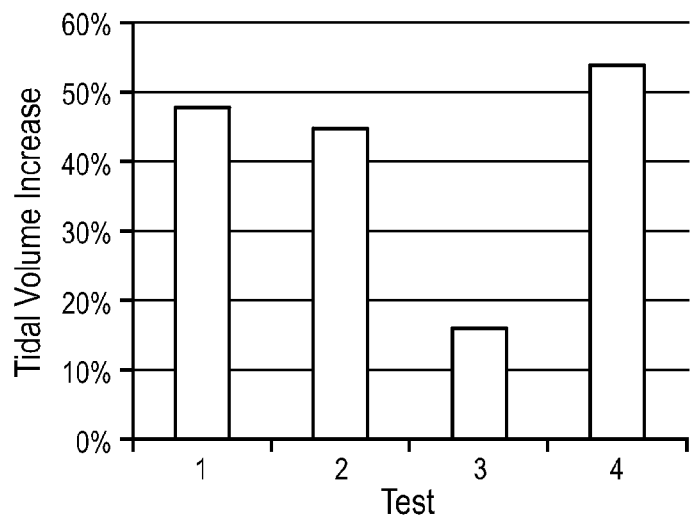
FIG. 108 graphically illustrates the lung volumes achieved with a nasal interface of the present invention on actual test subjects.

FIG. 108 graphically illustrates the lung volumes achieved with a nasal interface of the present invention on actual test subjects. Using embodiments of the present invention, tidal volume may increase by an average of approximately 41%.

Figure 109:
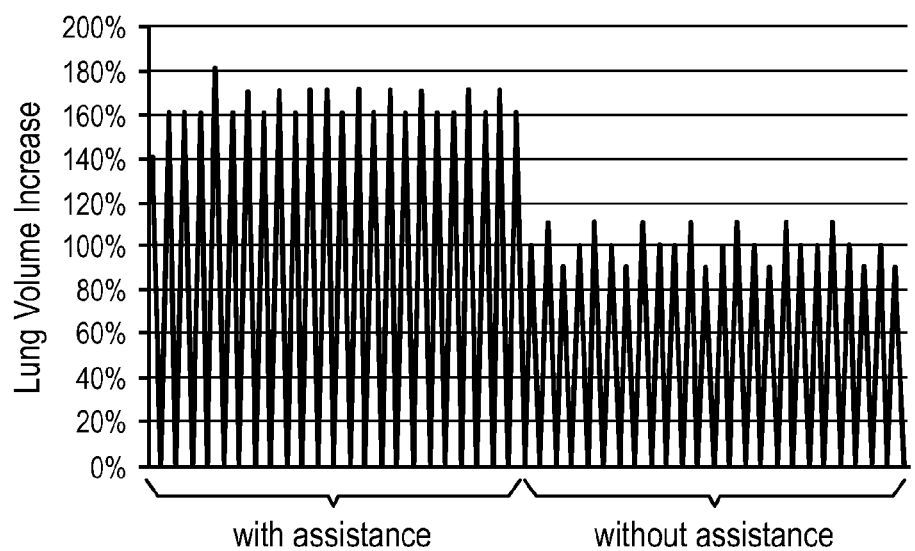
FIG. 109 graphically illustrates lung volumes achieved with a nasal interface of the present invention on a test subject using a chest impedance band to measure and display lung volume.

FIG. 109 graphically illustrates lung volumes achieved with a nasal interface of the present invention on a test subject using a chest impedance band to measure and display lung volume. To the left side of the graph, while spontaneously breathing the subject is receiving ventilation from the invention, and on the right side of the graph, the ventilation therapy may be turned off and the subject may be spontaneously breathing without the ventilation therapy, showing a marked increase the ventilation therapy causes over baseline, thus showing how NIOV can increase lung volumes.

Figure 110:
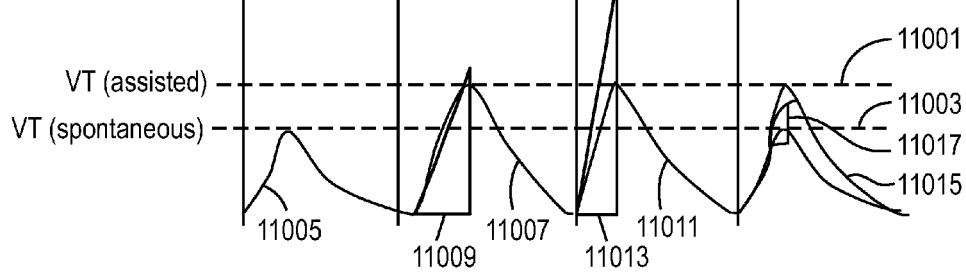
FIG. 110 graphically illustrates the lung volumes achieved with NIOV on a lung simulator bench model in comparison to conventional ventilation.

FIG. 110 graphically illustrates the lung volumes achieved with NIOV on a lung simulator bench model in comparison to conventional ventilation. In all the waveforms the simulated patient is spontaneously breathing at the same inspiratory effort which results in a tidal volume of 245 ml, and the clinical goal is to increase the patient's tidal volume from 245 ml 11001 to 380 ml 11003. In the first waveform 11005 from left to right in the graph, the patient's breath is un-assisted and thus the patient receives a tidal volume of 245 ml. In the next waveform 11007, the simulated patient with the same effort is assisted with a traditional closed system ventilator, such as with a sealed breathing mask or cuffed airway tube. The ventilator output 11009 is set to a level in order to achieve the desired "assisted" tidal volume of 380 ml. The ventilator is set to 420 ml to achieve this goal. In the third waveform 11011, a small leak is introduced in the conventional ventilator system, such as would be done in the case of weaning the patient off of the ventilator. To achieve the desired "assisted" tidal volume of 380 ml, the ventilator must now be set at 705 ml 11013. In the second and third waveforms, it can also be seen that all of the volume received by the patient's lung originates from the ventilator, which it must in these conventional systems. In the forth waveform 11015, the patient is assisted with the NIOV, and as can be seen, the NIOV ventilator output only has to be set at 90 ml 11017 to achieve desired "assisted" level of 380 ml. In this case, only some of the 380 ml tidal volume comes from the ventilator, and a substantial portion of the 380 ml comes from entrainment and spontaneously inspired ambient air, therefore making the NIOV system far more efficient, comfortable, and healthier, than the other systems.

Figure 111:
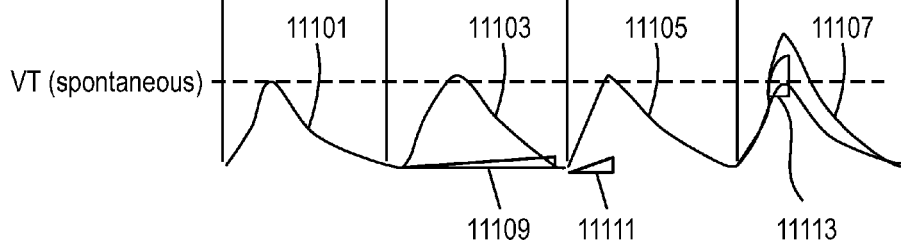
FIG. 111 graphically shows NIOV in comparison to oxygen therapy, using the lung simulator bench model.

FIG. 111 graphically shows NIOV in comparison to oxygen therapy, using the lung simulator bench model. In the first waveform on the left 11101, the patient is unassisted and breathes at an effort of −0.8 cmH2O, generating 248 ml of inspired tidal volume. In the second waveform 11103 and third waveform 11105, the patient receives continuous flow 11109 and pulsed flow 11111 of oxygen respectively via nasal cannula, with no or negligible effect on lung pressure and tidal volume. In the forth waveform 11107, NIOV 11113 is used which shows a marked increase in lung pressure and tidal volume, thus indicating that NIOV helps in the work-of-breathing as described earlier, despite the fact that NIOV is an open airway system.

Figure 112:
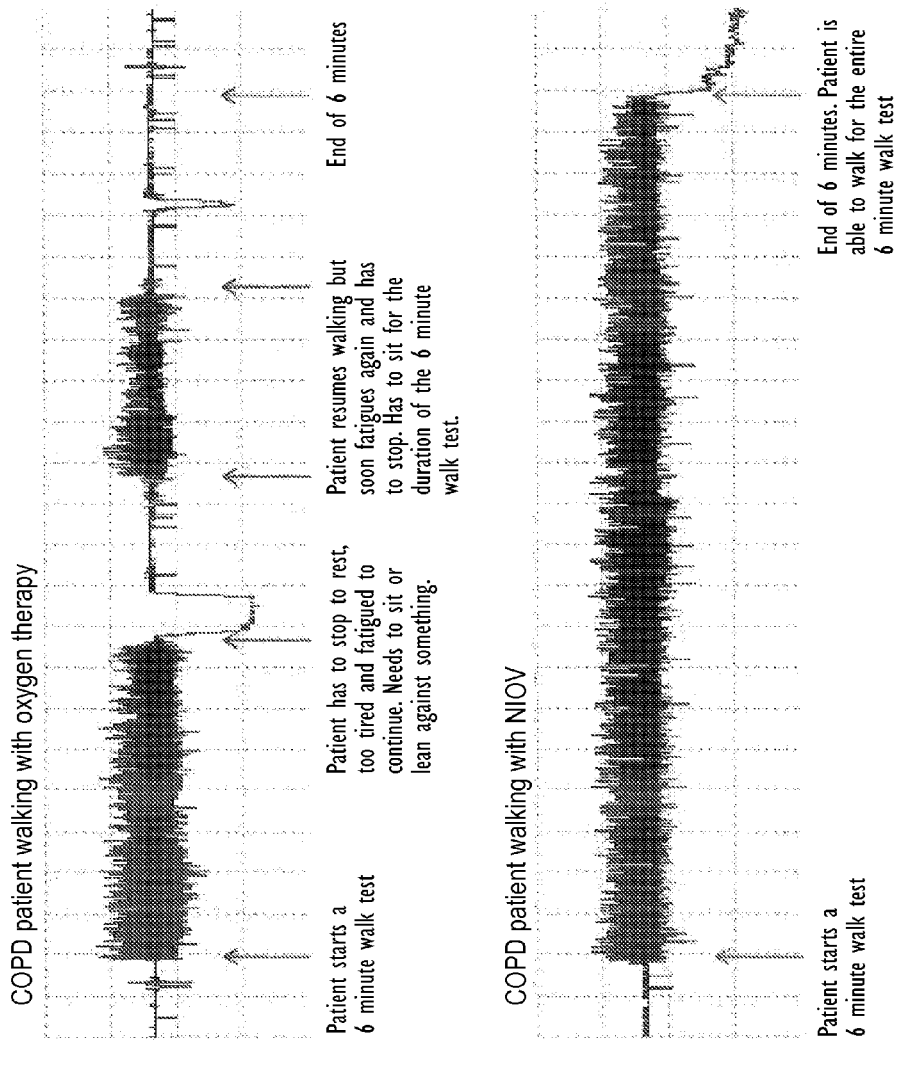
FIG. 112 graphically describes a typical COPD patient's ability to perform a 6 minute walk test using standard oxygen therapy and the NIOV therapy.

FIG. 112 includes two graphs that graphically describe a typical COPD patient's ability to perform a 6 minute walk test using standard oxygen therapy and the NIOV therapy described herein. In the oxygen therapy walk (top graph), the patient fatigues early and has to stop to rest, because the amount of energy the patient has to expend to breathe to overcome their reduced lung function, is just too difficult. The patient has to rest, and often sit down or lean against something. Typically, the heart rate and blood pressure are extremely elevated in addition to being fatigued, and the CO2 level is high because the patient cannot get enough air in and out, again, because of how much energy is required to breathe. The same patient performing the walk test using NIOV (bottom graph) may be able to walk the entire 6 minutes without walking, because NIOV is helping their respiratory muscles in the work of breathing. The COPD patient is typically able to walk 10-50% further with the NIOV, or 30-70 meters further. Because NIOV is a wear-able system, and because the patient interface is an open airway interface, the patient may be comfortable with the ventilator and interface and is able to leave the house and perform activities of daily living.

Figure 113A:
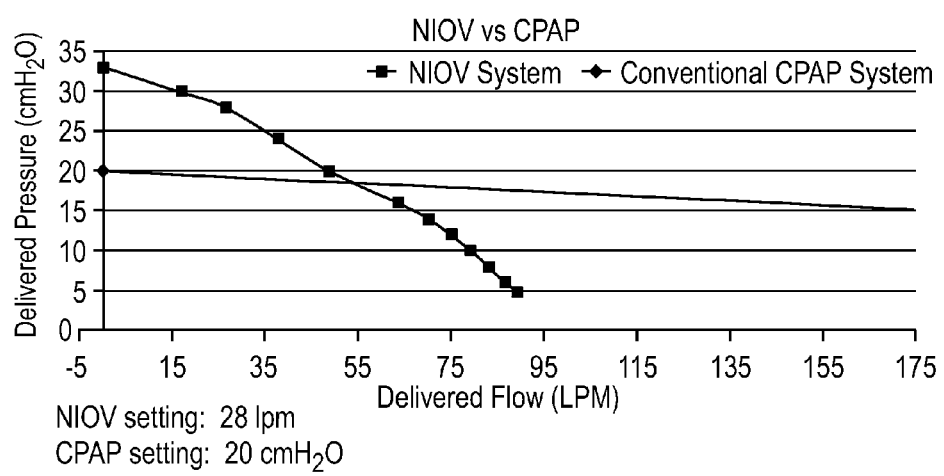
FIG. 113A describes lung pressure generated by NIOV compared to lung pressure generated by a conventional CPAP ventilator.

FIG. 113A describes lung pressure generated by NIOV compared to lung pressure generated by a conventional CPAP ventilator. Each ventilator is delivering flow through their respective gas delivery circuits and nasal masks. The NIOV system is set for the ventilator to output 28 lpm, and, as explained above, it entrains additional gas from ambient air before the gas enters the patient's airways. The CPAP system is set to 20 cmH2O, a relatively high but typical setting for CPAP therapy. When the mask is occluded, the pressure generated by the system is indicated in the graph at zero on the X axis. As can be seen the NIOV system is capable of generating at least as much pressure as the CPAP system. When the gas delivery circuits and masks are open to atmosphere, the NIOV system can generate 18 cmH2O easily while delivering approximately 55 lpm of gas, which is well within the capability of the NIOV system. Therefore, with NIOV a Respiratory Insufficiency patient or a Sleep Apnea patient can be ventilated just as well as with CPAP; however, with the convenience and minimal obtrusiveness of the NIOV system.

Figure 113B:
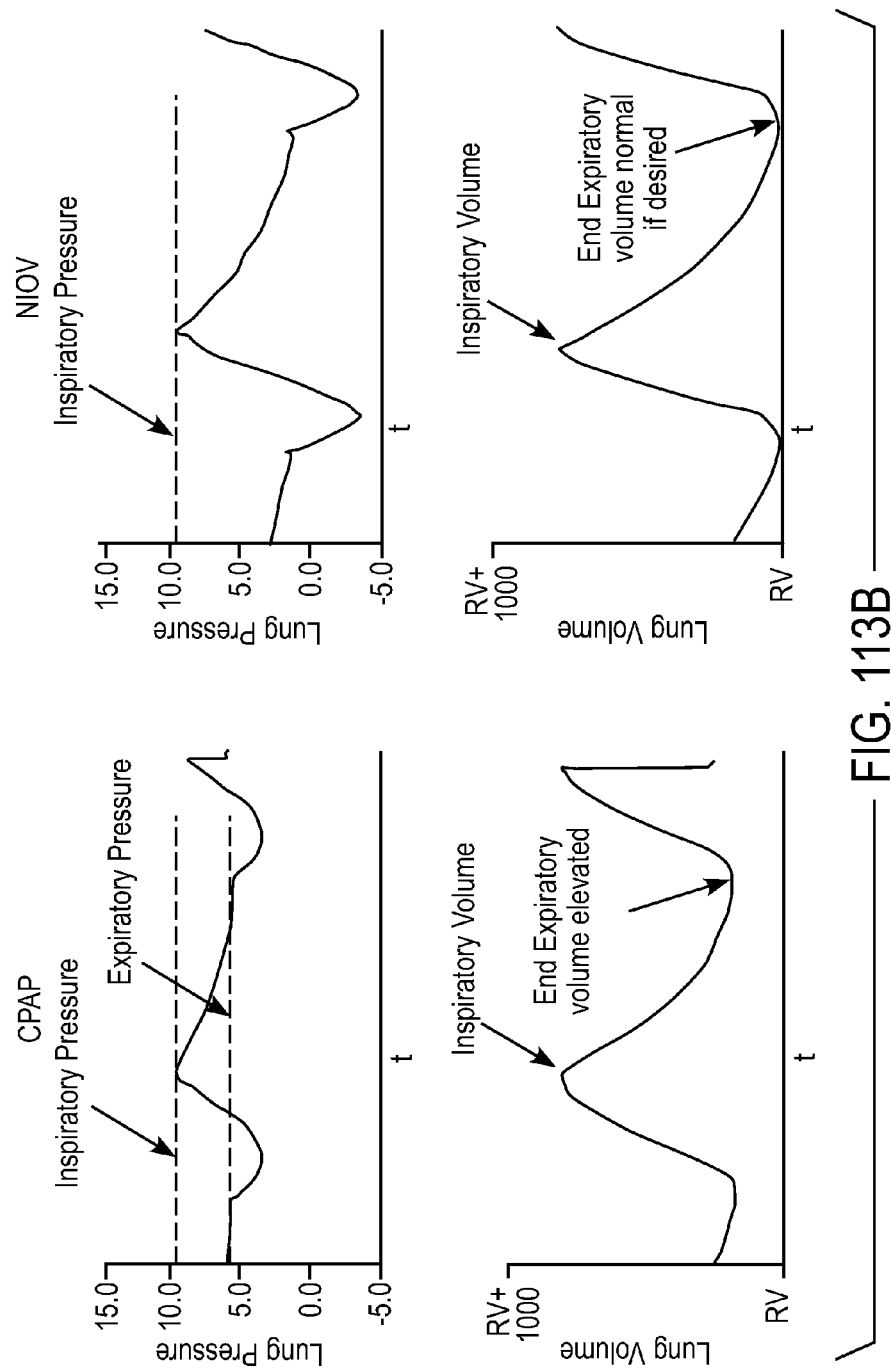
FIG. 113B describes lung volumes achieved with the NIOV system in comparison to conventional BiPAP.

FIG. 113B describes lung volumes achieved with the NIOV system in comparison to conventional CPAP. The CPAP system is set to an inspiratory pressure of 10 cmH2O and expiratory pressure of 5 cmH2O. The NIOV system is set to an inspiratory pressure of about 10 cmH2O, but is not set with an expiratory pressure, and hence the expiratory pressure is that of the spontaneously breathing patient. Alternatively, as explained earlier, the expiratory pressure with the NIOV system could also be set at a level elevated from spontaneous expiratory pressure. As can be seen in the graphs, the CPAP patient has an elevated RV because of the expiratory pressure and flow, whereas the NIOV patient has a normal RV. This can be very beneficial in COPD to prevent hyperinflation, or in OSA to maximize patient comfort and tolerance. Note that the same therapeutic inspiratory pressure can be reached in both cases.

FIGS. 114-153 graphically describe NIOV in more detail as it relates to providing mechanical ventilatory support for the patient. FIGS. 114-129 compare the invention with the prior art. FIGS. 114-117 compare delivery circuit drive pressure of NIOV to the prior art. FIGS. 118-121 compare inspiratory phase volume delivery of NIOV to the prior art. FIGS. 122-125 compare lung pressure of NIOV to the prior art. FIGS. 126-129 compare typical outer diameter of a delivery circuit of NIOV to the prior art.

FIGS. 114-117 describe the pressure signal in the gas delivery circuit of the invention. The pressure range in FIGS. 114 and 115 are typically in the 5-40 psi range, and the pressure range in FIG. 116 is typically in the 0.1-0.5 psi range. The pressure range in FIG. 117 can be either in the 5-40 psi range or in the 0.1-0.5 psi range depending on the exact therapy.

FIGS. 118-121 describe the volume delivered by prior art oxygen therapies, comparing NIOV to the prior art. This series of graphs show only the volume delivered to the patient by the therapy, and do not describe the additional spontaneous volume being inspired by the patient. The total volume being delivered to the lung is the combination of the volume being delivered by the therapy and the volume being spontaneous inspired by the patient, and in the case of NIOV the volume entrained by the therapy. For the purpose of this description, the total resultant lung volume is shown in the graphs in FIGS. 122-125, in terms of lung pressure, which is directly correlated to lung volume. The lung pressure resulting from the therapy is governed by a combination of factors: the gas delivery circuit pressure, the jet pump design and configuration, the patient's lung compliance and airway resistance, the timing of the ventilator output relative to the patient's inspiratory phase, and the ventilator output waveform. Typically, however, a gas delivery circuit pressure of 30 psi delivering 100 ml with a square waveform, and delivered for 500 msec starting at the beginning of the patient's inspiratory phase, may increase lung pressure by 5-15 cmH2O. And, typically a gas delivery circuit pressure of 30 psi delivering 250 ml with a square waveform, and delivered for 500 msec starting at the near the middle of the patient's inspiratory phase, may increase lung pressure by 10-25 cmH2O.

FIGS. 122-125 describe the effect that the therapies have on lung pressure. In FIG. 122, two potential lung pressure results caused by the invention are both depicted: less negative pressure shown by the solid line and positive pressure shown by the dotted line. Additional waveforms and resultant lung pressures conceived by the invention are shown in subsequent figures.

FIGS. 126-129 graphically represent the relative cross sectional area or profile required for the gas delivery circuits of the various therapies, providing an indication of the size and obtrusiveness of the interface. As can be seen by comparing the invention to pulsed dose oxygen therapy, for the same circuit delivery pressure conditions and an equal or even smaller gas delivery circuit profile, the invention may produce entrained flow, whereas oxygen therapy has negligible entrained flow, and the invention may provide greater volume delivery, and causes an mechanical effect on lung pressure, compared to oxygen therapy which has no effect on lung pressure. Comparing the invention with high flow oxygen therapy (FIGS. 116, 120, 124, 128), NIOV has the potential to have an equal or greater effect on the lung pressure and work-of-breathing, however with a significantly smaller delivery circuit profile and with much less gas consumption. 15 LPM or more of source gas may be consumed in the case of HFOT, whereas less than 8 LPM of source gas may be consumed in the case of NIOV, this making the invention at least equally efficacious, but with a more efficient design. For the sake of comparison, the volume depicted in the curve in FIG. 120 accounts for and describes the volume output of the HFOT system only during the patient's inspiratory time, even though the output is continuous flow as indicated in FIG. 116. Comparing NIOV with BiPAP ventilation therapy, the invention can approximate the effect on the lung that BiPAP therapy produces (FIGS. 121 and 125); however, with a significantly less obtrusive delivery system, and with a system that is potentially wearable and permits activities of daily living. FIG. 125 shows a range of lung pressures that can be created by BiPAP, ranging from the solid line to the dotted line.

FIGS. 130-153 graphically show different alternative ventilator output waveforms of the present invention, and the effect of the ventilator output on the patient's lung mechanics. The series of graphs in FIGS. 130-133 and 142-145 indicate a pressure waveform in the delivery circuit. The series of graphs in FIGS. 134-137 and 146-149 indicate the volume delivery, both delivered and entrained. The series of graphs in FIGS. 138-141 and 150-153 indicate a pressure level in the lung.

FIG. 130 describes a square pressure waveform output during the patient's spontaneous inspiratory phase, which entrains ambient air at approximately a 1:1 ratio effectively doubling the volume delivered to the patient, and resulting in an increase in lung pressure during inspiration from a negative pressure (when therapy is off) to a positive pressure (when therapy is on). FIG. 131 describes a rounded pressure delivery waveform, delivered during inspiration after a slight delay after the start of the inspiratory phase. The entrained air volume may be roughly equal to the ventilator output, and the resultant lung pressure may be increased from its normal negative value during inspiration to a positive value. The lung pressure may return to normal at the end of the gas delivery, to the patient's normal value. Alternatively, the waveform duration can be extended so that it ends coincident with the start of exhalation, or slightly into exhalation, such that the lung pressure remains positive when transitioning from inspiration to exhalation. FIG. 132 describes a square pressure output waveform delivered and completed in the first portion of the inspiratory phase, and completed before the transition to exhalation. In this case the lung pressure may be affected and becomes positive, and may return to its normal level when the ventilator delivery is completed.

FIGS. 133, 137 and 141 describe a multiple pressure amplitude delivery waveform, with a higher amplitude delivered during inspiration and transitioning to a lower amplitude delivered during exhalation. Two potential resultant lung pressure waveforms are both shown in FIG. 141, the solid line showing a relatively high pressure during exhalation, such as a PEEP pressure of 3-10 cmH2O, and the dotted line showing an attenuating and less pressure during exhalation, such as a pressure of 1-5 cmH2O. Delivered volume may be increased due to the entrainment as in the other waveform examples. Lung pressure may be increased during inspiration (less negative pressure is shown, however, zero pressure or positive pressure is also possible), and during exhalation positive pressure is maintained and or increased beyond the patient's normal expiratory pressure. The positive pressure during exhalation can help reduce dynamic hyperinflation by reducing airway collapse during exhalation, and or can help alveolar ventilation and lung recruitment, by keeping the lung lobule spaces biased open during all phases of breathing including the expiratory phase. While the example shows two discrete pressure levels, there may be multiple levels, or a variable level that adjusts as needed, and the transition from one level to another can be ramped rather than stepped as shown.

Figure 142:
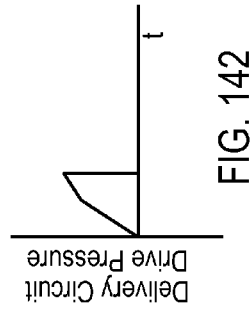
Figure 146:
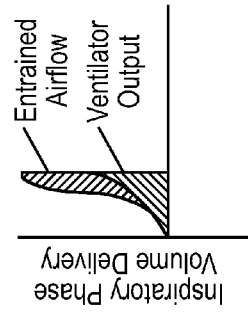
Figure 150:
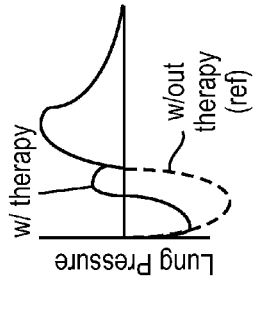

FIGS. 142, 146 and 150 describe an ascending pressure delivery waveform in which the pressure begins to be delivered at the onset of inspiration, and ramps up during the delivery period. The delivery period can be a portion of inspiratory phase, or all of inspiratory phase, or longer than inspiratory phase, depending on the clinical need and the comfort of the patient. The ramping waveform serves to match the patient's spontaneous breathing, such that the intervention feels comfortable and synchronized with the patient's demand, effort and need. Less gas may be entrained when using this waveform compared to some other waveforms, however, the total delivered volume is sufficient to increase lung pressure to a positive pressure if desired.

Figure 143:
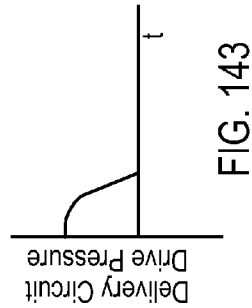
Figure 147:
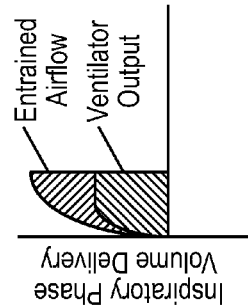
Figure 151:
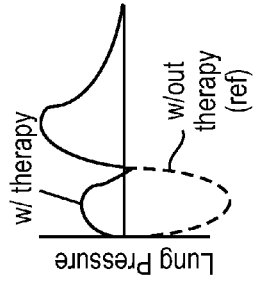

FIGS. 143, 147 and 151 describe a descending waveform, which may be preferred if the patient is breathing deep or heavy, such that the initial strong demand from the patient is matched with a strong output from the ventilator.

Figure 144:
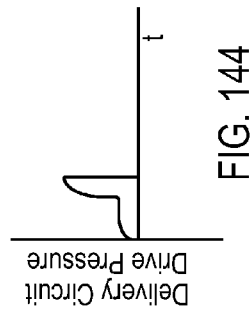
Figure 148:
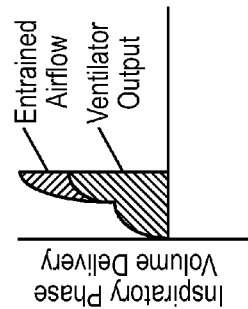
Figure 152:
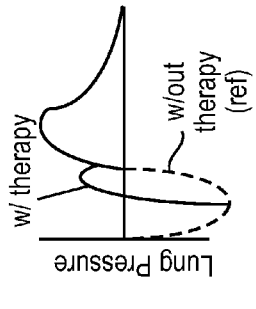

FIGS. 144, 148 and 152 describe a multiple pressure amplitudes delivery waveform, delivered within inspiration. The first pressure amplitude which is lower, comprises oxygen rich gas, such that the residence time of the oxygen in the lung is maximized to improve oxygenation and diffusion, and the second pressure amplitude which is higher and which can comprise just air or air/oxygen mixtures or just oxygen, is used to create a mechanical effect on pressure in the lung to help mechanically in the work of breathing. The second boost also serves to help the oxygen delivered in the first boost to penetrate the lung more effectively.

Figure 145:
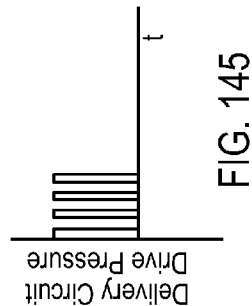
Figure 149:
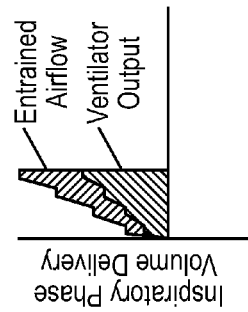
Figure 153:
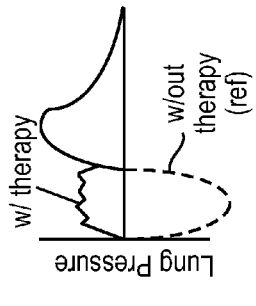

FIGS. 145, 149 and 153 describe an oscillatory multiple delivery waveform in which the pressure delivery is oscillated between off and on, or between a higher and lower value. This alternative waveform can improve gas source conservation and may have other beneficial effects, such as comfort and tolerance, entrainment values, penetration, drug delivery and humidification.

It should be noted that with respect to the ventilation system gas delivery waveforms shown in FIGS. 130-153, aspects or the whole of one waveform can be combined with aspects or the whole of another waveform. Also, the amplitude and timing values may vary. For example, the ventilator gas flow delivery can commence immediately at the beginning of inspiration or can commence with a delay or can be timed to be synchronized with a certain portion of the patient's inspiratory phase, such as when the inspiratory flow or inspiratory muscle effort reaches a certain percentage of maximum. Or, for example, the delivery can be within the inspiratory time, equal to the inspiratory time, or extend beyond the inspiratory time. Or, for example, the pressure created in the lung by the ventilator can be less negative than baseline (ventilator off), or zero pressure can be created, or positive pressure can be created, or combinations of less negative, zero and positive pressure can be created. The different waveforms can be combined and mixed, for example, pressure delivery can be delivered during exhalation in combination with an ascending pressure waveform being delivered during inspiration. In an optional embodiment of the invention, the ventilation gas delivery rate is selected to attempt to match to the patient's inspiratory demand. When the patient is breathing deeper and stronger, the ventilation output may be increased to match the demand. When the patient is breathing shallower and weak, the ventilation output may be decreased to match the need. In an optional embodiment, this flow rate matching can be used to create a zero pressure or close to zero pressure condition in the lung during inspiration, or alternatively, create a certain desired negative pressure, such as −2 cwp, or to create a certain desired positive pressure, such as +2 cwp. A biofeedback signal can also be used to titrate the ventilator output to the need of the patient, for example such as respiratory rate, depth of breathing as previously mentioned, walking or activity level, or oxygen saturation. In an additional embodiment, the sensor arrangement at the tip of the cannula can include the capability to measure and record the absolute or relative amount of entrained ambient air. Based on a collection of measurements such as nasal airway pressure, and other known values such as ventilator gas output parameters, the ventilation system can together with the entrained ambient air measurement, determine the total amount of gas being delivered and being spontaneous inspired into the patient. From this information tidal volume and FIO2 can be derived, and the ventilation status of the patient ascertained and the setting of the ventilator further titrated for improved efficacy.

Ventilation can be delivered in synchrony with inspiration, or in synchrony with exhalation, or both, or can be delivered at a high frequency, a constant flow, in a retrograde direction, and all possible combinations of the above. When synchronized with the patient's inspiratory or expiratory phase, the ventilator (V) may deliver volume in ranges from approximately 40-700 ml per cycle, preferably approximately 75-200 ml, in delivery times of approximately 0.2 to 1.2 seconds, preferably approximately 0.35-0.75 seconds, and with a catheter exit speed of approximately 50-300 m/sec., preferably approximately 150-250 m/sec. If delivered at a high frequency rates, the ventilator (V) may deliver volume at a rate of approximately 0.25 cycles per second to approximately 4 cycles per second, preferably at a rate of approximately 0.5 to 2 cycles per second, in the range of approximately 10 ml to 100 ml per cycle, preferably approximately 25-75 ml per cycle. When delivered at a constant flow, the ventilator V may deliver flow at a rate of approximately 0.5 LPM to 10 LPM, preferably approximately 2-6 LPM, and at a catheter exit speed of approximately 50 m/sec to 250 m/sec, preferably approximately 100-200 m/sec.

Optionally, high frequency low volume ventilation can be delivered by the ventilator and patient interface where very low volumes of gas are delivered at very fast frequencies, such as approximately 5-50 ml at approximately 12-120 cycles per minute, or preferably approximately 10-20 ml at approximately 30-60 cycles per minute. In this manner, substantial minute volumes can be delivered to the lung but while controlling the pressures achieved in the airway and lung more closely to a desired level, albeit in an open airway system. This delivery waveform can be continuous, or can be synchronized with the inspiratory phase of breathing. Again, different waveforms described can be combined in whole or in part, for example, volumes can be synchronized and delivered in one shot during inspiration, and then high frequency low volume ventilation can be delivered during exhalation. It should also be noted that ventilation gas delivery, when activated, can gradually ramp up so that it is not a sudden increase in amplitude, which could arouse the patient.

Further, as shown in FIG. 165, NIOV can include speaking detection capability, such as using airway pressure signal processing or sound or vibration sensors, and when speaking is detected, the ventilator output can switch from synchronized delivery during inspiratory phase, to either no delivery or continuous flow delivery, so that the ventilation gas delivery is not out of synchrony with the patient's breathing pattern. Also, the system can include a pause feature, so that the patient can speak, or eat, with the therapy off, for example for 10-20 seconds. The pause feature can turn the therapy output to zero, or to a continuous flow.

It should be noted that in the graphical examples provided, the respiration sensor waveform is exemplary only and actual waveforms can take on other characteristics, such as different I:E ratios, breath rates, random behavior, ascending and descending shapes of inspiratory and expiratory curves, and altering amplitudes. It is noted that because of the gas flow delivery from the cannula, a region of transient negative pressure may be generated near the catheter distal tip. The sensing signal processing may take this into account when determining the breath phase.

The current invention is also an improvement over existing sleep apnea ventilation therapies. The present invention may prevent or reduce obstruction of the airway, or alternatively may ventilate the lung during a complete or partial obstruction, with a cannula-based system that is less obtrusive than CPAP, thereby improving patient adherence, compliance and efficacy of the therapy. In addition, the invention may provide improved prediction of the onset of an apneic episode so that the therapy can intervene in a more precise, intelligent manner and a manner that is more tolerant to the patient. Embodiments of the present invention may include one or more of the following features: (1) catheter-based synchronized ventilation of the oropharyngeal airway and/or lung; (2) catheter-based pressurization of the oropharyngeal airway to prevent or reverse airway obstruction; (3) using breathing effort and breathing sensors for apnea prediction and detection and for regulating the therapeutic parameters; (4) using a minimum amount of ventilation gas to treat OSA, thereby creating less noise and providing a more normal breathing environment; (5) a ventilation delivery interface that is minimized in size to improve tolerance and comfort; (6) an open system so that the patient can feel like they are inhaling and exhaling ambient room air naturally.

FIGS. 154-161 graphically describe the ventilation parameters and their effect on respiration air flow, when the invention is used to treat sleep apnea SA. Similar parameters and techniques are used to treat obstructive sleep apnea (OSA) central sleep apnea (CSA) and mixed sleep apnea (MSA). FIGS. 154-156 illustrate the three basic treatment algorithms of the present invention used to detect and treat OSA: reaction/correction, preemption, and prevention, respectively. FIG. 154 describes intervening upon detection of apnea. FIG. 155 describes intervening upon detection of a precursor to an obstruction to prevent a complete obstruction. FIG. 156 describes intervening proactively in attempt to prevent obstructions. In this series of graphs, t is the time axis, Q is the airway flow signal, IQ is the inspiratory flow signal, EQ is the expiratory flow signal, VO is the ventilator output, 32 is the normal breathing flow curve, 34 is a breathing flow curve when the airway is partially obstructed, and 48 is an obstructed airflow signal and 40 is the ventilator output synchronized with the actual breath, and 44 is the ventilator output based on previous breath history or breathing effort. In the examples shown, the ventilation is delivered in synchrony with the patient's inspiratory breath effort, however this is exemplary only, and ventilation can also be delivered using constant flow or pressure, or variable flow or pressure, or any combination of the above. Additional details of the treatment algorithms are explained in subsequent descriptions.

In FIG. 154, the reaction and correction algorithm, the spontaneous breathing sensor may detect a shift in nasal airflow from a normal airflow signal 32 to a reduced airflow signal 34. As seen in the graph labeled "with intervention", immediately after the reduced airflow signal 34 is detected by the breathing sensor or, alternatively, after some desired delay, the gas delivery control system commands the ventilator to deliver ventilation flow/volume 44 at a rate based on past breath rate history. The ventilator gas flow together with ambient air entrainment may open the obstruction and restore respiration as seen in the graph labeled "with intervention" and restore ventilation to the lung. For contrast, the graph labeled "without intervention" shows the respiration signal eventually going to no airflow signal 48, thus indicating a substantially complete obstruction. In the example shown, during the period of partial or complete obstruction, the flow signal at the nares is not strong enough for the breathing sensors to detect respiration. Alternatively, during apnea, the ventilator gas flow can be delivered from the ventilator at a pre-determined back-up rate, or delivered as a continuous flow. In FIG. 155, the preemption algorithm, the breathing sensor detects a shift in nasal airflow from a normal airflow signal 32 to a reduced airflow signal 34. Either immediately or after some desired delay, the control unit may command the ventilator to deliver ventilator gas flow synchronized with inspiration 40. Alternatively, the ventilator gas flow can be delivered at a pre-determined back-up rate, or at a continuous flow. In FIG. 156, the prevention algorithm, ventilator gas flow is delivered in synchrony with the patient's spontaneous breathing, and when a reduction in airflow 34 occurs due to the onset of an obstruction, the cyclical rate of the ventilator prevents the obstruction from fully developing, and the breathing returns to normal 32. While the ventilator gas flow profiles described in FIGS. 154-155 indicate discrete gas volume outputs with intermittent delivery, other gas delivery profiles can exist, such as continuous flow and combinations of volume deliveries and continuous flow delivery, as will be describe in more detail subsequently. It should be noted that the three basic algorithms can be combined in whole or in part to create a hybrid treatment algorithm.

FIG. 157 graphically shows the patient and ventilator waveforms over a period of time, in which the ventilator is activated during the precursor to an apnea 34 or during periods of apnea or airway obstruction 48, and then is deactivated when normal breathing 32 is restored. The ventilator gas flow may be delivered cyclically when activated, as shown, or as described earlier can be delivered continuously. In an optional embodiment of the invention the ventilator control system includes a database describing the characteristic breath sensor signal waveforms or amplitudes or frequencies (collectively referred to as waveforms) that relate to the different phases of sleep. For example the database includes characteristic waveforms for an awake state, an S1, S2, S3 and S4 sleep state, and an REM state. The ventilator control system would compare the actual measured waveform with this database of characteristic waveforms. The ventilator would them make determinations to designate breaths as "apnea" breaths, versus "normal" breaths, versus "partial obstruction" breaths, versus other situations like snoring, coughing, etc. This feature would further allow the ventilation output treatment algorithm to be matched to the needs of the patient. For example, the algorithm in which the ventilator output is enabled during the detection of an onset of an apneic event, i.e., a partial obstruction, can then differentiate between a partial obstruction and simply a lighter stage of breathing. Alternatively, instead of a database, these characteristics could be determined in real time or learned by the ventilator. Or, alternatively, an additional sensor can be included in the invention which measures the stages of sleep, such as an EEG sensor or biorhythm sensor. In addition, the invention can include artifact detection and screening, so that the monitoring of the patient's status and control of the therapy is not fooled by an artifact. Such artifact detection and screening include for example snoring or breathing into a pillow.

The breath detection may be critical to the function of the invention when used to monitor and treat forms of SA. In OSA for example, during a partial obstruction, gas flow at the nares may be reduced due to the obstruction. The tracheal pressure signal may increase because of the increased pressure drop required to move air across the partial obstruction, or because of moving gas flow back and forth between the trachea and lung. Conversely, airflow at the nares reduces or stops. Therefore, an apneic event can be detected by the loss of a pressure of flow signal being measured at the nares, and a precursor to an apneic event is detected by a reduction in the signal amplitude. Using both a pressure and airflow sensor may be desired because the information can be crosschecked against each other, for example, a reduced airflow signal plus an increased pressure signal may correspond to the precursor of an obstruction event. In addition, another external respiration sensor may be used to detect respiratory muscle effort, such as a chest impedance or chest movement sensor. In this case, the effort signal may be compared to the nasal airflow and/or nasal pressure signal, and the comparison can determine exactly what the breathing condition is among all the possible conditions, for example, normal unobstructed breathing, partially obstructed breathing, complete obstructions, heavy unobstructed breathing and light unobstructed breathing. Also, OSA can be distinguished from CSA events particularly if using both a nasal sensor and muscles sensor, and comparing the signals. An external sensor can optionally be used in place of the nasal air flow sensor as the primary respiration sensor.

FIGS. 158-164 describe different gas flow delivery waveforms, or treatment algorithms, when the invention is used to treat OSA. The delivery waveforms can be used with each of the three basic treatment algorithms described earlier, i.e., reaction/correction, preemption, and prevention, or a hybrid of the three treatment algorithms. In each case, the ventilator gas output may be disabled when the user first connects the mask and gets in bed, and only when needed later when the patient is asleep or drowsey or after a period, does the ventilator gas output enable, thus allowing the patient to breathe freely through the mask without any therapy at the beginning of the night, to make the patient feel completely normal. Since the mask is a completely open mask, this is possible, whereas this is not possible with conventional CPAP and BiPAP sleep apnea masks and breathing circuits. The graphs labeled Q represent airflow in the airways, and the graphs labeled VO represent the ventilator gas output, either in pressure or in flow or volume. In FIG. 158, the ventilator output is increased 40 in response to a weakening airflow or breathing signal 34, thus preventing obstruction and restoring normal airflow 32. The ventilator output returns to its baseline amplitude at the desired subsequent time. In FIG. 159, the ventilator output switches from a synchronized cyclical on and off output 40 to delivering a continuous flow 47 between cycles, when the onset of an obstruction 34 is detected. In FIG. 160, the ventilator emits a continuous flow or pressure output 42 until the precursor to an apnea 34 is detected, at which time the ventilator boosts its output to deliver a greater amplitude of pressure, flow or volume synchronized with inspiration, while the reduced airflow 34 representing the partial obstruction is present. In FIG. 161, a variable ventilator pressure or continuous flow or pressure output 42 is delivered, which ramps 43 to a greater amplitude until the reduced airflow signal 34 is returned to a normal signal, after which time, the ventilator output can ramp down to its baseline value. In a preferred embodiment indicated in FIGS. 160 and 161, the ventilator output can ramp up from zero output, extending to the left of the scale shown in the graphs, when the user first attaches the interface and is awake, to a very small output when he or she falls asleep, and ramp to an increased output when the onset of an apneic event is detected, or, ramp from zero to a higher output only when the apneic onset is detected as described using a combination of FIG. 155 and FIG. 161. This capability is a significant advantage over conventional OSA PAP therapy in that the patient can comfortably and naturally breathe ambient air past or through the NIOV nasal interface when awake but in bed, and before the apneic or hypopneic breathing begins, without the ventilation gas being delivered. This is difficult and ill advised with conventional PAP therapy in which the patient breathes the significant majority of gas through the mask and hose, in which case it is best to always have the ventilation gas being delivered to the patient to prevent CO2 retention in the hose, mask and airways due to rebreathing. Other gas flow delivery waveforms are included in the invention, and the above ventilator output waveform examples can be combined in whole or in part to create hybrid waveforms or switching waveforms. For example, the ventilator output can be small gas volumes delivered in synchrony with inspiration, until the precursor to an obstruction is detected at which time the volume output is increased; if the obstruction gets worse or becomes completely obstructed, then the ventilator output switches to continuous flow which ramps from a starting amplitude to higher amplitudes until the obstruction is opened.

FIGS. 162 and 163 indicate additional treatment algorithms, specifically a continuous flow ramping algorithm and an inspiratory effort-synchronized algorithm respectively.

In FIG. 162 ramping is conducted during inspiratory phase only to make the increase more unnoticeable to the patient. The ventilator output ramps to a low-level non-therapeutic flow prior to ramping to the therapeutic flow, for the purpose of acclimating the patient to the feeling and sound of the therapy, and ramps during inspiration in order to minimize the sensation of increasing flow to the patient.

FIG. 163 indicates an algorithm in which non-therapeutic pulses of flow are delivered in synchrony with the patient's inspiratory effort, in order to condition or acclimate the patient to the feeling and or sound of the therapy. In addition, delivering non-therapeutic levels of gas earlier in the session also serves to provide information to the system regarding the fit and function of the nasal interface. For example, if the interface is attached correctly, the system will detect that and proceed normally, but if the interface is not attached or aligned correctly, the system will detect this with signal processing, and can alert the user to make adjustments before the patient enters a deep stage of sleep. Alternatively, the system can provide therapeutic levels of therapy soon after the nasal interface is attached, and determine if the interface is connected properly, and if not, instruct the patient to make the necessary adjustments. Once properly fitted, as determined by the signal processing of the system, the ventilation gas output is turned off until needed, as described in the foregoing. Alternatively, the breathing pressure signal can be used to ascertain if the interface is attached and aligned properly.

FIG. 164 graphically illustrates in closer detail an optional embodiment of the gas delivery waveform when using an inspiratory effort-synchronized therapy.

For SA treatment, some additional or alternative parameters are as follows: Volume delivery can be approximately 10 ml to 200 ml per ventilator cycle depending on the breathing status of the patient. If complete apnea occurs, volume delivery increases to approximately 200 ml to 500 ml per cycle, at a rate of approximately 6-20 cycles per minute. The flow rate of the gas being delivered is typically approximately 6-50 LPM during the actual delivery of the gas, and preferably approximately 10-20 LPM. Timing of the ventilator cycling can be in synch with the patient's breath rate, for example, approximately 6-30 BPM, or if not synchronized or if the patient is apneic, cycling can be approximately 8-20 cycles per minute unless high frequency low volume ventilation is used, which is described subsequently. The drive pressure at the ventilator output for the ventilation may be typically approximately 5-60 psi and preferably approximately 8-40, and most preferably approximately 10-15 psi, to create a desired oropharyngeal pressure of approximately 0-5 cmH2O under normal unobstructed conditions during inspiration and up to approximately 20 cmH2O during obstructed conditions. It should also be noted that while ventilator gas flow is often shown in synchrony with a breath cycle, the breath cycle may not be detectable due to a partial obstruction or apneic event, and, therefore, the ventilator gas flow is simply applied at a predetermined rate or a predicted rate. It should also be understood that depending on the sensor used, the breath effort may still be detectable even though there is no or very little airflow being inspired from ambient or being exhaled to ambient. However, the movement of air in the trachea in response to the breath effort in some cases, depending on the sensor technology being used, may be enough to register as an inspiratory effort and expiratory effort by the sensor. In fact, in some cases, depending on the sensor used, an obstruction may be accompanied by an increased negative pressure during inspiration, and, while there is reduced airflow in the trachea T because of the obstruction, the breath signal may be stronger. Therefore, in the present invention, the gas delivery control system and algorithms in the gas delivery control system takes all these matters into account while processing the sensor information and deciding whether there is normal or reduced breathing taking place at any given time. The ventilation pressures achieved in the upper airway by the delivery of the ventilator gas flow may be in the range of approximately 1-20 cmH2O, preferably approximately 2-5 cmH2O when delivered preemptively, and approximately 5-10 cmH2O when delivered in response to a detected obstruction event. The ventilation pressures achieved in the lower airways and lung may be similar to the pressures achieved in the upper airway by the ventilation gas delivery.

Optionally, high frequency low volume ventilation can be delivered by the ventilator and patient interface, where very low volumes of gas are delivered at very fast frequencies, such as approximately 5-50 ml at approximately 12-120 cycles per minute, or preferably approximately 10-20 ml at approximately 30-60 cycles per minute. In this manner, substantial minute volumes can be delivered to the lung but while controlling the pressures achieved in the airway and lung more closely to a desired level, albeit in an open airway system. This delivery waveform can be continuous, or can be synchronized with the inspiratory phase of breathing. Again, different waveforms described can be combined in whole or in part, for example, volumes can be synchronized and delivered in one shot during inspiration, and then high frequency low volume ventilation can be delivered during exhalation. It should also be noted that ventilation gas delivery, when activated, can gradually ramp up so that it is not a sudden increase in amplitude, which could arouse the patient.

In an optional embodiment, the methods and apparatus of the present invention can be used to treat OSA by determining a flow rate requirement needed to prevent airway obstructions, rather than determining and titrating a therapeutic pressure level as is done in existing systems. For example, a patient with a sleep apnea index greater than 10, or a negative inspiratory force of −10 cwp, or a certain upper airway compliance as determined by ultrasound or other means, a diagnostic measurement can be correlated to a therapeutic ventilation flow rate requirement that may prevent, preempt or correct an obstruction or onset of an obstruction. The correlation can be made automatically by the ventilation system for each user, or can be made in advance by a medical assessment.

It should be noted that in the graphical examples provided, the respiration sensor waveform is exemplary only and actual waveforms can take on other characteristics, such as different I:E ratios, breath rates, random behavior, ascending and descending shapes of inspiratory and expiratory curves, and altering amplitudes. It is noted that because of the gas flow delivery from the cannula, a region of transient negative pressure may be generated near the catheter distal tip. The sensing signal processing may take this into account when determining the breath phase.

It should be noted that the different embodiments described above can be combined in a variety of ways to deliver a unique therapy to a patient and while the invention has been described in detail with reference to the preferred embodiments thereof, it will be apparent to one skilled in the art that various changes and combinations can be made without departing for the present invention. Also, while the invention has been described as a means for mobile respiratory support for a patient, it can be appreciated that still within the scope of this invention, the embodiments can be appropriately scaled such that the therapy can provide higher levels of support for more seriously impaired and perhaps non-ambulatory patients or can provide complete or almost complete ventilatory support for non-breathing or critically compromised patients, or can provide support in an emergency, field or transport situation. Also, while the invention has mostly been described as being administered via a nasal interface it should be noted that the ventilation parameters can be administered with a variety of other airway interface devices such as ET tubes, tracheostomy tubes, laryngectomy tubes, cricothyrotomy tubes, endobronchial catheters, laryngeal mask airways, oropharyngeal airways, nasal masks, trans-oral cannula, nasal-gastric tubes, full face masks, etc. . . . And while the ventilation parameters disclosed in the embodiments have been mostly specified to be compatible with adult respiratory augmentation, it should be noted that with the proper scaling the therapy can be applied to pediatric and neonatal patients. Further, while the target disease states have mostly been described as respiratory insufficiency and SA, other breathing, lung and airway disorders can be treated by the therapy with the requisite adjustment in ventilation parameters, for example, ALS, neuromuscular disease, spinal cord injury, influenza, CF, ARDS, lung transplant bridging, and other diseases can be addressed with this therapy, as well as mass casualty, pandemic, military, bridge and transport applications. Lastly, while the invention has been described as a stand alone therapy, the therapy can be modular, for example a ventilation system can be adapted which can switch between invasive or NIV or other closed system ventilation modes and the non-invasive open ventilation mode described herein. Or, the therapy can be used simultaneously in conjunction with other modes of ventilation, such as during a conscious sedation medical procedure in which the patient is ventilated with a conventional ventilator as a back up means of respiration while the patient receives ventilation from the mode described herein.

In general, any of these interface devices may include one or more of the following design or feature elements: Noise reduction elements, diagnostic element(s) for positioning the mask, sensing flow, volume, sensing augmentation, sensing entrainment—(knowing how much entrainment is passing through the mask), incorporating the sensing of effort—sensing what the patient effort is, and feeding into patient diagnostic to help diagnose different forms of respiratory problems, Apnea back up or apnea detection. The system could react to the information it's gathering, Could analyze entrainment, etc., feedback for correct fitting, positioning, i:e ratio), detection that the mask needs to be adjusted due to fit, Congestion; Mustaches, facial hair; Plugged nose, etc.; Eating, Sneezing, Motion.

These devices, method and systems may also include the following and address the following problems: Adjusting the triggering sensitivity level, multi-axis pressure transducer capable of having more gain to handle motion of the device better; additional sensors such as blood pressure integral to the mask; temperature integral to the mask such as measuring temperature inside of the nose; speaker/microphone for communication; Video monitor for communication, customizing the mask or ventilator to unique physical shape; integrating part of the system into assisted walking devices for example attachment to walker, etc. For titration to the patient, an acquired signal obtained from the patient could autotitrate by determining quickly their best trigger time and waveform and matching the patient effort which may be important for compliance. Diagnostic capability could include monitoring and capturing coughing/sneezing. During sleep the system can monitoring sleep position. The system can include sensors to distinguish between mouth breathing and nose breathing and alert the patient to perform purse-lip breathing if it is detected that they are active and not breathing right. The system can include an element that helps the patient by coaching them through the different types of breathing/etc. The start up upon power on may gently ramp to the therapeutic level to avoid startling patient. The system could optimize adjustment by sound, using a microphone that detects when there is not optimal entrainment and positioning. An audiofile could play from the ventilator. The ventilator could record breathing/wheezing, speech, lung sounds. The gas jets could be fabricated to create a helical gas stream exit to reduce sound and increase power. Could play WAV files—of soothing therapist voice, etc with volume of the music triggered to biofeedback (based on the mental/anxiety state). There could be custom voice alert messages and instructions. There could be active noise cancelling. The mask could be fitted with pads on the sides of the nares—the pads can comprise Nitinol and could anchor the device. The ventilator could include an parts or replacement supply ordering communication feature, as well as a panic button or trouble button. The nasal pillows may insufflate that provide the seal, position the device to center it based on the velocity, allow to float and location. Jets can come in from the bottom and from the size. The system can include flesh-toned tubing and parts. There can be 'skins" for the system—personalize or individual system covers, etc. Additional sensors include glucose, blood pressure, electrolytes. The ventilator screen can include a mirror or camera and display to allow the user to adjust the mask. The video can record the mask fit. The ventilator can include GPS for safety and other reasons and have automatic communication to a remote location for dealing with problems. Wax can be used to help fit the mask. The mask can include a modular shield to help performance in windy situations. The pillow can be inflatable to center with nostril. Ventilator skins can be personalized and selectable from range of styles, mix/match, etc. The mask may have multiple jets that converge/direct flow for each nostril.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A non-invasive ventilation system, the system comprising:
    at least one outer tube with a proximal lateral end of the at least one outer tube adapted to extend to a side of a nose, wherein the at least one outer tube includes a wall and a throat section;
    at least one coupler at a distal section of the at least one outer tube for impinging at least one nostril and positioning the at least one outer tube relative to the at least one nostril;
    at least one jet nozzle positioned within the at least one outer tube at the proximal lateral end and in fluid communication with a pressurized gas supply;
    at least one pressure tap disposed within the at least one outer tube in fluid communication with a transducer;
    at least one opening in the distal section adapted to be in fluid communication with the at least one nostril; and
    at least one aperture defined through the wall of the at least one outer tube in fluid communication with ambient air, wherein the at least one aperture is in downstream proximity to the at least one pressure tap.

2. The system of claim 1, wherein the at least one outer tube further includes a first outer tube and a second outer tube extending in substantially opposite directions.

3. The system of claim 2, wherein at least one of the at least one jet nozzle is positioned within the first outer tube and another of the at least one jet nozzle is positioned within the second outer tube.

4. The system of claim 2, wherein the first outer tube is separated from the second outer tube by a divider.

5. The system of claim 1, wherein the at least one outer tube is a manifold.

6. The system of claim 5, wherein a gas flow path within the manifold is curved and devoid of abrupt angles and corners.

7. The system of claim 1, wherein the at least one coupler is a nasal pillow.

8. The system of claim 1, wherein the at least one coupler is adapted to seal the at least one nostril such that a patient spontaneously breathes through the at least one aperture.

9. The system of claim 1, wherein a distal tip of the at least one jet nozzle is positioned at the at least one aperture.

10. The system of claim 1, wherein the at least one jet nozzle directs pressurized gas in a substantially parallel direction with ambient air entering from the at least one aperture.

11. The system of claim 1, further comprising at least one secondary aperture in the at least one outer tube.

12. The system of claim 1, wherein the at least one jet nozzle directs pressurized gas coaxially to a primary gas flow pathway.

13. The system of claim 1, further comprising a filter.

14. The system of claim 1, further comprising at least one sensor for sensing spontaneous respiration.

15. The system of claim 14, further comprising a ventilator for delivering pressurized gas in synchrony with phases of breathing.

16. The system of claim 1, wherein a cross sectional area of the at least one aperture is larger than a cross sectional area of the throat section.

17. The system of claim 1, wherein the system further comprises a wearable ventilator.

18. The system of claim 1, wherein the system further comprises a ventilator, the ventilator comprises a control unit, and wherein the control unit adjusts an output of the ventilator to match a patient's ventilation needs based on information from at least one sensor.

19. The system of claim 1, wherein the system further comprises a ventilator, the ventilator comprises a control unit, and the control unit comprises a speaking mode sensing system, and wherein the control unit adjusts an output of the ventilator while the patient is speaking to not be asynchronous with a patient's spontaneous breathing.

20. The system of claim 1, wherein the system further comprises a ventilator, the ventilator comprises a control unit, and the control unit comprises an apnea or hypopnea sensing system, and wherein the control unit adjusts an output of the ventilator according to apnea or hypopnea.

21. The system of claim 1, wherein the at least one outer tube comprises sound reduction features selected from the group consisting of: a secondary aperture, a filter for the at least one aperture, textured surfaces, a muffler, sound absorbing materials, an angled jet nozzle, non-concentric jet nozzle positions, and combinations thereof.

22. The system of claim 1, wherein the system further comprises a ventilator, and the at least one outer tube comprises at least one gas delivery circuit in fluid communication with the ventilator.

23. The system of claim 22, wherein the at least one gas delivery circuit is bifurcated.

24. The system of claim 23, wherein the at least one outer tube further comprises a manifold in fluid communication with the ventilator, the manifold comprising at least one lateral proximal end in fluid communication with the at least one gas delivery circuit.

25. The system of claim 24, wherein at least one of the at least one aperture defined through the wall of the at least one outer tube in fluid communication with ambient air is disposed in the at least one lateral proximal end of the manifold.

26. The system of claim 25, wherein at least one of the at least one jet nozzle is aligned in parallel with each of the at least one gas delivery circuit and supplies ventilation gas proximate to the at least one of the at least one aperture defined through the wall of the at least one outer tube in fluid communication with ambient air.

27. The system of claim 26, wherein the ventilation gas and entrained ambient air elevates lung pressure, elevates lung volume, decreases work of breathing or increases airway pressure.

28. The system of claim 22, wherein the transducer is disposed within the ventilator.

* * * * *